(12) United States Patent
Moola et al.

(10) Patent No.: US 9,804,168 B2
(45) Date of Patent: *Oct. 31, 2017

(54) BIOMARKER DISCOVERY IN COMPLEX BIOLOGICAL FLUID USING BEAD OR PARTICLE BASED LIBRARIES AND DIAGNOSTIC KITS AND THERAPEUTICS

(75) Inventors: Muralidhar Reddy Moola, Jupiter, FL (US); Jessica Schilke, Jupiter, FL (US)

(73) Assignee: OPKO Pharmaceuticals, LLC, Maimi, FL (US)

( * ) Notice: Subject to any disclaimer, the term of this patent is extended or adjusted under 35 U.S.C. 154(b) by 793 days.

This patent is subject to a terminal disclaimer.

(21) Appl. No.: 13/428,313

(22) Filed: Mar. 23, 2012

(65) Prior Publication Data

US 2012/0270741 A1    Oct. 25, 2012

Related U.S. Application Data

(60) Provisional application No. 61/467,256, filed on Mar. 24, 2011, provisional application No. 61/491,717, filed on May 31, 2011, provisional application No. 61/583,881, filed on Jan. 6, 2012.

(51) Int. Cl.

| | |
|---|---|
| *C40B 40/10* | (2006.01) |
| *G01N 33/68* | (2006.01) |
| *C07K 7/06* | (2006.01) |
| *G01N 33/543* | (2006.01) |
| *G01N 33/566* | (2006.01) |
| *C07K 1/04* | (2006.01) |
| *G01N 33/574* | (2006.01) |
| *C40B 40/04* | (2006.01) |
| *C40B 60/12* | (2006.01) |

(52) U.S. Cl.
CPC ......... *G01N 33/6845* (2013.01); *C07K 1/047* (2013.01); *C07K 7/06* (2013.01); *C40B 40/04* (2013.01); *C40B 40/10* (2013.01); *C40B 60/12* (2013.01); *G01N 33/566* (2013.01); *G01N 33/57438* (2013.01); *G01N 2800/104* (2013.01); *G01N 2800/2821* (2013.01)

(58) Field of Classification Search
None
See application file for complete search history.

(56) References Cited

U.S. PATENT DOCUMENTS

| | | | |
|---|---|---|---|
| 5,834,318 | A | 11/1998 | Buettner |
| 6,329,510 | B1 | 12/2001 | Qin |
| 6,344,334 | B1 | 2/2002 | Ellman |
| 7,354,584 | B2 | 4/2008 | Reed |
| 7,776,313 | B2 | 8/2010 | Fish |
| 7,932,294 | B2 | 4/2011 | Satyam |
| 2002/0004215 | A1 | 1/2002 | Osbourn |
| 2002/0018778 | A1 | 2/2002 | Caplan |
| 2004/0101830 | A1 | 5/2004 | Hammond |
| 2004/0241759 | A1 | 12/2004 | Tozer |
| 2006/0046967 | A1 | 3/2006 | Satyam |
| 2006/0205674 | A2 | 3/2006 | Satyam |
| 2006/0121489 | A1 | 6/2006 | Gorenstein |
| 2006/0275753 | A1 | 6/2006 | Hammond |
| 2006/0275829 | A1 | 6/2006 | Hammond |
| 2007/0003954 | A1 | 1/2007 | Kodadek |
| 2007/0026402 | A1 | 2/2007 | Noble et al. |
| 2007/0054857 | A1 | 3/2007 | Satyam |
| 2007/0065913 | A1 | 3/2007 | Chen |
| 2007/0105152 | A1 | 5/2007 | Denu |
| 2007/0111322 | A1 | 5/2007 | Yang |
| 2009/0077763 | A1 | 3/2009 | Chang |
| 2009/0111102 | A1 | 4/2009 | Diehl |
| 2009/0246124 | A1 | 10/2009 | Kodadek |
| 2010/0266610 | A1 | 10/2010 | Zmuda |
| 2010/0303805 | A1 | 12/2010 | Moola |

(Continued)

FOREIGN PATENT DOCUMENTS

| | | |
|---|---|---|
| JP | 2009-195245 | 9/2009 |
| JP | 2010-71744 | 4/2010 |

(Continued)

OTHER PUBLICATIONS

Reddy et al., "Protein "fingerprinting" in complex mixtures with peptoid microarrays," Proc. Natl. Acad. Sci. U.S.A. 2005, 102:12672-12677.*
Simpson et al., "Selective Toxin Sequestrants for the Treatment of Bacterial Infections," J. Am. Chem. Soc. 2009, 131:5760-5762.*
U.S. Appl. No. 61/467,256, filed Mar. 24, 2011, Muralidhar Reddy Moola.
U.S. Appl. No. 61/491,717, filed May 31, 2011, Muralidhar Reddy Moola.
Eichler et al, "Peptide, peptidomimetic, and organic synthetic combinatorial libraries", Med Res Rev., 15(6):481-96, 1995.
Cho et al, "Cyclic and linear oligocarbomate ligands for human thrombin", BioorgMed Chem 7, 1171-1179, 1999.
Gallop et al, "Applications of combinatorial technologies to drug discovery. 1. Background and peptide combinatorial libraties", J. Med. Chem., 37(9)1233-1251, 1994.

(Continued)

*Primary Examiner* — Kaijiang Zhang
(74) *Attorney, Agent, or Firm* — Mark Cohen; Pearl Cohen Zedek Latzer Baratz LLP

(57) ABSTRACT

The present invention is useful in screening for biomarkers associated with any other disease or condition. Such diseases and conditions range from the neurological diseases, autoimmune diseases and cancers identified above as well as any other disease or condition that has a biomarker such as an antibody or other characterizing protein or biomolecule associated with the disease or progression of the disease. The large ligand libraries of the invention can be used directly in biological fluid, under the appropriate experimental conditions and according to the processes recited herein, to screen for such markers and without the need to use fewer support members (e.g. about 100,000 or less) or without the need to transfer such peptoids or ligands to a microarray before screening the biological fluid. In addition, the ligand libraries may also be used to screen for cell based receptors that specifically relate to a particular cell surface marker.

4 Claims, 65 Drawing Sheets

(56) References Cited

U.S. PATENT DOCUMENTS

| | | |
|---|---|---|
| 2010/0303835 A1 | 12/2010 | Gocke |
| 2011/0092384 A1 | 4/2011 | Kwon |
| 2011/0269709 A1 | 11/2011 | Satyam |
| 2011/0269722 A1 | 11/2011 | Satyam |
| 2011/0274695 A1 | 11/2011 | Satyam |

FOREIGN PATENT DOCUMENTS

| | | |
|---|---|---|
| JP | 2011-004743 | 1/2011 |
| WO | WO 2000/009464 | 2/2000 |
| WO | WO 2002/070662 A2 | 9/2002 |
| WO | WO 2003/021264 A1 | 3/2003 |
| WO | WO 2004/005319 | 1/2004 |
| WO | WO 2004/037848 A2 | 5/2004 |
| WO | WO 2005/045430 | 5/2005 |
| WO | WO 2006/055689 A2 | 5/2006 |
| WO | WO 2006/094093 | 9/2006 |
| WO | WO 2006/124644 | 11/2006 |
| WO | WO 2009/077763 A1 | 6/2009 |
| WO | WO 2010/014651 A1 | 2/2010 |
| WO | WO 2010/141421 A1 | 12/2010 |
| WO | WO 2011/044253 A1 | 4/2011 |

OTHER PUBLICATIONS

Garcia-Arraras et al. (Jul. 23, 1993), Enteric nerve fibers of holothurians are recognized by an antibody to acetylated alpha-tubulin. Neruoscience Letters, 1993, vol. 157, pp. 153-156.
Gordon et al, "Applications of combinatorial technologies to drug discovery. 2. Combinatorial organic synthesis, library screening strategies, and future directions", J. Med. Chem., 37(10)1 385-401, 1994.
Stewart, J.M.; Young, J.D. (1984). Solid phase peptide synthesis (2nd ed.). Rockford: Pierce Chemical Company. p. 91.
Ostergaard et al., "Peptorners: A versatile approach for the preparation of diverse combinatorial peptidomimetic bead libraries", Mol. Divers., 3:17-27, 1997.
LePlae et al, "Tolerance of acylic residues in the beta-peptide 12-helix: Access to diverse side-chain arrays for biological applications", J. Amer. Chem. Soc, 124:6820-6821, 2002.
Marani et al., "Screening of one-bead-one-peptide combinatorial library using red fluorescent dyes. Presence of positive and false positive beads", J. Comb. Chein,, 2009, 11 (1), pp. 146-150.
Merrifield, "Solid phase synthesis" Science, 232(4748):341-347, 1986.
Neumann et al. "SPR-based Fragment Screening: Advantages and Applications." Current Topics in Medicinal Chemistry, 2007, vol. 7, pp. 1630-1642.
Østergaard, S & Holm, A 1997, 'Synthesis and screening of an indexed motif-library containing non-proteinogenic amino acids' Journal of Peptide Science, vol. 3, pp. 123-132.
Reddy et al., "Identification of Candidate IgG Biomarkers for Alzheimer's Disease via Combinatorial Library Screening", Cell, Jan. 2011, 144, 132-142.
Tam et al, "$S_N2$ Deprotection of synthetic peptides with a low concentration of HF in dimethyl sulfide: evidence and application in peptide synthesis", J. Am. Chem. Soc, 105:6442, 1983.
Thompson et al., "Synthesis and Applications of Small Molecule Libraries" Chem. Rev., 1996, 96 (1), pp. 555-600.
Yang et al, "Novel turns and helices in peptides of chiral alpha-aminoxy acids", J. Amer. Chem. Soc, 121:589-590, 1999.
Zuckermann et al., "Efficient method for the preparation of peptoids [Oligo(N-substituted glycines)] by submonomer solid-phase synthesis", J. Am. Chem. Soc. 114, 10646-10647, 1992.
Liu et al., "A potent transactivation domain mimic with activity in living cells", Journal of the American Chemical Society, 2005, vol. 127, pp. 8254-8255.
Garske Adam et al., "SIRT1 top 40 hits: use of one-bead, one-compound acetyl-peptide libraries and quantum dots to probe deacetylase specificity", Biochemistry, American Chemical Society, vol. 45, No. 1, 2006, pp. 94-101.
Joo et al., "Synthesis and screening of support-bound combinatorial peptide libraries with free c-termini: determination of the sequence specificity of PDZ domains", Biochemistry, American Chemical Society, vol. 47, No. 9, 2008, pp. 3061-3072.
Hard et al,, "HDAC6 and Ubp-M BUZ Domains recognize specific c-terminal sequence of proteins", Biochemistry, vol. 49, No. 50, 2010, pp. 10737-10746.
Juskowiak et al., "Synthesis, screening and sequencing of cysteine-rich one-bead, one-compound peptide libraries", Journal of Combinatorial Chemistry, vol. 10, No. 5, 2008, pp. 726-731.
Lim et al., "Rapid identification of improved protein ligands using peptoid microarrays", Bioorganic and Medicinal Chemistry Letters, vol. 19, No. 14, 2009, pp. 3866-3869.
Olivos et al., "Microwave-assisted solid-phase synthesis of peptoids", Organic Letters, vol. 4, No. 23, 2002, pp. 4057-4059.
Kawakami et al. "Messenger RNA-programmed incorporation of multiple N-methyl-amino acids into linear and cyclic peptides" Chemistry & biology. Jan. 25, 2008;15(1):32-42.
Kopin et al. "Inter-and intraspecies polymorphisms in the cholecystokinin-B/gastrin receptor alter drug efficacy"Proceedings of the National Academy of Sciences 94.20 (1997): 11043-11048.
Lee et al. "Discovery of an orexin receptor positive potentiator" Chemical Science 1.1 (2010): 48-54.
Lee et al. "Discovery of an orexin receptor positive potentiator" Chemical Science 1.1 (2010): 48-54—Supplementary material.
Montoliu et al. "Prevention of in vivo excitotoxicity by a family of trialkylglycines, a novel class of neuroprotectants" Journal of Pharmacology and Experimental Therapeutics 301.1 (2002): 29-36.
Reddy et al. "Identification of candidate IgG biomarkers for Alzheimer's disease via combinatorial library screening" Cell 144.1 (2011): 132-142 — Supplementary Material.
Supplementary European Search Report for European Application No. 12761160.6 dated Jul. 28, 2016.
Thakkar et al. "High-throughput sequencing of peptoids and peptide-peptoid hybrids by partial edman degradation and mass spectrometry" J Comb Chem. Mar. 9, 2009;11(2):294-302.
Zuckermann et al. "Peptoids as potential therapeutics" Curr. Opin. Mol. Ther 11.3 (2009): 299-307.

* cited by examiner

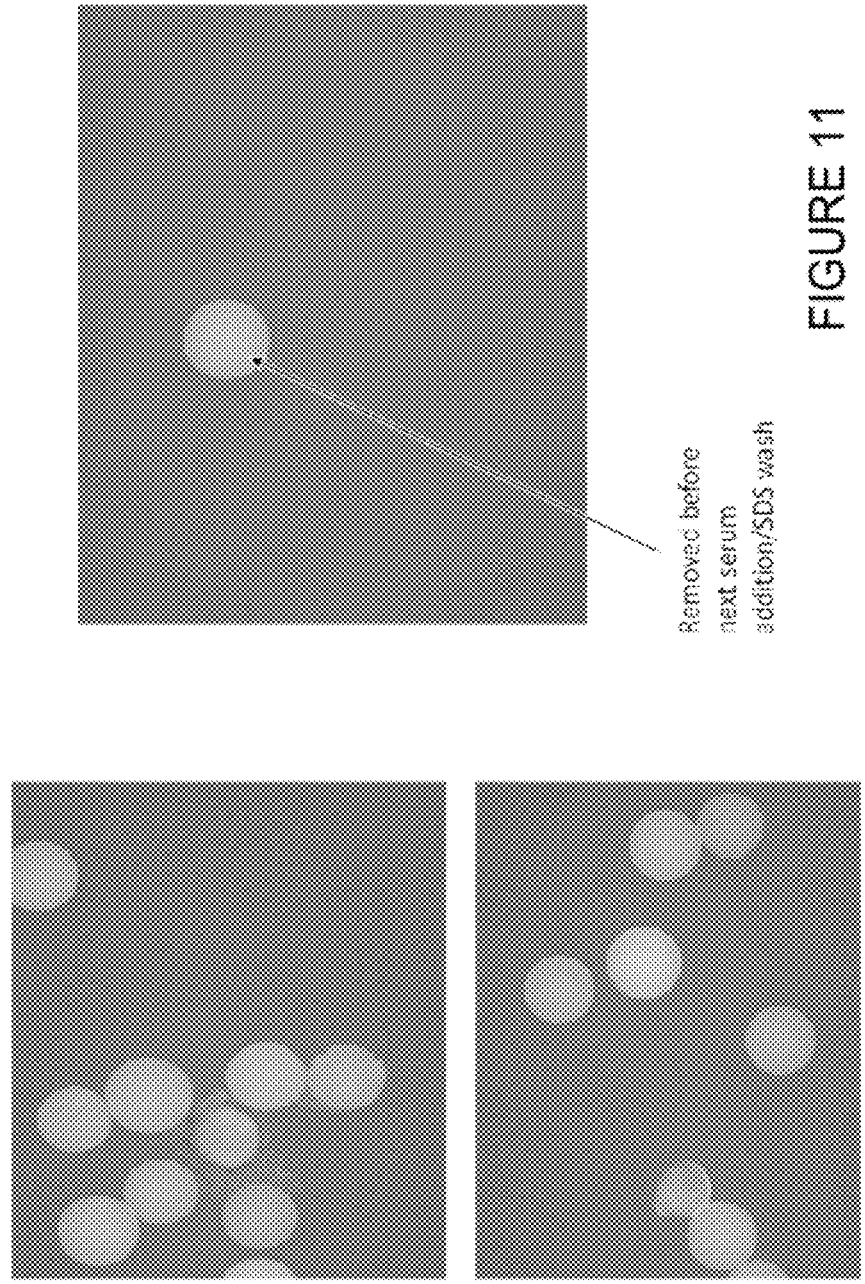

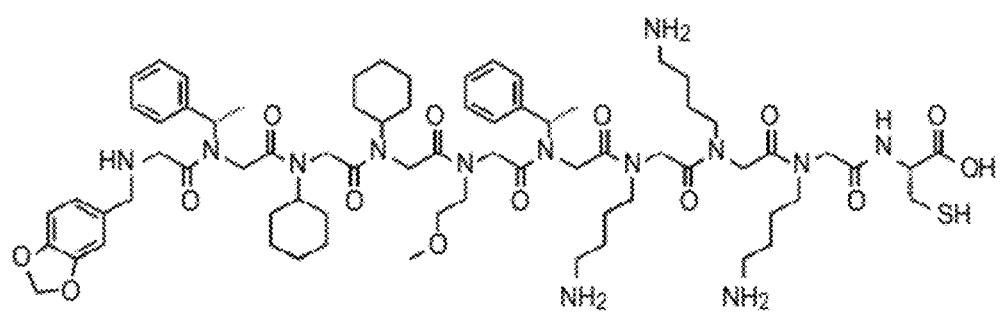
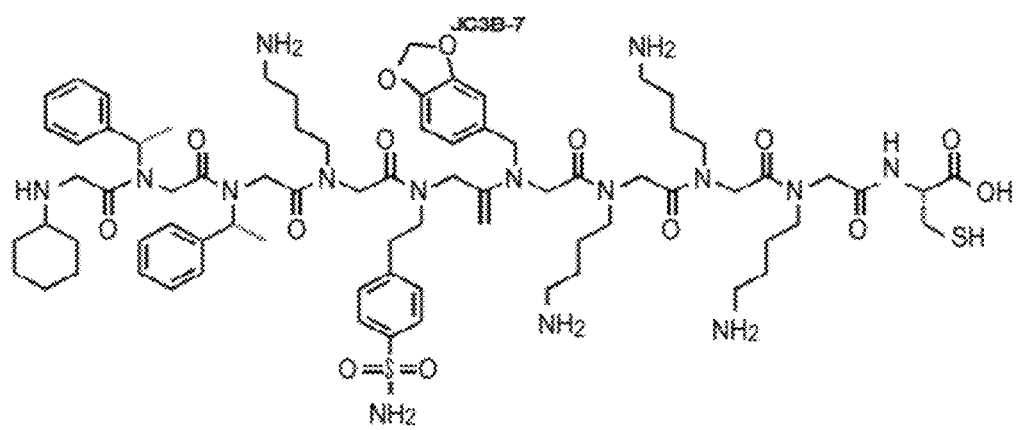
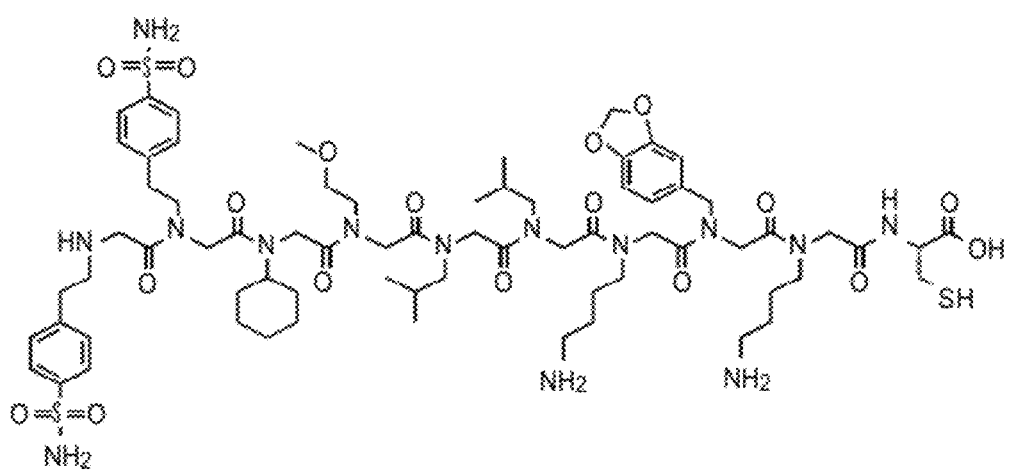
FIGURE 13B

KN1B SLE Hits

| KN1B-14 | KN1B-15 | KN1B-16 | KN1B-17 | KN1B-18 | KN1B-19 | KN1B-20 | KN1B-21 | KN1B-22 |
|---|---|---|---|---|---|---|---|---|
| Cysteine | Cysteine | Cysteine | Cysteine | Cysteine | Cysteine | Cysteine | Cysteine | Cysteine |
| Diaminobutane | Diaminobutane | Diaminobutane | Diaminobutane | Diaminobutane | Diaminobutane | Diaminobutane | Diaminobutane | Diaminobutane |
| Allylamine | Cyclohexylamine | Benzesulfonamide | Benzesulfonamide | Diaminobutane | Allylamine | Dimethoxyphenethylamine | Methylbenzylamine | Piperonylamine |
| Pyridinamine | Diaminobutane | Alkylamine | Dimethoxyphenethylamine | Piperonylamine | Methylbenzylamine | Isobutylamine | Benzesulfonamide | Benzylamine |
| Glycine | Diaminobutane | Diaminobutane | Diaminobutane | Methylbenzylamine | Methylbenzylamine | Methylbenzylamine | Piperonylamine | Piperonylamine |
| Benzesulfonamide | methoxyphenethylamine | Benzylamine | Benzesulfonamide | Cyclohexylamine | Diaminobutane | Diaminobutane | Diaminobutane | Benzylamine |
| Benzylamine | benzylamine | Methylbenzylamine | Diaminobutane | Benzylamine | Piperonylamine | Methylbenzylamine | Methylbenzylamine | Diaminobutane |
| Diaminobutane | Piperonylamine | Benzylamine | Benzylamine | Dimethoxyphenethylamine | Benzylamine | Benzylamine | Methylbenzylamine | Benzylamine |
| Isobutylamine | Diaminobutane | Methylbenzylamine | Methylbenzylamine | Diaminobutane | Piperonylamine | Piperonylamine | Diaminobutane | Cyclohexylamine |
| Benzesulfonamide | Diaminobutane | Diaminobutane | Benzylamine | Methylbenzylamine | Diaminobutane | Diaminobutane | Methylbenzylamine | Diaminobutane |

FIGURE 28

ELISA
Binding of KN1B-20-biotin-fluorescein to ELISA Plates
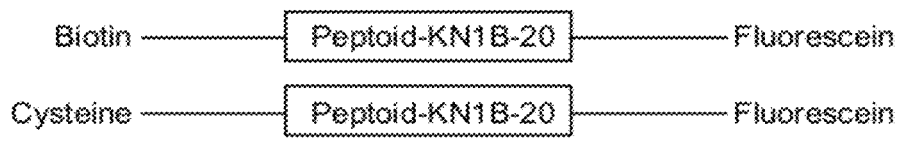
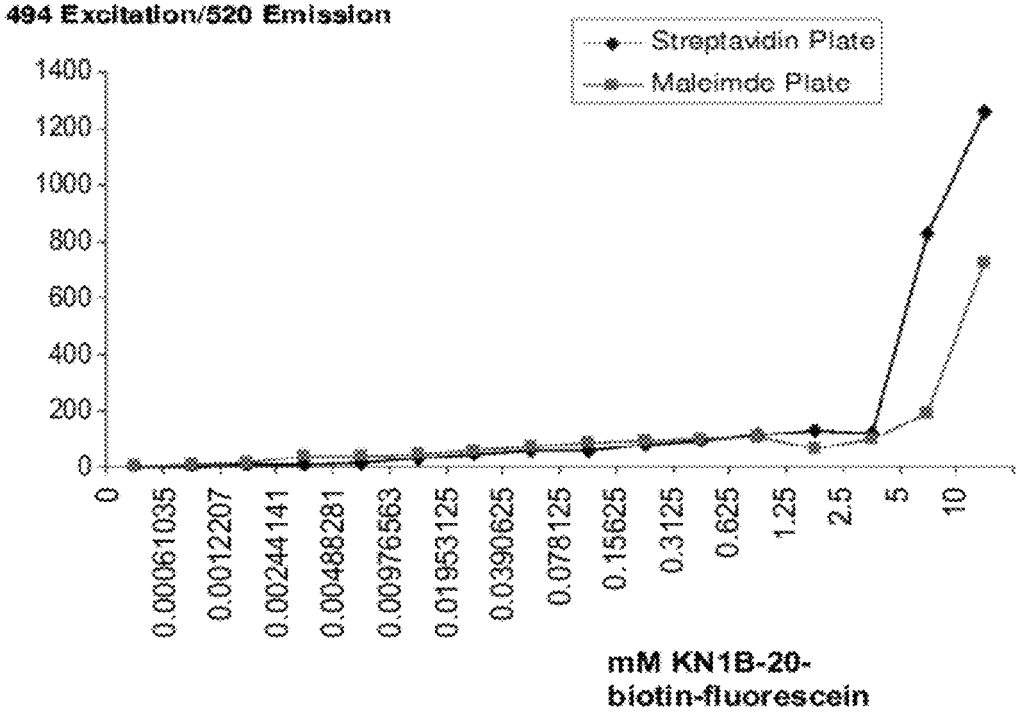
FIGURE 30

ELISA with 10mM ADP3

ELISA with 10mM SLE-KN1B-20

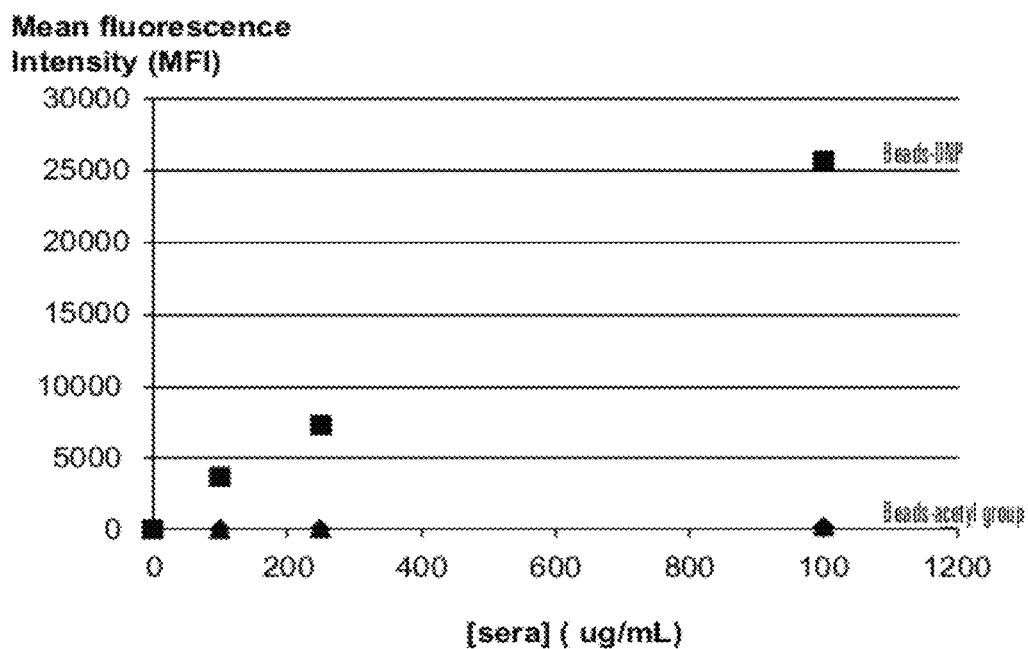
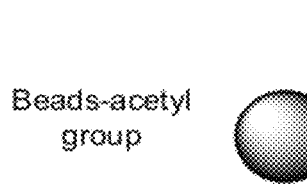
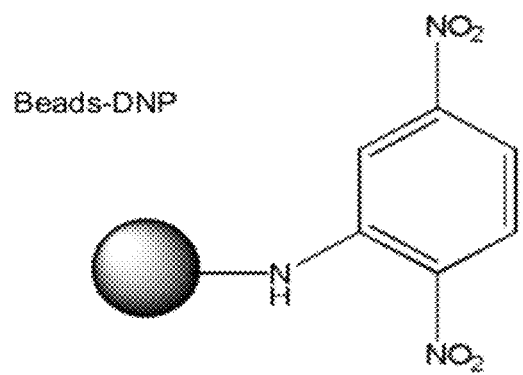
FIGURE 39

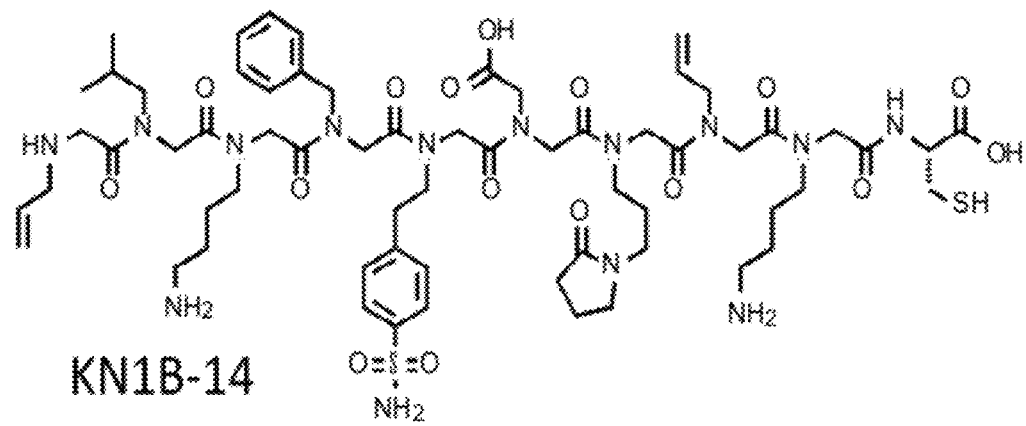
KN1B-14
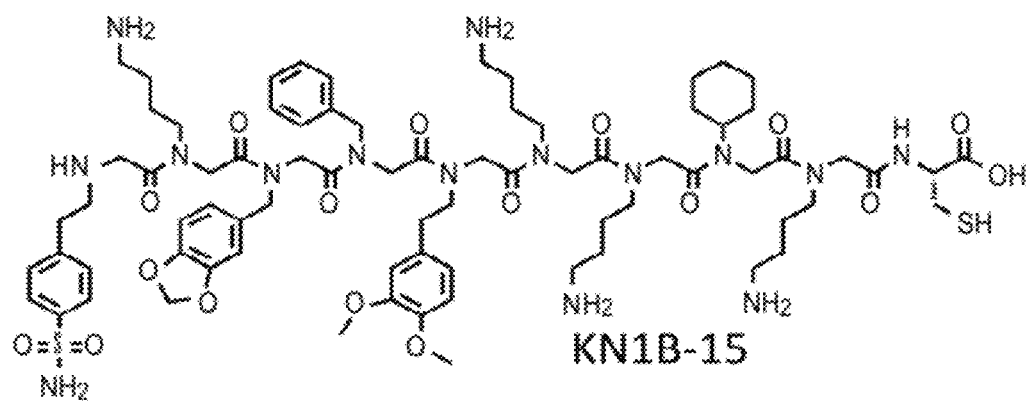
KN1B-15
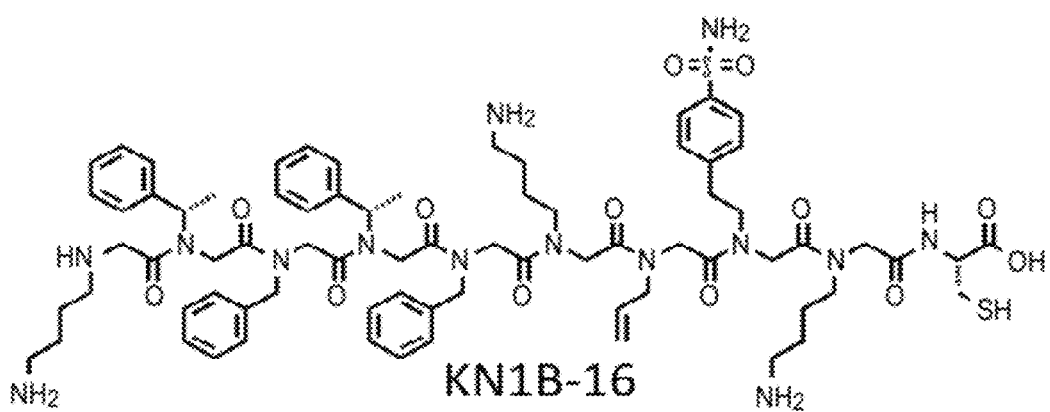
KN1B-16
FIGURE 43A

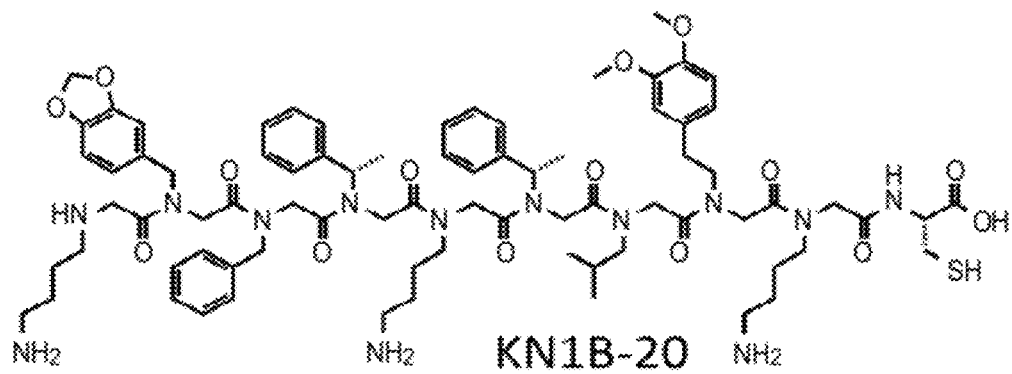
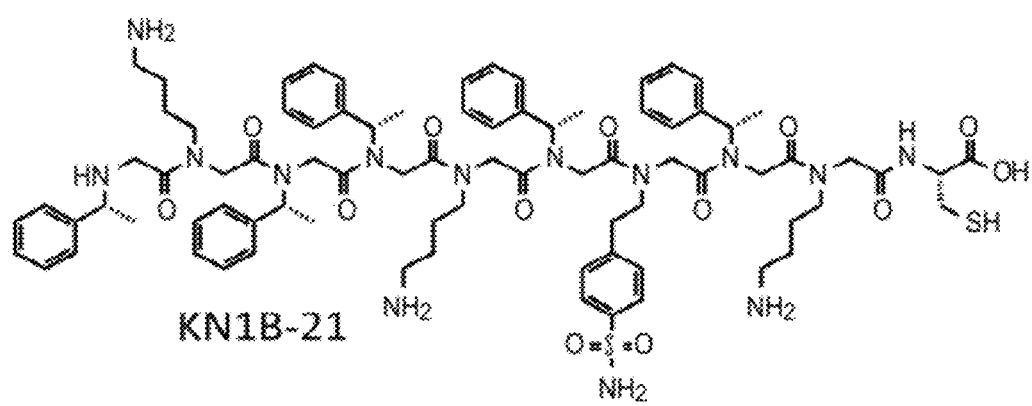
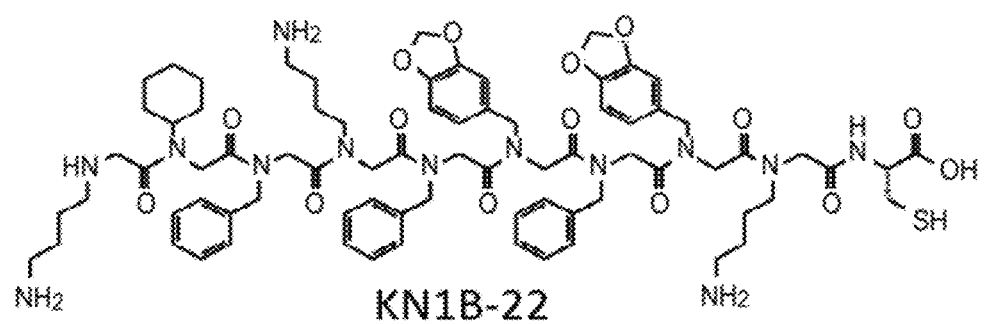
FIGURE 44

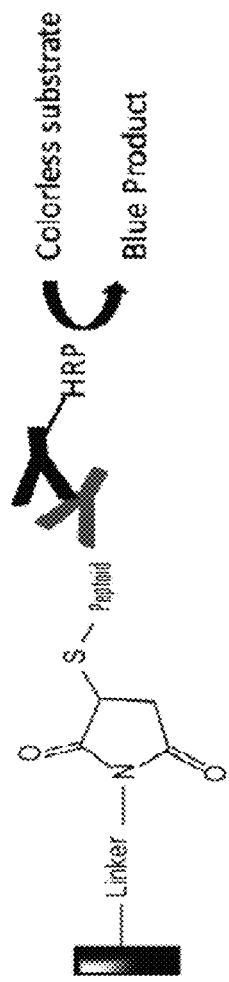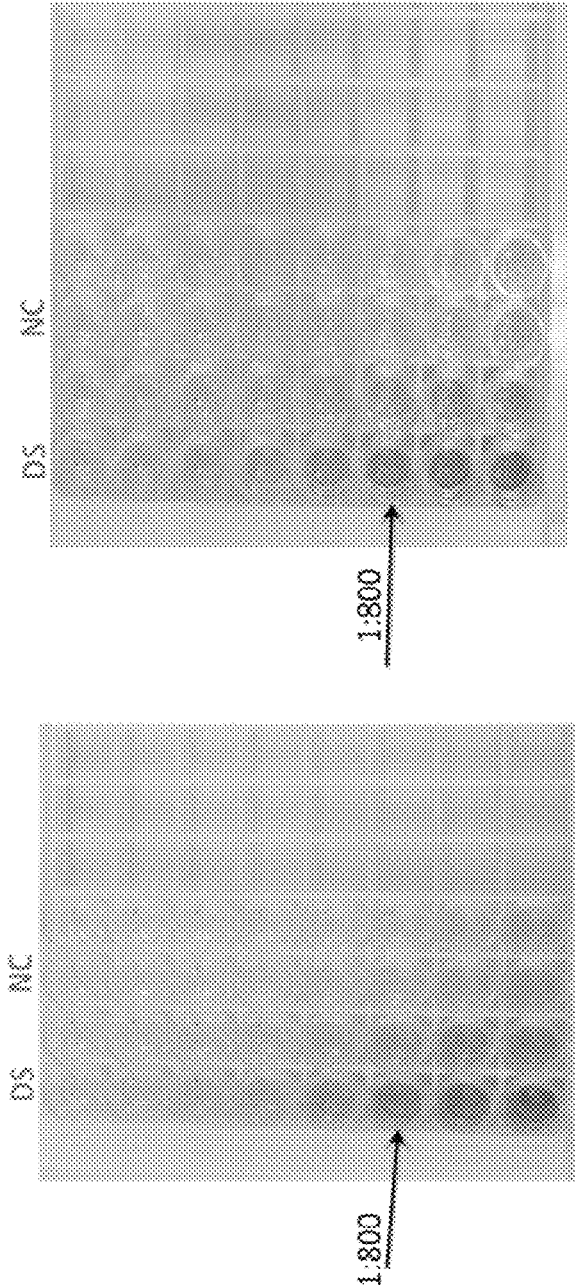
FIGURE 51

Diseased clinically
Opko: UND on single point. Titration: AD

Normal clinically (non-demented)
Opko: pre-AD even at single point

AD clinically (demented)
Opko: Not AD. Must be other dementia

AD Clinically
Opko: UND at single point. UND even after titration.

Summary of ELISA Analysis
Total Plasma Samples Tested = 106

| Clinical Diagnosis | Our prediction | Differences |
|---|---|---|
| 49 Alzheimer's | 42 | 7 (14%) |
| 57 Normal | 47 | 10 (17%) |

BIOMARKER DISCOVERY IN COMPLEX BIOLOGICAL FLUID USING BEAD OR PARTICLE BASED LIBRARIES AND DIAGNOSTIC KITS AND THERAPEUTICS

CROSS-REFERENCE TO RELATED APPLICATIONS

This application claims priority to U.S. Provisional Patent Applications 61/467,256, 61/491,717, and 61/583,881 filed Mar. 24, 2011, May 31, 2011, and Jan. 6, 2012, respectively, all of which are incorporated by reference herein in their entirety.

FIELD OF THE INVENTION

The present invention relates to a new screening methodology and diagnostic and therapeutic products derived therefrom. In particular, new large bead-based libraries containing a rich assortment of small molecules, peptides, peptoids and/or other oligomers are used to screen biological samples for disease related biomarkers. The invention allows for both rapid and direct screening of plasma, serum or other biological fluid to find disease associated antibodies in a host of diseases and further finds antibody-specific molecules, which can serve as diagnostic tools or as therapeutics for said diseases. Diagnostic kits containing such antibody specific molecules can be prepared for virtually any disease state that has an antibody or immunogenic component such as autoimmune diseases, central nervous system disorders and cancer. Such kits can be made from virtually any known support system provided said system can support or bind the antibody specific molecule such as a peptoid or other ligand binding moiety. Similarly, any known detection method including ELISA or other known detection means can be used to detect the antibody subsequent to either the initial screening to find putative hits and/or after a diagnostic screen using such putative hits in the diagnostic assay. Such methods may also be used to screen for other biomarkers including proteins and/or other biomolecules on the surface of cells to distinguish between cells expressing disease related markers versus healthy cells not expressing such markers.

BACKGROUND OF THE INVENTION

U.S. patent publication 2007/0003954 discloses protein and antibody profiling using small molecule microarrays. The application discloses ligands, which bind to ligand binding moieties wherein the ligands are arranged in arrays of synthetic molecules, which are used to screen for biomarkers and molecular fingerprints. The specific arrays described therein include, for example, a peptoid microarray having 7680 different compounds bound to the array. In that disclosure, bead based libraries were utilized as the initial means to make peptoids which were then transferred to microarrays with addressable locations on the microarray to screen biological fluids. The screening results in a unique pattern or molecular fingerprint on the array for any particular protein in a complex biological mixture. U.S. patent application 2010/0303805, hereby incorporated by reference, discloses certain peptoids and diagnostic arrays useful in screening biological fluids for biomarkers associated with central nervous system disorders. The specific monomers disclosed therein utilized to form the arrays therein may also be utilized in the new screening methodology of the present invention provided the libraries are enlarged to a much greater number of beads/peptoids or beads/ligands—e.g., between greater than 100K to 150 MM.

The present inventors have found that significantly larger bead based libraries (relative to microarray based screens for antibody biomarkers or bead based screens for cells) can, under the right conditions, be used to directly screen complex biological samples to find disease associated biomarkers as well as a significantly larger pool of ligands which bind to such ligand-binding moieties. This significantly larger pool includes a significantly improved number of high affinity ligands that serve as diagnostic tools as well as potential therapeutics. This approach also permits a significantly improved screening rate for any particular complex biological fluid because the need to make microarrays or similar addressable support systems is obviated in the first instance. Once the screening is performed, microarrays or other support systems including diagnostic arrays comprising the hits found in the screen may be manufactured and are included within the scope of this invention.

SUMMARY OF THE INVENTION

The present invention relates to a composition or a plurality of "compositions" comprising a large, random bead-based library of ligands. The library or plurality of libraries that form any particular "composition" is selected to screen for a target disease or condition and each library may be used to screen against a different disease or condition or the same libraries may be used to screen multiple disease states or conditions. The term "random" includes those libraries that have a rich assortment of side chains on the mono-substituted amines that form any particular monomer in an oligomeric chain. This assortment of R groups on the amine starting material is "random" even if some of the chemical and/or physical features on any particular monomer such as functionality/solubility are part of a desired feature or characteristic of the target oligomers. For plasma based screens or serum screens, for example, it is desired that any particular ligand bound to a bead has solubility characteristics which facilitate interaction, in solution, with a ligand binding moiety such as an antibody. In addition, the size of the oligomer is also a feature that is considered when forming a library of ligands that can bind to a ligand-binding moiety when the target moiety is, for example, an antibody or protein. The bead-based library comprises beads or similar support structures (i.e., polymeric resins) having bonded thereto (or to a linker on such resin) a ligand selected from the group consisting of small molecules, peptides, peptoids, polysaccharides or any oligomer based compound including nucleic acids or modified nucleic acid moieties. In a preferred embodiment, the bead-based library comprises peptoids. The peptoids are oligomers having monomeric units of between 5 to 15 monomers linked covalently to form the oligomer. The oligomer may have additional moieties linked to a terminal end of the oligomer to bond to a support or to a linker which links the oligomer to the support. The oligomeric peptoids are generated using, for example, a hybrid combination of a typical solid state peptide synthesis merged with a sub-monomer synthetic approach and comprise glycine or carbon substituted glycine-like moieties having a mono-substituted amide wherein the substituent on the amide nitrogen or α-carbon is selected from a wide range of moieties depending upon the monosubstituted amine or glycine α carbon substituent utilized in the synthesis. The peptoid libraries may generally be prepared as described in, for example, Kodadek and Reddy, Proceedings of the National Academy of Sciences, Sep. 6, 2005, volume 102, No. 36 or as described herein. As referenced above, the mono-substituted amine pool is generally selected from a wide range of monomers. The size of the library can range from about 200,000 to 150 MM beads having said number of distinct ligands per bead. Alternatively, and depending upon the size of the bead or support, each support or bead may have more than one ligand per bead/support and the ligand(s) may be the same ligand or distinct ligands.

The beads/supports having the ligand(s) which comprise the library are then taken further in the process of the invention. The invention comprises a process for screening a biological fluid for disease associated biomarkers comprising the steps of screening a biological control sample and a biological diseased sample with at least one bead-based ligand library and finding disease associated biomarkers using such a screen. The invention comprises a process for screening a complex biological sample for the presence of a disease-associated biomarker, which comprises exposing said sample to a plurality of ligand-bearing supports wherein at least one ligand detectably binds to the disease associated biomarker. The invention further comprises a method of screening a complex biological sample for disease associated biomarkers comprising the steps of (1) exposing a random ligand library to a control sample to identify and remove any non-specific ligand hits and (2) exposing the remaining ligand library to a diseased sample to identify any ligands which bind to a disease associated biomarker in the diseased sample. In particular, the invention comprises a process for screening a biological sample for a disease associated biomarker, comprising (1) pretreating a ligand-bearing bead (LBB) library with a suitable solvent to form treated LLBs; (2) exposing the treated LBBs to a normal control (NC) biological sample having control sample ligand binding moieties; (3) exposing the treated LBBs from the control sample to a Dynabead screen (iron tagged anti-IgG antibody) and removing the hits; (4) washing the remaining LBB library and exposing said library to an NC biological sample having any remaining control sample ligand binding moieties using quantam dot labeled secondary anti IgG antibodies and removing the hits; (5) washing the remaining LBB library and exposing said library to a biological sample from a patient having a disease; (6) exposing the treated LBBs from the diseased sample to a Dynabead screen and removing the hits; (7) washing the remaining LBBs and exposing said library to the biological sample from a patient having a disease; (8) adding quantam dot labeled secondary anti IgG antibodies to the washed LBBs and identifying the disease-associated ligand binding moieties bound to a ligand on the LBB and, optionally, after washing the Dynabeads from step (6), repeating step (8) using the Dynabead hits from step (6) and identifying the Dynabead Qdot hits. In a preferred embodiment, Tentagel beads (having embedded PEG linkers) are utilized in the preparation of the LBB. Alternative beads and/or particles and having different and/or optional linkers may also be utilized along with alternative detecting means. Beads may also be selected from, for example, Luminex beads. In a preferred process, the Dynabead steps are not utilized except as initial validation steps to confirm the Qdot hits.

Any or all of the separated hits from the step or steps identified above may be further characterized, chemically identified and synthesized as the same moiety or as a modified version thereof. In particular, the preferred characterization relates to taking the ligands on the LBB from step (8) and sequencing the particular oligomer or ligand bound to the biomarker or disease associated ligand-binding moiety. In a preferred embodiment, the ligand is a peptoid and the peptoid is sequenced to identify and/or confirm or reconfirm the identity of the putative diagnostic probe, which can be further utilized in a diagnostic kit or as the basis for a therapeutic drug or vaccine candidate depending upon the particular disease or condition. In a preferred embodiment, the ligand hit is sequenced, indentified and then resynthesized or synthesized in a larger scale using a bead or support based synthetic method to produce the identified/sequenced ligand. In this instance, the preferred synthetic ligand includes, for example, a cysteine amino acid as a functional ligand that is linked to a resin/bead or support (or to a linker on said support) and this amino acid is further treated with, for example, submonomers comprising bromoacetic acid and substituted amines having the selected R groups for the particular sequenced ligand (peptoid or α-substituted peptoid). The cysteine residue or other analogous amino acid residue provides a sulfhydryl, which can react with electrophilic groups on glass slides or supports. In a different manner, in the initial library formation and on tentagel beads or beads or resins without linkers, methionine is used as the first monomer to permit cleavage from the bead or resin following synthesis of the peptoid oligomer. The methionine forms part of the oligomer when cleaved from the resin or bead. Rink resins, on the other hand, have cleavage linkers or linkers that facilitate, under the right conditions, cleavage of the molecule from the linker and resin without also cleaving the other amide bonds in the oligomer.

The invention also comprises diagnostic kits using the ligands (or modified versions thereof) identified in the biological sample screening methodology. The power of the particular screen results in the rapid identification of a significant number of actual hits that are further utilized in such diagnostic kits. The term "rapid" in this instance means that the present process avoids the complicated and unnecessary step of building a microarray before having to analyze complex biological fluid, which thus results in a significant savings in time. In addition, the present method permits a much larger number of molecules to be screened against a complex biological fluid at any one time instead of being limited to a small number on a microarray. In addition to finding a significant number of hits, the discovered ligands include a significantly greater number of high affinity binders relative to those found using prior screening methodology, which did not directly screen or assay complex biological fluid(s) using such bead or particle based technology. Such ligands may be utilized in multiplex disease platforms comprising a first peptoid to screen for disease or condition A and at least one additional peptoid to screen for disease or condition B.

The range of diseases that may be screened for the presence of disease-associated antibodies or biomarkers in the organism of interest using the methodology of the invention includes virtually any disease and at any stage of development of the disease. The invention is useful in the diagnosis and progression of human and animal disease. Diagnostic kits comprising the ligands discovered and identified during the screening can comprise bead based diagnostic kits for point of care diagnostic screens and/or can comprise more elaborate diagnostic systems and/or multiplex systems built upon more complex support systems such as microarrays. In addition, diagnostic arrays built from the peptoids, α-substituted peptoids or ligands found in the initial screen may be used in clinical trials to identify or assist in identification of patient stratification and/or disease progression in any particular patient population or subpopulation. It is envisioned that such data derived from the primary and/or secondary or tertiary screens herein may accelerate drug development and sub-group or individualized patient care using pharmaceuticals that are specifically designed for a stage or certain stages of a disease, including early stage disease. Similarly, diagnostic kits derived from the ligands discovered herein may be used to identify early stage disease progression and/or any stage of the disease progression based upon the biomarker profile. Such information can be used to assist the physician in prescribing the most appropriate medical care for the individual patient or group of patients.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The following drawings are part of the present specification.

Figure 1A shows starting from a polystyrene bead having an amino group as the reactant (a PEG or equivalent or alternative linker may be formed between the bead and the terminal amino group). FIG. 1B shows the starting amino acid on the bead as methonine and which is then reacted to form the compound shown in B. FIG. 1C shows the submonomers (monomeric amines and haloacetic acids) utilized to form the oligomeric library of compounds.

FIG. 1A shows starting from a polystyrene bead having an amino group as the reactant (a PEG or equivalent or alternative linker may be formed between the bead and the terminal amino group). FIG. 1B shows the starting amino acid on the bead as methonine and which is then reacted to form the compound shown in B. FIG. 1C shows the submonomers (monomeric amines and haloacetic acids) utilized to form the oligomeric library of compounds. JC3B was also used to screen pancreatic cancer serum (data not shown).

FIG. 1A shows starting from a polystyrene bead having an amino group as the reactant (a PEG or equivalent or alternative linker may be formed between the bead and the terminal amino group). FIG. 1B shows the starting amino acid on the bead as methonine and which is then reacted to form the compound shown in B. FIG. 1C shows the submonomers (monomeric amines and haloacetic acids) utilized to form the oligomeric library of compounds.

FIG. 1A shows starting from a polystyrene bead having an amino group as the reactant (a PEG or equivalent or alternative linker may be formed between the bead and the terminal amino group). FIG. 1B shows the starting amino acid on the bead as methonine and which is then reacted to form the compound shown in B. FIG. 1C shows the submonomers (monomeric amines and haloacetic acids) utilized to form the oligomeric library of compounds. JC5B monomers included Isobutylamine, 2-Methoxyethylamine, Diaminobutane, Furfurylamine, Cyclohexylamine, R-Methylbenzylamine, Piperonylamine and 4-(Aminoethyl) Benzenesulfonamide.

FIG. 1A shows starting from a polystyrene bead having an amino group as the reactant (a PEG or equivalent or alternative linker may be formed between the bead and the terminal amino group). FIG. 1B shows the starting amino acid on the bead as methonine and which is then reacted to form the compound shown in B. FIG. 1C shows the submonomers (monomeric amines and haloacetic acids) utilized to form the oligomeric library of compounds.

FIG. 11 shows a reproducibility test which uses a diseased sample after SDS wash and QDOT addition.

FIG. 12 shows the peptoid sequences of the putative hits selected from the Alzheimer's screen from the JC3B library. The C-terminus is on the right side of the sheet and the N-terminus is on the left side.

FIG. 25 shows the pancreatic cancer screen hit sequences from the JC3B library.

FIG. 26 shows the pancreatic cancer screen hit sequences from the JC5B library.

FIG. 28 shows the SLE hits from the KN1B library. The C-terminus is on the right side of the sheet.

FIG. 30 shows the binding/detection of one of the SLE (lupus) peptoids to ELISA plates using two different binding methods at different concentrations of peptoid using a fluorescein tag.

FIG. 32 also shows validation of the TentaGel bead platform to distinguish between diseased and control sera.

FIG. 37 shows an SLE serum ELISA graph using 10 mM KN1B-20 prepared in DMSO at various serum dilutions. Separation between normal and diseased serum occurred over the dilution range of 1:200 through approximately 1:10,000. The starting dilutions were 1:200 (Group 1 SLE serum 0.367 mg/mL and non-diseased serum at 0.322 mg/mL).

FIG. 39 shows the degree of separation between beads having an acetyl group and beads having a 2,5-dintrophenyl group (DNP) at various concentrations of sera (100 ug/mL to 1,000 ug/mL) and in response to treatment with an anti-DNP labeled secondary antibody. The Mean fluorescence intensity (MFI) separation was greatest at the higher dilution of 1,000 ug/mL sera.

FIGS. 43 and 44 show the structures of the SLE (lupus) resynthesized peptoid ligand hits.

FIG. 51 shows ELISA experiments with a clear distinction between normal control and diseased serum at a serum dilution of 1:800 using horseradish peroxidase linked to a secondary antibody that detects the disease associated antibody-peptoid complex. The colorless substrate is added and changes color (blue) upon reaction with the bound HRP enzyme.

FIG. 56A shows the data for peptoids ADP3 and others as shown for a patient that was diseased clinically but for which the Opko peptoid P1aag4 was below 1.0 (UND at a single point; Titration AD positive). All other Opko peptoids were positive for AD (i.e., above 1.0). FIG. 56B shows that all Opko peptoids were positive for disease associated antibodies in a patient that was currently diagnosed as normal (non-demented) suggesting pre-AD. FIG. 56C shows that none of the Opko AD peptoids showed an intensity above 1 at any dilution point in a patient that was clinically diagnosed with AD suggesting that this patient had some other form of dementia. FIG. 56D shows that in a clinically positive AD patient, multiple Opko AD peptoids were not positive for disease associated antibodies but two peptoids (P1aag6 and P1aag4) were positive, thus UND at a single point and UND even after titration.

FIG. 57 also shows that the ADP3 peptoid is selected for disease associated antibodies associated with Alzheimer's disease and not Parkinsons or Lupus (SLE).

DETAILED DESCRIPTION OF THE INVENTION

Figure 1:
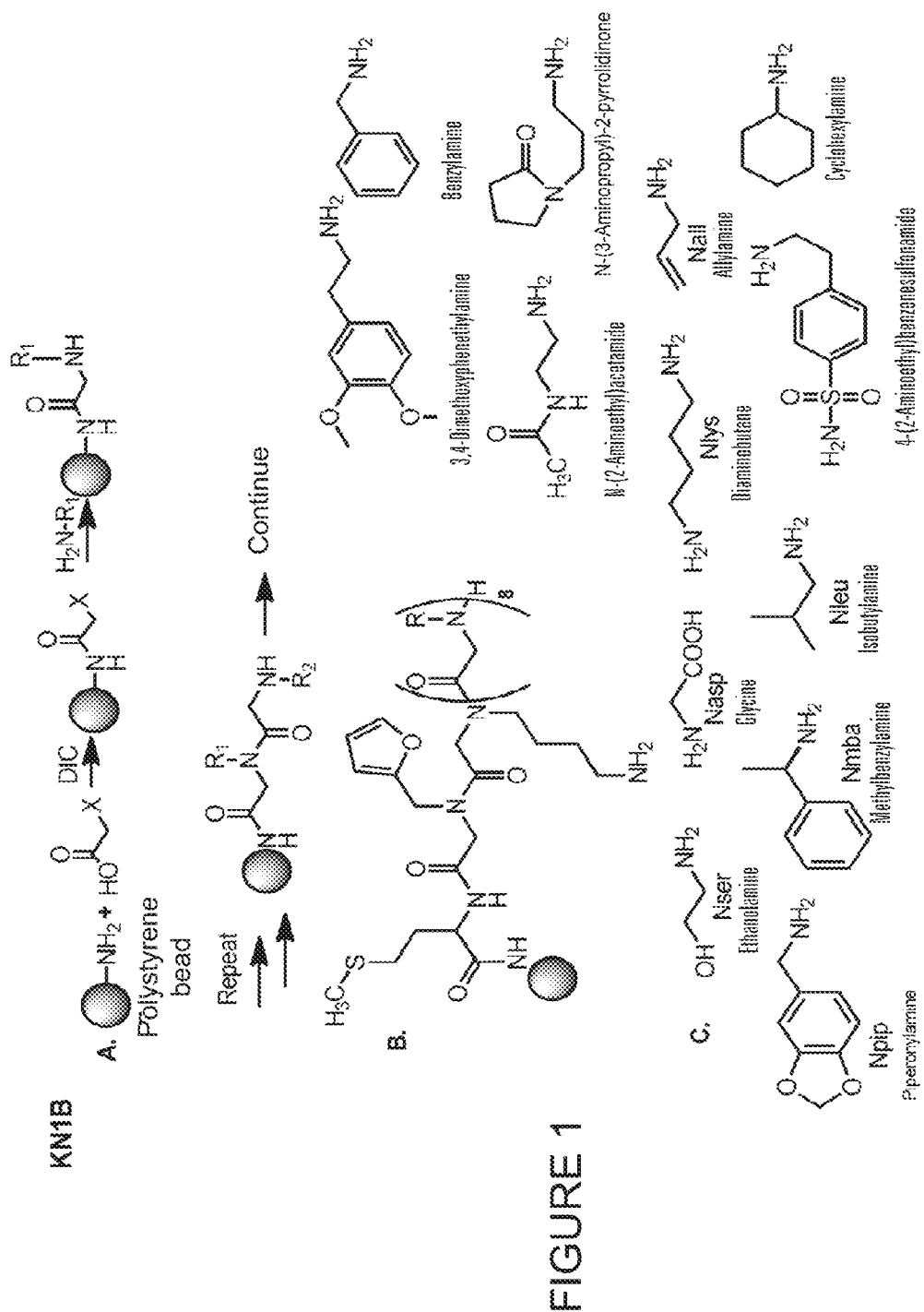
FIG. 1 shows a basic chemical schematic of the preparation of a library of Tentagel beads (KN1B) used to screen Alzheimer's serum samples.
Figure 2:
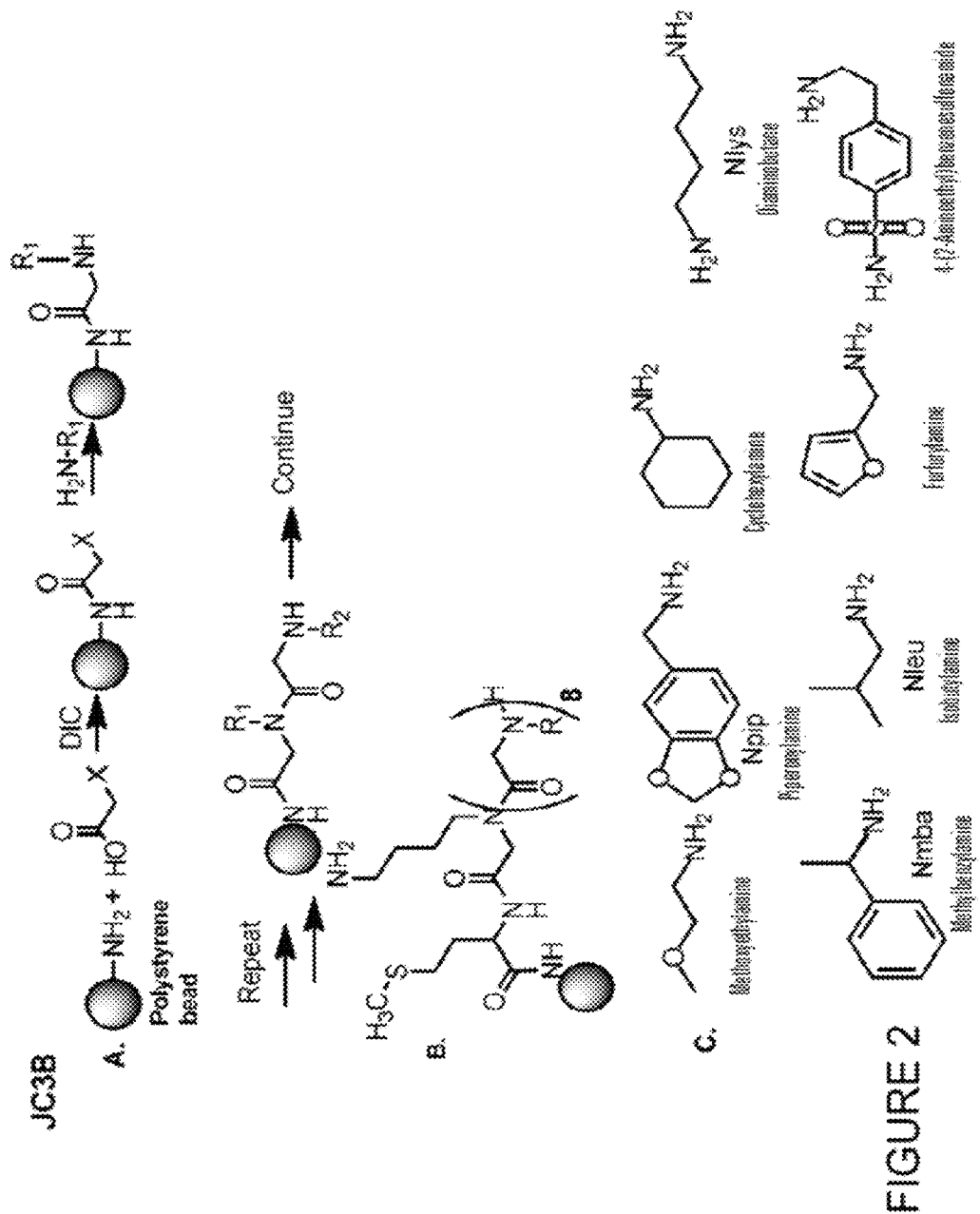
FIG. 2 shows a basic chemical schematic of the preparation of a library of Tentagel beads (JC3B) also used to screen Alzheimer's serum samples.
Figure 3:
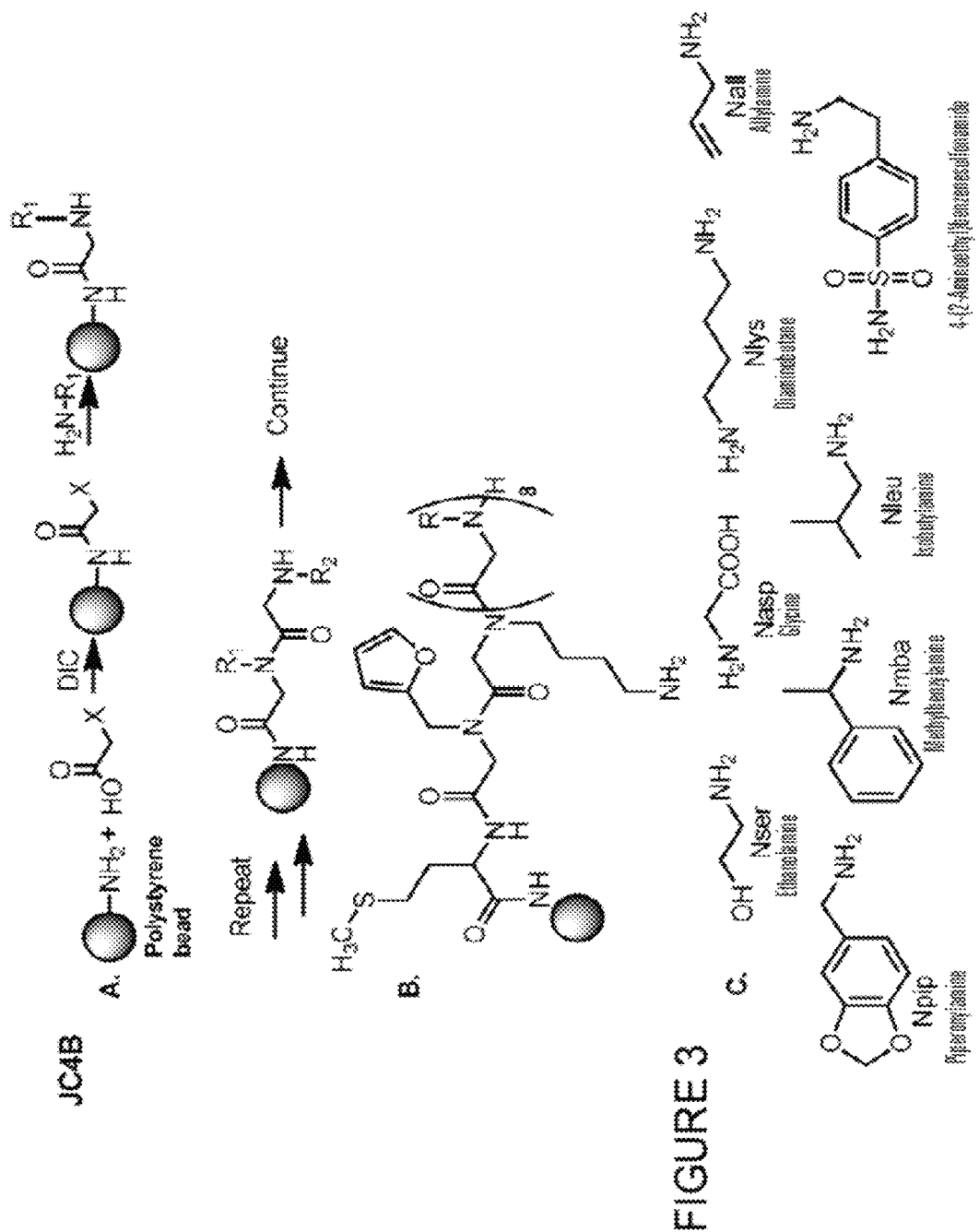
FIG. 3 shows a basic chemical schematic of the preparation of a library of Tentagel beads (JC4B) used to screen Alzheimer's serum samples.
Figure 4:
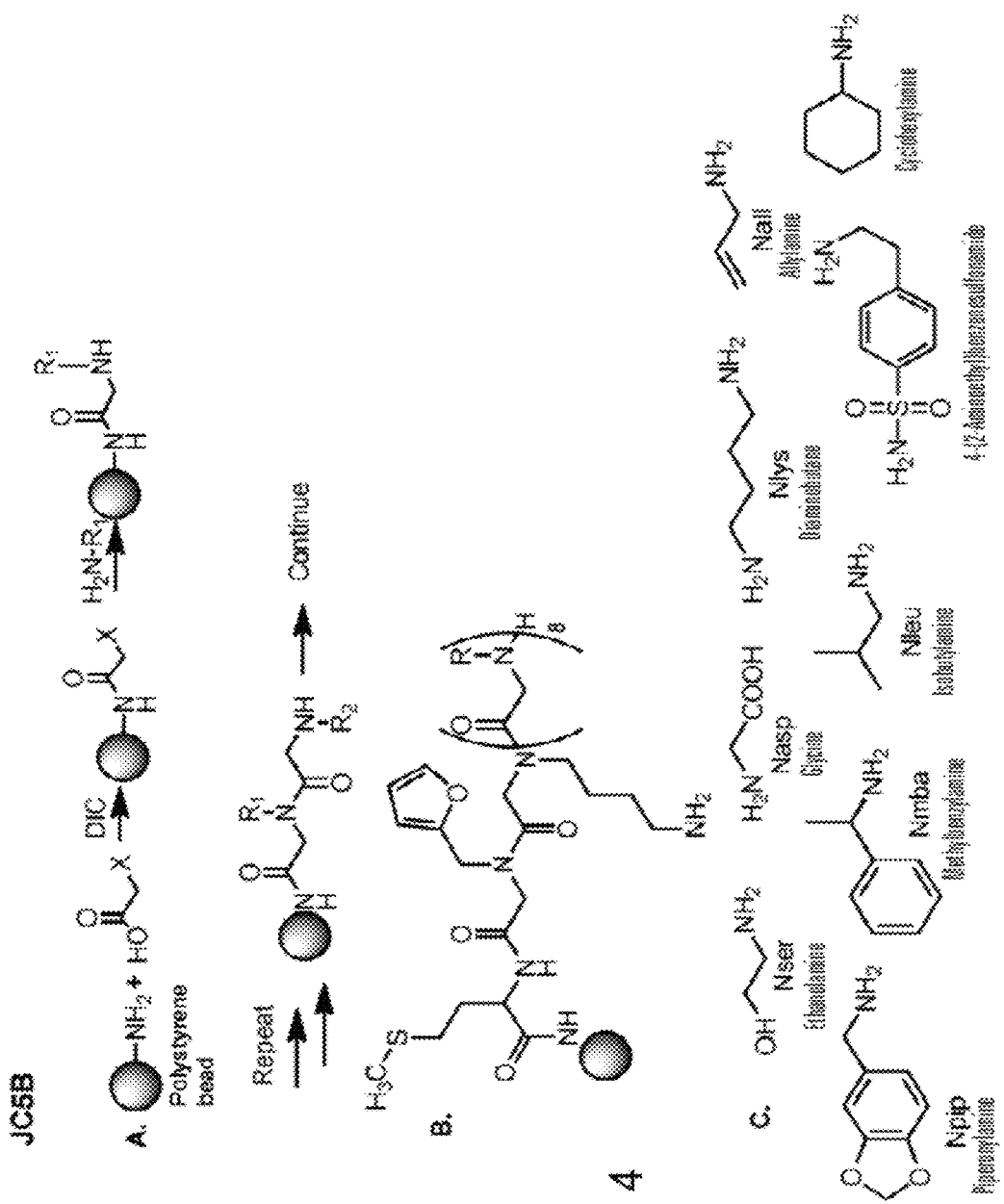
FIG. 4 shows a basic chemical schematic of the preparation of a library of Tentagel beads (JC5B) used to screen Alzheimer's serum samples.
Figure 5:
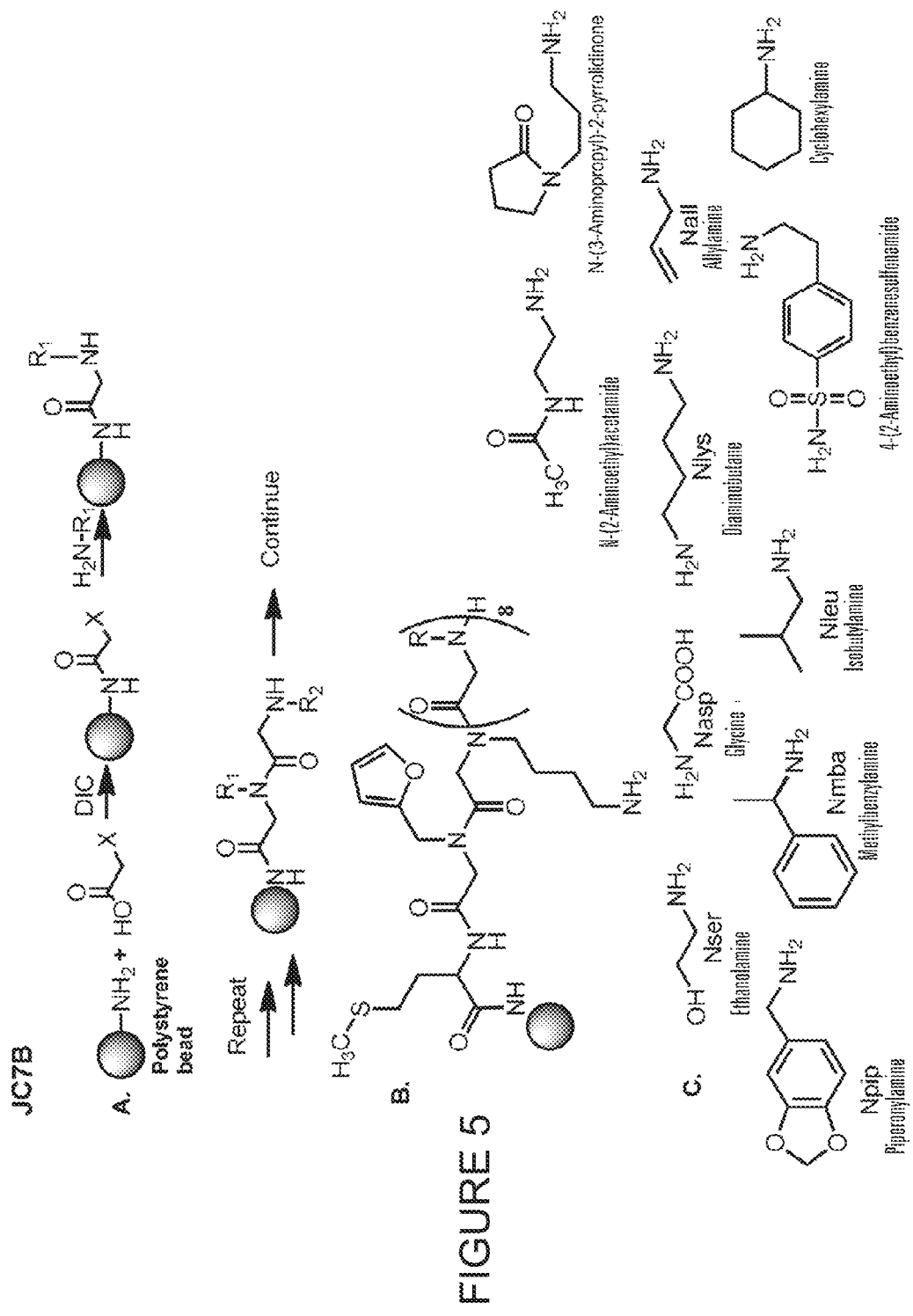
FIG. 5 shows a basic chemical schematic of the preparation of a library of Tentagel beads (JC7B) used to screen serum samples.

The present invention represents a significant advance in diagnostic and therapeutic discovery. In particular, the present inventor has discovered a screening methodology that eclipses prior approaches to the screening of complex biological samples. In particular, there is a need for improved methods of discovering disease associated biomarkers and for making diagnostic kits comprising high-affinity ligands for such biomarkers. The present invention relates to a method of screening for such biomarkers and for diagnosing disease and disease progression using the ligands to detect such biomarkers.

The invention comprises compositions which comprises particle based libraries of compounds selected from peptoids, peptides, oligomers, small molecules and any molecule naturally derived or synthetically made and which can be placed on a support system such as a bead or small particle. This "library" is then pretreated and exposed, under the right conditions and after exposure to a control plasma or serum sample to permit removal of non-selective ligands, to a complex biological fluid such as plasma or serum which is "screened" for the presence or absence of disease-associated biomarkers or other target biomarkers such as antibodies or proteins or other markers such as cell surface proteins. The blood samples or other biological fluid samples are taken from patients that may or may not have a particular disease and the results generated from the screen are compared to results taken from a control healthy patient or control diseased patient.

The primary screen results in a significant number of high-affinity ligands for any particular disease-associated biomarker such as an antibody. The invention further comprises a process for generating high affinity ligands which are useful in either a diagnostic setting for such disease state and/or are useful as ligands in their own right—e.g., as therapeutic vaccines or as drugs which can target said disease associated antibodies located in a particular region of the body or body tissue. Such drugs can be linked to other moieties such as chemotherapeutic agents or other agents that generate or can generate a localized immune response to remove and/or degrade auto-antibodies.

Alzheimer's Disease (AD) is a progressive and fatal brain disease that affects as many as 5.3 million Americans. AD destroys brain cells, causing problems with memory, thinking and behavior. These symptoms get worse over time, and ultimately the disease is fatal. Today, it is the sixth-leading cause of death in the United States and is the most common form of dementia, accounting for 50-70% of all dementia cases. Sadly, while treatments for symptoms exist, there is no cure.

Diagnosing Alzheimer's Disease is an empirical process that involves several types of evaluations and may take many days to weeks to complete. Evaluations include taking a detailed medical history and physical examination. In addition, standard laboratory tests including blood, urine and CSF tests are mainly designed to help eliminate other possible conditions. Neuropsychological testing, using a variety of tools to assess memory, problem-solving, attention, vision-motor coordination and abstract thinking, are also performed. Tests for depression should also be included. Finally, brain-imaging scans are recommended to rule out brain tumors or blood clots in the brain as the reason for symptoms. In sum, there is currently no single test that accurately diagnoses Alzheimer's Disease, with a definitive diagnosis of Alzheimer's possible only by examining brain tissue after death.

Parkinson's Disease (PD) is another degenerative disease of the brain (central nervous system) that often impairs motor skills, speech, and other functions. It affects movement (motor symptoms), but other typical symptoms include disorders of mood, behavior, thinking, and sensation (non-motor symptoms). Patient's individual symptoms may be quite dissimilar and progression of the disease is also distinctly individual. The symptoms of PD result from the loss (idiopathic or genetic, toxic or traumatic) of pigmented dopamine-secreting (dopaminergic) cells in the pars compacta region of the substantia nigra (literally "black substance"). These neurons project to the striatum and their loss leads to alterations in the activity of the neural circuits within the basal ganglia that regulate movement, in essence an inhibition of the direct pathway and excitation of the indirect pathway.

Diagnosis of PD presents similar if somewhat distinct challenges. When performing a neurologic examination to evaluate a patient with any movement disorder, the doctor should take a medical history and perform a physical examination. In addition, a neurologic exam is conducted to make a thorough evaluation of the nervous system, including observing aspects of the patient's movement, coordination and balance. Laboratory testing of the blood of patients with the symptoms typical of Parkinson's only rarely uncovers any abnormality. Electroencephalograms (EEG's) record some aspects of brain electrical activity, but they are not effective in spotting PD. The MRI and CAT scans of the brain produce remarkable and exquisite anatomic pictures, but the brains of people with PD disease appear normal even under this scrutiny because the changes associated with PD are microscopic and are not revealed by these scans. With no definitive diagnostic tests to provide specific answers, physicians must base their diagnosis of PD on judgment.

Thus, there remains a need for diagnostic procedures for both of these diseases and other neurological diseases that are (i) accurate and objective, (ii) simple and reproducible, and (iii) useful in both early and late stage case.

In accordance with the present invention, there is provided compositions comprising peptoid(s) that bind antibodies indicative of a neurodegenerative disease and methods of detecting antibodies in an antibody-containing sample comprising contacting an antibody-containing sample with a support having affixed thereto a peptoid. Ligand libraries can include compounds of formula I wherein the R groups on either the amine side chain or the alpha carbon are independently selected from the group consising of hydrogen; alkyl; allyl; methyl; ethyl; n-propyl; isopropyl; n-butyl; isobutyl; n-butylamine; sec-butyl; tert-butyl; pentyl; hexyl; isopentyl; aryl; hetero aryl; furanyl; indolyl; thiophenyl; thiazolyl; imidazolyl; isoxazoyl; oxazoyl; piperonyl; pyrazoyl; pyrrolyl; pyrazinyl; pyridyl; pyrimidyl; pyrimidinyl; purinyl; cinnolinyl; benzofuranyl; benzothienyl; benzotriazolyl; benzoxazolyl; quinoline; isoxazolyl; isoquinoline cycloalkyl; alkenyl; cycloalkenyl; phenyl; pyridyl; methoxyethyl; (R)-methylbenzyl; $C_{0-6}$ alkylaryl; $C_{0-6}$ alkylheteroaryl; $C_{1-6}$ alkyl substituted with a group selected from OH, SH, a halogen, $OR^{15}$, $COOR^{15}$, $NR^{15}$ (wherein $R^{15}$ is selected from the group consisting of H or $C_{1-6}$ alkyl or $C_{1-6}$ alkynl) or $R^{16}$ (wherein $R^{16}$ is selected from the group consisting of H or $C_{1-6}$ alkynl); $OC_{1-6}$ alkyl; $C_{2-6}$ alkenyl; $C_{2-6}$ alkynyl; $C_{2-6}$ alkenyl; and $C_{2-6}$ alkynyl—including one or more chemical group described in Tables 1 and 2 below.

Preferred ligand libraries of the invention for purposes of screening Alzheimer's disease comprise a random ligand library for screening a complex biological fluid comprising a compound of formula I on a support,

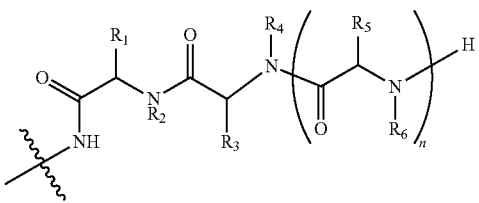

wherein $R_1$ is selected from an electron rich amino acid side chain Y;
$R_2$ is selected from H;
and $R_3$-$R_6$ are independently selected from the groups consisting of H, —$C_1$-$C_6$alkyl, —$C_1$-$C_6$alkylSCH$_3$, —$C_0$-$C_6$alkylC$_2$-$C_6$alkenyl, —$C_0$-$C_6$alkyl C$_2$-$C_6$alkynyl, —$C_1$-$C_6$ COOH, —$C_1$-$C_6$alkylOH, —$C_1$-$C_6$alkylN(R)$_2$, —$C_3$-$C_8$cyclo alkyl, —$C_1$-$C_6$alkylaryl, —$C_1$-$C_6$alkylhetero aryl, —$C_1$-$C_6$alkylNC(O)C$_1$-$C_6$alkyl, —$C_1$-$C_6$alkylcycloamide wherein any of the aryl or heteroaryl groups may be independently substituted with —OH, Cl, F, Br, —OCH$_3$, —SO$_2$NH$_2$ or —O—CH$_2$—O—.

Other peptoid libraries suitable for screening Alzheimer's disease include those libraries comprising:

A random ligand library for screening a complex biological fluid comprising a compound of formula I on a support,

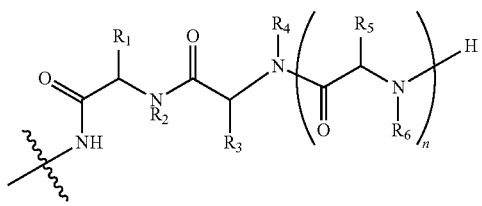

wherein the compounds are produced by a process which comprises use of a reactant selected from the group consisting of (A) furfurylamine; 3,4-dimethoxyethanolamine; benzylamine; N-(2-aminoethyl)acet amide; N-(3-aminopropyl)-2-pyrrolidinone; ethanolamine; glycine; diaminobutane; allylamine; piperonylamine; methylbenzylamine; isobutylamine; 4-(2-aminoethyl)benzenesulfonamide or cyclohexylamine; or (B) methoxyethylamine; piperonylamine; cyclohexylamine; diaminobutane; methylbenzylamine; isobutylamine; furfurylamine or 4-(2-aminoethyl)benzenesulfonamide; or (C) furfurylamine, ethanolamine; glycine; diaminobutane; allylamine; piperonylamine; methylbenzylamine; isobutylamine or 4-(2-aminoethyl)benzenesulfonamide; or (D) furfurylamine, N-(2-aminoethyl)acetamide; N-(3-aminoethyl)-2-pyrrolidinone; ethanolamine; glycine; diaminobutane; allylamine; piperonylamine; methylbenzylamine; isobutylamine; 4-(2-aminoethyl)benzenesulfonamide; or (E) cysteine, glycine, allylamine, ethanolamine, isobutylamine, methylbenzylamine, piperonylamine, methionine, cyclohexylamine, 3,4-dimethoxyphenethylamine, benzylamine, N-(2-aminoethyl)acetamide, N-(3-aminopropyl)-2-pyrrolidone, 4-(2-aminoethyl)benzenesulfonamide and furfurylamine; and wherein, $R_1$ is selected from the group consisting —$(C_1-C_6)SCH_3$;

$R_2$ is selected from H;

$R_3$ and $R_5$ are independently selected from the groups consisting of H, —$C_1$-$C_6$alkyl, —$C_1$-$C_6$alkylSCH$_3$, —$C_0$-$C_6$alkylC$_2$-$C_6$alkenyl, —$C_0$-$C_6$alkyl C$_2$-$C_6$alkynyl, —$C_1$-$C_6$COOH, —$C_1$-$C_6$alkylOH, —$C_1$-$C_6$alkylN(R)$_2$, —$C_3$-$C_8$cycloalkyl, —$C_1$-$C_6$alkylaryl, —$C_1$-$C_6$alkylheteroaryl, —$C_1$-$C_6$alkylNC(O)C$_1$-$C_6$alkyl, —$C_1$-$C_6$alkylcycloamide wherein any of the aryl or heteroaryl groups may be independently substituted with —OH, Cl, F, Br, —OCH$_3$, —SO$_2$NH$_2$ or —O—CH$_2$—O—;

$R_4$ is selected from the group consisting of furfuryl or —(C$_1$-C$_6$alkyl)NR$_7$R$_8$, $R_6$ is selected from the group consisting of H, 1-yl-allyl, 1-yl-2-hydroxyethyl, isobutyl, 1-yl-n-butylamine, methylbenzyl, piperonyl, cyclohexyl, 1-yl-2-(3,4-dimethoxyphenyl)ethyl, benzyl, 1-yl-2-(acetamide)ethyl, 1-yl-3-2-pyrrolidinone, 1-yl-2-(4-benzenesulfonamide)ethyl or furfuryl and n is 3-11.

In a more preferred embodiment, such libraries and/or compounds are selected from A compound having a formula Ia

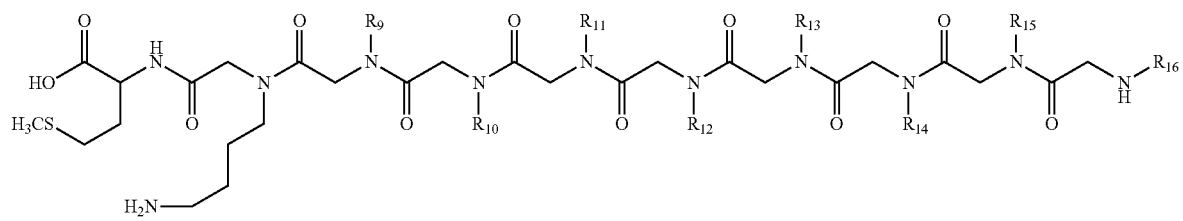

wherein the compound is selected from the group consisting of a compound of formula Ia wherein, (a) $R_9$ is n-butylamine; $R_{10}$ is 1-yl-n-butylamine; $R_{11}$ is piperonyl; $R_{12}$ is methylbenzyl; $R_{13}$ is piperonyl; $R_{14}$ is methylbenzyl; $R_{15}$ is 1-yl-2-(4(benzenesulfonamide)ethyl and $R_{16}$ is 1-yl-2-methoxyethyl;

(b) $R_9$ is 1-yl-n-butylamine; $R_{10}$ is 1-yl-2-(4(benzenesulfonamide)ethyl; $R_{11}$ is 1-yl-n-butylamine; $R_{12}$ is cyclohexyl; $R_{13}$ is 1-yl-2-methoxyethyl; $R_{14}$ is 1-yl-2,2-dimethylethyl (isobutyl); $R_{15}$ is 1-yl-2-(4(benzenesulfonamide)ethyl and $R_{16}$ is methylbenzyl;

(c) $R_9$ is 1-yl-n-butylamine; $R_{10}$ is 1-yl-n-butylamine; $R_{11}$ is piperonyl; $R_{12}$ is 1-yl-2-(4(benzenesulfonamide)ethyl; $R_{13}$ is 1-yl-n-butylamine; $R_{14}$ is methylbenzyl; $R_{15}$ is methylbenzyl and $R_{16}$ is cyclohexyl;

(d) $R_9$ is piperonyl; $R_{10}$ is 1-yl-n-butylamine; $R_{11}$ is isobutyl; $R_{12}$ is 1-yl-2-(4(benzenesulfonamide)ethyl; $R_{13}$ is methylbenzyl; $R_{14}$ is cyclohexyl; $R_{15}$ is isobutyl and $R_{16}$ is 1-yl-n-butylamine;

(e) $R_9$ is 1-yl-n-butylamine; $R_{10}$ is 1-yl-n-butylamine; $R_{11}$ is methylbenzyl; $R_{12}$ is 1-yl-2-methoxyethyl; $R_{13}$ is cyclohexyl; $R_{14}$ is cyclohexyl; $R_{15}$ is methylbenzyl and $R_{16}$ is piperonyl;

(f) $R_9$ is piperonyl; $R_{10}$ is 1-yl-n-butylamine; $R_{11}$ is isopropyl; $R_{12}$ is isopropyl; $R_{13}$ is 1-yl-2-methoxyethyl; $R_{14}$ is cyclohexyl; $R_{15}$ is 1-yl-2-(4(benzenesulfonamide)ethyl and $R_{16}$ is 1-yl-2-(4(benzenesulfonamide)ethyl;

(g) $R_9$ is 1-yl-n-butylamine; $R_{10}$ is 1-yl-n-butylamine; $R_{11}$ is piperonyl; $R_{12}$ is methylbenzyl; $R_{13}$ is piperonyl; $R_{14}$ is methylbenzyl; $R_{15}$ is 1-yl-2-(4(benzenesulfonamide)ethyl and $R_{16}$ is cyclohexyl;

(h) $R_9$ is 1-yl-n-butylamine; $R_{10}$ is 1-yl-n-butylamine; $R_{11}$ is methylbenzyl; $R_{12}$ is 1-yl-2-methoxyethyl; $R_{13}$ is cyclohexyl; $R_{14}$ is cyclohexyl; $R_{15}$ is methylbenzyl and $R_{16}$ is piperonyl;

(i) $R_9$ is 1-yl-n-butylamine; $R_{10}$ is methylbenzyl; $R_{11}$ is methylbenzyl; $R_{12}$ is 1-yl-n-butylamine; $R_{13}$ is 1-yl-n-butylamine; $R^{14}$ is cyclohexyl; $R^{15}$ is 1-yl-2-(4(benzenesulfonamide)ethyl and $R^{16}$ is cyclohexyl;

(j) $R_9$ is 1-yl-2-(4(benzenesulfonamide)ethyl; $R_{10}$ is methylbenzyl; $R_{11}$ is methylbenzyl; $R_{12}$ is cyclohexyl; $R_{13}$ is 1-yl-n-butylamine; $R_{14}$ is methylbenzyl; $R_{15}$ is isobutyl and $R_{16}$ is 1-yl-n-butylamine;

(k) $R_9$ is 1-yl-2-methoxyethyl; $R_{10}$ is isobutyl; $R_{11}$ is 1-yl-2-(4(benzenesulfonamide)ethyl; $R_{12}$ is piperonyl; $R_{13}$ is 1-yl-n-butylamine; $R_{14}$ is cyclohexyl; $R_{15}$ is methylbenzyl and $R_{16}$ is 1-yl-2-methoxyethyl;

(l) $R_9$ is 1-yl-n-butylamine; $R_{10}$ is 1-yl-2-(4(benzenesulfonamide)ethyl; $R_{11}$ is 1-yl-n-butylamine; $R_{12}$ is cyclohexyl; $R_{13}$ is 1-yl-2-methoxyethyl; $R_{14}$ is isobutyl; $R_{15}$ is 1-yl-2-(4(benzenesulfonamide)ethyl and $R_{16}$ is methylbenzyl;

(m) $R_9$ is 1-yl-2-methoxyethyl; $R_{10}$ is 1-yl-n-butylamine; $R_{11}$ is 1-yl-n-butylamine; $R_{12}$ is 1-yl-2-methoxyethyl; $R_{13}$ is methylbenzyl; $R_{14}$ is 1-yl-n-butylamine; $R_{15}$ is furfuryl and $R_{16}$ is furfuryl;

(n) $R_9$ is cyclohexyl; $R_{10}$ is cyclohexyl; $R_{11}$ is 1-yl-n-butylamine; $R_{12}$ is furfuryl; $R_{13}$ is 1-yl-2-methoxyethyl; $R_{14}$ is 1-yl-2-methoxyethyl; $R_{15}$ is 1-yl-2-(4(benzenesulfonamide)ethyl and $R_{16}$ is furfuryl;

(o) $R_9$ is 1-yl-n-butylamine; $R_{10}$ is piperonyl; $R_{11}$ is 1-yl-2-(4(benzenesulfonamide)ethyl; $R_{12}$ is 1-yl-2-methoxyethyl; $R_{13}$ is methylbenzyl; $R_{14}$ is 1-yl-n-butylamine; $R_{15}$ is 1-yl-2-methoxyethyl and $R_{16}$ is methylbenzyl;

(p) $R_9$ is cyclohexyl; $R_{10}$ is cyclohexyl; $R_{11}$ is piperonyl; $R_{12}$ is 1-yl-n-butylamine; $R_{13}$ is 1-yl-n-butylamine; $R_{14}$ is 1-yl-n-butylamine; $R_{15}$ is 1-yl-n-butylamine and $R_{16}$ is isobutyl;

(q) $R_9$ is piperonyl; $R_{10}$ is 1-yl-n-butylamine; $R_{11}$ is 1-yl-2-methoxyethyl; $R_{12}$ is 1-yl-2-(4(benzenesulfonamide)ethyl; $R_{13}$ is piperonyl; $R_{14}$ is 1-yl-n-butylamine; $R_{15}$ is methylbenzyl and $R_{16}$ is methylbenzyl;

(r) $R_9$ is methylbenzyl; $R_{10}$ is methylbenzyl; $R_{11}$ is methylbenzyl; $R_{12}$ is 1-yl-n-butylamine; $R_{13}$ is piperonyl; $R_{14}$ is 1-yl-n-butylamine; $R_{15}$ is piperonyl and $R_{16}$ is 1-yl-n-butylamine;

(s) $R_9$ is 1-yl-n-butylamine; $R_{10}$ is 1-yl-n-butylamine; $R_{11}$ is methylbenzyl; $R_{12}$ is 1-yl-n-butylamine; $R_{13}$ is methylbenzyl; $R_{14}$ is methylbenzyl; $R_{15}$ is 1-yl-2-methoxyethyl and $R_{16}$ is piperonyl;

(t) $R_9$ is methylbenzyl; $R_{10}$ is 1-yl-2-(4(benzenesulfonamide)ethyl; $R_{11}$ is 1-yl-n-butylamine; $R_{12}$ is 1-yl-2-(4(benzenesulfonamide)ethyl; $R_{13}$ is isobutyl; $R_{14}$ is 1-yl-n-butylamine; $R_{15}$ is methylbenzyl and $R_{16}$ is 1-yl-2-methoxyethyl;

(u) $R_9$ is 1-yl-2-methoxyethyl; $R_{10}$ is 1-yl-n-butylamine; $R_{11}$ is isobutyl; $R_{12}$ is isobutyl; $R_{13}$ is cyclohexyl; $R_{14}$ is 1-yl-n-butylamine; $R_{15}$ is 1-yl-2-(4(benzenesulfonamide)ethyl and $R_{16}$ is cyclohexyl;

(v) $R_9$ is isobutyl; $R_{10}$ is 1-yl-n-butylamine; $R_{11}$ is 1-yl-n-butylamine; $R_{12}$ is methylbenzyl; $R_{13}$ is 1-yl-n-butylamine; $R_{14}$ is 1-yl-n-butylamine; $R_{15}$ is piperonyl and $R_{16}$ is piperonyl;

(w) $R_9$ is 1-yl-2-(4(benzenesulfonamide)ethyl; $R_{10}$ is isobutyl; $R_{11}$ is methylbenzyl; $R_{12}$ is 1-yl-2-methoxyethyl; $R_{13}$ is 1-yl-2-(4(benzenesulfonamide)ethyl; $R_{14}$ is isobutyl; $R_{15}$ is 1-yl-2-methoxyethyl and $R_{16}$ is cyclohexyl;

(x) $R_9$ is furfuryl; $R_{10}$ is furfuryl; $R_{11}$ is piperonyl; $R_{12}$ is cyclohexyl; $R_{13}$ is piperonyl; $R_{14}$ is 1-yl-n-butylamine; $R_{15}$ is 1-yl-2-(4(benzenesulfonamide)ethyl and $R_{16}$ is cyclohexyl;

(y) $R_9$ is piperonyl; $R_{10}$ is piperonyl; $R_{11}$ is 1-yl-2-methoxyethyl; $R_{12}$ is 1-yl-2-methoxyethyl; $R_{13}$ is 1-yl-n-butylamine; $R_{14}$ is 1-yl-n-butylamine; $R_{15}$ is 1-yl-n-butylamine and $R_{16}$ is 1-yl-2-methoxyethyl;

(z) $R_9$ is piperonyl; $R_{10}$ is 1-yl-n-butylamine; $R_{11}$ is isobutyl; $R_{12}$ is 1-yl-2-(4(benzenesulfonamide)ethyl; $R_{13}$ is methylbenzyl; $R_{14}$ is cyclohexyl; $R_{15}$ is isobutyl and $R_{16}$ is 1-yl-n-butylamine;

(aa) $R_9$ is 1-yl-2-(4(benzenesulfonamide)ethyl; $R_{10}$ is 1-yl-2-(4(benzenesulfonamide)ethyl; $R_{11}$ is methylbenzyl; $R_{12}$ is methylbenzyl; $R_{13}$ is 1-yl-n-butylamine; $R_{14}$ is 1-yl-n-butylamine; $R_{15}$ is 1-yl-2-(4(benzenesulfonamide)ethyl and $R_{16}$ is 1-yl-2-(4(benzenesulfonamide)ethyl;

(bb) $R_9$ is 1-yl-n-butylamine; $R_{10}$ is 1-yl-2-methoxyethyl; $R_{11}$ is 1-yl-n-butylamine; $R_{12}$ is isobutyl; $R_{13}$ is cyclohexyl; $R_{14}$ is 1-yl-n-butylamine; $R_{15}$ is 1-yl-n-butylamine and $R_{16}$ is piperonyl;

(cc) $R_9$ is cyclohexyl; $R_{10}$ is methylbenzyl; $R_{11}$ is cyclohexyl; $R_{12}$ is piperonyl; $R_{13}$ is 1-yl-n-butylamine; $R_{14}$ is 1-yl-2-(4(benzenesulfonamide)ethyl; $R_{15}$ is 1-yl-n-butylamine and $R_{16}$ is 1-yl-2-methoxyethyl;

(dd) $R_9$ is 1-yl-2-methoxyethyl; $R_{10}$ is 1-yl-2-(4(benzenesulfonamide)ethyl; $R_{11}$ is 1-yl-n-butylamine; $R_{12}$ is 1-yl-2-methoxyethyl; $R_{13}$ is 1-yl-2-(4(benzenesulfonamide)ethyl; $R_{14}$ is 1-yl-2-methoxyethyl; $R_{15}$ is isobutyl and $R_{16}$ is cyclohexyl;

(ee) $R_9$ is 1-yl-2-methoxyethyl; $R_{10}$ is methylbenzyl; $R_{11}$ is 1-yl-n-butylamine; $R_{12}$ is 1-yl-n-butylamine; $R_{13}$ is piperonyl; $R_{14}$ is isobutyl; $R_{15}$ is 1-yl-2-(4(benzenesulfonamide)ethyl and $R_{16}$ is 1-yl-n-butylamine;

(ff) $R_9$ is 1-yl-n-butylamine; $R_{10}$ is methylbenzyl; $R_{11}$ is 1-yl-2-(4(benzenesulfonamide)ethyl; $R_{12}$ is methylbenzyl; $R_{13}$ is 1-yl-n-butylamine; $R_{14}$ is 1-yl-2-(4(benzenesulfonamide)ethyl; $R_{15}$ is 1-yl-2-(4(benzenesulfonamide)ethyl and $R_{16}$ is cyclohexyl;

(gg) $R_9$ is 1-yl-n-butylamine; $R_{10}$ is 1-yl-2-methoxyethyl; $R_{11}$ is 1-yl-n-butylamine; $R_{12}$ is 1-yl-2-(4(benzenesulfonamide)ethyl; $R_{13}$ is 1-yl-2-methoxyethyl; $R_{14}$ is 1-yl-2-methoxyethyl; $R_{15}$ is 1-yl-n-butylamine and $R_{16}$ is methylbenzyl;

(hh) $R_9$ is cyclohexyl; $R_{10}$ is cyclohexyl; $R_{11}$ is methylbenzyl; $R_{12}$ is 1-yl-n-butylamine; $R_{13}$ is methylbenzyl; $R_{14}$ is cyclohexyl; $R_{15}$ is methylbenzyl and $R_{16}$ is 1-yl-n-butylamine;

(ii) $R_9$ is 1-yl-n-butylamine; $R_{10}$ is furfuryl; $R_{11}$ is methylbenzyl; $R_{12}$ is 1-yl-2-(4(benzenesulfonamide)ethyl; $R_{13}$ is furfuryl; $R_{14}$ is cyclohexyl; $R_{15}$ is methylbenzyl and $R_{16}$ is cyclohexyl;

(jj) $R_9$ is 1-yl-n-butylamine; $R_{10}$ is methylbenzyl; $R_{11}$ is 1-yl-n-butylamine; $R_{12}$ is 1-yl-2-(4(benzenesulfonamide)ethyl; $R_{13}$ is 1-yl-2-methoxyethyl; $R_{14}$ is methylbenzyl; $R_{15}$ is 1-yl-2-methoxyethyl and $R_{16}$ is isobutyl;

(kk) $R_9$ is 1-yl-2-(4(benzenesulfonamide)ethyl; $R_{10}$ is 1-yl-n-butylamine; $R_{11}$ is 1-yl-n-butylamine; $R_{12}$ is methylbenzyl; $R_{13}$ is methylbenzyl; $R_{14}$ is cyclohexyl; $R_{15}$ is 1-yl-2-(4(benzenesulfonamide)ethyl and $R_{16}$ is methylbenzyl;

(ll) $R_9$ is 1-yl-2-(4(benzenesulfonamide)ethyl; $R_{10}$ is 1-yl-2-(4(benzenesulfonamide)ethyl; $R_{11}$ is 1-yl-n-butylamine; $R_{12}$ is 1-yl-n-butylamine; $R_{13}$ is methylbenzyl; $R_{14}$ is 1-yl-n-butylamine; $R_{15}$ is methylbenzyl and $R_{16}$ is 1-yl-n-butylamine;

(mm) $R_9$ is 1-yl-n-butylamine; $R_{10}$ is 1-yl-2-(4(benzenesulfonamide)ethyl; $R_{11}$ is 1-yl-2-(4(benzenesulfonamide)ethyl; $R_{12}$ is 1-yl-2-methoxyethyl; $R_{13}$ is 1-yl-n-butylamine; $R_{14}$ is cyclohexyl; $R_{15}$ is 1-yl-2-(4(benzenesulfonamide)ethyl and $R_{16}$ is methylbenzyl;

(nn) $R_9$ is 1-yl-n-butylamine; $R_{10}$ is 1-yl-n-butylamine; $R_{11}$ is piperonyl; $R_{12}$ is 1-yl-2-(4(benzenesulfonamide)ethyl; $R_{13}$ is 1-yl-n-butylamine; $R_{14}$ is methylbenzyl; $R_{15}$ is methylbenzyl and $R_{16}$ is cyclohexyl;

(oo) $R_9$ is 1-yl-2-(4(benzenesulfonamide)ethyl; $R_{10}$ is methylbenzyl; $R_{11}$ is methylbenzyl; $R_{12}$ is 1-yl-n-butylamine; $R_{13}$ is methylbenzyl; $R_{14}$ is piperonyl; $R_{15}$ is 1-yl-n-butylamine and $R_{16}$ is 1-yl-2-methoxyethyl;

(pp) $R_9$ is piperonyl; $R_{10}$ is 1-yl-n-butylamine; $R_{11}$ is 1-yl-n-butylamine; $R_{12}$ is methylamine; $R_{13}$ is piperonyl; $R_{14}$ is 1-yl-n-butylamine; $R_{15}$ is piperonyl and $R_{16}$ is 1-yl-2-methoxyethyl;

(qq) $R_9$ is cyclohexyl; $R_{10}$ is cyclohexyl; $R_{11}$ is furfuryl; $R_{12}$ is 1-yl-2-methoxyethyl; $R_{13}$ is isobutyl; $R_{14}$ is cyclohexyl; $R_{15}$ is methylbenzyl and $R_{16}$ is methylbenzyl;

(rr) $R_9$ is piperonyl; $R_{10}$ is 1-yl-n-butylamine; $R_{11}$ is isobutyl; $R_{12}$ is isobutyl; $R_{13}$ is 1-yl-2-methoxyethyl; $R_{14}$ is cyclohexyl; $R_{15}$ is 1-yl-2-(4(benzenesulfonamide)ethyl and $R_{16}$ is 1-yl-2-(4(benzenesulfonamide)ethyl;

(ss) $R_9$ is cyclohexyl; $R_{10}$ is cyclohexyl; $R_{11}$ is 1-yl-n-butylamine; $R_{12}$ is methylbenzyl; $R_{13}$ is 1-yl-n-butylamine; $R_{14}$ is methylbenzyl; $R_{15}$ is cyclohexyl and $R_{16}$ is piperonyl;

and pharmaceutically acceptable salts thereof.

In a more preferred embodiment and for screening for disease associated biomarkers in patients having or suspected of having Alzheimer's using kits and/or diagnostic machines and/or instruments, the following compounds are preferred:

A compound of the formula:

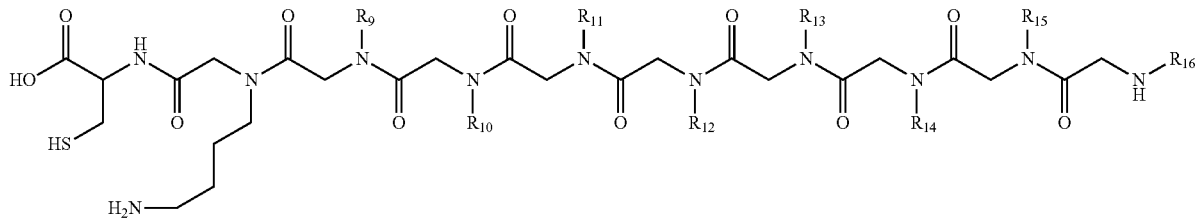

II wherein the compound is selected from the group consisting of a compound of formula II wherein, (a) $R_9$ is n-butylamine; $R_{10}$ is 1-yl-n-butylamine; $R_{11}$ is piperonyl; $R_{12}$ is methylbenzyl; $R_{13}$ is piperonyl; $R_{14}$ is methylbenzyl; $R_{15}$ is 1-yl-2-(4(benzenesulfonamide)ethyl and $R_{16}$ is 1-yl-2-methoxyethyl;

(b) $R_9$ is 1-yl-n-butylamine; $R_{10}$ is 1-yl-2-(4(benzenesulfonamide)ethyl; $R_{11}$ is 1-yl-n-butylamine; $R_{12}$ is cyclohexyl; $R_{13}$ is 1-yl-2-methoxyethyl; $R_{14}$ is 1-yl-2,2-dimethylethyl (isobutyl); $R_{15}$ is 1-yl-2-(4(benzenesulfonamide)ethyl and $R_{16}$ is methylbenzyl;

(c) $R_9$ is 1-yl-n-butylamine; $R_{10}$ is 1-yl-n-butylamine; $R_{11}$ is piperonyl; $R_{12}$ is 1-yl-2-(4(benzenesulfonamide)ethyl; $R_{13}$ is 1-yl-n-butylamine; $R_{14}$ is methylbenzyl; $R_{15}$ is methylbenzyl and $R_{16}$ is cyclohexyl;

(d) $R_9$ is piperonyl; $R_{10}$ is 1-yl-n-butylamine; $R_{11}$ is isobutyl; $R_{12}$ is 1-yl-2-(4(benzenesulfonamide)ethyl; $R_{13}$ is methylbenzyl; $R_{14}$ is cyclohexyl; $R_{15}$ is isobutyl and $R_{16}$ is 1-yl-n-butylamine;

(e) $R_9$ is 1-yl-n-butylamine; $R_{10}$ is 1-yl-n-butylamine; $R_{11}$ is methylbenzyl; $R_{12}$ is 1-yl-2-methoxyethyl; $R_{13}$ is cyclohexyl; $R_{14}$ is cyclohexyl; $R_{15}$ is methylbenzyl and $R_{16}$ is piperonyl;

(f) $R_9$ is piperonyl; $R_{10}$ is 1-yl-n-butylamine; $R_{11}$ is isopropyl; $R_{12}$ is isopropyl; $R_{13}$ is 1-yl-2-methoxyethyl; $R_{14}$ is cyclohexyl; $R_{15}$ is 1-yl-2-(4(benzenesulfonamide)ethyl and $R_{16}$ is 1-yl-2-(4(benzenesulfonamide)ethyl;

(g) $R_9$ is 1-yl-n-butylamine; $R_{10}$ is 1-yl-n-butylamine; $R_{11}$ is piperonyl; $R_{12}$ is methylbenzyl; $R_{13}$ is piperonyl; $R_{14}$ is methylbenzyl; $R_{15}$ is 1-yl-2-(4(benzenesulfonamide)ethyl and $R_{16}$ is cyclohexyl;

(h) $R_9$ is 1-yl-n-butylamine; $R_{10}$ is 1-yl-n-butylamine; $R_{11}$ is methylbenzyl; $R_{12}$ is 1-yl-2-methoxyethyl; $R_{13}$ is cyclohexyl; $R_{14}$ is cyclohexyl; $R_{15}$ is methylbenzyl and $R_{16}$ is piperonyl;

(i) $R_9$ is 1-yl-n-butylamine; $R_{10}$ is methylbenzyl; $R_{11}$ is methylbenzyl; $R_{12}$ is 1-yl-n-butylamine; $R_{13}$ is 1-yl-n-butylamine; $R^{14}$ is cyclohexyl; $R^{15}$ is 1-yl-2-(4(benzenesulfonamide)ethyl and $R^{16}$ is cyclohexyl;

(j) $R_9$ is 1-yl-2-(4(benzenesulfonamide)ethyl; $R_{10}$ is methylbenzyl; $R_{11}$ is methylbenzyl; $R_{12}$ is cyclohexyl; $R_{13}$ is 1-yl-n-butylamine; $R_{14}$ is methylbenzyl; $R_{15}$ is isobutyl and $R_{16}$ is 1-yl-n-butylamine;

(k) $R_9$ is 1-yl-2-methoxyethyl; $R_{10}$ is isobutyl; $R_{11}$ is 1-yl-2-(4(benzenesulfonamide)ethyl; $R_{12}$ is piperonyl; $R_{13}$ is 1-yl-n-butylamine; $R_{14}$ is cyclohexyl; $R_{15}$ is methylbenzyl and $R_{16}$ is 1-yl-2-methoxyethyl;

(l) $R_9$ is 1-yl-n-butylamine; $R_{10}$ is 1-yl-2-(4(benzenesulfonamide)ethyl; $R_{11}$ is 1-yl-n-butylamine; $R_{12}$ is cyclohexyl; $R_{13}$ is 1-yl-2-methoxyethyl; $R_{14}$ is isobutyl; $R_{15}$ is 1-yl-2-(4(benzenesulfonamide)ethyl and $R_{16}$ is methylbenzyl;

(m) $R_9$ is 1-yl-2-methoxyethyl; $R_{10}$ is 1-yl-n-butylamine; $R_{11}$ is 1-yl-n-butylamine; $R_{12}$ is 1-yl-2-methoxyethyl; $R_{13}$ is methylbenzyl; $R_{14}$ is 1-yl-n-butylamine; $R_{15}$ is furfuryl and $R_{16}$ is furfuryl;

(n) $R_9$ is cyclohexyl; $R_{10}$ is cyclohexyl; $R_{11}$ is 1-yl-n-butylamine; $R_{12}$ is furfuryl; $R_{13}$ is 1-yl-2-methoxyethyl; $R_{14}$ is 1-yl-2-methoxyethyl; $R_{15}$ is 1-yl-2-(4(benzenesulfonamide)ethyl and $R_{16}$ is furfuryl;

(o) $R_9$ is 1-yl-n-butylamine; $R_{10}$ is piperonyl; $R_{11}$ is 1-yl-2-(4(benzenesulfonamide)ethyl; $R_{12}$ is 1-yl-2-methoxyethyl; $R_{13}$ is methylbenzyl; $R_{14}$ is 1-yl-n-butylamine; $R_{15}$ is 1-yl-2-methoxyethyl and $R_{16}$ is methylbenzyl;

(p) $R_9$ is cyclohexyl; $R_{10}$ is cyclohexyl; $R_{11}$ is piperonyl; $R_{12}$ is 1-yl-n-butylamine; $R_{13}$ is 1-yl-n-butylamine; $R_{14}$ is 1-yl-n-butylamine; $R_{15}$ is 1-yl-n-butylamine and $R_{16}$ is isobutyl;

(q) $R_9$ is piperonyl; $R_{10}$ is 1-yl-n-butylamine; $R_{11}$ is 1-yl-2-methoxyethyl; $R_{12}$ is 1-yl-2-(4(benzenesulfonamide)ethyl; $R_{13}$ is piperonyl; $R_{14}$ is 1-yl-n-butylamine; $R_{15}$ is methylbenzyl and $R_{16}$ is methylbenzyl;

(r) R$_9$ is methylbenzyl; R$_{10}$ is methylbenzyl; R$_{11}$ is methylbenzyl; R$_{12}$ is 1-yl-n-butylamine; R$_{13}$ is piperonyl; R$_{14}$ is 1-yl-n-butylamine; R$_{15}$ is piperonyl and R$_{16}$ is 1-yl-n-butylamine;

(s) R$_9$ is 1-yl-n-butylamine; R$_{10}$ is 1-yl-n-butylamine; R$_{11}$ is methylbenzyl; R$_{12}$ is 1-yl-n-butylamine; R$_{13}$ is methylbenzyl; R$_{14}$ is methylbenzyl; R$_{15}$ is 1-yl-2-methoxyethyl and R$_{16}$ is piperonyl;

(t) R$_9$ is methylbenzyl; R$_{10}$ is 1-yl-2-(4(benzenesulfonamide)ethyl; R$_{11}$ is 1-yl-n-butylamine; R$_{12}$ is 1-yl-2-(4(benzenesulfonamide)ethyl; R$_{13}$ is isobutyl; R$_{14}$ is 1-yl-n-butylamine; R$_{15}$ is methylbenzyl and R$_{16}$ is 1-yl-2-methoxyethyl;

(u) R$_9$ is 1-yl-2-methoxyethyl; R$_{10}$ is 1-yl-n-butylamine; R$_{11}$ is isobutyl; R$_{12}$ is isobutyl; R$_{13}$ is cyclohexyl; R$_{14}$ is 1-yl-n-butylamine; R$_{15}$ is 1-yl-2-(4(benzenesulfonamide)ethyl and R$_{16}$ is cyclohexyl;

(v) R$_9$ is isobutyl; R$_{10}$ is 1-yl-n-butylamine; R$_{11}$ is 1-yl-n-butylamine; R$_{12}$ is methylbenzyl; R$_{13}$ is 1-yl-n-butylamine; R$_{14}$ is 1-yl-n-butylamine; R$_{15}$ is piperonyl and R$_{16}$ is piperonyl;

(w) R$_9$ is 1-yl-2-(4(benzenesulfonamide)ethyl; R$_{10}$ is isobutyl; R$_{11}$ is methylbenzyl; R$_{12}$ is 1-yl-2-methoxyethyl; R$_{13}$ is 1-yl-2-(4(benzenesulfonamide)ethyl; R$_{14}$ is isobutyl; R$_{15}$ is 1-yl-2-methoxyethyl and R$_{16}$ is cyclohexyl;

(x) R$_9$ is furfuryl; R$_{10}$ is furfuryl; R$_{11}$ is piperonyl; R$_{12}$ is cyclohexyl; R$_{13}$ is piperonyl; R$_{14}$ is 1-yl-n-butylamine; R$_{15}$ is 1-yl-2-(4(benzenesulfonamide)ethyl and R$_{16}$ is cyclohexyl;

(y) R$_9$ is piperonyl; R$_{10}$ is piperonyl; R$_{11}$ is 1-yl-2-methoxyethyl; R$_{12}$ is 1-yl-2-methoxyethyl; R$_{13}$ is 1-yl-n-butylamine; R$_{14}$ is 1-yl-n-butylamine; R$_{15}$ is 1-yl-n-butylamine and R$_{16}$ is 1-yl-2-methoxyethyl;

(z) R$_9$ is piperonyl; R$_{10}$ is 1-yl-n-butylamine; R$_{11}$ is isobutyl; R$_{12}$ is 1-yl-2-(4(benzenesulfonamide)ethyl; R$_{13}$ is methylbenzyl; R$_{14}$ is cyclohexyl; R$_{15}$ is isobutyl and R$_{16}$ is 1-yl-n-butylamine;

(aa) R$_9$ is 1-yl-2-(4(benzenesulfonamide)ethyl; R$_{10}$ is 1-yl-2-(4(benzenesulfonamide)ethyl; R$_{11}$ is methylbenzyl; R$_{12}$ is methylbenzyl; R$_{13}$ is 1-yl-n-butylamine; R$_{14}$ is 1-yl-n-butylamine; R$_{15}$ is 1-yl-2-(4(benzenesulfonamide)ethyl and R$_{16}$ is 1-yl-2-(4(benzenesulfonamide)ethyl;

(bb) R$_9$ is 1-yl-n-butylamine; R$_{10}$ is 1-yl-2-methoxyethyl; R$_{11}$ is 1-yl-n-butylamine; R$_{12}$ is isobutyl; R$_{13}$ is cyclohexyl; R$_{14}$ is 1-yl-n-butylamine; R$_{15}$ is 1-yl-n-butylamine and R$_{16}$ is piperonyl;

(cc) R$_9$ is cyclohexyl; R$_{10}$ is methylbenzyl; R$_{11}$ is cyclohexyl; R$_{12}$ is piperonyl; R$_{13}$ is 1-yl-n-butylamine; R$_{14}$ is 1-yl-2-(4(benzenesulfonamide)ethyl; R$_{15}$ is 1-yl-n-butylamine and R$_{16}$ is 1-yl-2-methoxyethyl;

(dd) R$_9$ is 1-yl-2-methoxyethyl; R$_{10}$ is 1-yl-2-(4(benzenesulfonamide)ethyl; R$_{11}$ is 1-yl-n-butylamine; R$_{12}$ is 1-yl-2-methoxyethyl; R$_{13}$ is 1-yl-2-(4(benzenesulfonamide)ethyl; R$_{14}$ is 1-yl-2-methoxyethyl; R$_{15}$ is isobutyl and R$_{16}$ is cyclohexyl;

(ee) R$_9$ is 1-yl-2-methoxyethyl; R$_{10}$ is methylbenzyl; R$_{11}$ is 1-yl-n-butylamine; R$_{12}$ is 1-yl-n-butylamine; R$_{13}$ is piperonyl; R$_{14}$ is isobutyl; R$_{15}$ is 1-yl-2-(4(benzenesulfonamide)ethyl and R$_{16}$ is 1-yl-n-butylamine;

(ff) R$_9$ is 1-yl-n-butylamine; R$_{10}$ is methylbenzyl; R$_{11}$ is 1-yl-2-(4(benzenesulfonamide)ethyl; R$_{12}$ is methylbenzyl; R$_{13}$ is 1-yl-n-butylamine; R$_{14}$ is 1-yl-2-(4(benzenesulfonamide)ethyl; R$_{15}$ is 1-yl-2-(4(benzenesulfonamide)ethyl and R$_{16}$ is cyclohexyl;

(gg) R$_9$ is 1-yl-n-butylamine; R$_{10}$ is 1-yl-2-methoxyethyl; R$_{11}$ is 1-yl-n-butylamine; R$_{12}$ is 1-yl-2-(4(benzenesulfonamide)ethyl; R$_{13}$ is 1-yl-2-methoxyethyl; R$_{14}$ is 1-yl-2-methoxyethyl; R$_{15}$ is 1-yl-n-butylamine and R$_{16}$ is methylbenzyl;

(hh) R$_9$ is cyclohexyl; R$_{10}$ is cyclohexyl; R$_{11}$ is methylbenzyl; R$_{12}$ is 1-yl-n-butylamine; R$_{13}$ is methylbenzyl; R$_{14}$ is cyclohexyl; R$_{15}$ is methylbenzyl and R$_{16}$ is 1-yl-n-butylamine;

(ii) R$_9$ is 1-yl-n-butylamine; R$_{10}$ is furfuryl; R$_{11}$ is methylbenzyl; R$_{12}$ is 1-yl-2-(4(benzenesulfonamide)ethyl; R$_{13}$ is furfuryl; R$_{14}$ is cyclohexyl; R$_{15}$ is methylbenzyl and R$_{16}$ is cyclohexyl;

(ii) R$_9$ is 1-yl-n-butylamine; R$_{10}$ is methylbenzyl; R$_{11}$ is 1-yl-n-butylamine; R$_{12}$ is 1-yl-2-(4(benzenesulfonamide)ethyl; R$_{13}$ is 1-yl-2-methoxyethyl; R$_{14}$ is methylbenzyl; R$_{15}$ is 1-yl-2-methoxyethyl and R$_{16}$ is isobutyl;

(kk) R$_9$ is 1-yl-2-(4(benzenesulfonamide)ethyl; R$_{10}$ is 1-yl-n-butylamine; R$_{11}$ is 1-yl-n-butylamine; R$_{12}$ is methylbenzyl; R$_{13}$ is methylbenzyl; R$_{14}$ is cyclohexyl; R$_{15}$ is 1-yl-2-(4(benzenesulfonamide)ethyl and R$_{16}$ is methylbenzyl;

(ll) R$_9$ is 1-yl-2-(4(benzenesulfonamide)ethyl; R$_{10}$ is 1-yl-2-(4(benzenesulfonamide)ethyl; R$_{11}$ is 1-yl-n-butylamine; R$_{12}$ is 1-yl-n-butylamine; R$_{13}$ is methylbenzyl; R$_{14}$ is 1-yl-n-butylamine; R$_{15}$ is methylbenzyl and R$_{16}$ is 1-yl-n-butylamine;

(mm) R$_9$ is 1-yl-n-butylamine; R$_{10}$ is 1-yl-2-(4(benzenesulfonamide)ethyl; R$_{11}$ is 1-yl-2-(4(benzenesulfonamide)ethyl; R$_{12}$ is 1-yl-2-methoxyethyl; R$_{13}$ is 1-yl-n-butylamine; R$_{14}$ is cyclohexyl; R$_{15}$ is 1-yl-2-(4(benzenesulfonamide)ethyl and R$_{16}$ is methylbenzyl;

(nn) R$_9$ is 1-yl-n-butylamine; R$_{10}$ is 1-yl-n-butylamine; R$_{11}$ is piperonyl; R$_{12}$ is 1-yl-2-(4(benzenesulfonamide)ethyl; R$_{13}$ is 1-yl-n-butylamine; R$_{14}$ is methylbenzyl; R$_{15}$ is methylbenzyl and R$_{16}$ is cyclohexyl;

(oo) R$_9$ is 1-yl-2-(4(benzenesulfonamide)ethyl; R$_{10}$ is methylbenzyl; R$_{11}$ is methylbenzyl; R$_{12}$ is 1-yl-n-butylamine; R$_{13}$ is methylbenzyl; R$_{14}$ is piperonyl; R$_{15}$ is 1-yl-n-butylamine and R$_{16}$ is 1-yl-2-methoxyethyl;

(pp) R$_9$ is piperonyl; R$_{10}$ is 1-yl-n-butylamine; R$_{11}$ is 1-yl-n-butylamine; R$_{12}$ is methylamine; R$_{13}$ is piperonyl; R$_{14}$ is 1-yl-n-butylamine; R$_{15}$ is piperonyl and R$_{16}$ is 1-yl-2-methoxyethyl;

(qq) R$_9$ is cyclohexyl; R$_{10}$ is cyclohexyl; R$_{11}$ is furfuryl; R$_{12}$ is 1-yl-2-methoxyethyl; R$_{13}$ is isobutyl; R$_{14}$ is cyclohexyl; R$_{15}$ is methylbenzyl and R$_{16}$ is methylbenzyl;

(rr) R$_9$ is piperonyl; R$_{10}$ is 1-yl-n-butylamine; R$_{11}$ is isobutyl; R$_{12}$ is isobutyl; R$_{13}$ is 1-yl-2-methoxyethyl; R$_{14}$ is cyclohexyl; R$_{15}$ is 1-yl-2-(4(benzenesulfonamide)ethyl and R$_{16}$ is 1-yl-2-(4(benzenesulfonamide)ethyl;

(ss) R$_9$ is cyclohexyl; R$_{10}$ is cyclohexyl; R$_{11}$ is 1-yl-n-butylamine; R$_{12}$ is methylbenzyl; R$_{13}$ is 1-yl-n-butylamine; R$_{14}$ is methylbenzyl; R$_{15}$ is cyclohexyl and R$_{16}$ is piperonyl;

and pharmaceutically acceptable salts thereof.

In a more preferred embodiment, the following compounds are selected as peptoid ligands for Alzheimer's disease screening and/or detection:

The compound according to claim 35 wherein said compound of formula II is selected from the group having R$_9$-R$_{16}$ as (a) R$_9$ is n-butylamine; R$_{10}$ is 1-yl-n-butylamine; R$_{11}$ is piperonyl; R$_{12}$ is methylbenzyl; R$_{13}$ is piperonyl; R$_{14}$ is methylbenzyl; $R_{15}$ is 1-yl-2-(4(benzenesulfonamide) ethyl and $R_{16}$ is 1-yl-2-methoxyethyl;

(b) $R_9$ is 1-yl-n-butylamine; $R_{10}$ is 1-yl-2-(4(benzenesulfonamide)ethyl; $R_{11}$ is 1-yl-n-butylamine; $R_{12}$ is cyclohexyl; $R_{13}$ is 1-yl-2-methoxyethyl; $R_{14}$ is 1-yl-2,2-dimethylethyl (isobutyl); $R_{15}$ is 1-yl-2-(4(benzenesulfonamide)ethyl and $R_{16}$ is methylbenzyl;

(c) $R_9$ is 1-yl-n-butylamine; $R_{10}$ is 1-yl-n-butylamine; $R_{11}$ is piperonyl; $R_{12}$ is 1-yl-2-(4(benzenesulfonamide) ethyl; $R_{13}$ is 1-yl-n-butylamine; $R_{14}$ is methylbenzyl; $R_{15}$ is methylbenzyl and $R_{16}$ is cyclohexyl;

(d) $R_9$ is piperonyl; $R_{10}$ is 1-yl-n-butylamine; $R_{11}$ is isobutyl; $R_{12}$ is 1-yl-2-(4(benzenesulfonamide)ethyl; $R_{13}$ is methylbenzyl; $R_{14}$ is cyclohexyl; $R_{15}$ is isobutyl and $R_{16}$ is 1-yl-n-butylamine;

(e) $R_9$ is 1-yl-n-butylamine; $R_{10}$ is 1-yl-n-butylamine; $R_{11}$ is methylbenzyl; $R_{12}$ is 1-yl-2-methoxyethyl; $R_{13}$ is cyclohexyl; $R_{14}$ is cyclohexyl; $R_{15}$ is methylbenzyl and $R_{16}$ is piperonyl;

(f) $R_9$ is piperonyl; $R_{10}$ is 1-yl-n-butylamine; $R_{11}$ is isopropyl; $R_{12}$ is isopropyl; $R_{13}$ is 1-yl-2-methoxyethyl; $R_{14}$ is cyclohexyl; $R_{15}$ is 1-yl-2-(4(benzenesulfonamide)ethyl and $R_{16}$ is 1-yl-2-(4(benzenesulfonamide) ethyl and pharmaceutically acceptable salts thereof.

Autoimmune Diseases

The present invention also provides for the identification of molecules that can bind autoimmune T-cells and/or antibodies from a variety of autoimmune disease states or conditions. Though the examples are directed to EAE, an animal model for MS, this invention should be useful in the context of a variety of autoimmune diseases, some of which are discussed below. In certain aspects, disease states include, but are not limited to diseases such as acute disseminated encephalomyelitis (ADEM), acute necrotizing hemorrhagic leukoencephalitis, Addison's disease, agammaglobulinemia, allergic asthma, allergic rhinitis, alopecia areata, amyloidosis, ankylosing spondylitis, anti-GBM/anti-TBM nephritis, antiphospholipid syndrome (APS), autoimmune aplastic anemia, autoimmune dysautonomia, autoimmune hepatitus, autoimmune hyperlipidemia, autoimmune immunodeficiency, autoimmune inner ear disease (AIED), autoimmune myocarditis, autoimmune pancreatitis, autoimmune retinopathy, autoimmune thrombocytopenic purpura (ATP), autoimmune thyroid disease, axonal & neuronal neuropathies, Balo disease, Behcet's disease, bullous pemphigoid, cardiomyopathy, Castlemen disease, celiac sprue (non-tropical), Chagas disease, chronic fatigue syndrome, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogan's syndrome, cold agglutinin disease, congenital heart block, coxsackie myocarditis, CREST disease, essential mixed cryoglobulinemia, demyelinating neuropathies, dermatomyositis, Devic's disease (neuromyelitis optica), discoid lupus, Dressler's syndrome, endometriosis, eosinophillic fasciitis, erythema nodosum, experimental allergic encephalomyelitis, Evan's syndrome, fibromyalgia, fibrosing alveolitis, giant cell arteritis (temporal arteritis), glomerulonephritis, Goodpasture's syndrome, Grave's disease, Guillain-Barre syndrome, Hashimoto's encephalitis, Hashimoto's thyroiditis, hemolytic anemia, Henock-Schoniein purpura, herpes gestationis, hypogammaglobulinemia, idiopathic thrombocytopenic purpura (ITP), IgA nephropathy, immunoregulatory lipoproteins, inclusion body myositis, insulin-dependent diabetes (type 1), interstitial cystitis, juvenile arthritis, juvenile diabetes, Kawasaki syndrome, Lambert-Eaton syndrome, leukocytoclastic vasculitis, lichen planus, lichen sclerosus, ligneous conjunctivitis, linear IgA disease (LAD), Lupus (SLE), Lyme disease, Meniere's disease, microscopic polyangitis, mixed connective tissue disease (MCTD), Mooren's ulcer, Mucha-Habermann disease, multiple sclerosis, myasthenia gravis, myositis, narcolepsy, neuromyelitis optica (Devic's), neutropenia, ocular cicatricial pemphigoid, optic neuritis, palindromic rheumatism, PANDAS (Pediatric Autoimmune Neuropsychiatric Disorders Associated with Streptococcus), paraneoplastic cerebellar degeneration, paroxysmal nocturnal hemoglobinuria (PNH), Parry Romberg syndrome, Parsonnage-Turner syndrome, pars plantis (peripheral uveitis), pemphigus, peripheral neuropathy, perivenous encephalomyelitis, pernicious anemia, POEMS syndrome, polyarteritis nodosa, type I, II & III autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynaud's phenomena, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Slogren's syndrome, sperm and testicular autoimmunity, stiff person syndrome, subacute bacterial endocarditis (SBE), sympathetic ophthalmia, Takayasu's arteritis, temporal arteritis/giant cell arteries, thrombocytopenic purpura (TPP), Tolosa-Hunt syndrome, transverse myelitis, ulcerative colitis, undifferentiated connective tissue disease (UCTD), uveitis, vasculitis, vesiculobullous dermatosis, vitiligo or Wegener's granulomatosis or, chronic active hepatitis, primary biliary cirrhosis, cadilated cardiomyopathy, myocarditis, autoimmune polyendocrine syndrome type I (APS-I), cystic fibrosis vasculitides, acquired hypoparathyroidism, coronary artery disease, pemphigus foliaceus, pemphigus vulgaris, Rasmussen encephalitis, autoimmune gastritis, insulin hypoglycemic syndrome (Hirata disease), Type B insulin resistance, acanthosis, systemic lupus erythematosus (SLE), pernicious anemia, treatment-resistant Lyme arthritis, polyneuropathy, demyelinating diseases, atopic dermatitis, autoimmune hypothyroidism, vitiligo, thyroid associated ophthalmopathy, autoimmune coeliac disease, ACTH deficiency, dermatomyositis, Sjogren syndrome, systemic sclerosis, progressive systemic sclerosis, morphea, primary antiphospholipid syndrome, chronic idiopathic urticaria, connective tissue syndromes, necrotizing and crescentic glomerulonephritis (NCGN), systemic vasculitis, Raynaud syndrome, chronic liver disease, visceral leishmaniasis, autoimmune C1 deficiency, membrane proliferative glomerulonephritis (MPGN), prolonged coagulation time, immunodeficiency, atherosclerosis, neuronopathy, paraneoplastic pemphigus, paraneoplastic stiff man syndrome, paraneoplastic encephalomyelitis, subacute autonomic neuropathy, cancer-associated retinopathy, paraneoplastic opsoclonus myoclonus ataxia, lower motor neuron syndrome and Lambert-Eaton myasthenic syndrome.

Peptoid libraries of the invention for purposes of screening for lupus associated antibodies comprise the library(ies) specified above and further comprise a random ligand library for screening a complex biological fluid comprising a compound of formula I on a support,

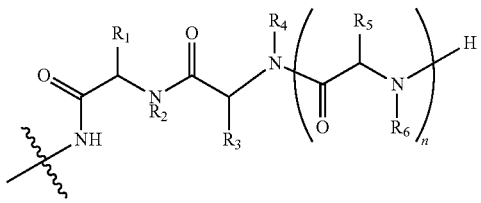

wherein $R_1$ is selected from an electron rich amino acid side chain Y;

$R_2$ is selected from H;

and $R_3$-$R_6$ are independently selected from the groups consisting of H, —$C_1$-$C_6$alkyl, —$C_1$-$C_6$alkylSCH$_3$, —$C_0$-$C_6$alkyl$C_2$-$C_6$alkenyl, —$C_0$-$C_6$alkyl $C_2$-$C_6$alkynyl, —$C_1$-$C_6$ COOH, —$C_1$-$C_6$alkylOH, —$C_1$-$C_6$alkylN(R)$_2$, —$C_3$-$C_8$cyclo alkyl, —$C_1$-$C_6$alkylaryl, —$C_1$-$C_6$alkylhetero aryl, —$C_1$-$C_6$alkylNC(O)$C_1$-$C_6$alkyl, —$C_1$-$C_6$alkylcycloamide wherein any of the aryl or heteroaryl groups may be independently substituted with —OH, Cl, F, Br, —OCH$_3$, —SO$_2$NH$_2$ or —O—CH$_2$—O—.

Other peptoid libraries suitable for screening for SLE (lupus) include those libraries comprising:

a random ligand library for screening a complex biological fluid comprising a compound of formula I on a support,

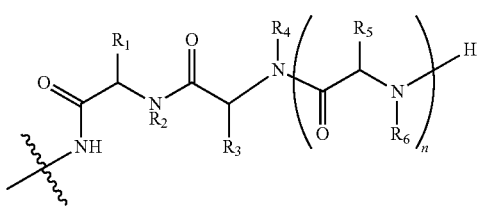

wherein the compounds are produced by a process which comprises use of a reactant selected from the group consisting of (A) furfurylamine; 3,4-dimethoxyethanolamine; benzylamine; N-(2-aminoethyl)acetamide; N-(3-aminopropyl)-2-pyrrolidinone; ethanolamine; glycine; diaminobutane; allylamine; piperonylamine; methylbenzylamine; isobutylamine; 4-(2-aminoethyl)benzenesulfonamide or cyclohexylamine; or (B) methoxyethylamine; piperonylamine; cyclohexylamine; diaminobutane; methylbenzylamine; isobutylamine; furfurylamine or 4-(2-aminoethyl)benzenesulfonamide; or (C) furfurylamine, ethanolamine; glycine; diaminobutane; allylamine; piperonylamine; methylbenzylamine; isobutylamine or 4-(2-aminoethyl)benzenesulfonamide; or (D) furfurylamine, N-(2-aminoethyl)acetamide; N-(3-aminoethyl)-2-pyrrolidinone; ethanolamine; glycine; diaminobutane; allylamine; piperonylamine; methylbenzylamine; isobutylamine; 4-(2-aminoethyl)benzenesulfonamide; or (E) cysteine, glycine, allylamine, ethanolamine, isobutylamine, methylbenzylamine, piperonylamine, methionine, cyclohexylamine, 3,4-dimethoxyphenethylamine, benzylamine, N-(2-aminoethyl)acetamide, N-(3-aminopropyl)-2-pyrrolidone, 4-(2-aminoethyl)benzenesulfonamide and furfurylamine; and wherein, $R_1$ is selected from the group consisting —($C_1$-$C_6$)SCH$_3$;

$R_2$ is selected from H;

$R_3$ and $R_5$ are independently selected from the groups consisting of H, —$C_1$-$C_6$alkyl, —$C_1$-$C_6$alkylSCH$_3$, —$C_0$-$C_6$alkyl$C_2$-$C_6$alkenyl, —$C_0$-$C_6$alkyl $C_2$-$C_6$alkynyl, —$C_1$-$C_6$ COOH, —$C_1$-$C_6$alkylOH, —$C_1$-$C_6$alkylN(R)$_2$, —$C_3$-$C_8$cycloalkyl, —$C_1$-$C_6$alkylaryl, —$C_1$-$C_6$alkylheteroaryl, —$C_1$-$C_6$alkylNC(O)$C_1$-$C_6$alkyl, —$C_1$-$C_6$alkylcycloamide wherein any of the aryl or heteroaryl groups may be independently substituted with —OH, Cl, F, Br, —OCH$_3$, —SO$_2$NH$_2$ or —O—CH$_2$—O—;

$R_4$ is selected from the group consisting of furfuryl or —($C_1$-$C_6$alkyl)NR$_7$R$_8$, $R_6$ is selected from the group consisting of H, 1-yl-allyl, 1-yl-2-hydroxyethyl, isobutyl, 1-yl-n-butylamine, methylbenzyl, piperonyl, cyclohexyl, 1-yl-2-(3,4-dimethoxyphenyl)ethyl, benzyl, 1-yl-2-(acetamide)ethyl, 1-yl-3-2-pyrrolidinone, 1-yl-2-(4-benzenesulfonamide)ethyl or furfuryl and n is 3-11.

Preferred embodiments for initial screening purposes comprise:

A compound of the formula:

IIIa

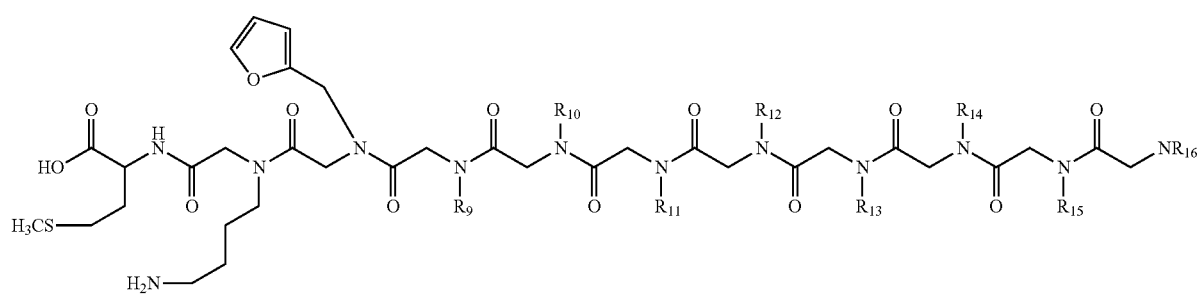

wherein, in a compound of formula IIIa, $R_9$-$R_{16}$ are selected from, (a) $R_9$ is 1-yl-allyl; $R_{10}$ is 1-yl-3N-(2-pyrrolidinone)propyl; $R_{11}$ is acetic acid; $R_{12}$ is 1-yl-2-(4(benzenesulfonamide)ethyl; $R_{13}$ is benzyl; $R_{14}$ is 1-yl-n-butylamine; $R_{15}$ is isobutyl and $R_{16}$ is 1-yl-allyl;

(b) $R_9$ is cyclohexyl; $R_{10}$ is 1-yl-n-butylamine; $R_{11}$ is 1-yl-n-butylamine; $R_{12}$ is 1-yl-2-(3,4-dimethoxyphenyl)ethyl; $R_{13}$ is benzyl; $R_{14}$ is piperonyl; $R_{15}$ is 1-yl-n-butylamine and $R_{16}$ is 1-yl-2-(4(benzenesulfonamide)ethyl;

(c) $R_9$ is 1-yl-2-(4(benzenesulfonamide)ethyl; $R_{10}$ is 1-yl-allyl; $R_{11}$ is 1-yl-n-butylamine; $R_{12}$ is benzyl; $R_{13}$ is methylbenzyl; $R_{14}$ is benzyl; $R_{15}$ is methylbenzyl and $R_{16}$ is 1-yl-n-butylamine;
(d) $R_9$ is 1-yl-2-(4(benzenesulfonamide)ethyl; $R_{10}$ is 1-yl-2-(3,4-dimethoxyphenyl)ethyl; $R_{11}$ is 1-yl-n-butylamine; $R_{12}$ is 1-yl-2-(4(benzenesulfonamide)ethyl; $R_{13}$ is 1-yl-n-butylamine; $R_{14}$ is benzyl; $R_{15}$ is methylbenzyl and $R_{16}$ is benzyl;
(e) $R_9$ is piperonyl; $R_{10}$ is piperonyl; $R_{11}$ is 1-yl-n-butylamine; $R_{12}$ is cyclohexyl; $R_{13}$ is benzyl; $R_{14}$ is 1-yl-2-(3,4-dimethoxyphenyl)ethyl; $R_{15}$ is 1-yl-n-butylamine and $R_{16}$ is methylbenzyl;
(f) $R_9$ is 1-yl-allyl; $R_{10}$ is methylbenzyl; $R_{11}$ is methylbenzyl; $R_{12}$ is 1-yl-n-butylamine; $R_{13}$ is piperonyl; $R_{14}$ is benzyl; $R_{15}$ is piperonyl and $R_{16}$ is 1-yl-n-butylamine;
(g) $R_9$ is 1-yl-2-(3,4-dimethoxyphenyl)ethyl; $R_{10}$ is isobutyl; $R_{11}$ is methylbenzyl; $R_{12}$ is 1-yl-n-butylamine; $R_{13}$ is methylbenzyl; $R_{14}$ is benzyl; $R_{15}$ is piperonyl and $R_{16}$ is 1-yl-n-butylamine;
(h) $R_9$ is methylbenzyl; $R_{10}$ is 1-yl-2-(4(benzenesulfonamide)ethyl; $R_{11}$ is methylbenzyl; $R_{12}$ is 1-yl-n-butylamine; $R_{13}$ is methylbenzyl; $R_{14}$ is methylbenzyl; $R_{15}$ is 1-yl-n-butylamine and $R_{16}$ is methylbenzyl;
(i) $R_9$ is piperonyl; $R_{10}$ is benzyl; $R_{11}$ is piperonyl; $R_{12}$ is benzyl; $R_{13}$ is 1-yl-n-butylamine; $R_{14}$ is benzyl; $R_{15}$ is cyclohexyl and $R_{16}$ is 1-yl-n-butylamine and
pharmaceutically acceptable salts thereof.

Preferred embodiments for purposes of kits and/or other diagnostic methods include:
A compound of the formula:

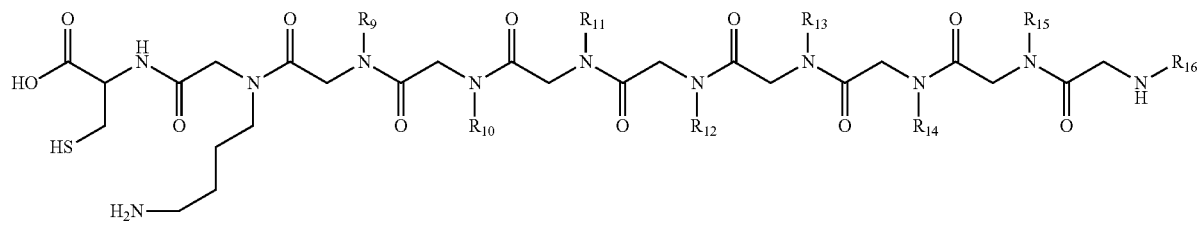

II wherein, in a compound of formula II, $R_9$-$R_{16}$ are selected from,
(a) $R_9$ is 1-yl-allyl; $R_{10}$ is 1-yl-3N-(2-pyrrolidinone)propyl; $R_{11}$ is acetic acid; $R_{12}$ is 1-yl-2-(4(benzenesulfonamide)ethyl; $R_{13}$ is benzyl; $R_{14}$ is 1-yl-n-butylamine; $R_{15}$ is isobutyl and $R_{16}$ is 1-yl-allyl;
(b) $R_9$ is cyclohexyl; $R_{10}$ is 1-yl-n-butylamine; $R_{11}$ is 1-yl-n-butylamine; $R_{12}$ is 1-yl-2-(3,4-dimethoxyphenyl)ethyl; $R_{13}$ is benzyl; $R_{14}$ is piperonyl; $R_{15}$ is 1-yl-n-butylamine and $R_{16}$ is 1-yl-2-(4(benzenesulfonamide)ethyl;
(c) $R_9$ is 1-yl-2-(4(benzenesulfonamide)ethyl; $R_{10}$ is 1-yl-allyl; $R_{11}$ is 1-yl-n-butylamine; $R_{12}$ is benzyl; $R_{13}$ is methylbenzyl; $R_{14}$ is benzyl; $R_{15}$ is methylbenzyl and $R_{16}$ is 1-yl-n-butylamine;
(d) $R_9$ is 1-yl-2-(4(benzenesulfonamide)ethyl; $R_{10}$ is 1-yl-2-(3,4-dimethoxyphenyl)ethyl; $R_{11}$ is 1-yl-n-butylamine; $R_{12}$ is 1-yl-2-(4(benzenesulfonamide)ethyl; $R_{13}$ is 1-yl-n-butylamine; $R_{14}$ is benzyl; $R_{15}$ is methylbenzyl and $R_{16}$ is benzyl;
(e) $R_9$ is piperonyl; $R_{10}$ is piperonyl; $R_{11}$ is 1-yl-n-butylamine; $R_{12}$ is cyclohexyl; $R_{13}$ is benzyl; $R_{14}$ is 1-yl-2-(3,4-dimethoxyphenyl)ethyl; $R_{15}$ is 1-yl-n-butylamine and $R_{16}$ is methylbenzyl;
(f) $R_9$ is 1-yl-allyl; $R_{10}$ is methylbenzyl; $R_{11}$ is methylbenzyl; $R_{12}$ is 1-yl-n-butylamine; $R_{13}$ is piperonyl; $R_{14}$ is benzyl; $R_{15}$ is piperonyl and $R_{16}$ is 1-yl-n-butylamine;
(g) $R_9$ is 1-yl-2-(3,4-dimethoxyphenyl)ethyl; $R_{10}$ is isobutyl; $R_{11}$ is methylbenzyl; $R_{12}$ is 1-yl-n-butylamine; $R_{13}$ is methylbenzyl; $R_{14}$ is benzyl; $R_{15}$ is piperonyl and $R_{16}$ is 1-yl-n-butylamine;
(h) $R_9$ is methylbenzyl; $R_{10}$ is 1-yl-2-(4(benzenesulfonamide)ethyl; $R_{11}$ is methylbenzyl; $R_{12}$ is 1-yl-n-butylamine; $R_{13}$ is methylbenzyl; $R_{14}$ is methylbenzyl; $R_{15}$ is 1-yl-n-butylamine and $R_{16}$ is methylbenzyl;
(i) $R_9$ is piperonyl; $R_{10}$ is benzyl; $R_{11}$ is piperonyl; $R_{12}$ is benzyl; $R_{13}$ is 1-yl-n-butylamine; $R_{14}$ is benzyl; $R_{15}$ is cyclohexyl and $R_{16}$ is 1-yl-n-butylamine and
pharmaceutically acceptable salts thereof.

Cancer

The present invention is also useful in identifying and/or characterizing the presence or absence of biomarkers associated with cancer or pre-cancerous conditions. These cancers are selected from the group consisting of, for example,
Acute lymphoblastic leukemia, Acute myeloid leukemia, Adrenocortical carcinoma, AIDS-related cancers, AIDS-related lymphoma, Anal cancer, Appendix cancer, Astrocytoma, childhood cerebellar or cerebral, Basal cell carcinoma, Bile duct cancer, extrahepatic, Bladder cancer, Bone cancer, Osteosarcoma/Malignant fibrous histiocytoma, Brainstem glioma, Brain tumor, Brain tumor, cerebellar astrocytoma, Brain tumor, cerebral astrocytoma/malignant glioma, Brain tumor, ependymoma, Brain tumor, medulloblastoma, Brain tumor, supratentorial primitive neuroectodermal tumors, Brain tumor, visual pathway and hypothalamic glioma, Breast cancer, Bronchial adenomas/carcinoids, Burkitt lymphoma, Carcinoid tumor, childhood, Carcinoid tumor, gastrointestinal, Carcinoma of unknown primary, Central nervous system lymphoma, primary, Cerebellar astrocytoma, childhood, Cerebral astrocytoma/Malignant glioma, childhood, Cervical cancer, Childhood cancers, Chronic lymphocytic leukemia, Chronic myelogenous leukemia, Chronic myeloproliferative disorders, Colon Cancer, Cutaneous T-cell lymphoma, Desmoplastic small round cell tumor, Endometrial cancer, Ependymoma, Esophageal cancer, Ewing's sarcoma in the Ewing family of tumors, Extracranial germ cell tumor, Childhood, Extragonadal Germ cell tumor, Extrahepatic bile duct cancer, Eye Cancer, Intraocular melanoma, Eye Cancer, Retinoblastoma, Gallbladder cancer, Gastric (Stomach) cancer, Gastrointestinal Carcinoid Tumor, Gastrointestinal stromal tumor (GIST), Germ cell tumor: extracranial, extragonadal, or ovarian, Gestational trophoblastic tumor, Glioma of the brain stem, Glioma, Childhood Cerebral Astrocytoma, Glioma, Childhood Visual Pathway and Hypothalamic, Gastric carcinoid, Hairy cell leukemia, Head and neck cancer, Heart cancer, Hepatocellular (liver) cancer, Hodgkin lymphoma, Hypopharyngeal cancer, Hypothalamic and visual pathway glioma, childhood, Intraocular Melanoma, Islet Cell Carcinoma (Endocrine Pancreas), Kaposi sarcoma, Kidney cancer (renal cell cancer), Laryngeal Cancer, Leukemias, Leukemia, acute lymphoblastic (also called acute lymphocytic leukemia), Leukemia, acute myeloid (also called acute myelogenous leukemia), Leukemia, chronic lymphocytic (also called chronic lymphocytic leukemia), Leukemia, chronic myelogenous (also called chronic myeloid leukemia), Leukemia, hairy cell, Lip and Oral Cavity Cancer, Liver Cancer (Primary), Lung Cancer, Non-Small Cell, Lung Cancer, Small Cell, Lymphomas, Lymphoma, AIDS-related, Lymphoma, Burkitt, Lymphoma, cutaneous T-Cell, Lymphoma, Hodgkin, Lymphomas, Non-Hodgkin (an old classification of all lymphomas except Hodgkin's), Lymphoma, Primary Central Nervous System, Marcus Whittle, Deadly Disease, Macroglobulinemia, Waldenström, Malignant Fibrous Histiocytoma of Bone/Osteosarcoma, Medulloblastoma, Childhood, Melanoma, Melanoma, Intraocular (Eye), Merkel Cell Carcinoma, Mesothelioma, Adult Malignant, Mesothelioma, Childhood, Metastatic Squamous Neck Cancer with Occult Primary, Mouth Cancer, Multiple Endocrine Neoplasia Syndrome, Childhood, Multiple Myeloma/Plasma Cell Neoplasm, Mycosis Fungoides, Myelodysplastic Syndromes, Myelodysplastic/Myeloproliferative Diseases, Myelogenous Leukemia, Chronic, Myeloid Leukemia, Adult Acute, Myeloid Leukemia, Childhood Acute, Myeloma, Multiple (Cancer of the Bone-Marrow), Myeloproliferative Disorders, Chronic, Nasal cavity and paranasal sinus cancer, Nasopharyngeal carcinoma, Neuroblastoma, Non-Hodgkin lymphoma, Non-small cell lung cancer, Oral Cancer, Oropharyngeal cancer, Osteosarcoma/malignant fibrous histiocytoma of bone, Ovarian cancer, Ovarian epithelial cancer (Surface epithelial-stromal tumor), Ovarian germ cell tumor, Ovarian low malignant potential tumor, Pancreatic cancer, Pancreatic cancer, islet cell, Paranasal sinus and nasal cavity cancer, Parathyroid cancer, Penile cancer, Pharyngeal cancer, Pheochromocytoma, Pineal astrocytoma, Pineal germinoma, Pineoblastoma and supratentorial primitive neuroectodermal tumors, childhood, Pituitary adenoma, Plasma cell neoplasia/Multiple myeloma, Pleuropulmonary blastoma, Primary central nervous system lymphoma, Prostate cancer, Rectal cancer, Renal cell carcinoma (kidney cancer), Renal pelvis and ureter, transitional cell cancer, Retinoblastoma, Rhabdomyosarcoma, childhood, Salivary gland cancer, Sarcoma, Ewing family of tumors, Sarcoma, Kaposi, Sarcoma, soft tissue, Sarcoma, uterine, Sézary syndrome, Skin cancer (nonmelanoma), Skin cancer (melanoma), Skin carcinoma, Merkel cell, Small cell lung cancer, Small intestine cancer, Soft tissue sarcoma, Squamous cell carcinoma—see Skin cancer (nonmelanoma), Squamous neck cancer with occult primary, metastatic, Stomach cancer, Supratentorial primitive neuroectodermal tumor, childhood, T-Cell lymphoma, cutaneous—see Mycosis Fungoides and Sézary syndrome, Testicular cancer, Throat cancer, Thymoma, childhood, Thymoma and Thymic carcinoma, Thyroid cancer, Thyroid cancer, childhood, Transitional cell cancer of the renal pelvis and ureter, Trophoblastic tumor, gestational, Unknown primary site, carcinoma of, adult, Unknown primary site, cancer of, childhood, Ureter and renal pelvis, transitional cell cancer, Urethral cancer, Uterine cancer, endometrial, Uterine sarcoma, Vaginal cancer, Visual pathway and hypothalamic glioma, childhood, Vulvar cancer, Waldenström macroglobulinemia, Wilms tumor (kidney cancer), childhood.

Peptoid libraries of the invention for purposes of screening for pancreatic cancer in addition to those libraries described above are comprised of a random ligand library for screening a complex biological fluid comprising a compound of formula I on a support,

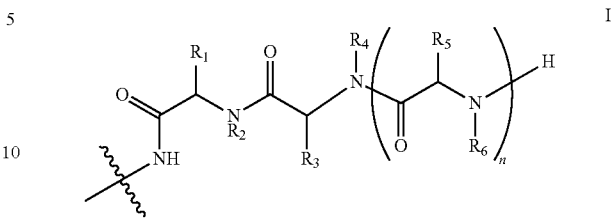

wherein $R_1$ is selected from an electron rich amino acid side chain Y;
$R_2$ is selected from H;
and $R_3$-$R_6$ are independently selected from the groups consisting of H, —$C_1$-$C_6$alkyl, —$C_1$-$C_6$alkylSCH$_3$, —$C_0$-$C_6$alkylC$_2$-$C_6$alkenyl, —$C_0$-$C_6$alkyl C$_2$-$C_6$alkynyl, —$C_1$-$C_6$COOH, —$C_1$-$C_6$alkylOH, —$C_1$-$C_6$alkylN(R)$_2$, —$C_3$-$C_8$cycloalkyl, —$C_1$-$C_6$alkylaryl, —$C_1$-$C_6$alkylheteroaryl, —$C_1$-$C_6$alkylNC(O)C$_1$-$C_6$alkyl, —$C_1$-$C_6$alkylcycloamide wherein any of the aryl or heteroaryl groups may be independently substituted with —OH, Cl, F, Br, —OCH$_3$, —SO$_2$NH$_2$ or —O—CH$_2$—O—.

Other peptoid libraries suitable for screening for cancer include those libraries comprising:
a random ligand library for screening a complex biological fluid comprising a compound of formula I on a support,

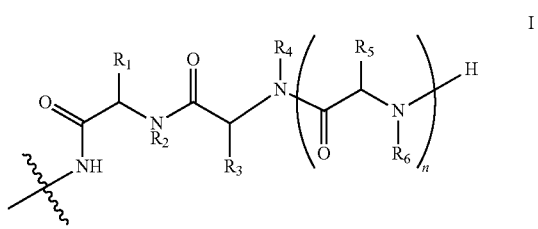

wherein the compounds are produced by a process which comprises use of a reactant selected from the group consisting of
(A) furfurylamine; 3,4-dimethoxyethanolamine; benzylamine; N-(2-aminoethyl)acetamide; N-(3-aminopropyl)-2-pyrrolidinone; ethanolamine; glycine; diaminobutane; allylamine; piperonylamine; methylbenzylamine; isobutylamine; 4-(2-aminoethyl)benzenesulfonamide or cyclohexylamine; or
(B) methoxyethylamine; piperonylamine; cyclohexylamine; diaminobutane; methylbenzylamine; isobutylamine; furfurylamine or 4-(2-aminoethyl)benzenesulfonamide; or
(C) furfurylamine, ethanolamine; glycine; diaminobutane; allylamine; piperonylamine; methylbenzylamine; isobutylamine or 4-(2-aminoethyl)benzenesulfonamide; or
(D) furfurylamine, N-(2-aminoethyl)acetamide; N-(3-aminoethyl)-2-pyrrolidinone; ethanolamine; glycine; diaminobutane; allylamine; piperonylamine; methylbenzylamine; isobutylamine; 4-(2-aminoethyl)benzenesulfonamide; or
(E) cysteine, glycine, allylamine, ethanolamine, isobutylamine, methylbenzylamine, piperonylamine, methionine, cyclohexylamine, 3,4-dimethoxyphenethylamine, benzylamine, N-(2-aminoethyl)acetamide, N-(3-aminopropyl)-2-pyrrolidone, 4-(2-aminoethyl)benzenesulfonamide and furfurylamine; and wherein,
R$_1$ is selected from the group consisting —(C$_1$-C$_6$)SCH$_3$;
R$_2$ is selected from H;
R$_3$ and R$_5$ are independently selected from the groups consisting of H, —C$_1$-C$_6$alkyl, —C$_1$-C$_6$alkylSCH$_3$, —C$_0$-C$_6$alkylC$_2$-C$_6$alkenyl, —C$_0$-C$_6$alkyl C$_2$-C$_6$alkynyl, —C$_1$-C$_6$COOH, —C$_1$-C$_6$alkylOH, —C$_1$-C$_6$alkylN(R)$_2$, —C$_3$-C$_8$cycloalkyl, —C$_1$-C$_6$alkylaryl, —C$_1$-C$_6$alkylheteroaryl, —C$_1$-C$_6$alkylNC(O)C$_1$-C$_6$alkyl, —C$_1$-C$_6$alkylcycloamide wherein any of the aryl or heteroaryl groups may be independently substituted with —OH, Cl, F, Br, —OCH$_3$, —SO$_2$NH$_2$ or —O—CH$_2$—O—;
R$_4$ is selected from the group consisting of furfuryl or —(C$_1$-C$_6$alkyl)NR$_7$R$_8$,
R$_6$ is selected from the group consisting of H, 1-yl-allyl, 1-yl-2-hydroxyethyl, isobutyl, 1-yl-n-butylamine, methylbenzyl, piperonyl, cyclohexyl, 1-yl-2-(3,4-dimethoxyphenyl)ethyl, benzyl, 1-yl-2-(acetamide)ethyl, 1-yl-3-2-pyrrolidinone, 1-yl-2-(4-benzenesulfonamide)ethyl or furfuryl and n is 3-11.

Preferred embodiments for purposes of preliminary screening include those peptoids comprising:
A compound of the formula:

ethyl; R$_{12}$ is methylbenzyl; R$_{13}$ is 1-yl-n-butylamine; R$_{14}$ is 1-yl-n-butylamine; R$_{15}$ is cyclohexyl and R$_{16}$ is isobutyl;
(e) R$_9$ is 1-yl-n-butylamine; R$_{10}$ is methylbenzyl; R$_{11}$ is methylbenzyl; R$_{12}$ is methylbenzyl; R$_{13}$ is 1-yl-2-methoxyethyl; R$_{14}$ is 1-yl-n-butylamine; R$_{15}$ is cyclohexyl and R$_{16}$ is methylbenzyl;
(f) R$_9$ is cyclohexyl; R$_{10}$ is cyclohexyl; R$_{11}$ is methylbenzyl; R$_{12}$ is 1-yl-2-methoxyethyl; R$_{13}$ is methylbenzyl; R$_{14}$ is methylbenzyl; R$_{15}$ is 1-yl-n-butylamine and R$_{16}$ is 1-yl-n-butylamine;
(g) R$_9$ is furfuryl; R$_{10}$ is furfuryl; R$_{11}$ is isobutyl; R$_{12}$ is 1-yl-n-butylamine; R$_{13}$ is 1-yl-n-butylamine; R$_{14}$ is methylbenzyl; R$_{15}$ is methylbenzyl and R$_{16}$ is methylbenzyl;
(h) R$_9$ is methylbenzyl; R$_{10}$ is 1-yl-2-(4(benzenesulfonamide)ethyl; R$_{11}$ is cyclohexyl; R$_{12}$ is cyclohexyl; R$_{13}$ is 1-yl-n-butylamine; R$_{14}$ is 1-yl-2-methoxyethyl; R$_{15}$ is 1-yl-n-butylamine and R$_{16}$ is methylbenzyl;
(i) R$_9$ is isobutyl; R$_{10}$ is methylbenzyl; R$_{11}$ is methylbenzyl; R$_{12}$ is 1-yl-n-butylamine; R$_{13}$ is 1-yl-n-butylamine; R$_{14}$ is isobutyl; R$_{15}$ is isobutyl and R$_{16}$ is 1-yl-n-butylamine;

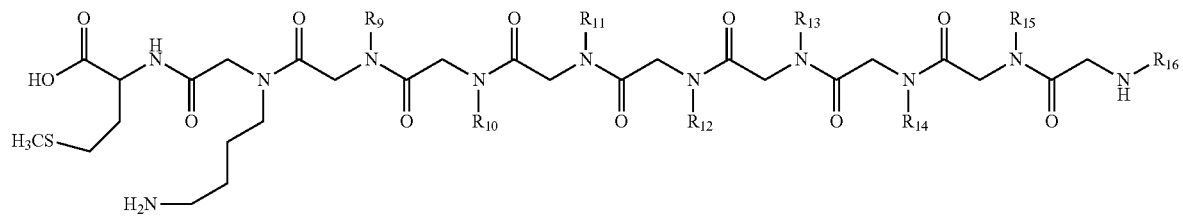

IIa wherein the compound is selected from the group consisting of a compound of formula IIa wherein,
(a) R$_9$ is 1-yl-n-butylamine; R$_{10}$ is piperonyl; R$_{11}$ is methylbenzyl; R$_{12}$ is 1-yl-n-butylamine; R$_{13}$ is cyclohexyl; R$_{14}$ is isobutyl; R$_{15}$ is methylbenzyl and R$_{16}$ is 1-yl-n-butylamine;
(b) R$_9$ is methylbenzyl; R$_{10}$ is 1-yl-n-butylamine; R$_{11}$ is 1-yl-2-(4(benzenesulfonamide)ethyl; R$_{12}$ is 1-yl-2-(4(benzenesulfonamide)ethyl; R$_{13}$ is isobutyl; R$_{14}$ is 1-yl-n-butylamine; R$_{15}$ is methylbenzyl and R$_{16}$ is 1-yl-n-butylamine;
(c) R$_9$ is 1-yl-n-butylamine; R$_{10}$ is 1-yl-n-butylamine; R$_{11}$ is 1-yl-2-methoxyethyl; R$_{12}$ is 1-yl-2-methoxyethyl; R$_{13}$ is isobutyl; R$_{14}$ is 1-yl-2-methoxyethyl; R$_{15}$ is 1-yl-n-butylamine and R$_{16}$ is 1-yl-2-methoxyethyl;

(j) R$_9$ is isobutyl; R$_{10}$ is 1-yl-n-butylamine; R$_{11}$ is methylbenzyl; R$_{12}$ is methylbenzyl; R$_{13}$ is methylbenzyl; R$_{14}$ is cyclohexyl; R$_{15}$ is methylbenzyl and R$_{16}$ is 1-yl-n-butylamine;
(k) R$_9$ is cyclohexyl; R$_{10}$ is cyclohexyl; R$_{11}$ is methylbenzyl; R$_{12}$ is methylbenzyl; R$_{13}$ is 1-yl-n-butylamine; R$_{14}$ is isobutyl; R$_{15}$ is 1-yl-n-butylamine and R$_{16}$ is isobutyl;
(l) R$_9$ is cyclohexyl; R$_{10}$ is cyclohexyl; R$_{11}$ is isobutyl; R$_{12}$ is 1-yl-n-butylamine; R$_{13}$ is 1-yl-n-butylamine; R$_{14}$ is methylbenzyl; R$_{15}$ is 1-yl-n-butylamine and R$_{16}$ is 1-yl-2-methoxyethyl;

and pharmaceutically acceptable salts thereof.
Preferred embodiments for purposes of screening for pancreatic cancer in kits comprise:
A compound of the formula:

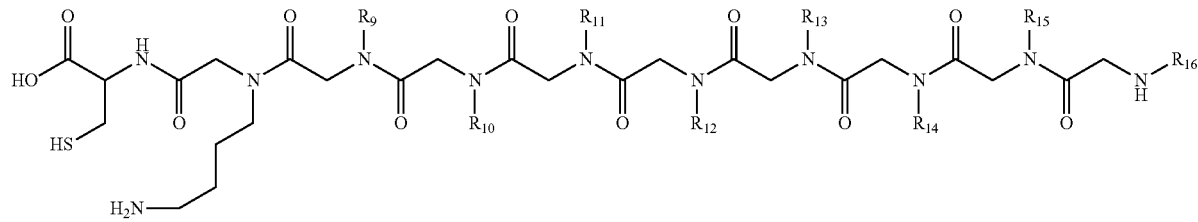

II (d) R$_9$ is methylbenzyl; R$_{10}$ is 1-yl-2-(4(benzenesulfonamide)ethyl; R$_{11}$ is 1-yl-2-(4(benzenesulfonamide)

wherein the compound is selected from the group consisting of a compound of formula II wherein, (a) $R_9$ is 1-yl-n-butylamine; $R_{10}$ is piperonyl; $R_{11}$ is methylbenzyl; $R_{12}$ is 1-yl-n-butylamine; $R_{13}$ is cyclohexyl; $R_{14}$ is isobutyl; $R_{15}$ is methylbenzyl and $R_{16}$ is 1-yl-n-butylamine;

(b) $R_9$ is methylbenzyl; $R_{10}$ is 1-yl-n-butylamine; $R_{11}$ is 1-yl-2-(4(benzenesulfonamide)ethyl; $R_{12}$ is 1-yl-2-(4(benzenesulfonamide)ethyl; $R_{13}$ is isobutyl; $R_{14}$ is 1-yl-n-butylamine; $R_{15}$ is methylbenzyl and $R_{16}$ is 1-yl-n-butylamine;

(c) $R_9$ is 1-yl-n-butylamine; $R_{10}$ is 1-yl-n-butylamine; $R_{11}$ is 1-yl-2-methoxyethyl; $R_{12}$ is 1-yl-2-methoxyethyl; $R_{13}$ is isobutyl; $R_{14}$ is 1-yl-2-methoxyethyl; $R_{15}$ is 1-yl-n-butylamine and $R_{16}$ is 1-yl-2-methoxyethyl;

(d) $R_9$ is methylbenzyl; $R_{10}$ is 1-yl-2-(4(benzenesulfonamide)ethyl; $R_{11}$ is 1-yl-2-(4(benzenesulfonamide)ethyl; $R_{12}$ is methylbenzyl; $R_{13}$ is 1-yl-n-butylamine; $R_{14}$ is 1-yl-n-butylamine; $R_{15}$ is cyclohexyl and $R_{16}$ is isobutyl;

(e) $R_9$ is 1-yl-n-butylamine; $R_{10}$ is methylbenzyl; $R_{11}$ is methylbenzyl; $R_{12}$ is methylbenzyl; $R_{13}$ is 1-yl-2-methoxyethyl; $R_{14}$ is 1-yl-n-butylamine; $R_{15}$ is cyclohexyl and $R_{16}$ is methylbenzyl;

(f) $R_9$ is cyclohexyl; $R_{10}$ is cyclohexyl; $R_{11}$ is methylbenzyl; $R_{12}$ is 1-yl-2-methoxyethyl; $R_{13}$ is methylbenzyl; $R_{14}$ is methylbenzyl; $R_{15}$ is 1-yl-n-butylamine and $R_{16}$ is 1-yl-n-butylamine;

(g) $R_9$ is furfuryl; $R_{10}$ is furfuryl; $R_{11}$ is isobutyl; $R_{12}$ is 1-yl-n-butylamine; $R_{13}$ is 1-yl-n-butylamine; $R_{14}$ is methylbenzyl; $R_{15}$ is methylbenzyl and $R_{16}$ is methylbenzyl;

(h) $R_9$ is methylbenzyl; $R_{10}$ is 1-yl-2-(4(benzenesulfonamide)ethyl; $R_{11}$ is cyclohexyl; $R_{12}$ is cyclohexyl; $R_{13}$ is 1-yl-n-butylamine; $R_{14}$ is 1-yl-2-methoxyethyl; $R_{15}$ is 1-yl-n-butylamine and $R_{16}$ is methylbenzyl;

(i) $R_9$ is isobutyl; $R_{10}$ is methylbenzyl; $R_{11}$ is methylbenzyl; $R_{12}$ is 1-yl-n-butylamine; $R_{13}$ is 1-yl-n-butylamine; $R_{14}$ is isobutyl; $R_{15}$ is isobutyl and $R_{16}$ is 1-yl-n-butylamine;

(j) $R_9$ is isobutyl; $R_{10}$ is 1-yl-n-butylamine; $R_{11}$ is methylbenzyl; $R_{12}$ is methylbenzyl; $R_{13}$ is methylbenzyl; $R_{14}$ is cyclohexyl; $R_{15}$ is methylbenzyl and $R_{16}$ is 1-yl-n-butylamine;

(k) $R_9$ is cyclohexyl; $R_{10}$ is cyclohexyl; $R_{11}$ is methylbenzyl; $R_{12}$ is methylbenzyl; $R_{13}$ is 1-yl-n-butylamine; $R_{14}$ is isobutyl; $R_{15}$ is 1-yl-n-butylamine and $R_{16}$ is isobutyl;

(l) $R_9$ is cyclohexyl; $R_{10}$ is cyclohexyl; $R_{11}$ is isobutyl; $R_{12}$ is 1-yl-n-butylamine; $R_{13}$ is 1-yl-n-butylamine; $R_{14}$ is methylbenzyl; $R_{15}$ is 1-yl-n-butylamine and $R_{16}$ is 1-yl-2-methoxyethyl;

and pharmaceutically acceptable salts thereof.

Other alternative embodiments for purposes of preliminary screens for the detection of pancreatic cancer autoantibodies include:

A compound of the formula:

IIIa

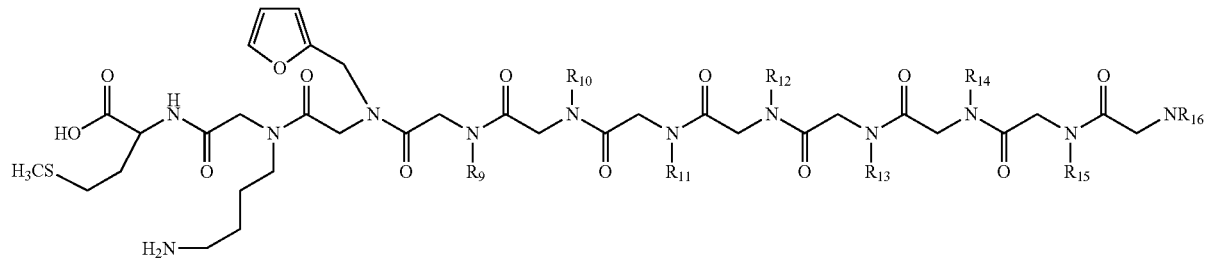

wherein said compounds are selected from the group consisting of compounds having $R_9$-$R_{16}$ as, (a) $R_9$ is piperonyl; $R_{10}$ is cyclohexyl; $R_{11}$ is 1-yl-n-butylamine; $R_{12}$ is 1-yl-n-butylamine; $R_{13}$ is 1-yl-2-(4(benzenesulfonamide)ethyl; $R_{14}$ is 1-yl-n-butylamine; $R_{15}$ is isobutyl and $R_{16}$ is 1-yl-n-butylamine;

(b) $R_9$ is piperonyl; $R_{10}$ is piperonyl; $R_{11}$ is cyclohexyl; $R_{12}$ is 1-yl-n-butylamine; $R_{13}$ is 1-yl-allyl; $R_{14}$ is isobutyl; $R_{15}$ is cyclohexyl and $R_{16}$ is 1-yl-n-butylamine;

(c) $R_9$ is methylbenzyl; $R_{10}$ is piperonyl; $R_{11}$ is cyclohexyl; $R_{12}$ is piperonyl; $R_{13}$ is piperonyl; $R_{14}$ is methylbenzyl; $R_{15}$ is 1-yl-n-butylamine and $R_{16}$ is 1-yl-n-butylamine;

(d) $R_9$ is isobutyl; $R_{10}$ is cyclohexyl; $R_{11}$ is isobutyl; $R_{12}$ is 1-yl-2-(4(benzenesulfonamide)ethyl; $R_{13}$ is 1-yl-allyl; $R_{14}$ is 1-yl-n-butylamine; $R_{15}$ is 1-yl-allyl and $R_{16}$ is piperonyl;

(e) $R_9$ is piperonyl; $R_{10}$ is isobutyl; $R_{11}$ is piperonyl; $R_{12}$ is cyclohexyl; $R_{13}$ is 1-yl-2-(4(benzenesulfonamide)ethyl; $R_{14}$ is 1-yl-n-butylamine; $R_{15}$ is 1-yl-n-butylamine and $R_{16}$ is piperonyl;

(f) $R_9$ is 1-yl-n-butylamine; $R_{10}$ is 1-yl-n-butylamine; $R_{11}$ is 1-yl-n-butylamine; $R_{12}$ is piperonyl; $R_{13}$ is methylbenzyl; $R_{14}$ is 1-yl-n-butylamine; $R_{15}$ is 1-yl-n-butylamine and $R_{16}$ is 1-yl-2-hydroxyethyl;

(g) $R_9$ is 1-yl-2-hydroxyethyl; $R_{10}$ is methylbenzyl; $R_{11}$ is cyclohexyl; $R_{12}$ is 1-yl-n-butylamine; $R_{13}$ is piperonyl; $R_{14}$ is methylbenzyl; $R_{15}$ is methylbenzyl and $R_{16}$ is 1-yl-n-butylamine;

(h) $R_9$ is methylbenzyl; $R_{10}$ is piperonyl; $R_{11}$ is methylbenzyl; $R_{12}$ is 1-yl-n-butylamine; $R_{13}$ is methylbenzyl; $R_{14}$ is 1-yl-n-butylamine; $R_{15}$ is 1-yl-n-butylamine and $R_{16}$ is piperonyl;

(i) $R_9$ is methylbenzyl; $R_{10}$ is 1-yl-allyl; $R_{11}$ is piperonyl; $R_{12}$ is piperonyl; $R_{13}$ is 1-yl-n-butylamine; $R_{14}$ is 1-yl-2-(4(benzenesulfonamide)ethyl; $R_{15}$ is 1-yl-n-butylamine and $R_{16}$ is methylbenzyl;

(j) $R_9$ is methylbenzyl; $R_{10}$ is methylbenzyl; $R_{11}$ is piperonyl; $R_{12}$ is methylbenzyl; $R_{13}$ is piperonyl; $R_{14}$ is 1-yl-n-butylamine; $R_{15}$ is methylbenzyl and $R_{16}$ is 1-yl-n-butylamine;

(k) $R_9$ is 1-yl-2-(4(benzenesulfonamide)ethyl; $R_{10}$ is methylbenzyl; $R_{11}$ is methylbenzyl; $R_{12}$ is methylbenzyl; $R_{13}$ is piperonyl; $R_{14}$ is 1-yl-n-butylamine; $R_{15}$ is 1-yl-n-butylamine and $R_{16}$ is isobutyl;

(l) $R_9$ is 1-yl-allyl; $R_{10}$ is methylbenzyl; $R_{11}$ is 1-yl-n-butylamine; $R_{12}$ is cyclohexyl; $R_{13}$ is piperonyl; $R_{14}$ is 1-yl-n-butylamine; $R_{15}$ is 1-yl-n-butylamine and $R_{16}$ is piperonyl;

(m) $R_9$ is 1-yl-n-butylamine; $R_{10}$ is 1-yl-2-hydroxyethyl; $R_{11}$ is isobutyl; $R_{12}$ is 1-yl-n-butylamine; $R_{13}$ is 1-yl-2-hydroxyethyl; $R_{14}$ is 1-yl-2-(4(benzenesulfonamide)ethyl; $R_{15}$ is 1-yl-n-butylamine and $R_{16}$ is cyclohexyl;

(n) $R_9$ is 1-yl-n-butylamine; $R_{10}$ is 1-yl-2-hydroxyethyl; $R_{11}$ is methylbenzyl; $R_{12}$ is 1-yl-2-hydroxyethyl; $R_{13}$ is 1-yl-n-butylamine; $R_{14}$ is 1-yl-n-butylamine; $R_{15}$ is piperonyl and $R_{16}$ is 1-yl-2-hydroxyethyl; and pharmaceutically acceptable salts thereof.

Preferred embodiments for purposes of kits and diagnostics include:

A compound of the formula:

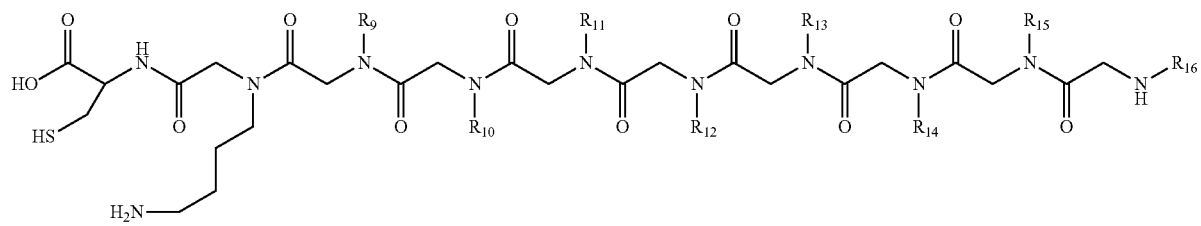

II wherein said compounds are selected from the group consisting of compounds having $R_9$-$R_{16}$ as, (a) $R_9$ is piperonyl; $R_{10}$ is cyclohexyl; $R_{11}$ is 1-yl-n-butylamine; $R_{12}$ is 1-yl-n-butylamine; $R_{13}$ is 1-yl-2-(4(benzenesulfonamide)ethyl; $R_{14}$ is 1-yl-n-butylamine; $R_{15}$ is isobutyl and $R_{16}$ is 1-yl-n-butylamine;

(b) $R_9$ is piperonyl; $R_{10}$ is piperonyl; $R_{11}$ is cyclohexyl; $R_{12}$ is 1-yl-n-butylamine; $R_{13}$ is 1-yl-allyl; $R_{14}$ is isobutyl; $R_{15}$ is cyclohexyl and $R_{16}$ is 1-yl-n-butylamine;

(c) $R_9$ is methylbenzyl; $R_{10}$ is piperonyl; $R_{11}$ is cyclohexyl; $R_{12}$ is piperonyl; $R_{13}$ is piperonyl; $R_{14}$ is methylbenzyl; $R_{15}$ is 1-yl-n-butylamine and $R_{16}$ is 1-yl-n-butylamine;

(d) $R_9$ is isobutyl; $R_{10}$ is cyclohexyl; $R_{11}$ is isobutyl; $R_{12}$ is 1-yl-2-(4(benzenesulfonamide)ethyl; $R_{13}$ is 1-yl-allyl; $R_{14}$ is 1-yl-n-butylamine; $R_{15}$ is 1-yl-allyl and $R_{16}$ is piperonyl;

(e) $R_9$ is piperonyl; $R_{10}$ is isobutyl; $R_{11}$ is piperonyl; $R_{12}$ is cyclohexyl; $R_{13}$ is 1-yl-2-(4(benzenesulfonamide)ethyl; $R_{14}$ is 1-yl-n-butylamine; $R_{15}$ is 1-yl-n-butylamine and $R_{16}$ is piperonyl;

(f) $R_9$ is 1-yl-n-butylamine; $R_{10}$ is 1-yl-n-butylamine; $R_{11}$ is 1-yl-n-butylamine; $R_{12}$ is piperonyl; $R_{13}$ is methylbenzyl; $R_{14}$ is 1-yl-n-butylamine; $R_{15}$ is 1-yl-n-butylamine and $R_{16}$ is 1-yl-2-hydroxyethyl;

(g) $R_9$ is 1-yl-2-hydroxyethyl; $R_{10}$ is methylbenzyl; $R_{11}$ is cyclohexyl; $R_{12}$ is 1-yl-n-butylamine; $R_{13}$ is piperonyl; $R_{14}$ is methylbenzyl; $R_{15}$ is methylbenzyl and $R_{16}$ is 1-yl-n-butylamine;

(h) $R_9$ is methylbenzyl; $R_{10}$ is piperonyl; $R_{11}$ is methylbenzyl; $R_{12}$ is 1-yl-n-butylamine; $R_{13}$ is methylbenzyl; $R_{14}$ is 1-yl-n-butylamine; $R_{15}$ is 1-yl-n-butylamine and $R_{16}$ is piperonyl;

(i) $R_9$ is methylbenzyl; $R_{10}$ is 1-yl-allyl; $R_{11}$ is piperonyl; $R_{12}$ is piperonyl; $R_{13}$ is 1-yl-n-butylamine; $R_{14}$ is 1-yl-2-(4(benzenesulfonamide)ethyl; $R_{15}$ is 1-yl-n-butylamine and $R_{16}$ is methylbenzyl;

(j) $R_9$ is methylbenzyl; $R_{10}$ is methylbenzyl; $R_{11}$ is piperonyl; $R_{12}$ is methylbenzyl; $R_{13}$ is piperonyl; $R_{14}$ is 1-yl-n-butylamine; $R_{15}$ is methylbenzyl and $R_{16}$ is 1-yl-n-butylamine;

(k) $R_9$ is 1-yl-2-(4(benzenesulfonamide)ethyl; $R_{10}$ is methylbenzyl; $R_{11}$ is methylbenzyl; $R_{12}$ is methylbenzyl; $R_{13}$ is piperonyl; $R_{14}$ is 1-yl-n-butylamine; $R_{15}$ is 1-yl-n-butylamine and $R_{16}$ is isobutyl;

(l) $R_9$ is 1-yl-allyl; $R_{10}$ is methylbenzyl; $R_{11}$ is 1-yl-n-butylamine; $R_{12}$ is cyclohexyl; $R_{13}$ is piperonyl; $R_{14}$ is 1-yl-n-butylamine; $R_{15}$ is 1-yl-n-butylamine and $R_{16}$ is piperonyl;

(m) $R_9$ is 1-yl-n-butylamine; $R_{10}$ is 1-yl-2-hydroxyethyl; $R_{11}$ is isobutyl; $R_{12}$ is 1-yl-n-butylamine; $R_{13}$ is 1-yl-2-hydroxyethyl; $R_{14}$ is 1-yl-2-(4(benzenesulfonamide)ethyl; $R_{15}$ is 1-yl-n-butylamine and $R_{16}$ is cyclohexyl;

(n) $R_9$ is 1-yl-n-butylamine; $R_{10}$ is 1-yl-2-hydroxyethyl; $R_{11}$ is methylbenzyl; $R_{12}$ is 1-yl-2-hydroxyethyl; $R_{13}$ is 1-yl-n-butylamine; $R_{14}$ is 1-yl-n-butylamine; $R_{15}$ is piperonyl and $R_{16}$ is 1-yl-2-hydroxyethyl; and pharmaceutically acceptable salts thereof.

The present invention is also useful in screening for biomarkers associated with any other disease or condition. Such diseases and conditions range from the neurological diseases, autoimmune diseases and cancers identified above as well as any other disease or condition that has a biomarker such as an antibody or other characterizing protein or biomolecule associated with the disease or progression of the disease. These diseases and conditions specifically include inflammatory disease, infectious disease, cardiovascular disease and metabolic disease. Specific infectious diseases include AIDS, anthrax, botulism, brucellosis, chancroid, chlamydial infection, cholera, coccidioidomycosis, cryptosporidiosis, cyclosporiasis, dipheheria, ehrlichiosis, arboviral encephalitis, enterohemorrhagic *Escherichia coli*, giardiasis, gonorrhea, dengue fever, haemophilus influenza, Hansen's disease (Leprosy), hantavirus pulmonary syndrome, hemolytic uremic syndrome, hepatitis A, hepatitis B, hepatitis C, human immunodeficiency virus, legionellosis, listeriosis, lyme disease, malaria, measles. Meningococcal disease, mumps, pertussis (whooping cough), plague, paralytic poliomyelitis, psittacosis, Q fever, rabies, rocky mountain spotted fever, rubella, congenital rubella syndrome (SARS), shigellosis, smallpox, streptococcal disease (invasive group A), streptococcal toxic shock syndrome, streptococcus pneumonia, syphilis, tetanus, toxic shock syndrome, trichinosis, tuberculosis, tularemia, typhoid fever, vancomycin intermediate resistant staphylocussus aureus, varicella, yellow fever, variant Creutzfeldt-Jakob disease (vCJD), Eblola hemorrhagic fever, Echinococcosis, Hendra virus infection, human monkeypox, influenza A, H5N1, lassa fever, Margurg hemorrhagic fever, Nipah virus, O'nyong fever, Rift valley fever, Venezuelan equine encephalitis and West Nile virus.

The large ligand libraries of the invention can be used directly in biological fluid, under the appropriate experimental conditions, to screen for such markers and without the need to use fewer support members (e.g. about 100,000 or less) or requirement to transfer such peptoids or ligands to a microarray before screening the biological fluid. In addition, the ligand libraries may also be used to screen for cell based receptors that specifically relate to a particular cell surface marker. The present invention, unlike prior methods, permits the inclusion of greater numbers of beads/resins and thus larger libraries in either the ligand binding agent screen or the cell receptor screen to directly screen the complex biological samples. The present invention thus also comprises a method of monitoring disease progression comprising the steps of screening a patient's biological sample at timepoint 1 followed by screening said patient's biological sample at timepoint 2 or any subsequent time to follow and/or monitor the presence or absence of the disease associated biomarker in said patient at any point in time using or kit or instrument or device having at least one ligand derived from the rapid screening methodology of the invention.

Ligands

As previously described with respect to microarray systems, virtually any molecule or compound may be used to build a random bead or resin based library. These "molecules" or "compounds" may include natural products or man-made compounds or synthetically derived molecules. The source of such molecules can be from biological systems as well as non-biologically derived sources. The preferred ligands for purposes of the initial screen using large bead libraries under the conditions claimed in the present invention are made, in part, from submonomers, which are selected from any known monomeric amine and from any known acetic acid halide or substituted acetic acid halide. For example, Table 1 provides a range of R groups on a monosubstituted amine that may be selected:

TABLE 1

Side chain modifications for peptoids

Amine Side Chain,
NH$_2$R (Ref. No.)
n-Bu[1]
(Heine, Tetrahedron 59 (2003) 9919-9930)
s-Bu
—Cy
—CH$_2$CH$_2$—CH(Ph)$_2$
—CH$_2$Ph
—CH$_2$CH$_2$OH
—OH

[structure: p-methylphenyl-OPh]

[structure: p-methylphenyl-OH]

[structure: CH$_2$CH$_2$-phenyl-OPh]

TABLE 1-continued

Side chain modifications for peptoids

[structure: CH(CH$_2$OH)$_2$]

[structure: (CH$_2$)$_n$NHBoc, n = 0-4]

[structure: (CH$_2$)$_n$C(O)Ot-Bu]

[structure: (CH$_2$)$_n$C(O)NH$_2$]

[structure: indol-3-yl-propyl]

[structure: imidazol-4-yl-ethyl]

[structure: thiazol-2-yl]

[structure: thiophen-2-yl-methyl]

-i-Bu
—CH$_2$Cy

[structure: tetrahydrofuran-2-yl-methyl]

—CH2OClPh
—CH$_2$pOCH$_3$Ph
—CHCH$_3$Ph
—CH$_2$CH$_2$CH$_2$NHBoc

TABLE 1-continued
Side chain modifications for peptoids
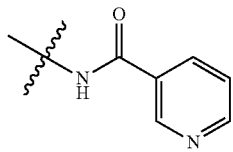 [SMILES: *NC(=O)c1cccnc1]
—CH₂CH₂OMe
—CH₂CH₂CH₂OH
—CH(CH₃)CH₂OH
—CH₂CHOHCH₂OH
—CH₂CH(OH)Ph
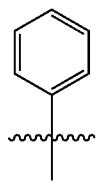
(Kirshenbaum etal JACS Nov. 17, 2008)
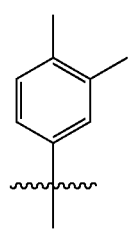 [SMILES: *c1ccc(C)c(C)c1]
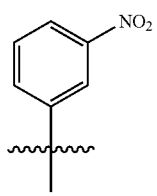 [SMILES: *c1cccc([N+](=O)[O-])c1]
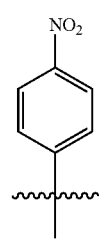
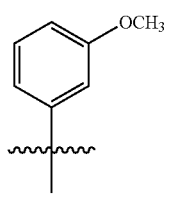 [SMILES: *c1cccc(OC)c1]
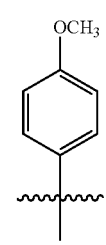
TABLE 1-continued
Side chain modifications for peptoids
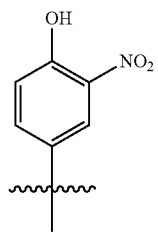 [SMILES: *c1ccc(O)c([N+](=O)[O-])c1]
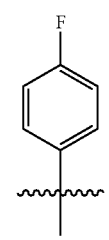 [SMILES: *c1ccc(F)cc1]
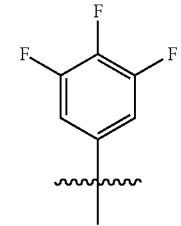 [SMILES: *c1cc(F)c(F)c(F)c1]
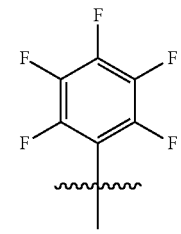 [SMILES: *c1c(F)c(F)c(F)c(F)c1F]
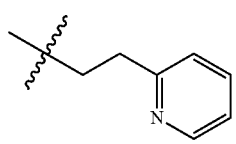
(Disney et. al. ACS Chem. Biol. Mar. 11, 2009)
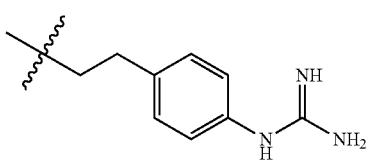 [SMILES: *CCc1ccc(NC(=N)N)cc1]
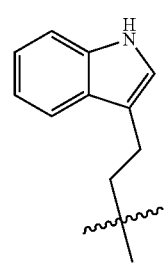 [SMILES: *CCc1c[nH]c2ccccc12]

TABLE 1-continued
Side chain modifications for peptoids
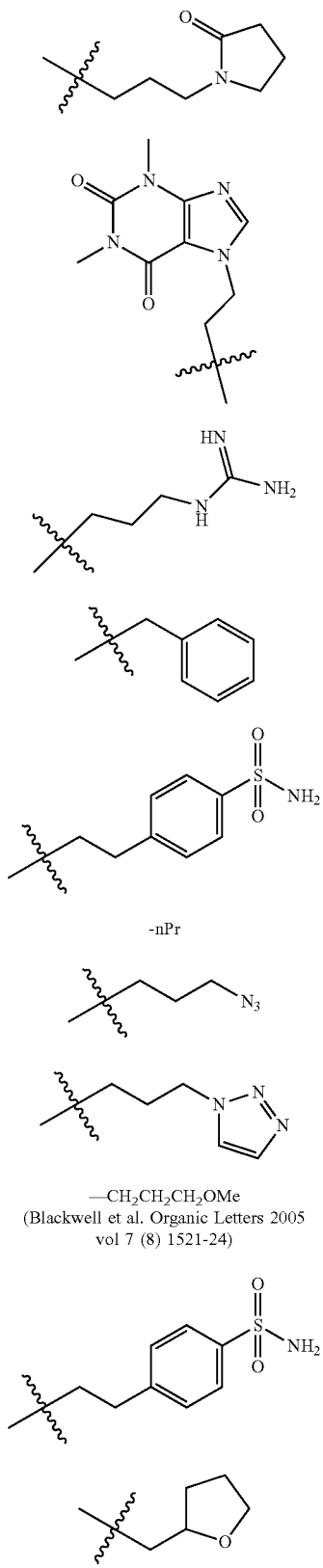
-nPr
—CH₂CH₂CH₂OMe
(Blackwell et al. Organic Letters 2005
vol 7 (8) 1521-24)
TABLE 1-continued
Side chain modifications for peptoids
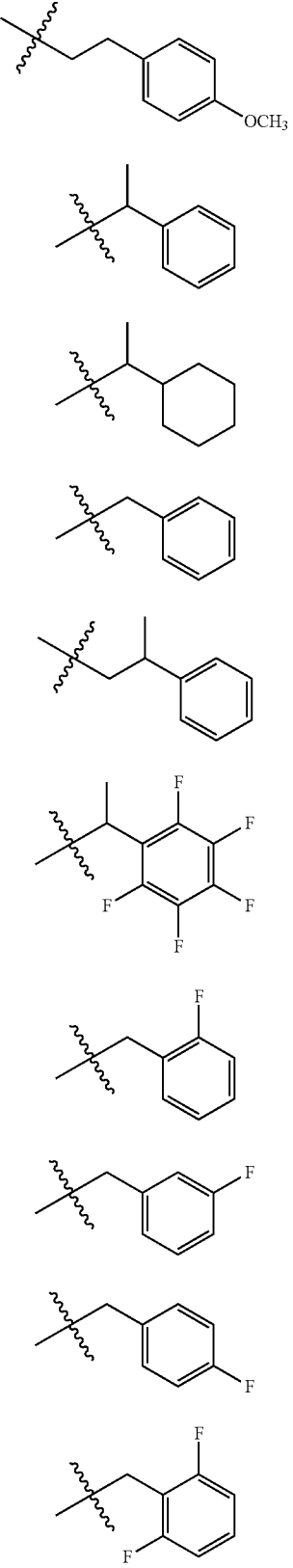

TABLE 1-continued
Side chain modifications for peptoids
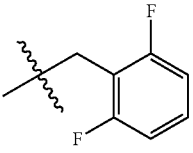 [SMILES: *Cc1c(F)cccc1F]
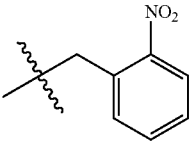 [SMILES: *Cc1ccccc1[N+](=O)[O-]]
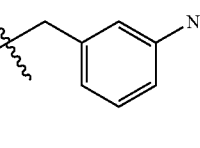
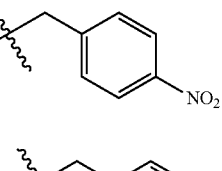
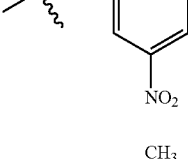
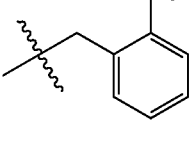
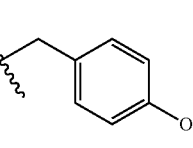
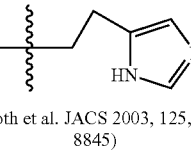
(Burkoth et al. JACS 2003, 125, 8841-8845)
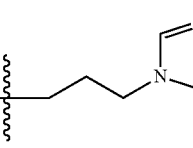
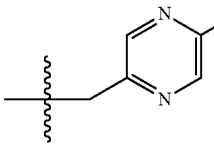
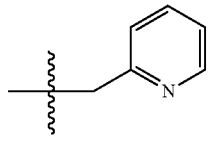 [SMILES: *Cc1ccccn1]
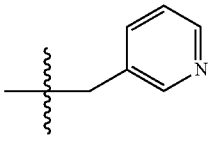
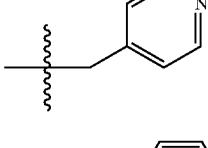
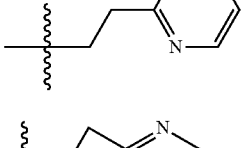
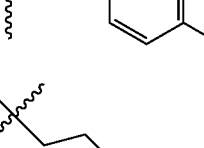
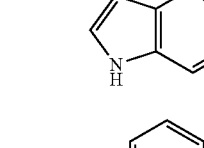
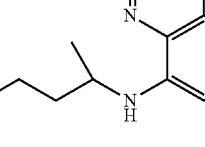
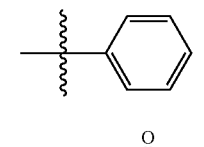
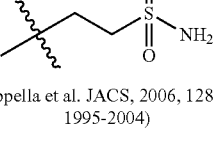
(Appella et al. JACS, 2006, 128(6), 1995-2004)
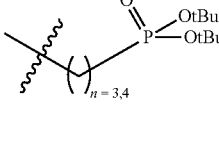

TABLE 1-continued
Side chain modifications for peptoids
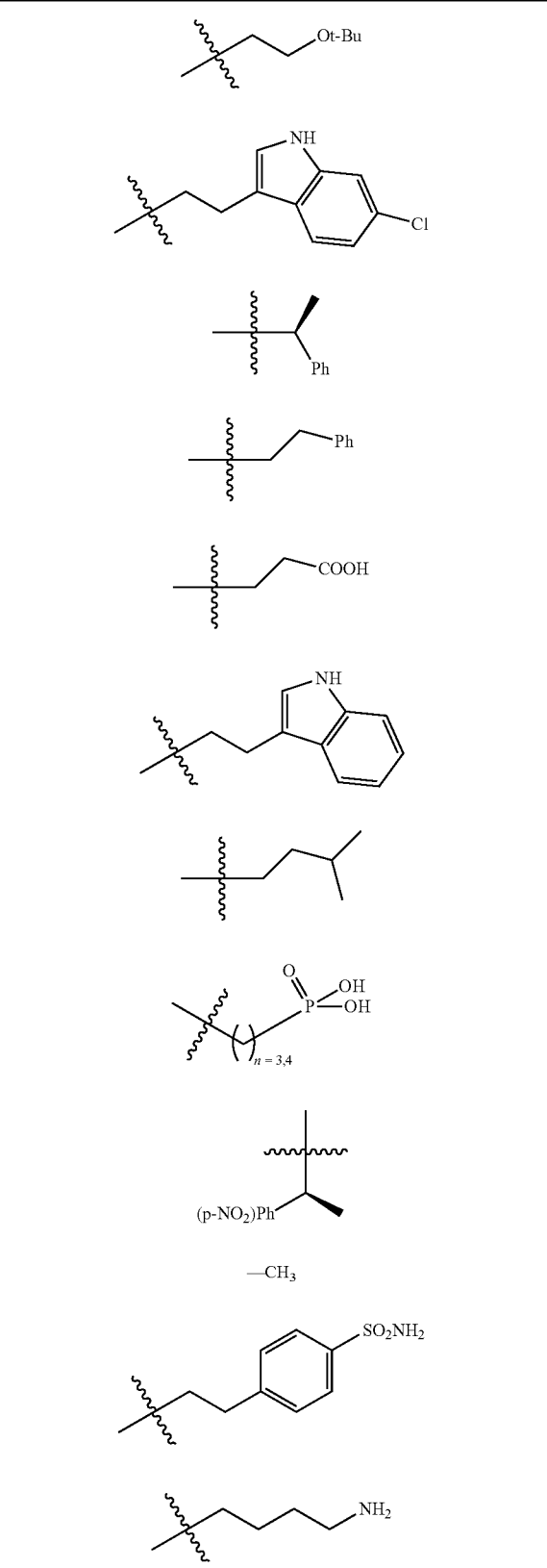
TABLE 1-continued
Side chain modifications for peptoids
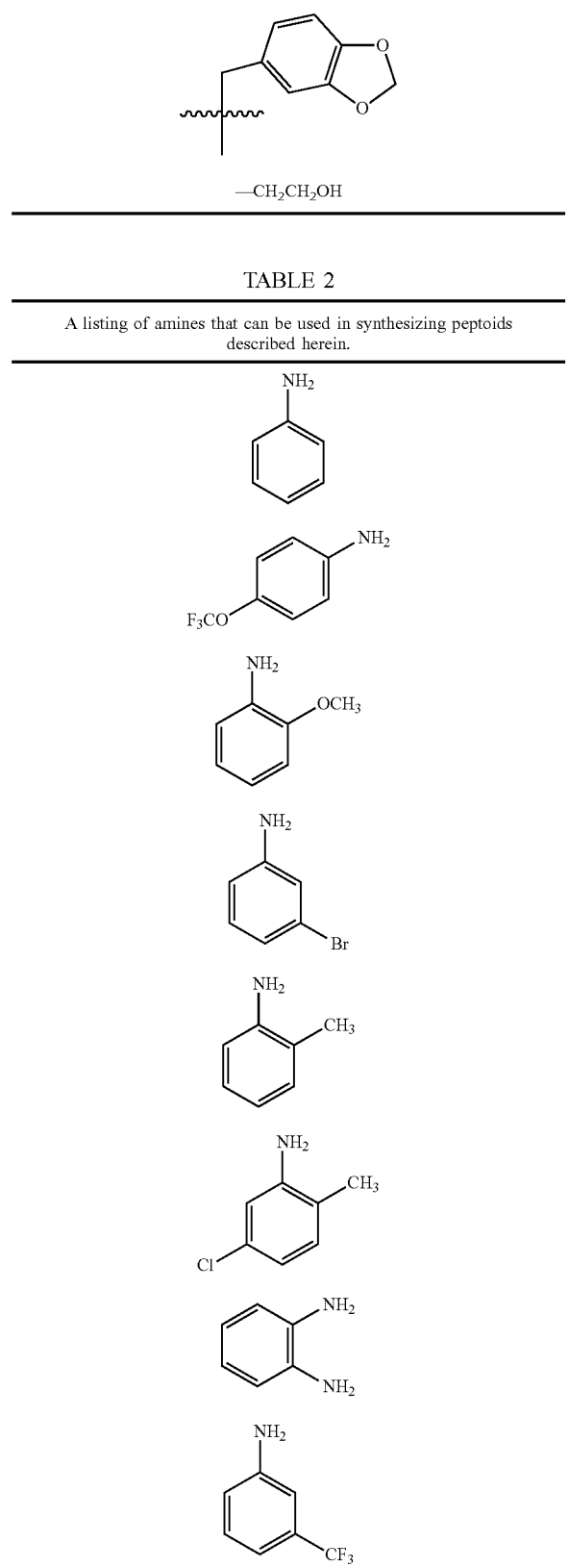
TABLE 2
A listing of amines that can be used in synthesizing peptoids described herein.

TABLE 2-continued
A listing of amines that can be used in synthesizing peptoids described herein.
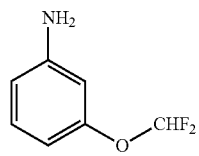 [SMILES: Nc1cccc(OC(F)F)c1]
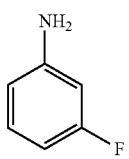
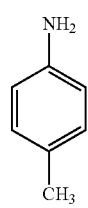
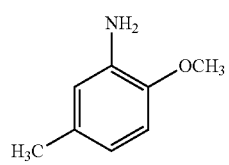
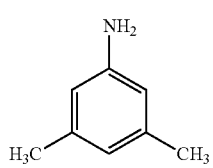
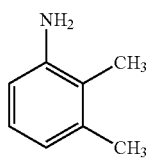
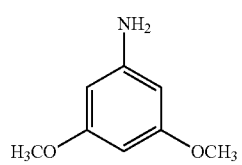
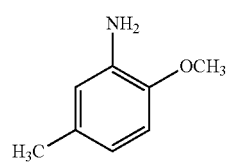
TABLE 2-continued
A listing of amines that can be used in synthesizing peptoids described herein.
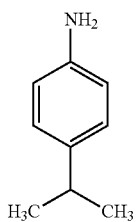
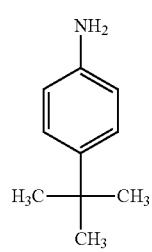
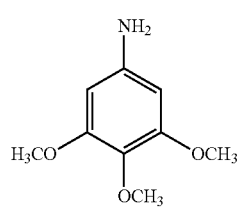 [SMILES: COc1cc(N)cc(OC)c1OC]
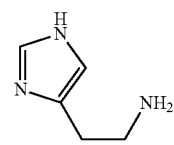
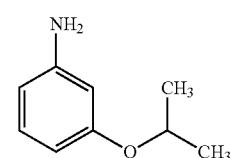
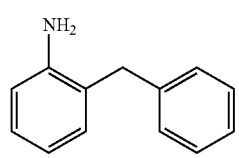 [SMILES: Nc1ccccc1Cc1ccccc1]
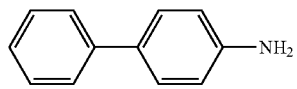 [SMILES: Nc1ccc(-c2ccccc2)cc1]
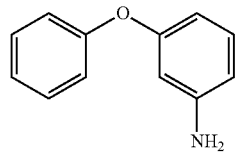 [SMILES: Nc1cccc(Oc2ccccc2)c1]

TABLE 2-continued
A listing of amines that can be used in synthesizing peptoids described herein.
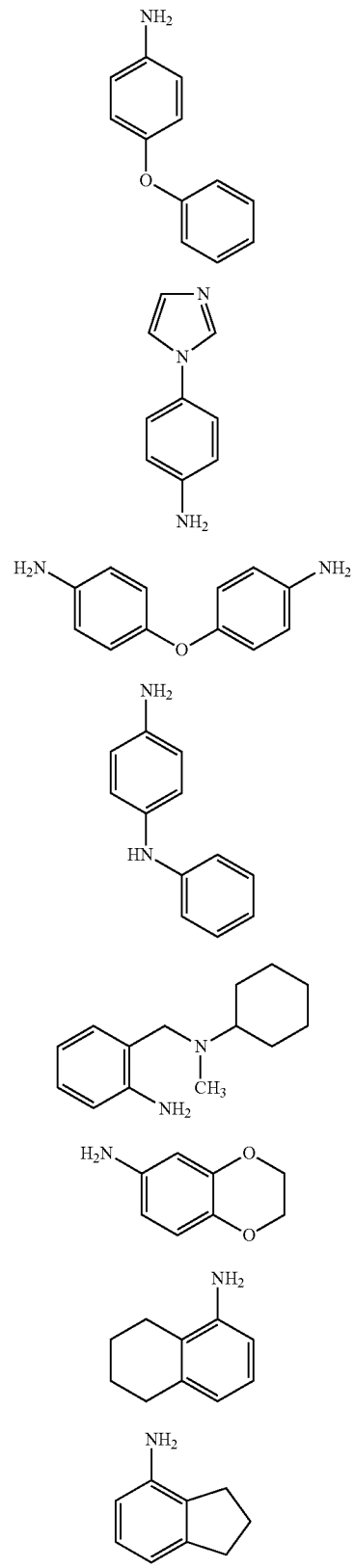
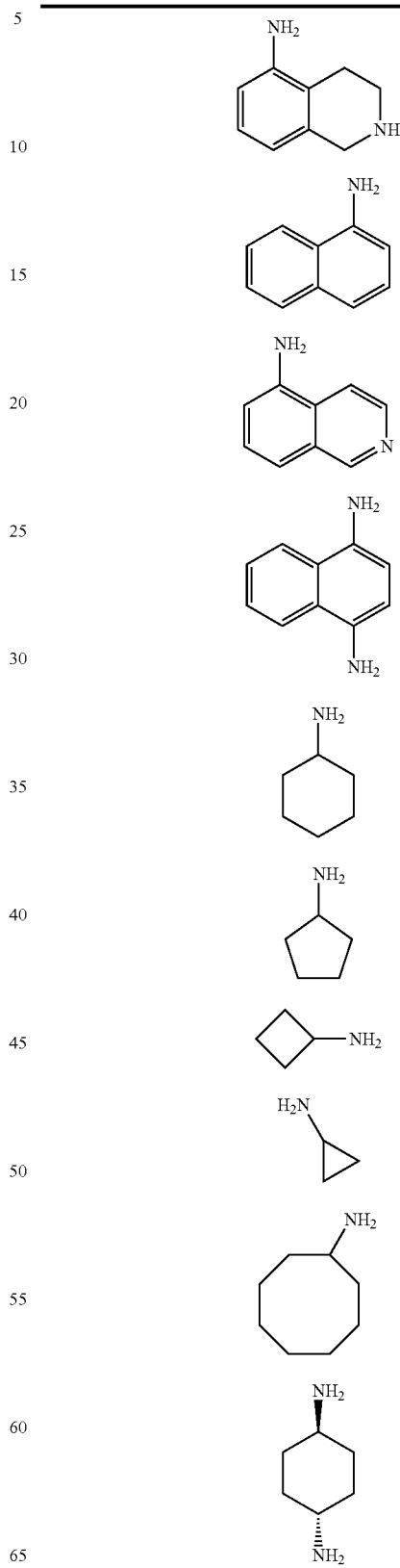

TABLE 2-continued
A listing of amines that can be used in synthesizing peptoids described herein.
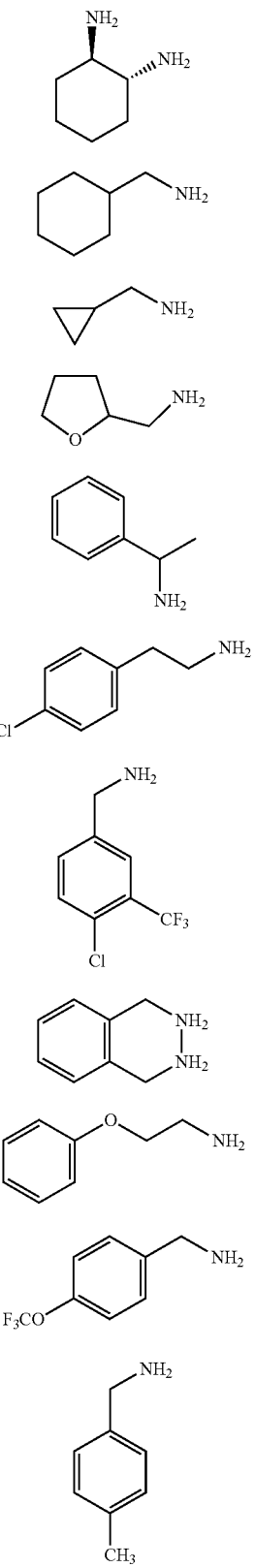
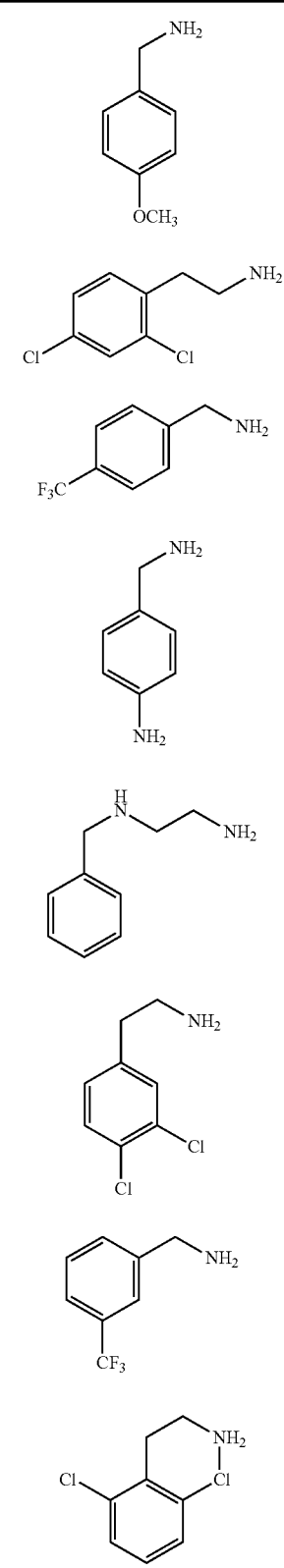

TABLE 2-continued

A listing of amines that can be used in synthesizing peptoids described herein.

TABLE 2-continued
A listing of amines that can be used in synthesizing peptoids described herein.
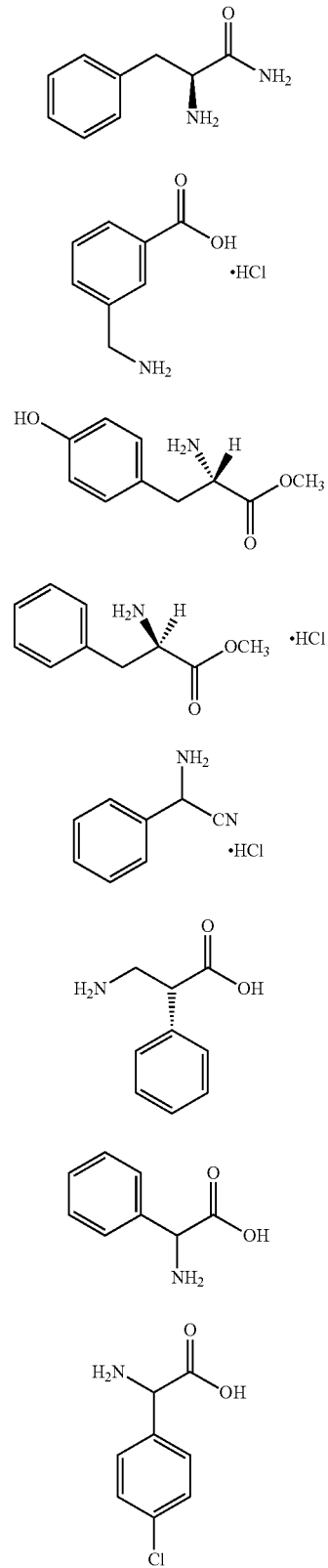
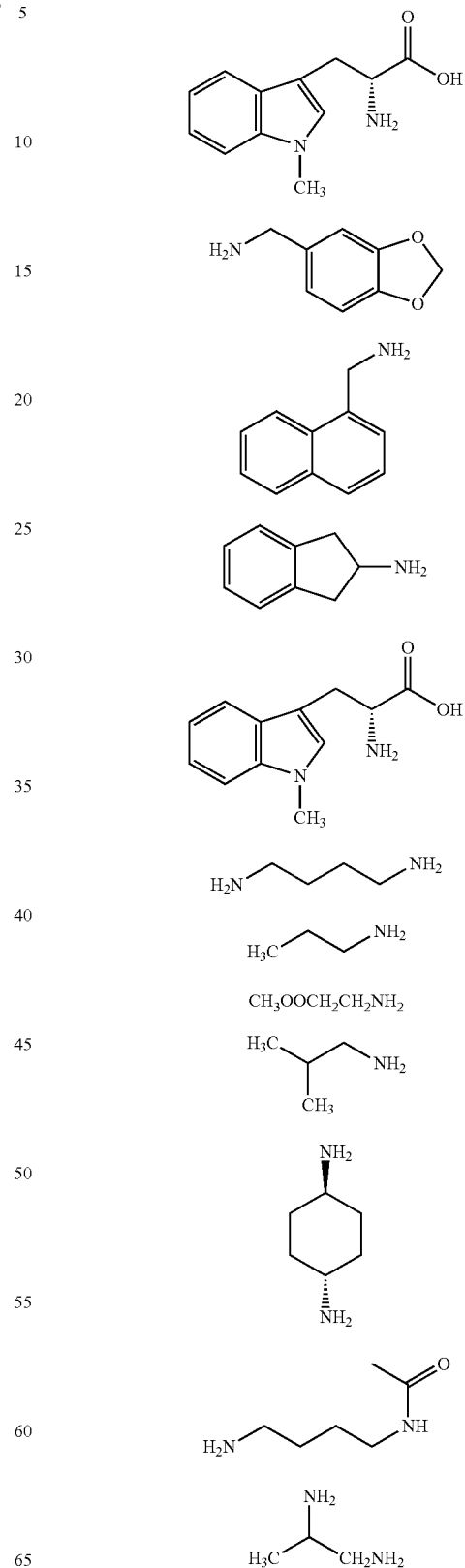

TABLE 2-continued

A listing of amines that can be used in synthesizing peptoids described herein.

H₂N–CH₂CH₂–NH₂

CH₃(CH₂)₄CH₂NH₂

H₂N–CH₂CH₂–NH–CH₂CH₂–NH₂

NH₂CH₂CH₂CH₂NHCH₃

H₃C–CH(NH₂)–CH₂–N(CH₃)₂

(CH₃)₂N–CH₂CH₂–NH₂

(CH₃)₂CH–NH–CH₂CH₂CH₂–NH₂

(CH₃)₂N–CH₂CH₂CH₂–NH₂

H₂N–C(=O)–CH₂–NH₂

H₂N–C(=O)–CH₂CH₂–NH₂

(CH₃CH₂)₂N–CH₂CH₂–NH₂

H₂N–CH₂CH₂–O–CH₂CH₂–O–CH₂CH₂–NH₂

2-aminobenzylamine 4-aminobenzylamine

TABLE 2-continued

A listing of amines that can be used in synthesizing peptoids described herein.

N-(2-aminoethyl)aniline

H₂N–CH₂–CH=CH₂ (allylamine)

H₂N–CH₂–C≡CH (propargylamine)

propylamine (n-PrNH₂)

CF₃CH₂NH₂

(CH₃)₂CH–NH₂ (isopropylamine)

CH₃(CH₂)₄CH₂NH₂

(CH₃)₃C–CH₂CH₂–NH₂

(CH₃)₂CH–CH₂CH₂–NH₂

CH₃–CH(NH₂)–CH₂CH₂–CH₃

HO–C(=O)–CH₂–NH₂ (glycine)

H₂N–C(=O)–CH₂–NH₂

H₃CO–C(=O)–CH₂–NH₂

Any amino acid furfurylamine (2-aminomethylfuran)

4-(2-aminoethyl)benzenesulfonamide

H₂N–CH₂CH₂–O–CH₃

TABLE 2-continued

A listing of amines that can be used in synthesizing peptoids described herein.

TABLE 2-continued

A listing of amines that can be used in synthesizing peptoids described herein.

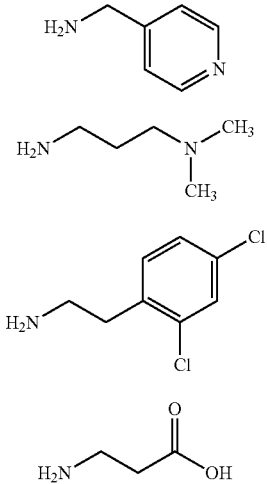

The preferred monomers and/or submonomers for purposes of the AD screen, the pancreatic cancer screen and the lupus screen (preliminary and/or diagnostic) are selected from the group consisting of cysteine, glycine, methionine, allylamine, ethanolamine, is obutylamine, diaminobutane, methylbenzylamine (racemic or enantiomeric), piperonylamine, cyclohexylamine, 3,4 dimethoxyphenethylamine, benzylamine, N-(2-aminoethyl)acetamide, N-(3-aminopropyl)-2-pyrrolidinone, 4-(2-aminoethyl)benzenesulfonamide or furfurylamine.

Acetic acid halides and/or R substituted acetic acid halides wherein R is selected from any amino acid side chain or from any other group including those groups or variables on the monosubstituted amines are also utilized as submonomers. Alternatively, the combination of any amine and any acetic acid halide may be reacted to form a monomer, which is then reacted, with another reactive monomer on a growing peptoid chain to form an oligomer of the invention.

Combinatorial Libraries of Peptoids May be Prepared as Follows:

Peptoids having a cysteine or methionine monomeric amino acid attached to a support or a linker on a support or resin or bead may be prepared by first adding the protected amino acid to a support or linker on a support. Following addition of said amino acid (or any amino acid desired which can serve a functional or other purpose in the oligomer or a diagnostic having said oligomer), remaining monomers can be added using standard peptide chemistry or using submonomers of bromoacetic acid (or α-substituted bromoacetic acid or similar reactant) and a monosubstituted amine wherein the amine is substituted with an R group. The R group may be selected from any known peptoid substitutent including those described in, for example, U.S. Pat. Publication Nos. 2010/0303805 or 2010/0303835 and/or those described in Zuckermann and various Kodadek publications. The preferred amines are those selected from the libraries recited herein wherein particular monomeric amines are added to each library to build 1-2 MM bead or resin libraries.

The process to make each peptoid generally involves (1) preparation of an amino acid reactant on a support (including an optional linker on a support); (2) reaction of the amino acid moiety on said support with an acyl halide such as bromoacetic acid or chloroacetic acid to form a halogenated derivative (3) reaction of the halogenated derivative with a monosubstitued amine to form an amide and (4) repeat of steps (2) and (3) to form a peptoid. Methionine containing peptoids are generally made in the large libraries. Cysteine containing peptoids are typically made when larger scale quantities of high affinity peptoids are desired and following the initial screening of the large bead or resin libraries. In the large bead based libraries used to initially screen complex biological fluid such as serum, there is no need for or requirement for a long PEG linker which is typically necessary for microarray screens. A PEG linker may be on the bead or resin provided it is a short linker of less than about 10 monomeric units. In the diagnostic kits comprising beads or tentagel beads of less than about 50 microns (e.g. 10 microns), it is useful to use both short PEG linkers (e.g. between 2-10 PEG monomers) or longer PEG oligomers may be utilized.

The conditions used to perform each step in the oligomer building process utilize solvents such as DMF or acetonitrile or dichloromethane. Trifluoroacetic acid is utilized for cleavage purposes and piperidine or other suitable base is used as a base in the reaction between a bromo derivative and an amine. Various protecting groups are utilized in the preparation of the amino acid reactant. In a preferred embodiment, diaminobutane is utilized as the first amine submonomer in the chain adjacent to the cysteine residue at the C-terminus of the peptoid. In the first step of the process, the selected beads or resins (in gram or milligram quantities) are swollen in a suitable solvent such as DMF. If the beads are "protected" with a protecting group on the reactive amine on said bead, a base solution such as piperidine is repeatedly added with subsequent washing with DMF to deprotect the bead. Once the bead is deprotected or if a bead such as a tentagel bead is initially utilized, it may be reacted with a suitable amino acid such as cysteine or methionine (protected with Fmoc or other suitable protecting group on the nitrogen and protected with Trt (triphenylmethyl) on the sulfur and in sufficient molar quantities to react with each bead) in a suitable solvent such as DMF. HBTU (tetramethyluronium hexafluorophosphate (coupling reagent) and 4-methylmorpholine (base) along with the protected amino acid are added to the bead solution in a beaker (or tube or flask) and shaken at room temperature to form the Fmoc/Trt protected amino acid on the resin (or on a linker on the resin). The beads are then washed multiple times in a solvent such as DMF. The Fmoc group is then deprotected using a suitable reagent which permits reaction of the amine on the amino acid with another reactant such as another protected amino acid or a submonomer such as bromoacetic acid and an activating agent e.g. DIC (3-isopropylcarbodiimide) in a suitable solvent under heat (microwave with stirring). The resultant beads are then washed multiple times and then treated with a desired monomeric amine (in slight mole excess) in a suitable solvent under heat. The resultant beads are washed multiple times and then treated repeatedly with bromoacetic acid and the amine of choice to build the oligomer and oligomeric library. The peptoids may be cleaved from the beads using triflouroacetic acid. An alternative or other suitable process for peptoids comprising a preferred embodiment—e.g., those peptoids having cysteine adjacent to a monomer having a 1-yl-n-butylamine includes building a peptoid having two amino acids on the C-terminus followed by a process that further includes adding any of the monomers built in a submonomer process wherein the second amino acid is lysine. This further includes the selection of any monomer or submonomer to make α-substituted bromoacetic acid submonomers wherein the carbon substituents may be selected from typical amino acid side chains to form, after reaction of the reactants, α-substituted peptoids wherein an R group is found on either or both of the carbon on the peptoid chain or the nitrogen on the peptoid chain.

Combinatorial libraries of small molecules may be obtained commercially or prepared using methods known in the art. See for example, Eichler et al., 1995; Cho et al., 1999; LePlae et al., 2002; Ostergaard and Holm, 1997; Yang et al., 1999). In addition, U.S. Pat. No. 6,344,334 and publications Gallop et al., (1994), Gordon et al., (1994); Thompson and Ellman (1996) are also sources of such molecules and libraries.

Combinatorial libraries of peptides may be obtained commercially or prepared using methods known in the art. See, for example, Stewart and Young (1984); Tam et al. (1983); Merrifield (1986); and Barany and Merrifield (1979), each of which are hereby incorporated by reference.

Combinatorial libraries of nucleic acids including RNA or DNA may be obtained commercially or prepared using methods known in the art. Combinatorial libraries of oligosaccharides may be obtained commercially or prepared using methods known in the art.

In each instance, the "ligands" or random ligands may be added to support resins or beads to form screening libraries can be used, under the conditions described herein, to screen for biomarkers in complex biological fluid. The preferred ligands are peptoid ligands.

In addition to building and/or using such libraries, it may be necessary or desired to characterize, purify and/or synthesize or re-synthesize any such ligand. Such methods are known in the art and include the entire gamut of purification methods such as HPLC via chromatographic means or purification methods via chemical means; characterization methods such as mass spec or NMR or combinations of any of these methods. Such methods are further described in, for example, US Pat. Publication 2007/0003954, which is hereby incorporated by reference. In such cases, any such purified ligand may be referred to as a compound or substantially purified compound.

In the initial screening methodology of the invention, beads and/or resins are utilized as the support means having an oligomer operably coupled to said support. In diagnostic kits or other kits having "hits" or "putative hits" from such initial screen, the support systems can be broadened to virtually any support system including microarrays or any other known diagnostic platforms. In these cases, it is necessary to ensure that such kits or other support systems with the putative hits also have or are adapted to have a detector or detection methods to permit detection of ligands having ligand binding moieties attached to such ligands. The preferred detection methods include, for example, ELISA or other methods which involve the use of labeled secondary antibodies.

Supports can be made of any suitable material. Materials utilized to make such supports can include, for example, glass, plastic, ceramic or polymeric resins or beads. Supports may also include materials such as nickel, brass, steel or other metals or mixtures of metals. The supports may also be conditioned to have linkers and/or other means to bind to or connect to or react with a ligand or active group on a ligand. Such groups are also described in U.S. Pat. Pub. No. 2007/0003954. In the present invention, the number of resins or beads having individual ligands bonded thereto or to a linker and then to said support ranges from greater than 100 K to about 150 million (MM). The preferred number utilized in the initial screening methods of the invention ranges between 1 MM and 2 MM ligands/resins.

TentaGel® resins are most preferred for the large ligand screening methodology of the invention. These resins are grafted copolymers consisting of a low crosslinked polystyrene matrix on which polyethylene glycol (PEG or POE) is grafted. TentaGel resins are commercially available (Rapp Polymere GmbH). As PEG is a "cameleon type" polymer with hydrophobic and hydrophilic properties, the graft copolymer shows modified chemical properties. According to the manufacturer, there are in principle two ways to introduce PEG onto the modified polystyrene matrix. The simplest immobilization procedure is to couple PEG via one of its terminal hydroxyl groups to chloromethylated polystyrene according to the classical ether synthesis or to use other bifunctional PEG's for coupling onto the solid support. The manufacturor found that by means of anionic graft copolymerization setting up the PEG step by step directly on the matrix, PEG chains of molecular masses up to 20 kilo dalton have been immobilized on functionalized crosslinked polystyrenes. Graft copolymers with PEG chains of about 2000-3000 dalton proved to be optimal in respect of kinetic rates, mobility, swelling and resin capacity. As there is no procedure to get monodisperse PEG with more than 10 ethylene oxide units by any polymerization techniques, there is theoretically no way to introduce monodisperse PEG chains with more than 10 ethylene oxide units to the resin or to get monodisperse PEG by direct polymerization onto the polystyrene backbone (monodisperse is defined as: PEG without any molecular weight distribution). These graft copolymers are pressure stable and can be used in batch processes as well as under continuous flow conditions. The copolymer contains about 50-70% PEG (w/w). The properties of these polymers are highly dominated by the properties of PEG and versus by the polystyrene matrix.

Setting up a chemical library or peptide library by the "one bead one compound" approach it is essential to know the number of beads which are available within a certain amount of resin as well as the capacity of single beads. Table 2 summarizes some particle sizes and correlates them to the corresponding capacity of a single bead. The calculations are based on a typical loading of TentaGel beads which are in the range of 0.25-0.3 mmol/g. For analytical characterization at least 5 pmol of resin-bound peptide are needed for sequencing on a bead. In order to estimate the optimum resin quantity for the library, which can be handled economically one, has to take into account the bead sizes and bead capacities. In respect to homogeneity of diffusion process and kinetic rates as well as for single bead analysis and single bead quantification, all our beads show a very narrow size distribution.

TABLE 3

| resin | size [μm] | beads/g | capacity/bead |
|---|---|---|---|
| TentaGel NH$_2$ | 750 μm | 4.62 × 10$^3$ | 65 nmol |
| TentaGel NH$_2$ | 500 μm | 1.5 × 10$^4$ | 19 nmol |
| TentaGel NH$_2$ | 300 μm | 6.4 × 10$^4$ | 4 nmol |
| TentaGel NH$_2$ | 200 μm | 2.15 × 10$^5$ | 1.3 nmol |
| TentaGel NH$_2$ | 130 μm | 8.87 × 10$^5$ | 280-330 pmol |
| TentaGel NH$_2$ | 90 μm | 2.86 × 10$^6$ | 80-100 pmol |
| TentaGel M NH$_2$ | 35 μm | 4.55 × 10$^7$ | 5.5 pmol |
| TentaGel M NH$_2$ | 20 μm | 2.4 × 10$^8$ | 1.0 pmol |
| TentaGel M NH$_2$ | 10 μm | 1.95 × 10$^9$ | 0.13 pmol |

Correlation of particle size, number of beads per gram resin and capacity per single bead. Calculation of single bead capacity is based on a capacity of 0.25-0.3 mmol/g resin There are several types of TentaGel resins available showing tailored properties dependent on their application:

TentaGel S Resins:

The PEG spacer is attached to the polystyrene backbone via an alkyl linkage. This linkage is not sensitive to acids or bases. This type of resin is a standard type of resin used for peptide synthesis, solid phase organic synthesis or combinatorial chemistry.

TentaGel PAP Resins:

The PEG is attached to the polystyrene backbone via a benzyl ether linkage. This benzyl ether linkage is sensitive to harsh acid conditions like 100% TFA or mixtures of TFA/TMSBr.

These specially tailored resins are used for immunization procedures or for synthesizing PEG modified derivatives (PEG Attached Products). Using harsh acid conditions, the PEG spacer is cleaved together with the synthesized compound from the solid support to get soluble PEG modified compounds by applying solid phase conditions (e.g. PEG modified peptides).

TentaGel N Resins:

The PEG spacer is attached to the polystyrene backbone via a benzyl ether linkage. These tailored resins are used in oligonucleotide chemistry for small and large scale oligonucleotide synthesis. In comparison to CPG glass the capacity is increased by a factor of 10.

As TentaGel resins are copolymers composed from polystyrene and polyethylene glycol, chemical and physico chemical properties of both base polymers have to be taken in account.

PEG itself is a hygroscopic polymer. It is known from literature that PEG esters are not very stable and easily hydrolyzed. Dependent on the storage conditions and storage time, PEG itself can be oxidized along the polyether chain to form peroxides or esters. Consequently, acid treatment or treatment with bases hydrolyzes the formed PEG—esters which result in a small amount of "PEG-leakage". This leakage can be noticed by MS or NMR as PEG signals and impurities in the final product. This chemical behavior is true to all PEG's—and PEG based polymers.

TABLE 4

| | |
|---|---|
| TentaGel S: | "S" means Standard resin, applicable to a large number of applications, useful in batch and flow through systems. |
| TentaGel R: | a special suited resin for research purpose synthesis. The resin shows an increased swelling volume but is less pressure resistant. Well suited for large peptides and difficult sequences. |
| TentaGel HL: | this highloaded version of TentaGel combines a significant higher capacity with the advantages of TentaGel resins. |
| TentaGel MB: | TentaGel Macrobeads are highlighted by extraordinary large particle diameters and high capacities based on the TentaGel technology and designed for single bead synthesis and single bead analysis. |
| TentaGel N: | this resin type is designed for automated large scale oligonucleotide synthesis. |
| TentaGel J: | this resin type has been developed for polymeric immunoconjugates. |
| TentaGel M: | the microspherical shape of 10, 20, 30 µm of this TentaGel and it's monodispersity allows applications in automated sorters, for creating huge libraries, high speed synthesis etc. |

TABLE 4-continued

| | |
|---|---|
| TentaGel B: | describes bifunctional TentaGel resins, where the reactive sites on the outer surface of the bead is orthogonally protected to the reactive sites located in the internal volume of the bead and hybrid resins for sequentional cleavage. |

In addition to TentaGel beads, other resins and/or particles may be utilized build a one ligand per bead library. For example, lightly cross-linked polystyrene resins or polyamide resins may be utilized. The group that joins the substrate to the resin bead can be an essential part of solid phase synthesis. The linker is a specialized protecting group, in that much of the time, the linker will tie up a functional group, only for it to reappear at the end of the synthesis. The linker must not be affected by the chemistry used to modify or extend the attached compound. And finally the cleavage step should proceed readily and in a good yield. The best linker must allow attachment and cleavage in quantitative yield.

In certain aspects, the support may be a bead, a plate, a dipstick, a filter, a membrane a pin, or a well. The sample may be blood, serum, saliva or CSF. Detecting may comprise RIA, FIA, ELISA, Western blot, flow cytometry, FRET, or surface plasmon resonance.

Carboxylic Acid Linkers

The first linking group used for peptide synthesis bears the name of the father of solid phase synthesis. Merrifield resin is cross-linked polystyrene functionalised with a chloromethyl group. The carbonyl group is attached by the nucleophilic displacement of the chloride with a cesium carboxylate salt in DMF. Cleavage to regenerate the carboxylic acid is usually achieved by hydrogen fluoride.

The second class of linker used for carboxylic acid is the Wang linker. This linker is generally attached to cross-linked polystyrene, TentaGel and polyacrylamide to form Wang resin. It was designed for the synthesis of peptide carboxylic acids using the Fmoc-protection strategy, and due to the activated benzyl alcohol design, the carboxylic acid product can be cleaved with TFA. A more acid-labile form of the Wang resin has been developed. The SASRIN resin has the same structure as the Wang linker but with the addition of a methoxy group to stabilise the carbonium ion formed during acid catalysed cleavage.

Carboxamide Linkers

The rink linker is generally preferred for generating primary carboxamide on solid phase. In the present invention, this linker is utilized when manufacturing or resynthesizing the hits or putative hits from the primary screen of the invention. In such cases, cysteine is the first monomer reacted with the rink linker and then the process involves either subsequent monomer addition to build the oligomer or subsequent submonomer chemistry to build the oligomer. The greater acid sensitivity in the rink linker is a consequence of the two additional electron donating methoxy groups. In the generation of primary carboxamide, the starting material is attached to the linker as a carboxylic acid and after synthetic modification is cleaved from the resin with TFA.

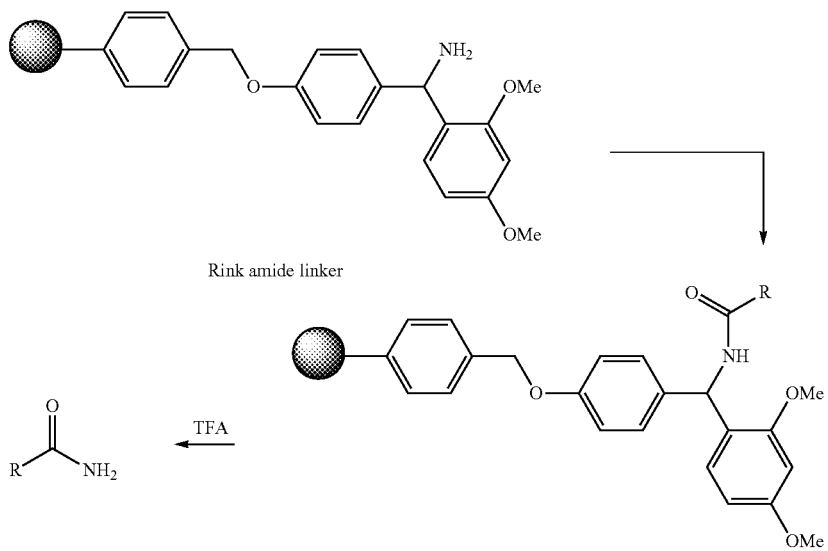

Rink amide linker

The use of Rink resin to produce carboxamide following TFA-catalysed cleavage.

Alcohol Linkers

A hydroxyl linker based on the tetrahydropyranyl (THP) protecting group has been developed by Thompson and Ellmann. All type of alcohols readily add to dihydropyran and the resulting THP protecting group is stable to strong base, but easily cleaved with acid. This linker is attached to a Merrifield resin. The trityl group is a good acid-labile protecting group for a lot of heteroatoms. The trityl group has been used to anchor alcohols in the synthesis of a library of β-mercaptoketones.

Carbamates and Amines Linker

Carbamates linker has been used for the synthesis of a combinatorial library of 576 polyamines prepared in the search of inhibitors of trypanosomal parasitic infections. Two linkers were investigated. One based on hydroxymethylbenzoic acid 1, and the other one, an electron-donating group has been added 2. The last one allowed cleavage by TFA while the first one could be cleaved with strong acidic conditions.

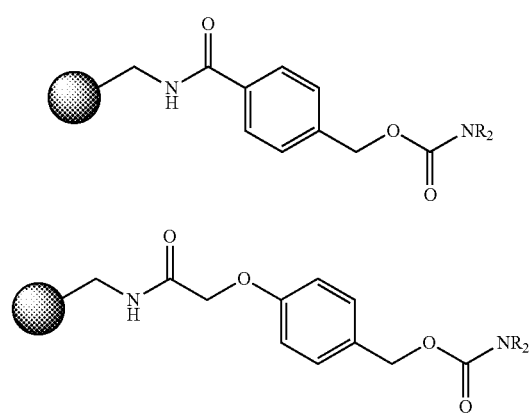

A very useful linker has been recently developed for the generation of tertiary amine. (Tertiary amines are commonly used in drug molecules.) Primary and secondary amines are introduced to the linker by Michael addition. The amine may be alkylated to gives a resin-bound quaternary ammonium ion. In mildly basic condition, Hoffmann elimination occurs to give a tertiary amines of high purity.

Traceless Linkers

In some case, the starting materials are loaded onto the resin in one form, such as carboxylic acid, and cleaved in another form; a carboxamide for example. This is perfectly acceptable if the target compound requires the released function. (Peptides invariably contain a carboxylic acid or carboxamide.) However, the growth in interest in combinatorial libraries of low molecular weight non-peptides has elicited a need in new types of linker. These linkers show non-specific function after cleavage. Traceless linkers are so called because an examination of the final compound reveals no trace of the point of linkage to the solid phase.

Samples

As discussed previously, the complex biological fluids prepared for analysis in the process of the invention include or can include a host of potential biomarkers including markers expressed on cells (non-adherent cells, including T-cells or other immune effector cells), microorganisms, proteins, peptides, lipids, polysaccharides, small molecules, organic molecules, inorganic molecules, biological molecules and including any detectable or reactable moiety in such complex milieu. In a preferred embodiment, such markers are antibodies and, in particular, are antibodies generated as a result of a disease or condition. In a preferred embodiment, body fluids such as serum, plasma, saliva or other fluids or samples derived from a patient or animal or organism are the source of such markers. Each sample or tissue or biologically derived or environmentally derived or obtained sample is conditioned or treated or diluted or otherwise handled in order to expose said sample to either the initial screening or any subsequent screening using putative hits or ligands which have affinity for such biomarkers. The samples are diluted pursuant to the methods recited herein to provide or permit sufficient distinction between background levels or noise and signals associated with the binding of a ligand to a ligand binding moiety.

The time and/or conditions necessary to expose the ligands/supports to such samples depend upon the particular sample and other factors. The preferred conditions for the process of the claimed invention are further described herein. In almost all cases, washing or eluting steps and other conditioning means are utilized following exposure of the biological fluid to the large ligand library and/or ligands or kits derived from such library. Aqueous solutions are utilized including buffered solutions such as HEPES buffer, Tris buffer or phosphate buffered saline. Support systems may also be treated with energy absorbing materials to facilitate desorption or ionization of a "complex" from a support surface. Chemical means are also utilized to decouple or remove ligand-ligand binding moiety complexes from supports.

Detection methods for detecting ligand-ligand binding moiety complexes on a support include photometric and non-photometric means. Such methods include ensuring that the process includes a method to detect and measure absorbance, fluorescence, refractive index, polarization or light scattering. These include direct and/or indirect means to measure such parameters. Methods involving fluorescence include fluorescent tagging in immunological methods such as ELISA or sandwich assay. Methods involving refractive index include surface Plasmon resonance (SPR), grating coupled methods (e.g. sensors uniform grating couplers, wavelength-interrogated optical sensors (WIOS) and chirped grating couplers), resonant minor and interferometric techniques. Methods involving polarization include ellipsometry. Light scattering methods may also be used. Other means for tagging and/or separating and/or detecting can also include magnetic means. Magnetic resonance imaging, gas phase ion spectrometry, MRI may all be used.

Analysis of the data generated typically involves quantification of a signal due to the detected biomarker versus a control or reference. The data can be analyzed by any suitable means. Computers and computer programs may be utilized to generate and analyze the data. Beads and/or other supports may be computer coded or coded for identification purposes. Data analysis includes analysis of signal strength under the particular conditions of the assay or detection method. Ligands, ligand binding moieties or reference moieties and/or secondary detection moieties may be labeled or radio-labeled or tagged with a detectable moiety. One of ordinary skill in the art can assess the difference and/or distinction between biological fluid samples that have disease associated biomarkers versus those control or healthy patient samples that do not contain such markers. One of ordinary skill in the art can also determine, pursuant to the methods described herein, the presence of false positives or other hits that are or may be found in control samples to account for and/or remove such "hits" and one of ordinary skill in the art, pursuant to the methods described herein, can continue the process of determining or finding disease associated biomarkers in patient samples having any disease or condition. The "detection" of such hits, in all cases, is accomplished by means for detecting the binding of a ligand-binding moiety such as a disease associated biomarker or other marker to ligands in a ligand library such as those described herein.

Biomarkers associated with the diseases and/or conditions recited herein will vary depending upon the particular stage of the disease and/or condition of the particular patient or animal or other organism assessed. The ligands, which are the putative hits and the compounds recited herein, are expected to, in most cases, mimic the natural antigen that initiates the immune response and/or formation of antibodies or immune cells in the first instance. The present invention and screening process claimed and recited herein does not require knowledge of either the particular antigen or the antibody generated in response to the antigen. The ligands, however, may be useful in their own right as vaccines or drug candidates in addition to being useful in the screens and diagnostic methods recited herein. The present invention thus includes compounds and pharmaceutical compositions.

Peptoid Screens:

To screen one-bead-one-compound (OBOC) combinatorial peptoid libraries, tens of thousands to millions of peptoid bearing beads are prepared and then mixed with a complex biological sample. The initial complex biological sample is preferably a control sample and a subsequent complex biological sample treated with a ligand library that has "removed" the control hits is then treated and/or screened against a diseased complex biological sample. The ligands/beads that interact with at least one disease associated biomarker are then detected, identified and isolated and/or characterized. In a preferred embodiment, a Tentagel screening protocol is used which comprises (1) bead preparation, (2) screening of complex biological fluid and (3) detection of hits.

Peptide Screens:

To screen one-bead-one-compound (OBOC) combinatorial peptide libraries, tens of thousands to millions of peptide bearing beads are prepared and then mixed with a complex biological sample following the processes described herein. The beads that interact with disease associated biomarkers are then identified and isolated for compound structure determination. For example, OBOC peptide library screening using streptavidin (SA) as probe protein, labeled with a red fluorescent dye and using the COPAS BIO-BEAD flow sorting equipment to separate fluorescent from nonfluorescent beads may be performed. See Marani et al., *J. Comb. Chem.*, 2009, 11 (1), pp 146-150. The red dyes which may be used are ATTO 590 and Texas Red. After incubating the library with the SA-red fluorescent dye conjugate, positive beads caused by peptide-SA interaction are obtained. The beads are analyzed by matrix-assisted laser desorption ionization time-of-flight mass spectrometry (MALDI-TOF MS). Thus, peptide libraries may be used in a manner that is analogous to the process described herein with peptoids wherein initial control biological fluid samples are used to remove any ligand/bead hits from the starting compound library and wherein the remaining members of the library are used to then screen for any hits in a diseased complex biological fluid sample. These hits are the putative hits which are then carried forward in any diagnostic kits.

In a similar manner, any ligand may be screened on the beads or supports using the processes described herein. These ligands include, in addition to peptoids or peptides, nucleic acid oligomers, polysaccharides, small molecules and/or any combination thereof which can be build into libraries and, under the conditions recited herein, used to screen complex biological fluid.

Kits and Diagnostic Tools

Any of the compounds or compositions described herein may be further utilized in diagnostic kits either in a clinical or laboratory setting. These kits can range from simple point of care diagnostic assays to complex and multiplex instruments or probes. The support systems and "packaging" surrounding the core support/ligand system can be selected from current commercial kits that are designed to include the putative hits and or hits that are resynthesized and installed on such suitable platforms or they can be used in newly designed diagnostic kits. The kits will typically be accompanied by all suitable reagents and instructions to use the kits to screen for and/or diagnosis the particular disease or condition the kit is designed for. Any such kit or method will comprise at least one putative hit or ligand that has been identified pursuant to the screening method recited herein. This ligand or plurality of ligands may be selected from the same ligand or a mixture of ligands which comprise the compounds of the invention. The ligands may be selected based upon their affinity for a disease associated biomarker for one particular disease state or a group or battery of diseases or conditions. The preferred ligands are peptoid ligands. The kits will also contain instructions for the physicians diagnosing a particular disease or condition and specific labeling for the particular kit and disease state or condition. The present invention thus includes a combination of a kit including all of its essential components such as the putative peptoids or ligands found from an initial screening using any one of the libraries disclosed herein and/or known pursuant to the specific methods recited herein and labeling instructions. It is also envisioned that the particular processes and methods and materials disclosed herein may be utilized in a clinical and laboratory setting under the supervision of a skilled operator. The kits and/or instruments or equipment comprise ligands such as peptoids that are specific for disease associated antibodies and/or cells. The "kit" may comprise a complete diagnostic kit and or screening kit or the "kit" may comprise components or subcomponents containing or comprising the diagnostic peptoids, antibodies discovered and characterized through such peptoids or native antigens that are discovered and purified and/or characterized as a result of interaction with and discovery from the autoantibody. Such antibodies and purified antigens comprise part of the present invention.

Diagnostic Methods

The ligand libraries of the present invention are utilized to find and determine ligands that bind to disease associated biomarkers. Such ligands are then utilized in the kits and/or methods described generally above to assess, screen or diagnose disease states or conditions. These diagnostic methods typically involve screening for and finding disease associated biomarkers which comprise antibodies and/or other biological markers. As stated above, these antibodies can be further identified and characterized using the ligands of the invention on suitable columns to pull out or remove such antibodies from blood samples. The antibodies can in turn be used to probe for and discover the native antigen associated with such antibody. The present invention thus includes both the antibodies and purified antigens associated with such antibodies and which are discovered, isolated and characterized using the methods of the invention.

Kits and/or other means to screen for and/or diagnose disease states or conditions must, in the first instance, be assessed against patient samples. These patient samples may be derived from normal control samples or from patient samples wherein said patient has been identified as a patient that has or is suspected of having that disease or condition. The patient may have other symptoms associated with the disease beyond the "presence" of a disease associated biomarker. The patient may be in an early stage of the disease, may not have the disease or condition at all or may be in a late stage of a particular disease. In any clinical context and under appropriate guidelines and controls, patient and clinical samples may be provided in a blinded fashion and then assessed using the compounds of the invention. The data generated as a result of the screening may then be analyzed after un-blinding to find or not find statistically significant results or correlations with known or underlying data about any particular patient or group of patients. The present invention comprises a method of screening for the presence of a disease or condition comprising (1) screening a biological sample from a patient with at least one compound of the invention; (2) screening a control biological sample under the same conditions using said at least one compound and (3) comparing the healthy control data versus the patient data to determine the presence or absence of a disease associated biomarker. A group of patients or patient samples having or suspected of having disease X may be screened against a kit or diagnostic probe having at least one compound of the invention and the data generated with respect to each patient may be utilized on a case by case basis to confirm or validate a disease state or condition or lack thereof. Such data generated herein may be used in combination with the total information known about that particular patient to assess the patient's condition and to provide guidance to the medical practitioner providing treatment options. The "information" generated as a result of any such screen may be used in the clinical trial setting to assess individual patients that are taking drug therapy. The present invention thus includes a method of assessing clinical trial progression comprising use of a screen performed according to the methods described herein. In a preferred embodiment, the present invention relates to a method of screening for or diagnosing an early disease state comprising use of a screen or compound claimed herein to detect a disease associated biomarker. The invention is particular useful in the context of early cancer intervention wherein detection of such biomarkers is expected to occur well before aggressive progression of the disease. In another context, early intervention in cardiovascular disease and/or metabolic disease as well as neurological disease is expected to save lives and prevent or be useful for preventing further development of such diseases without early medical intervention or treatment.

The present invention also includes methods to increase the resolution or efficiency of the difference between a control or standard solution and the complex biological fluid containing the disease associated biomarker. For example, methods include preconditioning or pre-treating or pre-blocking the system/serum with buffers and/or conditioning agents such as *E coli* lysate and/or lysine.

In yet another embodiment, there is provided a method of treating a subject suspected of having a disease comprising (a) contacting an antibody-containing sample from said subject with one or more supports having affixed thereto a peptoid comprising a peptoid of the formulas recited herein (b) detecting antibodies bound to said peptoids; and (c) making a treatment decision based on the result of step (b). The method may further comprise obtaining said sample from a subject. The method may also further comprise making a diagnosis of a disease for a subject from which said sample was obtained if antibody binding to the peptoid is greater than that observed for control non-diseased patients. The method may also further comprise making a treatment decision for said subject. The sample may be contacted with more than one peptoid of formulas recited herein. The sample may be contacted with a multiplex platform for the purposes of diagnosing multiple disease states or conditions. The support may be a bead, a plate, a dipstick, a filter, a membrane a pin, or a well. The sample may be blood, serum, saliva or CSF. Detecting may comprise RIA, FIA, ELISA, Western blot, flow cytometry, FRET, or surface plasmon resonance.

A further embodiment is directed to an antibody composition isolated from a biological fluid that is indicative of a disease. In certain embodiments the antibody are isolated by contacting a sample having such antibodies with a peptoid composition that specifically binds antibodies indicative or associated with a disease. The antibodies can be removed, isolated, or purified from other non-antibody and non-D specific components. The antibodies can then be washed and/or disassociated from the peptoid capture agent(s).

In certain embodiments, a peptoid array made from the peptoids discovered in the process described herein is hybridized with a biological sample that has been supplemented with a bacterial lysate, e.g., an *E. coli* lysate. The biological sample includes a control sample and a sample having a marker for a central nervous system disorder. For example, microarray slides are covered with a hybridization chamber and equilibrated with 1×TBST (50 mM Tris, pH 8.0, 150 mM NaCl, 0.1% Tween20) for about 15 minutes. The slides are then blocked with a bacterial lysate at a concentration at least, at most, or about 0.5, 1, 1.5, 2 mg/ml of lysate. The lysate is removed and the slides are incubated with about a milliliter of biological sample (having a an approximate protein concentration of 5, 10, 15, 20 or 25 g/ml including all ranges and values there between) in bacterial lysate with gentle shaking. Microarrays are then washed with 1×TBST and hybridized with labeled Anti-IgG antibodies (e.g., at 1:400 dilution). The slides are then washed with an appropriate buffer. The slides are dried using a centrifuge (e.g., 5 min spin at 1500 rpm) and scanned on a microarray scanner, for example, using a 635-nm laser at 100% power and a 600 or 650 photomultiplier tube gain. The present invention thus also relates to a method of reducing background antisera noise in a diagnostic assay comprising treating the control plasma sample and the diseased sample with an *E. coli* lysate and contacting said samples with a peptoid or ligand array. It is believed that this process can be used to support treatment of any array used to detect and distinguish antibodies in sera in the context of comparing a control sample to a diseased sample.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions and kits of the invention can be used to achieve methods of the invention.

Throughout this application, the term "about" is used to indicate that a value includes the inherent variation of error for the device, the method being employed to determine the value, or the variation that exists among the study subjects.

Vaccines and Drugs

It is understood that any one of the putative hits or peptoids discovered through the process recited herein may also be a therapeutic drug or vaccine candidate. The present invention thus relates to a process for discovering drug candidates or vaccines comprising use of the screen pursuant to the methods described herein.

Example 1 Library Preparation

Protocol for Peptoid Synthesis (Cyst-Peptoid or Methionine-Peptoid)

The following example demonstrates how peptoid libraries of the invention were generated. The materials utilized in the example include reaction flasks or beakers, plastic tubing, 10-15 3 ml syringes with needles, Latex gloves, 10-15 15 ml polypropylene test tubes and micropipettes with solvent safe tips (1000 µl), glass pipettes and Resin beads. The chemicals and/or reagents utilized included N,N Dimethylformamide, Bromoacetic acid (BMA), Anhydrous Dimethylformamide, Piperidine, Acetonitrile, 3-diisopropylcarbodiimide (DIC), Trifluoroacetic acid, 5(6)-Carboxyfluorescein, Dichloromethane (DCM) and 4-Methylmorpholine (NMM). The various amines utilized in each library preparation were also used as well as HBTU (Tetramethyluronium Hexafluorophosphate) and triethylsilane.

Peptoid Preparation

The concentration of each amine used in the process is calculated using following the formula:

$$V = FW/d/1000 \times 2M \times 5 \text{ ml}$$

Procedure:
Step 1
Swelling of the Resin Beads.
(a) 250 milligrams of resin beads were placed into a clean dried reaction flask and 5 mls of hydrous DMF was added to the beads which were allowed to swell over a period of an hour or less. The beads were then washed with DMF multiple times (2 or 3×) under vaccum.

Step 2
Steps (b), (c) and (d) were omitted when "unprotected beads" (e.g., Tenta-Gel) were used. 20% solution of Piperidine (base) using anhydrous DMF as the solvent was used in the following process:
The following process comprising steps (b), (c) and (d) was done 2 times when using "protected beads"
(b) 2.5 ml of 20% piperidine solution was added to the protected beads;
(c) After adding piperidine, the reaction flask was placed on a shaker/incubator for 20 minutes, set at 200 rpm @25° C.
(d) the reaction flask was then washed 8-10 times with hydrous DMF using 5 mls of DMF.

The following solutions were also prepared:
1. 468 mg Fmoc-Cys(Trt)-OH in anhydrous DMF (2 ml volume) (solution A).
2. 161.6 mg of NMM, in anhydrous DMF 2 ml
3. 303.2 mg HBTU was added to NMM vial (solution B).
Addition of HBTU/NMM and Fmoc-Cys
1 ml of each of solution A and solution B was added to the beads—(HBTU/NMM) and Fmoc-Cys(Trt)-OH) and shake for 1 hour.
The beads were washed in DMF 5-10 times.
The remaining 1 ml solution of solution A and B were added to the beads which were shaken for a period of 1 hour and then washed again in DMF 5-10 times.
The following solutions were also prepared:
20% Piperidine (in anhydrous DMF)
2M Bromoacetic acid
50% DIC/A. DMF
2M solution of each amine
The following steps (a), (b) and (c) were performed 2 times.
2.5 ml of 20% piperidine solution was added; (b) the reaction flask was shaken at 200 rpm at 25 degrees C. and then (c) the beads were washed with DMF 8× to 10×.
A 10 ml solution of 2M Bromoacetic acid was prepared.
A 10 ml solution of 50% 3.2M DIC/anhydrous DMF (v/v) was also prepared.
2M amine solutions were prepared of each amine in and for each library.

For peptoid synthesis, 1 ml of 2M stock solution was used each time an amine was added on the peptoid chain.

Step 3

(a) 1 ml of Bromoacetic acid was added to the reaction vessel;
(b) 1 ml of 50% DIC/DMF solution was then added and the resultant solution was (c) microwaved for 15 seconds @ 10% power.

Step (c) was performed 2 times swirling the flask side to side between sets of microwaving.

A white precipitate was formed after each microwaving step. The beads were then washed 8-10 times with DMF.

Step 4

One ml of the first amine in the sequence was added to the reaction flask containing the bromo intermediate from the preceding step and the vessel was shaken to evenly distribute the amine on the beads. The reaction was then initiated using the microwave for 15 seconds @ 10% power 2 times. The reacted beads were then washed with hydrous DMF 8-10 times.

Steps 3 and 4 were repeated until all amines were added to make the target peptoids.

Step 5

The beads were then washed with dichloromethane (DCM) 3 times and allowed to dry.

Step 6

The peptoids were then cleaved from the beads using a 95% TFA solution (5 mls). The peptoids were then collected off the beads which were washed with a solvent (CH3CN and water) to remove residual peptoids. Argon gas was used to remove any residual TFA. The peptoids were then lyophilized and characterized and purified as necessary.

The reaction conditions specified above may be modified on an as-needed basis depending upon the quantities needed for any particular bead composition.

FIGS. 1-5 generally demonstrate how the library of the invention was prepared for AD diagnostics, pancreatic cancer diagnostics and lupus. In general, the beads having an amine moiety were linked to an amino acid residue through a series of steps using standard peptide chemistry which was then reacted with an activated carbonyl moiety having a halide group which was then reacted with a monomeric amine having an R group. Steps 2 and 3 of the cycle were repeated as shown in the Figures to create large peptoid libraries having 1 MM to 2 MM distinct ligands. The initial screening library prepared on Tentagel resin or beads typically had a methionine amino acid as the first monomer in the chain. The present inventor uses such an amino acid to facilitate cleavage from a bead or resin that does not have a cleavable linker. The Rink resin used to build the cysteine containing peptoids have linkers which do not need or require the use of methionine as the first amino acid. The cysteine containing peptoids were typically resynthesized after the initial screen found the putative hits. The cysteine sulfur group permits reaction of the peptoid chain with, for example, another reactive moiety on a diagnostic platform substrate. The peptoids which were resynthesized also contained a 1-yl-n-butylamino moiety as the first side chain in the chain after the amino acid amine. It is believed this group is necessary to display the peptoid and to solubilize the peptoid in aqueous containing solutions.

Example 2 General Screening Methodology 160 micron Tentagel beads attached to a peptoid of choice were swelled overnight in DMF. Beads were then washed ten times in a reaction vessel with Millipore water and vigorous shaking. Fresh Millipore water was added each time, and on the 10$^{th}$ wash, beads were allowed to shake overnight at 150-200 rpm. The next day, beads were washed in the same fashion with 1×TBST and allowed to shake at 150-200 rpm for at least 3 hours.

Beads were then split evenly into 15 ml conical tubes, about 0.5 grams per tube in 1×TBST. TBST was removed, and 4 ml of diluted normal human serum was added to each tube. Serum stock made in 1×TBST was Nano-dropped to get desired concentration of 20 ug/ml. Tubes containing serum and beads were then tumbled overnight at 4 degrees Celsius in the dark. Serum was then pipetted out of the tubes, and replaced with 4 ml 1×TBST. Tubes were then slowly inverted to re-suspend then beads, and then allowed to settle. TBST was removed and added twice more, for a total of three TBST washes.

Secondary antibody solution was then prepared, by preparing 5 ul of goat anti-human IgG Qdot 655 per 1 ml 1×TBST. Once the last TBST addition was removed from the beads, 4 ml of the Qdot solution was added, and beads were tumbled for 2 hours at four degrees Celsius in the dark. The beads were then allowed to settle, and the Qdot solution was removed. The beads were then washed three times with 4 ml of 1×TBST. Beads were then poured into a clear Petri dish of viewed under a UV microscope containing a DAPI filter. All beads stained red were removed.

After the first screen was completed, beads were poured back into 15 ml conical tubes, and tumbled at four degrees Celsius for at least four hours before the next serum sample addition. Disease serum was then added to the beads in the same fashion as normal serum addition, with the exception that the serum was diluted in PBS starting block as opposed to 1×TBST. However, the original stock was prepared in 1×TBST in order to obtain the proper concentration with the nanodrop. The serum addition and secondary antibody addition is the same as with the normal serum.

Once diseased "hits" were removed, they were pooled into a 1.5 ml eppendorf tube, and heated at 95 degrees Celsius for 25-30 minutes in 1% SDS. The SDS was then removed from the tube, and replaced with Millipore water. Beads were then tumbled for 15 minutes at four degrees Celsius. The water was then replaced with fresh water, and beads were tumbled for another 15 minutes. The water was then removed and replaced with 50/50 Acetonitrile/water solution and allowed to tumble another 15 minutes. Beads were then separated into individual wells in a 96 well plate and allowed to dry.

A solution of 20-30 mg Cyanogen Bromide, 500 ul Acetonitrile, 400 ul Glacial Acetic Acid, and 100 ul Millipore water was made, and 20 ul of solution was added to each well containing a hit bead. The plate was covered and allowed to shake for 16 hours at 100 rpm. The cover was then removed, and the cleavage solution was evaporated from the wells. The hits were then spotted onto a MSMS plate and sequenced using a 4800 MALDI/TOF/TOF analyzer.

Figure 6:
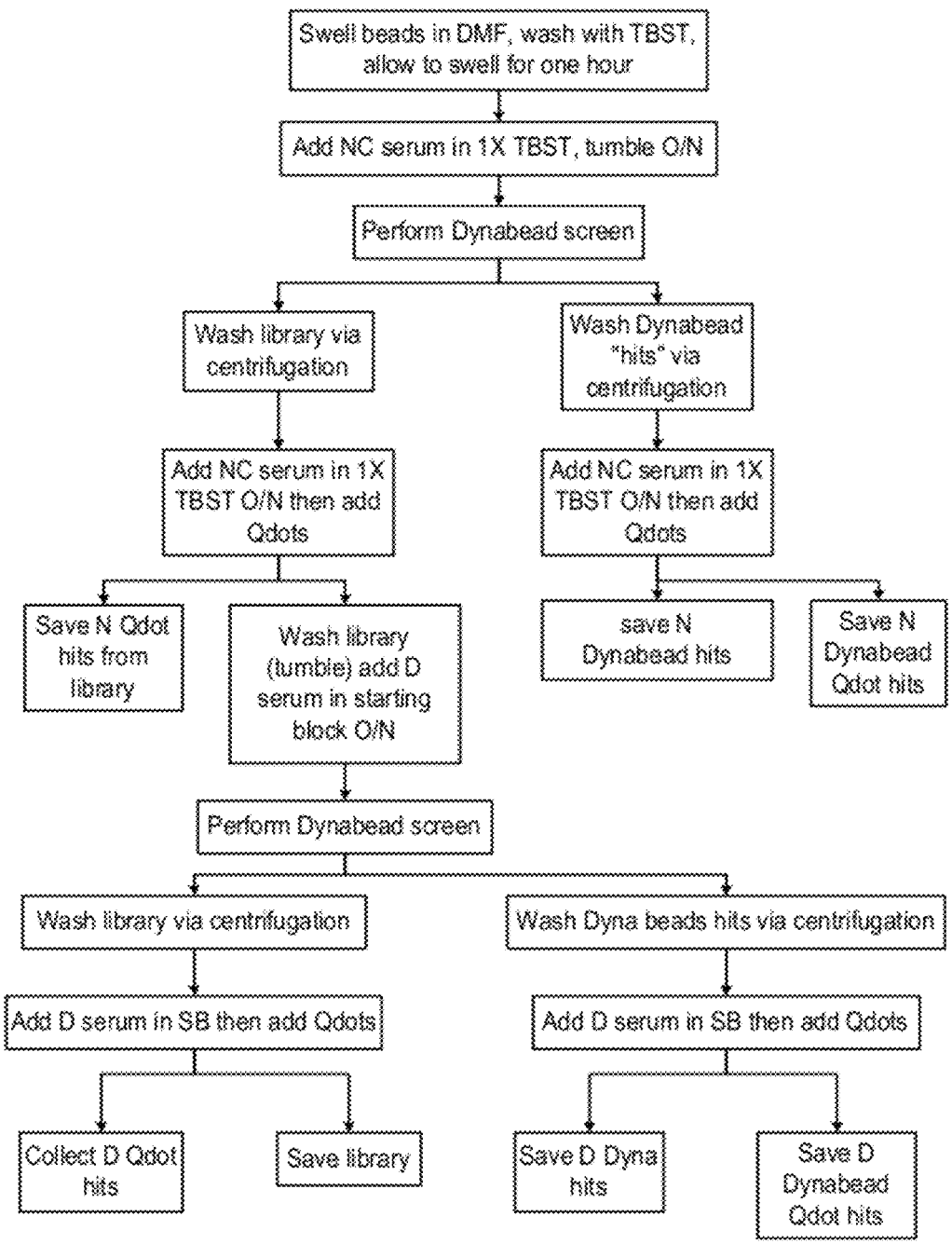
FIG. 6 shows a schematic of the process of the invention to screen a complex biological sample using bead based libraries of peptoid ligands.

FIG. 6 provides a general schematic of the screening methodology disclosed and claimed herein.

Example 3 Alzheimer's Disease Screening

Tentagel Magnetic Screen

Five hundred milligrams of 160 micron Tentagel beads (JC3B library) was added to a fifteen milliliter conical tube. Five milliliters of DMF was added to the tube, and the beads were allowed to sit overnight to swell. The next day, DMF was pipetted out of the tube and replaced with five milliliters of 1×TBST. The tube was inverted to mix, and beads were then allowed to settle to the bottom and 1×TBST was removed. Five milliliters of 1×TBST was added and removed five more times.

Normal AD serum samples were prepared by adding 4 milliliters of PBS starting block to a tube, and adding 7 ul of each of four separate AD samples to the same tube. The serum was added to the washed beads and beads and serum were allowed to tumble overnight at four degrees Celsius in the dark. The next morning, beads were removed from the tumbler and allowed to settle before the serum was pippeted out of the tube. Four milliliters of 1×TBST was added to the tube, and the tube was inverted to mix. The TBST was then pipetted out of the tube and replaced with four milliliters of fresh 1×TBST and removed again.

DYNA-bead solution was then prepared by adding 50 ul of well-mixed goat anti-human IgG DYNA beads to four milliliters of 1×TBST. The mixture was then added to the washed beads. The beads were then allowed to tumble for two hours at four degrees Celsius in the dark.

Without washing the beads, the DYNA beads screen was performed. The tube was placed in a magnet holder and filled to the brim with 1×TBST. The magnet and tube were slowly agitated for two minutes, and the beads were allowed to settle in the magnet holder. The TBST and free beads that settled to the bottom were removed carefully, to not touch the hit beads attached to the sides by the magnet, and replaced with fresh 1×TBST. The process was repeated two to three times, until no beads could be seen attached to the sides of the tube. The hit beads were then combined into one tube.

Remaining non-hit beads were divided into 1.5 milliliter tubes, inverted and quickly pulsed centrifuged. The supernatant was removed and replaced with fresh 1×TBST. This process repeated 6-8 times until no more DYNA beads were visible in the bead/TBST solution. The hit beads were washed in the same fashion.

Beads were combined back into a 15 ml tube, and normal serum was added to the beads in the same way as previously stated, and allowed to tumble overnight at 4 degrees Celsius in the dark. In addition, three Milliliters of each four normal AD samples was added to 1 milliliter of PBS starting block, and this solution was added to the DYNA bead "hit" bead tube. The next day, beads were washed in the same fashion as with the normal serum addition.

20 ul of goat-anti human IgG Quantum Dot 655 was diluted in 4 milliliter 1×TBST (20 ul Qdot in 1 Ml 1×TBST for the "hit" tube), and added to the beads. The solution was tumbled for two hours at four degrees Celsius in the dark. Both hit and non-hit tube was washed four times with 1×TBST and screened for bright red beads under a UV microscope. Remaining beads were tumbled in four milliliters of 1×TBST for one hour, and disease AD serum was added in the same fashion as the normal serum. The magnetic screen and Qdot additions were performed in the same manner as previously stated. The hits were then sequenced on a MALDI TOF/TOF mass spectrometer.

Figure 7:
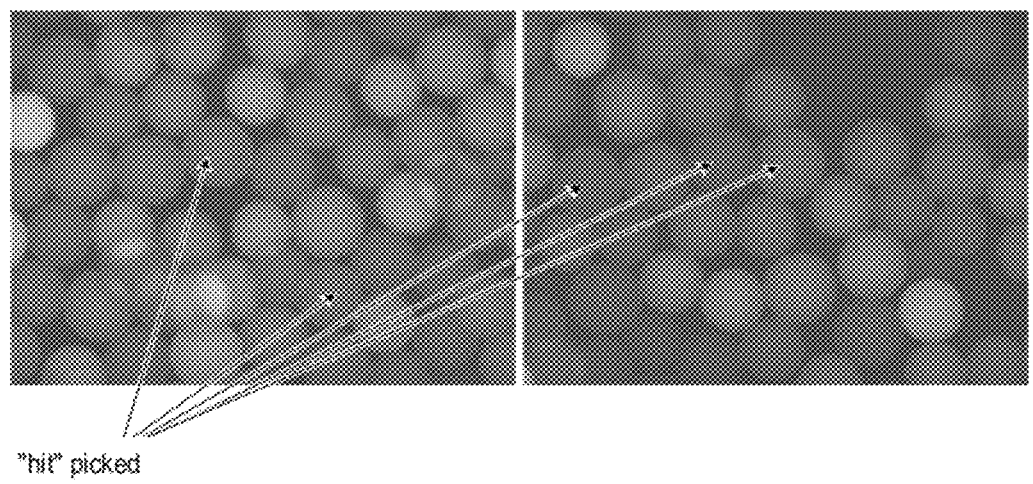
FIG. 7 shows normal control (NC) Dynabead hits after QDot addition in a peptoid library (JC3B) prepared to screen against an Alzheimer's normal control serum sample and Alzheimer's diseased serum sample. The hits were picked out and the remaining ligand bound beads were used in the disease based screen.

FIG. 7 shows pooled normal control serum samples that were incubated overnight with beads from a peptoid library (JC3B). An initial secondary antibody DYNA bead screen using goat anti-human IgG tagged with DYNA beads was performed to remove non-specific bead hits. These non-specific hits were then re-confirmed using a different secondary antibody. In this case, goat anti-human IgG tagged with Quantum Dot 655 (Invitrogen) was detected unto a UV microscope containing a DAPI filter. The red colored beads indicate hits that were re-confirmed; the blue beads indicate beads that did not reconfirm. The percentage of re-confirmed beads was continually low, so the DYNA bead screen was eventually discontinued.

Figure 8:
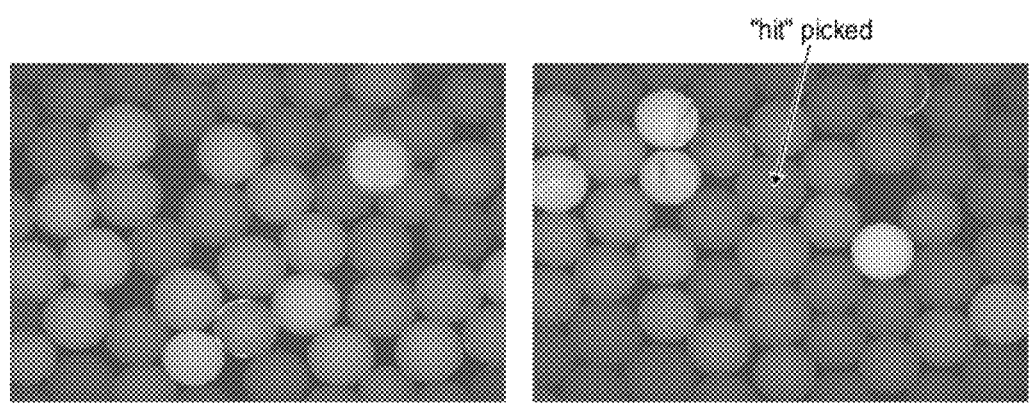
FIG. 8 shows the Tentagel bead screening of diseased serum from Alzheimer's patient blood samples after the NC hits were removed. The hits are shown in red, which is the Qdot secondary antibody bound to the disease associated biomarker (antibody) in the serum which is bound to a peptoid linked through a PEG linker to the bead.

FIG. 8 shows a peptoid library that was incubated with serum from AD patients. Afterwards, the library was incubated with a secondary detection antibody (goat anti-human IgG tagged with Quantum dot 655 (Invitrogen). Hit beads were detected under a UV microscope containing a DAPI filter, and beads that were red in color were picked as hits to be sequenced for further testing.

Figure 9:
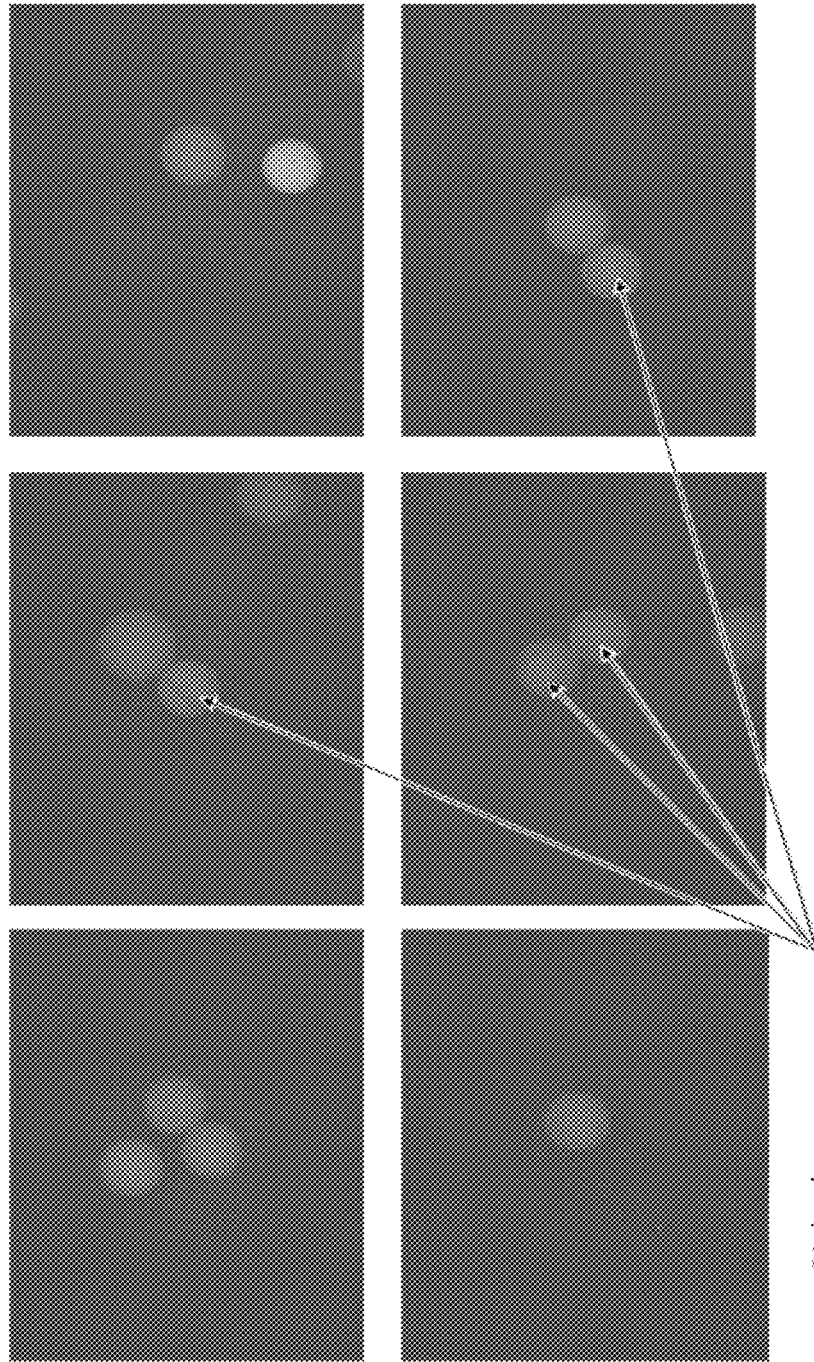
FIG. 9 shows a reproducibility test which uses a normal control sample (NC 030093) after SDS wash and QDOT addition. The arrow shows which NC peptoid hits were picked to sequence.
Figure 10:
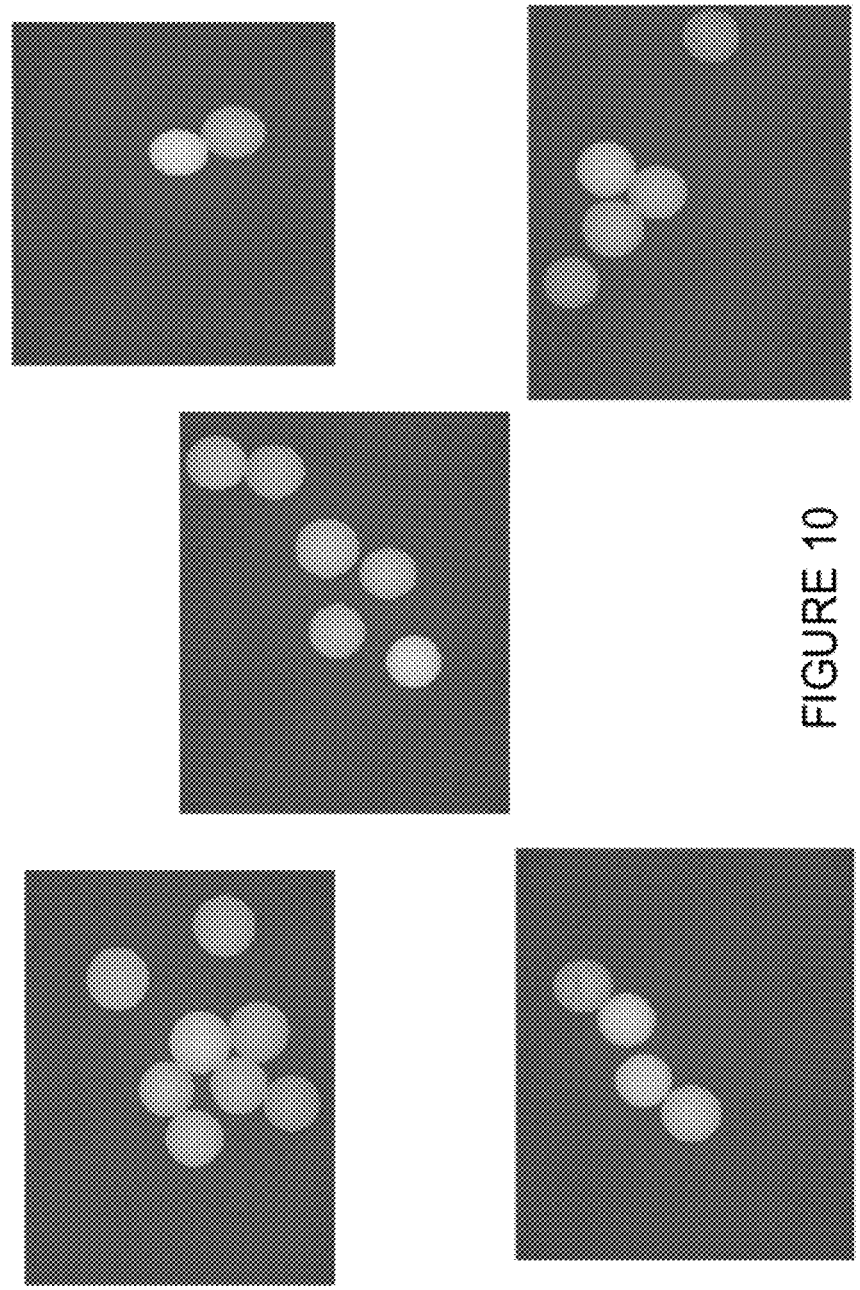
FIG. 10 shows a reproducibility test which uses a normal control sample (NC 050047) after SDS wash and QDOT addition.

FIGS. 9, 10 and 11 show that after Disease hits were isolated from the peptoid library, a 1% SDS wash was performed to strip the hits from any residual antibody. Beads were then incubated with individual Disease samples, and then with goat anti-human IgG Quantum dot 655. Beads were then visualized under a UV microscope to determine if hits would re-confirm with individual samples. The consistently reconfirmed hits were chosen to sequence.

Figure 12A:
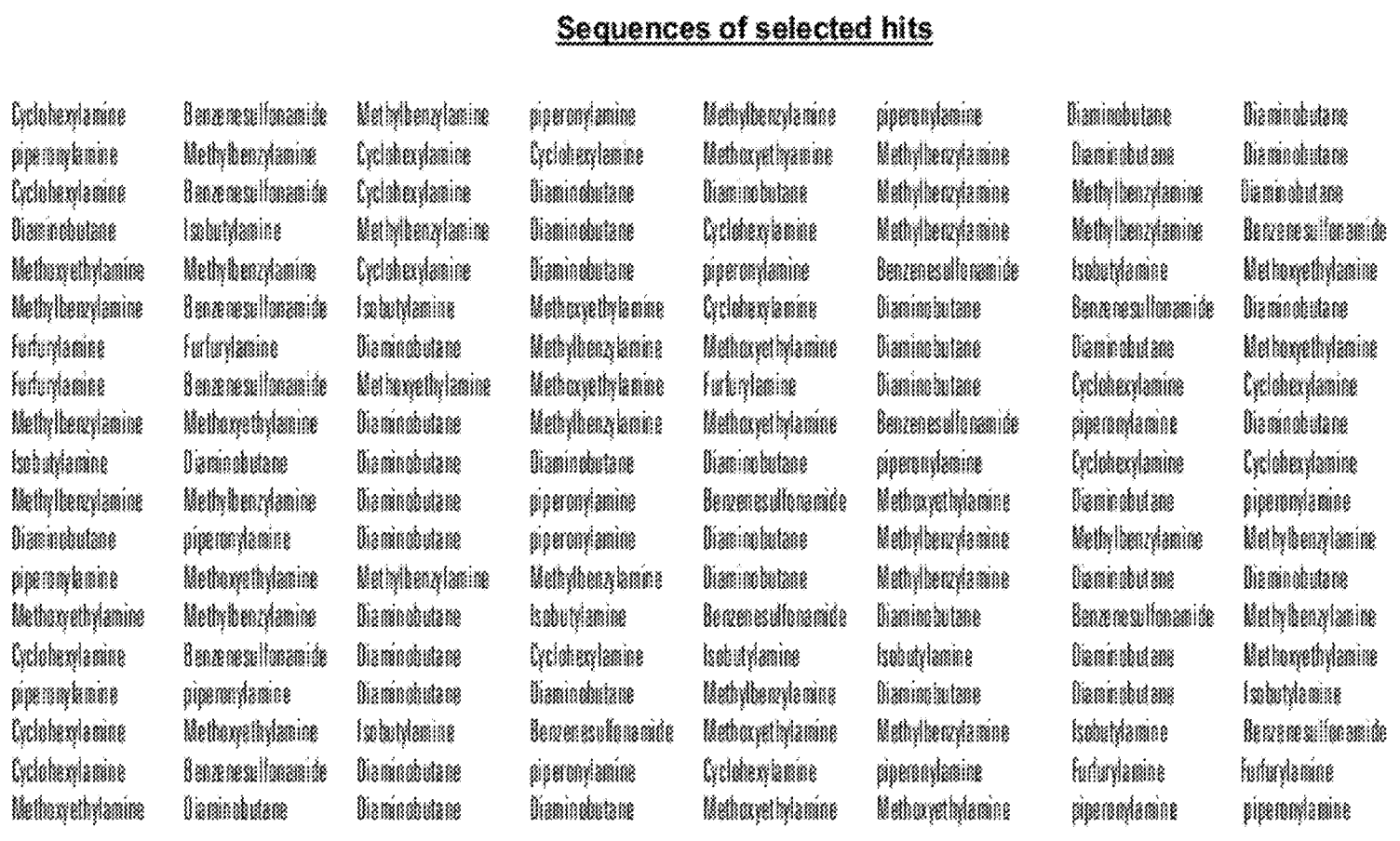
Figure 12B:
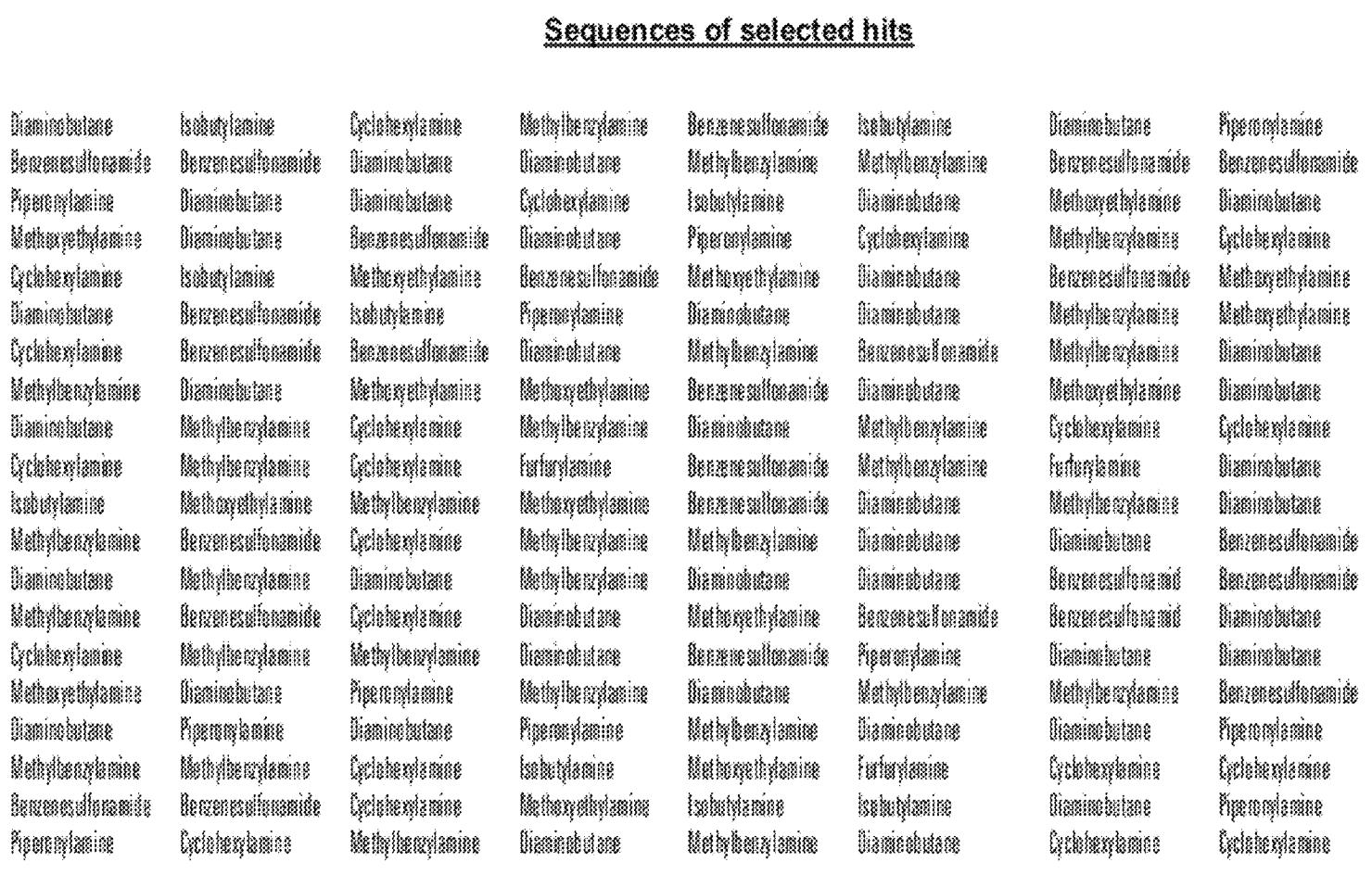

FIG. 12 shows the sequences of all of the selected hits in the Alzheimer's screen of JC3B library.

Figure 13A:
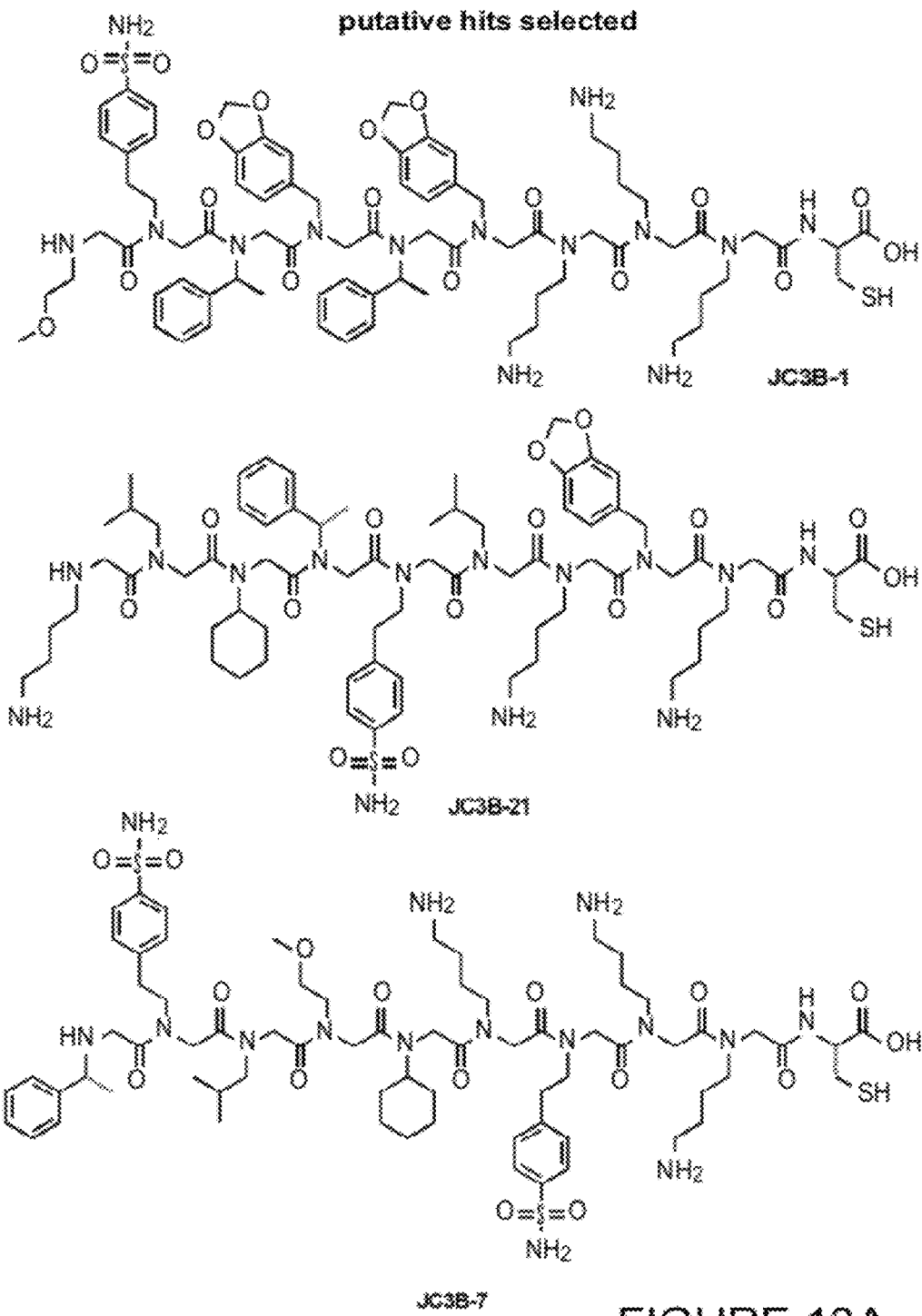
FIG. 13 shows the chemical structures of the preferred high affinity hits from the Alzheimer's screen from the JC3B library. In this example, the structures shown have a cysteine residue and were resynthesized after determining the structure of the initial hit in the preliminary screen. The JC3B library contained an analous peptoid but which had a methionine residue on the C-terminus and not a cysteine residue.

FIG. 13 shows the chemical structures of the putative hits selected in the Alzheimer's screen.

Figure 14:
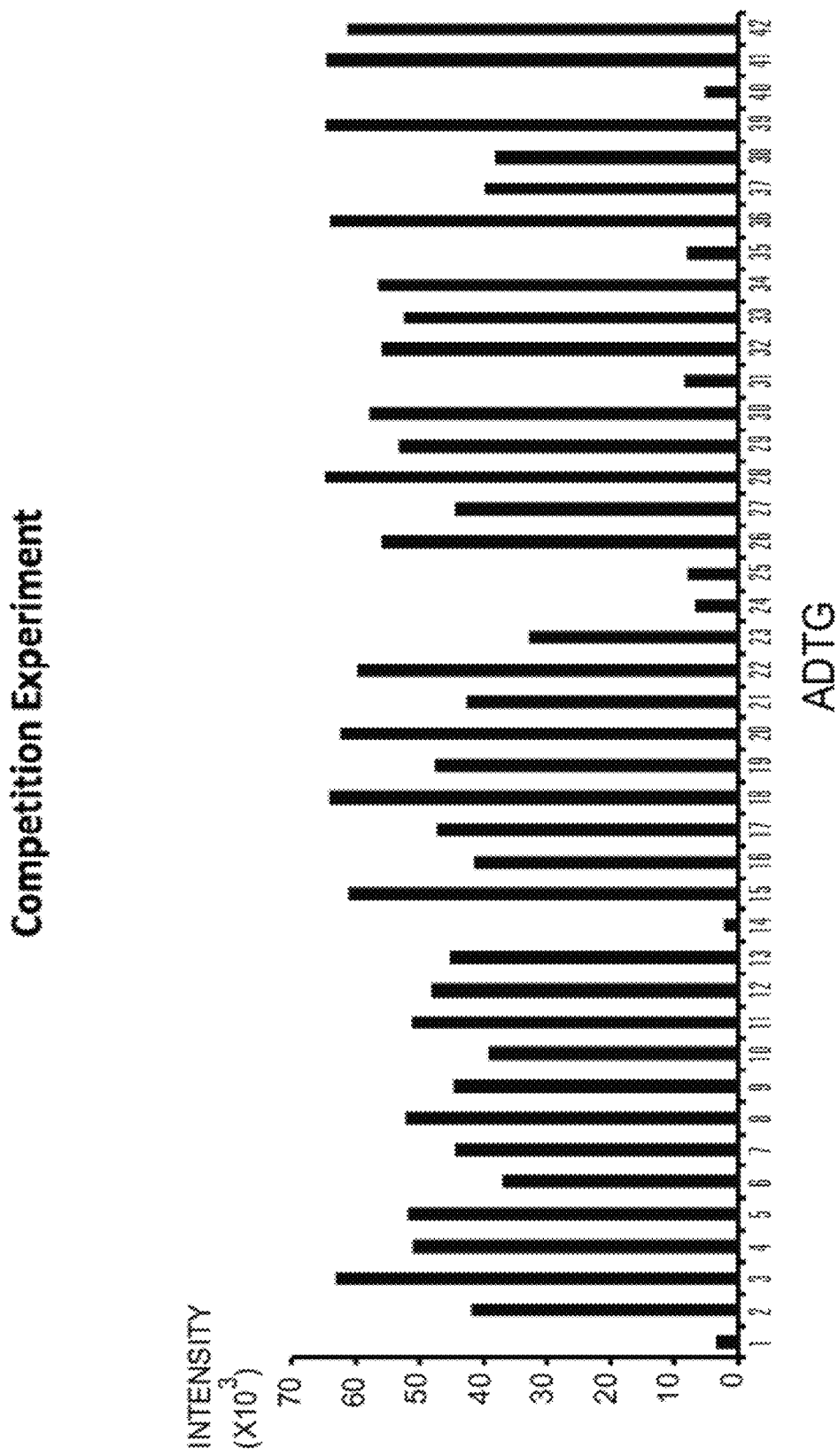
FIG. 14 shows a competition experiment between a high affinity ligand (ADTG1) in solution versus ADTG-1-ADTG-42 on a microarray support. The competition experiment shows that ADTG1 in solution bonded to the same antibody that would have bound to peptoids ADTG-1, ADTG14, ADTG24, ADTG25, ADTG31, ADTG35 and ADTG40 on the microarray. Similar experiments were conducted on each of the peptoids to find four sets of peptoids, which bound to four distinct Alzheimer's autoantibodies (data not shown).

FIG. 14 shows a competition experiment between peptoid ADTG1 in solution versus those peptoids designated as ADTG1-42 on a microarray. The data shows that peptoids ADTG1, 14, 24, 25, 31, 35 and 40 are binding to the same autoantibody. The same experiment was conducted for each of the peptoids on the array and this process determined that the peptoids are binding to seven distinct autoantibodies to Alzheimer's antigens.

Figure 15A:
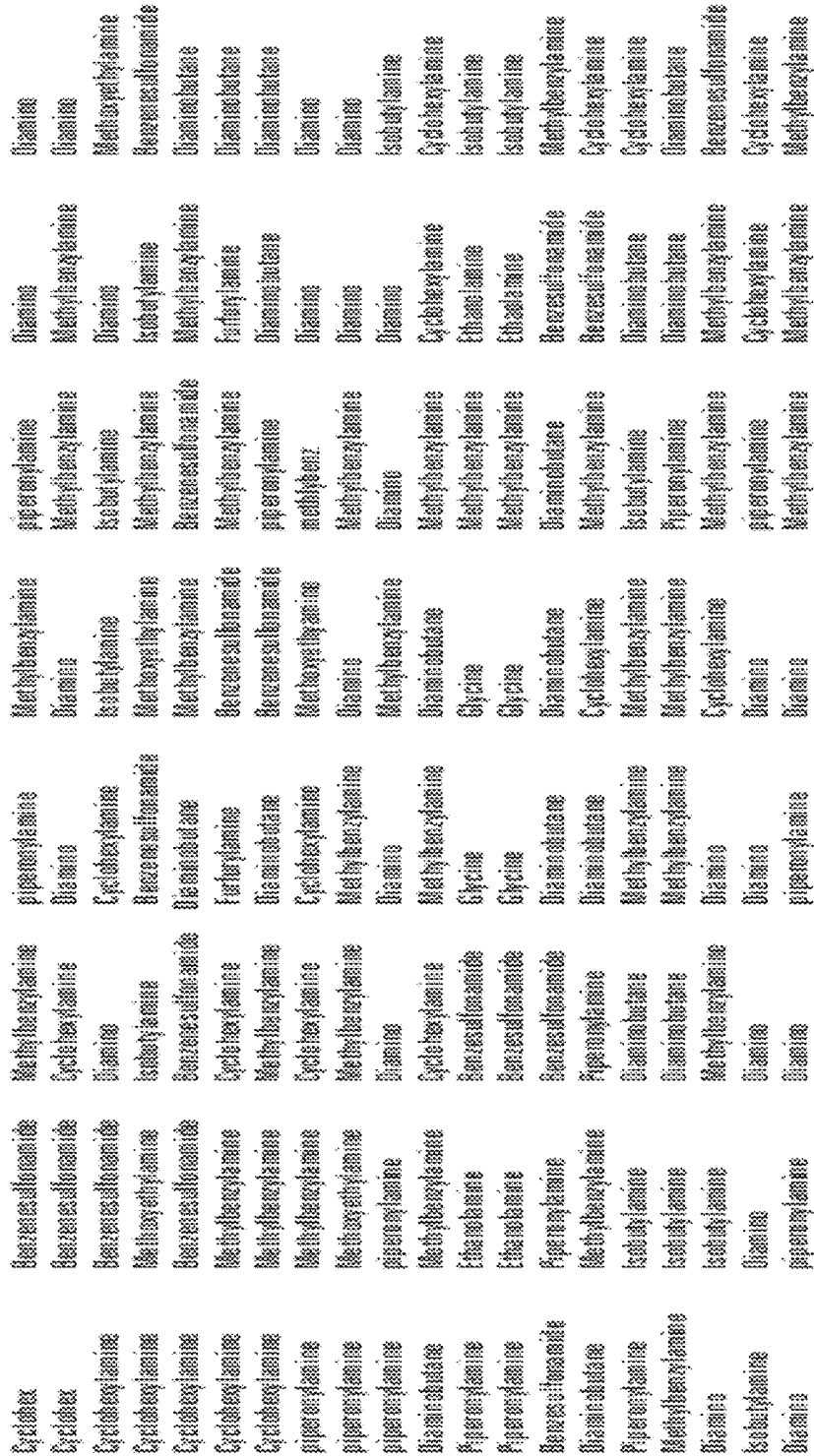
FIG. 15 shows the four groups of distinct peptoids, which bind to different autoantibodies in the Alzheimer's screen. Each group on the figure has the higher affinity binder at the top.

FIG. 15 shows the sequences of 41 of these peptoids which are, from the topline, designated as more active to less active and which are presented in four distinct groups based upon the results of the competition experiments which found that the ligands are binding to four distinct antibody biomarkers for AD. ADP1-3 were previously found in a microarray screen (data not shown but previously described in U.S. Pat. Publication No. 2010/0303805) and were discovered to bind to two distinct antibody biomarkers for AD. ADP1 and ADP3 were found to bind to the same antibody while ADP2 bound to a separate antibody. The new ligands discovered in the new screening methodology of this invention (all other ligands in FIG. 15 and as shown in FIG. 13) also bound in groups to distinct antibodies. Two new antibody biomarkers were discovered and some of the new ligands bound to either of the same antibody that ADP1 and ADP3 bind to or to the antibody that ADP2 binds to.

AD Data Analysis: Microarray Data with A Single Measurement

Microarrays were prepared as described in U.S. Pat. Publication No. 2010/0303805 which is hereby incorporated by reference. Microarray slides are covered with hybridization chamber and equilibrated with 1×TBST (50 mM Tris, pH 8.0, 150 mM NaCl, 0.1% Tween20) for 15 minutes. The slides are then blocked with 1 ml of blocking buffer for 1 hour at 4° C. The blocking buffer is removed and the slides are incubated with 1 ml of serum (20 mg/ml) for 16 hours at 4° C. with gentle shaking. In an alternative method, the slides are blocked with 1 ml of E. coli lysate (1.5 mg/ml) for 1 hour at 4° C. The E. coli lysate is removed and the slides are incubated with 1 ml of serum (15 mg/ml) in E. coli lysate (1.5 mg/ml) for 18 hours at 4° C. with gentle shaking. Microarrays are then washed three times with 1×TBST and hybridized with Alexa-647 labeled Anti IgG antibody (5 mg/ml) for 2 hours on orbital shaker at 4° C. The chamber cassettes were removed from microarray slides and washed with 1×TBST (3×15 min) followed by 0.1×TBST (1×10).

The slides are then dried on centrifuge (5 min at 1500 RPM) and scanned on microarray scanner (Gene Pix Autoloader 4200) by using 635-nm laser at 100% power and 600 or 650 photomultiplier tube gain. All the scanned images were analyzed by the Gene Pix Pro 6.0 software and Genespring software.

The new peptoids or ligands built on the microarrays and tested against patient samples pursuant to the method described above in a blinded study. FIGS. 16-20 provide the results of these screening assays. The serum samples were taken from a pool of 34 patients. Each sample resulted in the intensity or lack thereof as shown in FIGS. 16-18. Two of the new peptoids (P1aag4 and P1aag2) were compared against known peptoids ADP3 and ADP2 in the same patient pool. These results show a direct correlation between the new peptoids versus the previous peptoids that had been validated in an unblinded study which proved a direct correlation between the presence of the AD associated antibody and the clinical symptoms or presence of the disease.

Figure 16A:
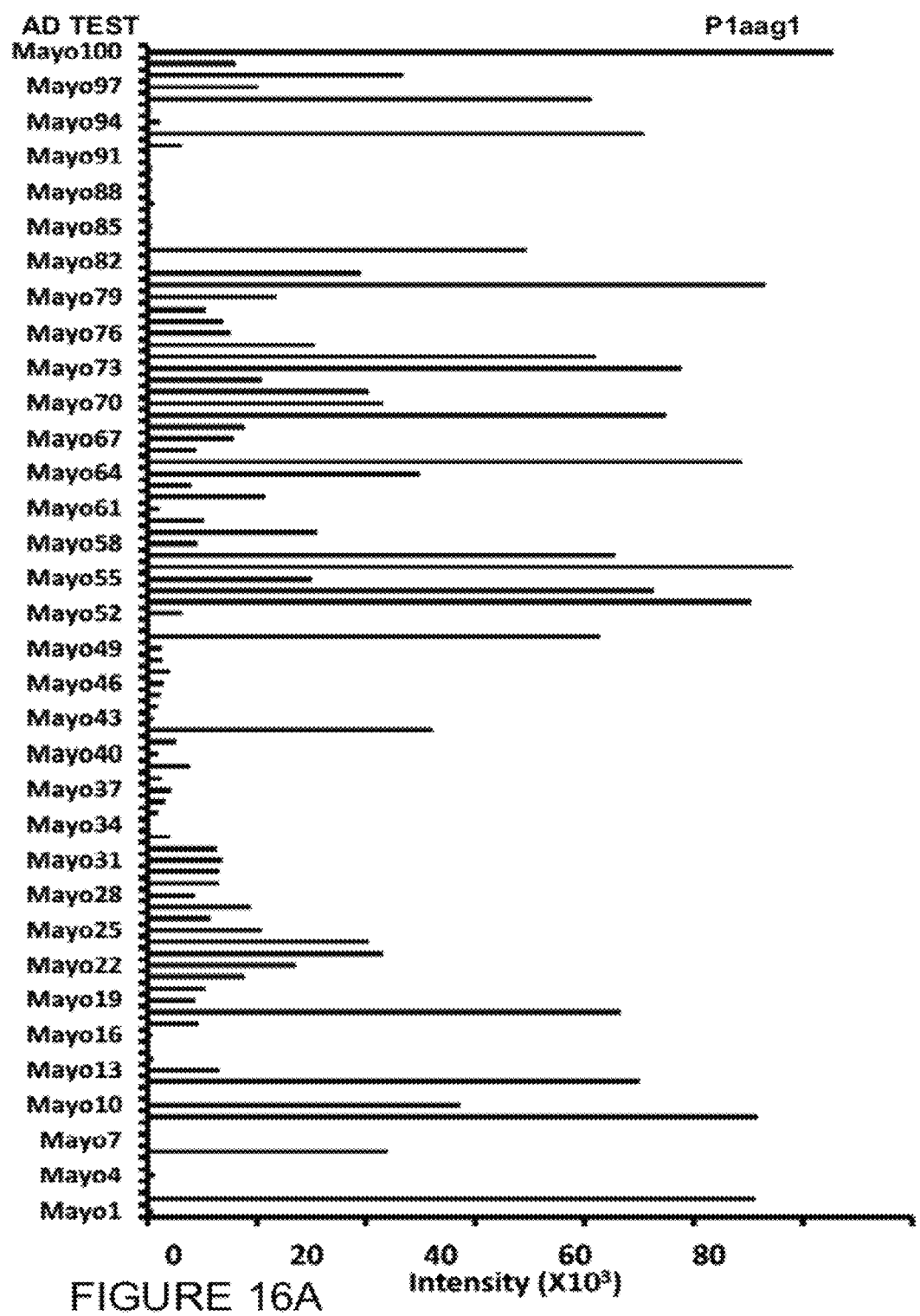
FIG. 16A shows AD test data (blinded) for a pool of patients using P1aag1 (JC3B-1) peptoid and FIG. 16B shows test data (blinded) for the same pool of AD patients using P1aag2 (JC3B-21). Each peptoid is presented on a microarray.
Figure 16B:
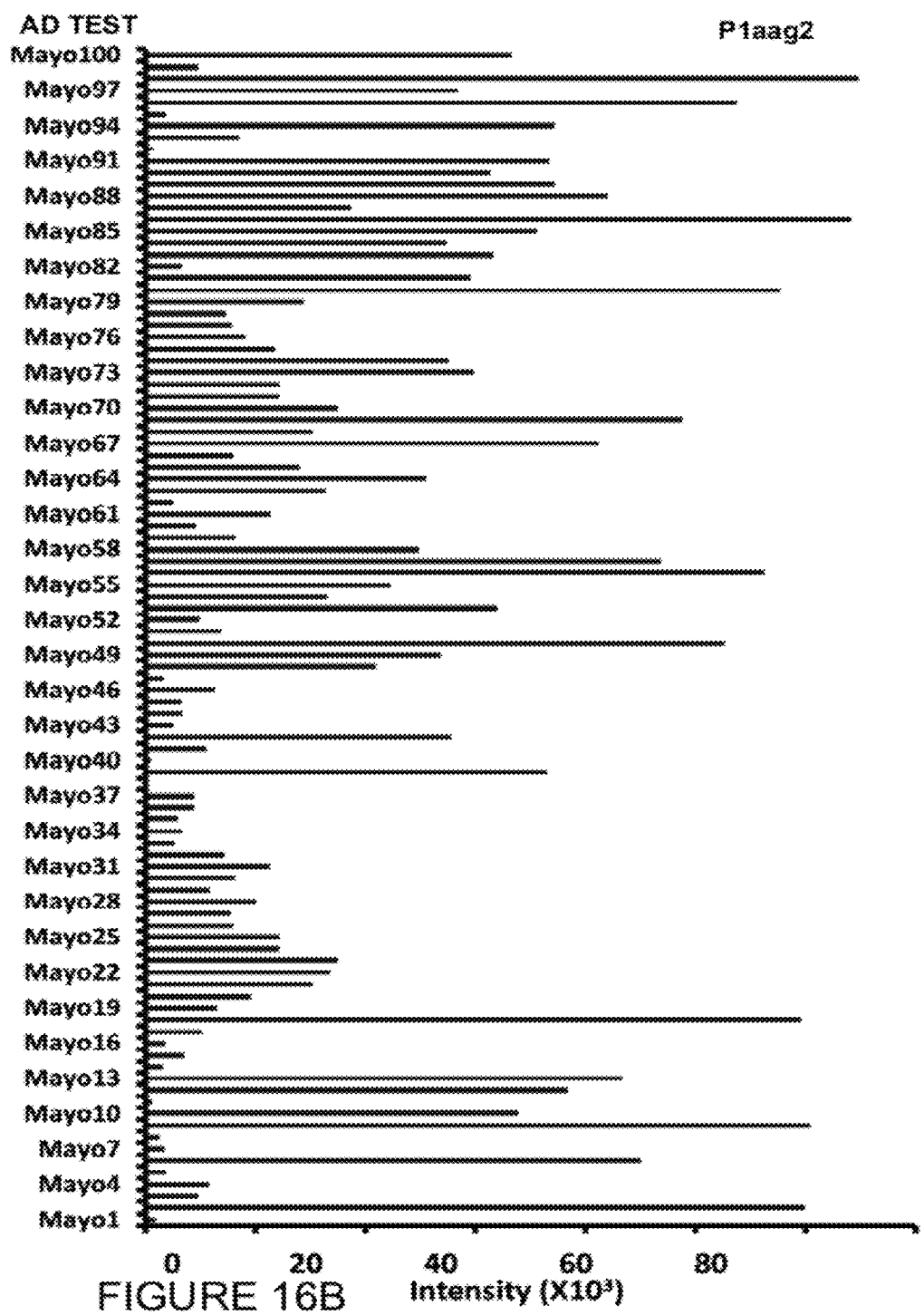

FIG. 16A shows the data for a group of serum samples (20 ug/mL) from 34 subjects screened with peptoid P1aag1 on a microarray. FIG. 16B shows the data for a group of serum samples from 34 subjects screened with peptoid P1aag2 on a microarray.

Figure 17A:
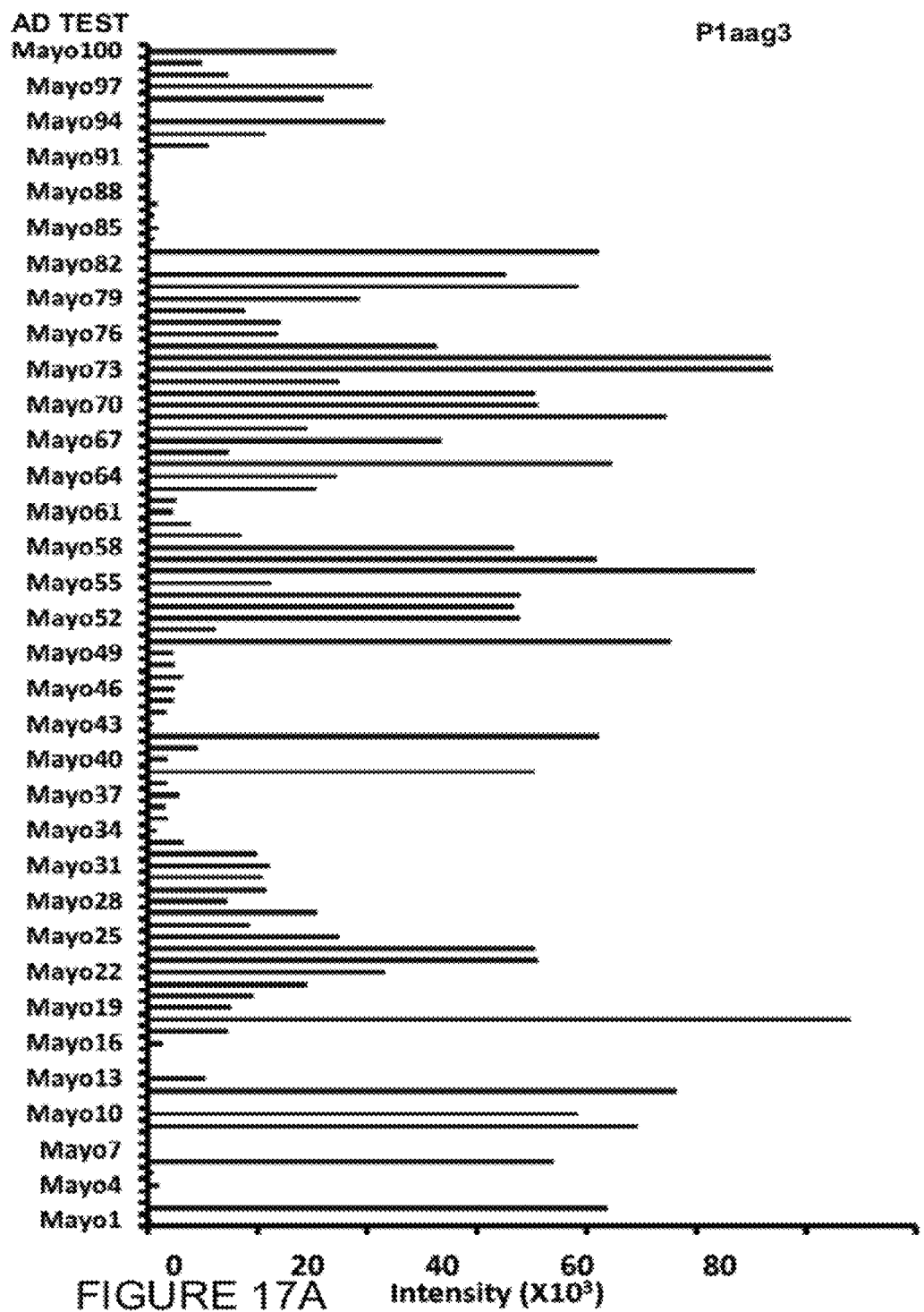
FIG. 17A shows AD test data (blinded) for a pool of patients using P1aag3 (JC3B-7) peptoid and FIG. 17B shows test data (blinded) for the same pool of AD patients using P1aag4 (JC3B-5). Each peptoid is presented on a microarray.
Figure 17B:
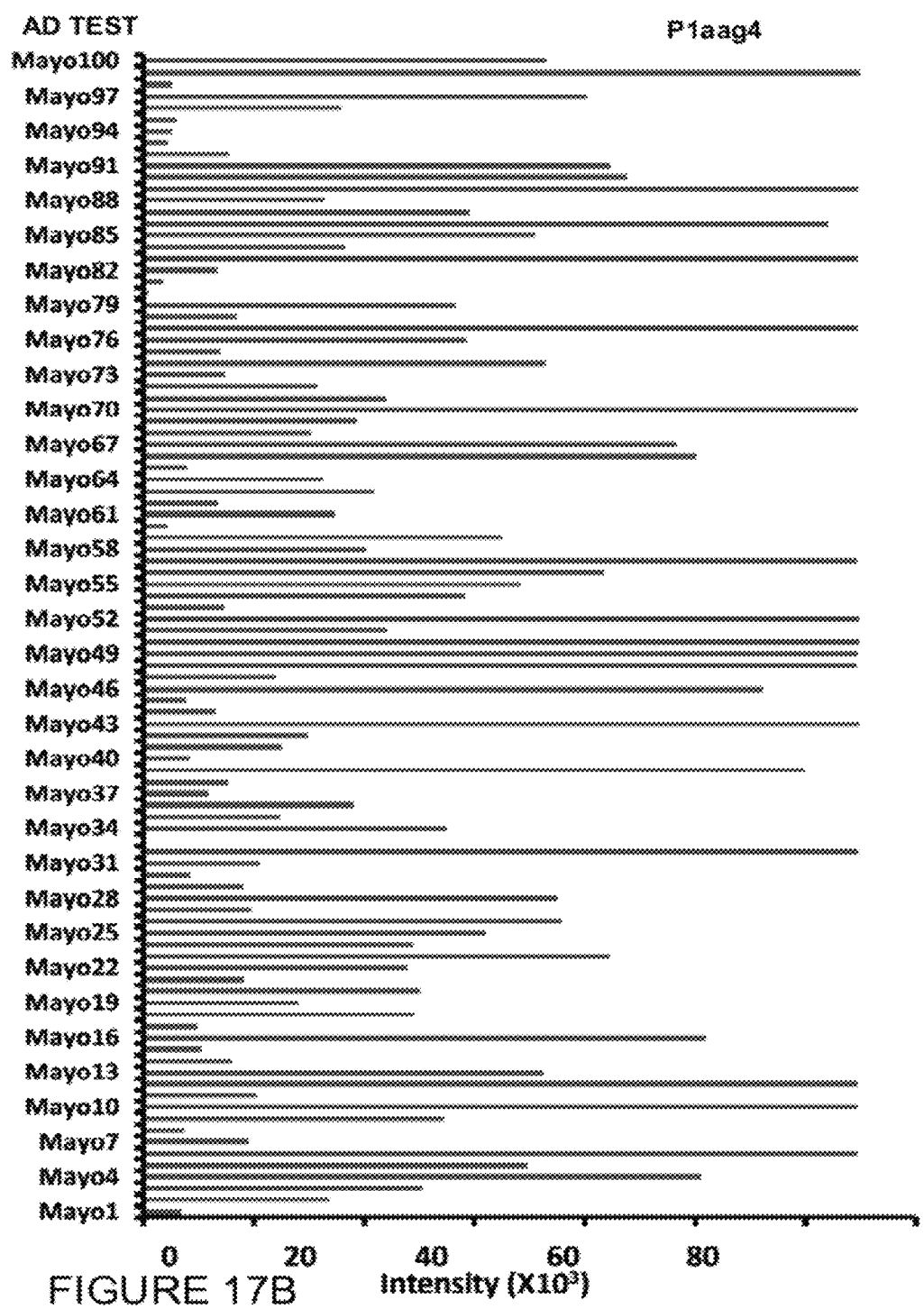

FIG. 17A shows the data for a group of serum samples from 34 subjects screened with peptoid P1aag3 on a microarray. FIG. 17B shows the data for a group of serum samples from 34 subjects screened with peptoid P4aag1 on a microarray.

Figure 18A:
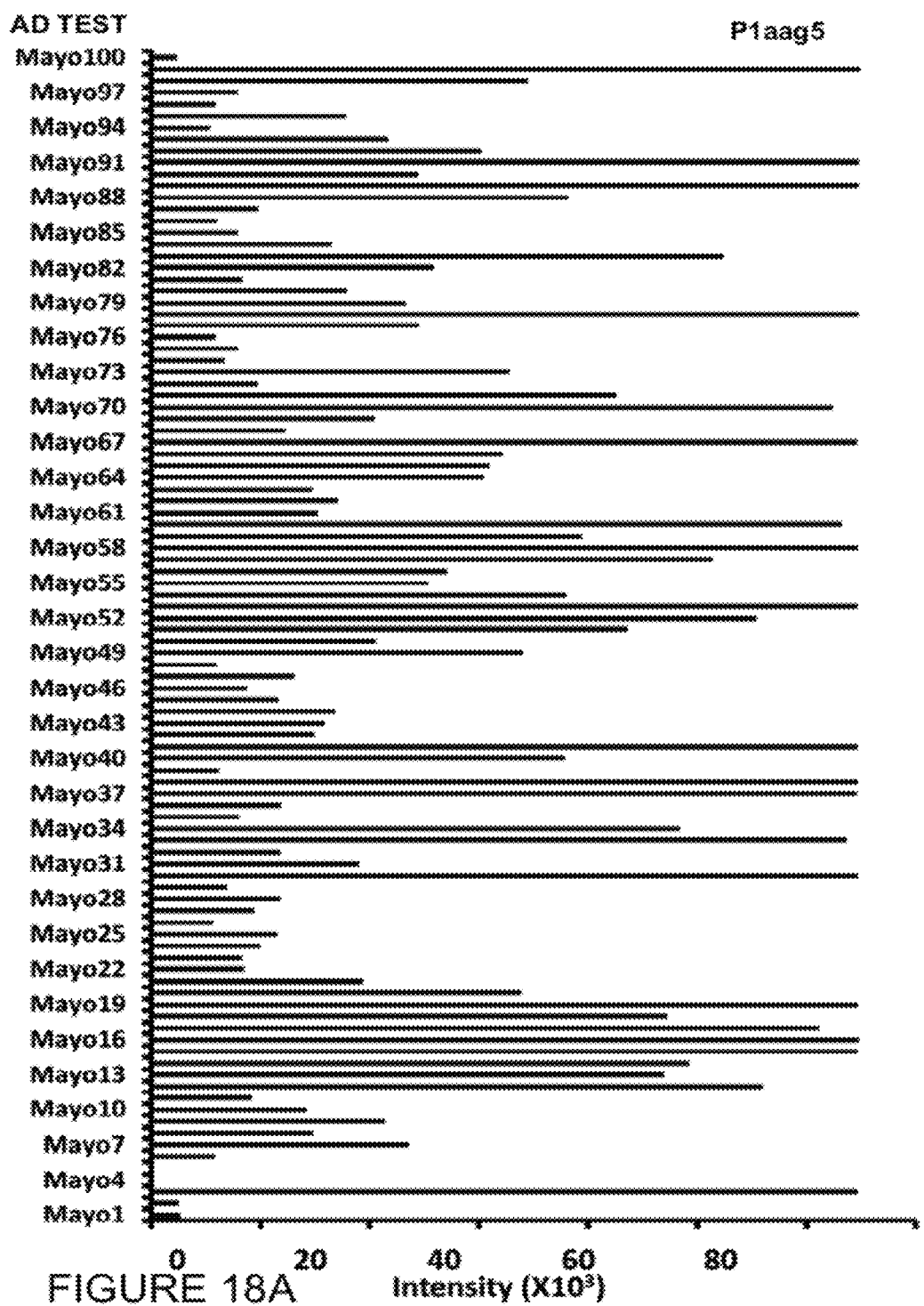
FIG. 18A shows AD test data (blinded) for a pool of patients using P1aag5 (JC3B-R8) peptoid and FIG. 18B shows test data (blinded) for the same pool of AD patients using P1aag6 (JC3B-R12). Each peptoid is presented on a microarray.
Figure 18B:
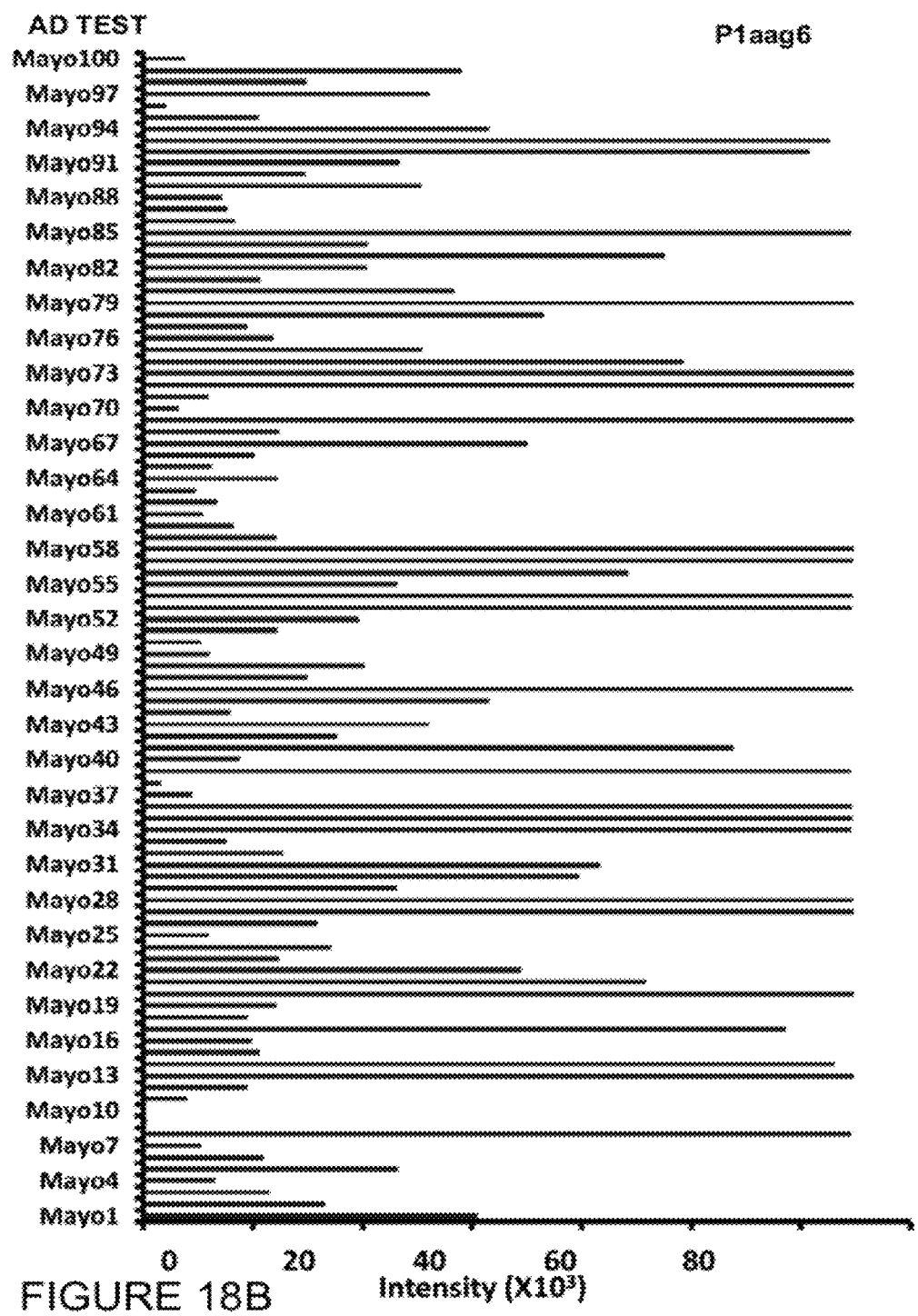

FIG. 18A shows the data for a group of serum samples from 34 subjects screened with peptoid P1aag5 on a microarray. FIG. 18B shows the data for a group of serum samples from 34 subjects screened with peptoid P1aag6 on a microarray.

Each of these peptoids is otherwise shown in FIG. 13. P1aag1 is JC3B-1; P1aag2 is JC3B-21; P1aag3 is JC3B-7; P1aag4 is JC3B-5; P1aag5 is JC3B-R8 and P1aag6 is JC3B-R12.

Figure 19A:
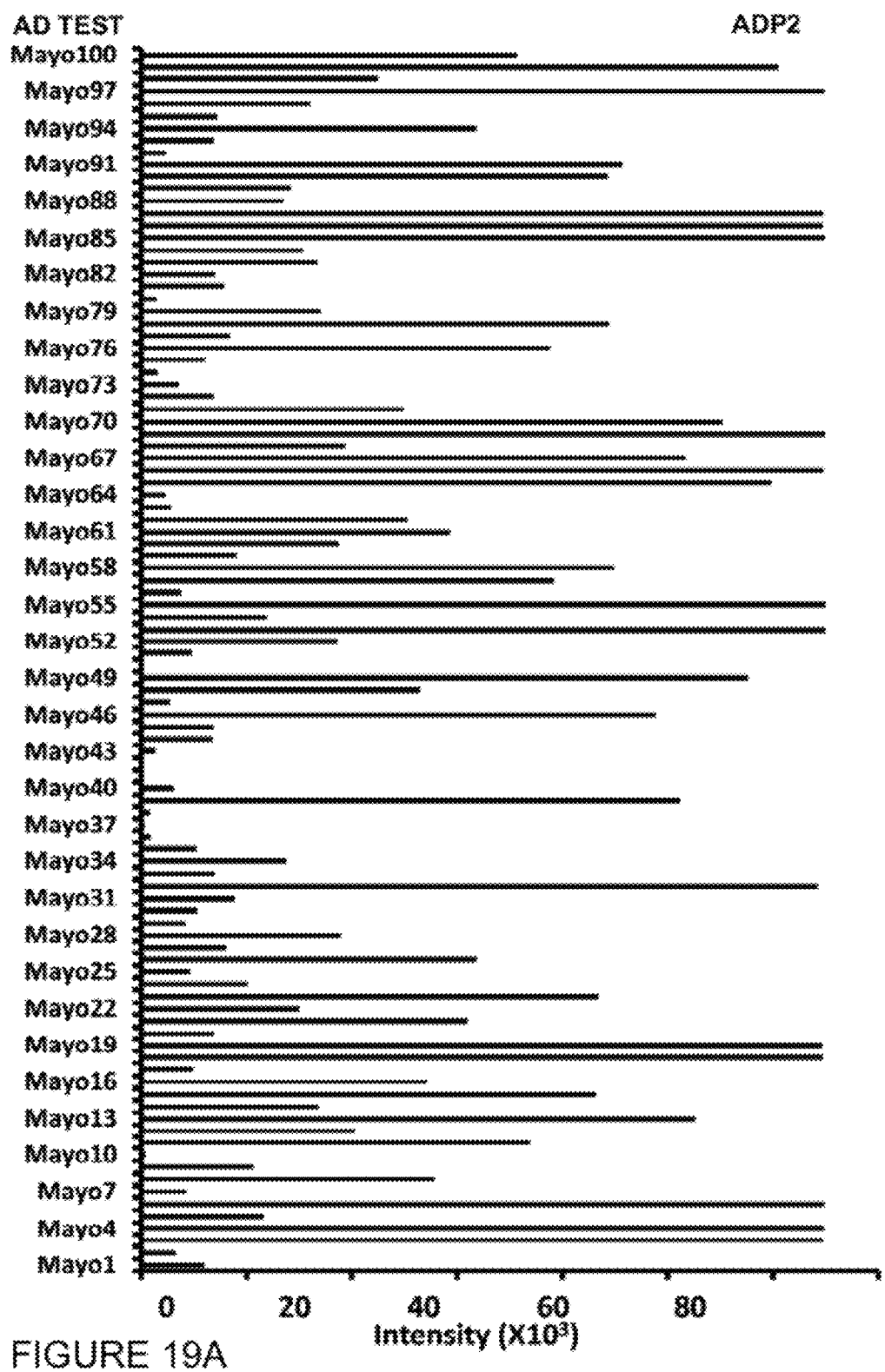
FIG. 19A shows microarray data for ADP2 in the same pool of patients for the tests conducted using P1aag1-6.
Figure 19B:
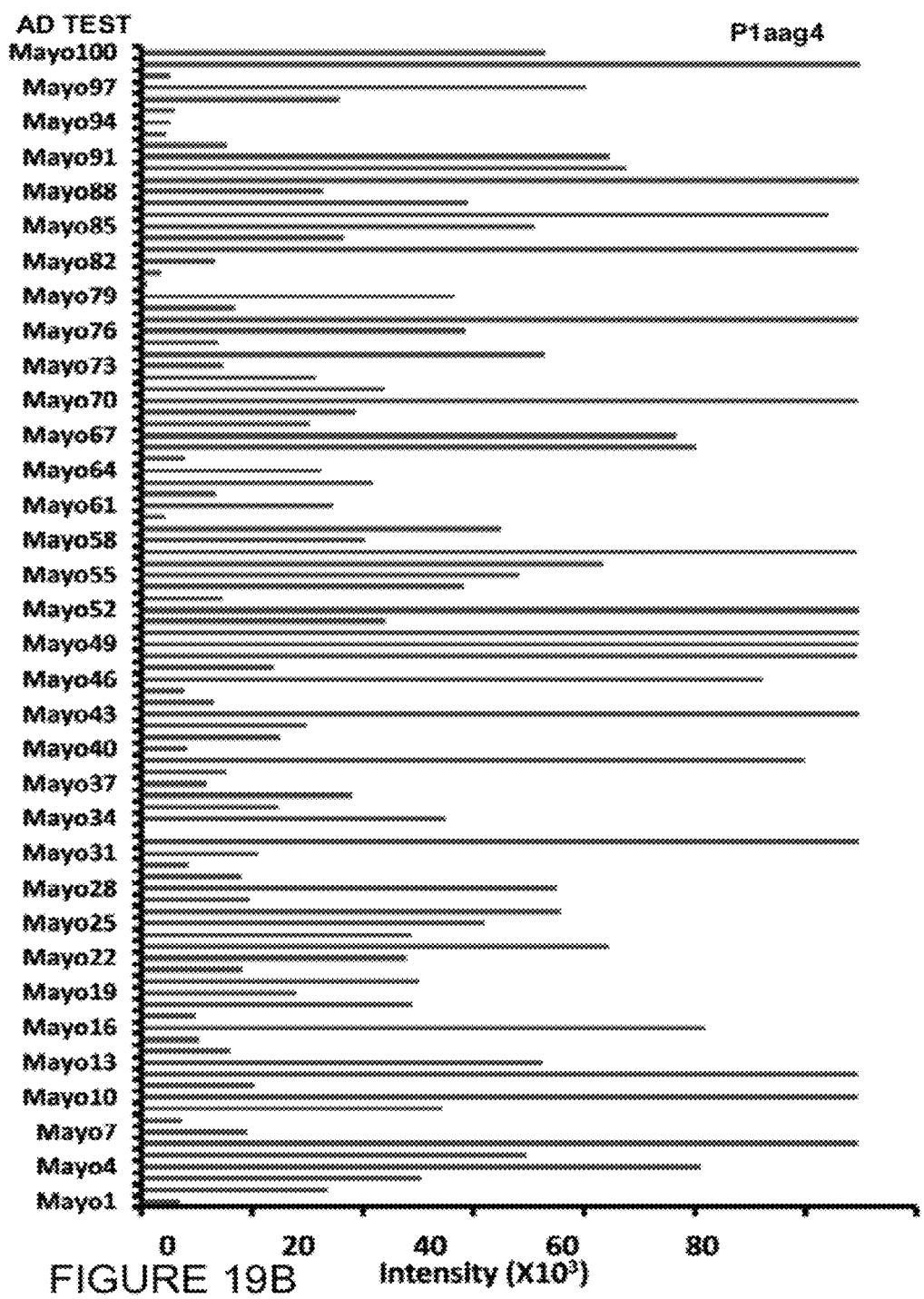
FIG. 19B shows comparative data using P1aag4 with the same set of patients. The data shows a clear correlation between the results achieved with a previously identified ADP2 and the newly identified P1aag4 in the same patient pool.

FIG. 19A shows ADP2 microarray data. FIG. 19B shows P1aag4 microarray data using patient serum from the same patient pool. There is at least a 90% correlation between the data set on the left with ADP2 and the dataset on the right with P1aag4.

Figure 20A:
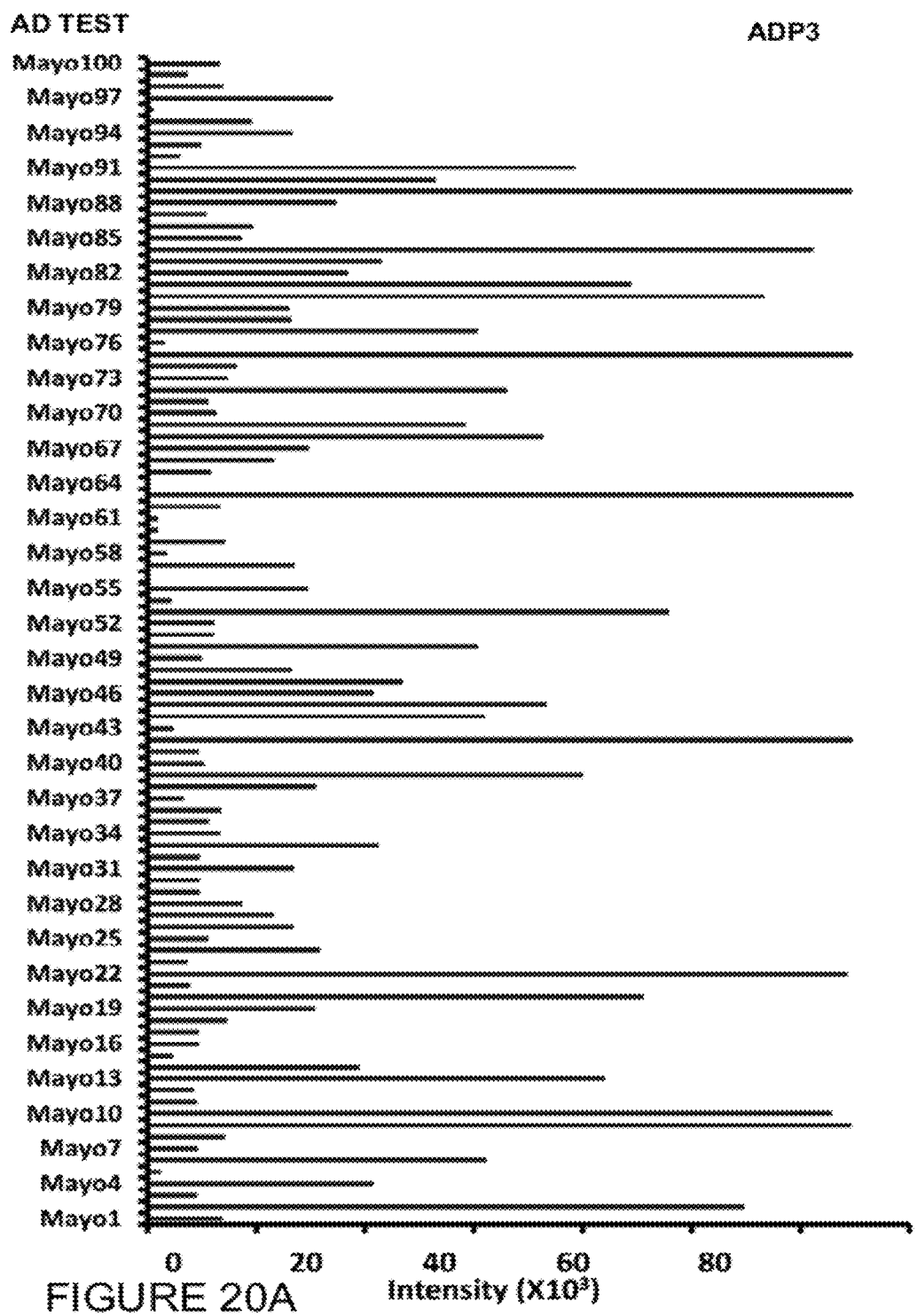
FIG. 20A shows microarray data for ADP3 in the same pool of patients for the tests conducted using P1aag1-6.
Figure 20B:
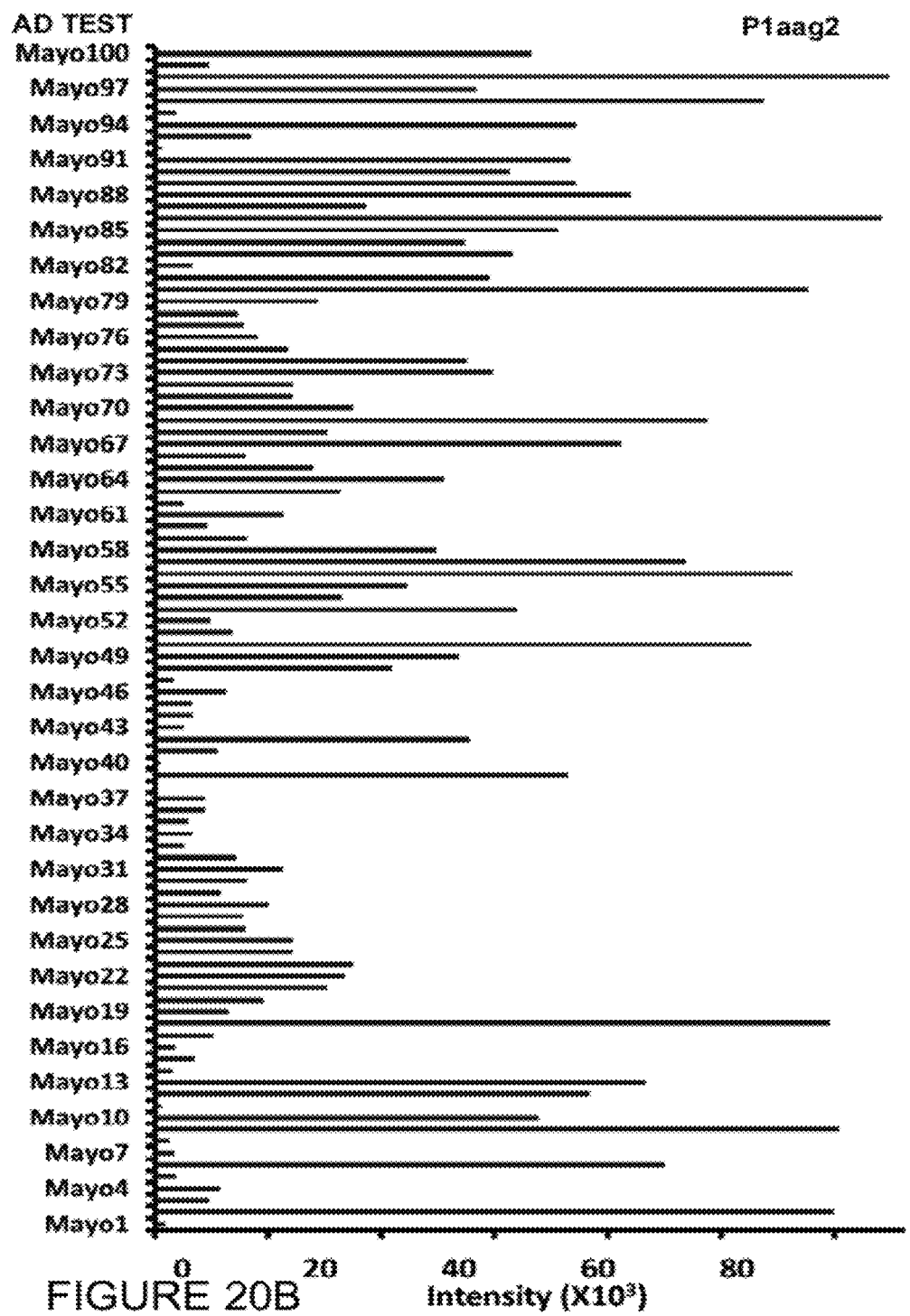
FIG. 20B shows comparative data using P1aag2 with the same set of patients. The data shows a clear correlation between the results achieved with a previously identified ADP3 and the newly identified P1aag2 in the same patient pool.

FIG. 20A shows ADP3 microarray data. FIG. 20B shows P1aag2 microarray data using patient serum samples in the same patient pool. There is at least a 90% correlation between the data set on the left with ADP3 and the dataset on the right with P1aag2.

Figure 21:
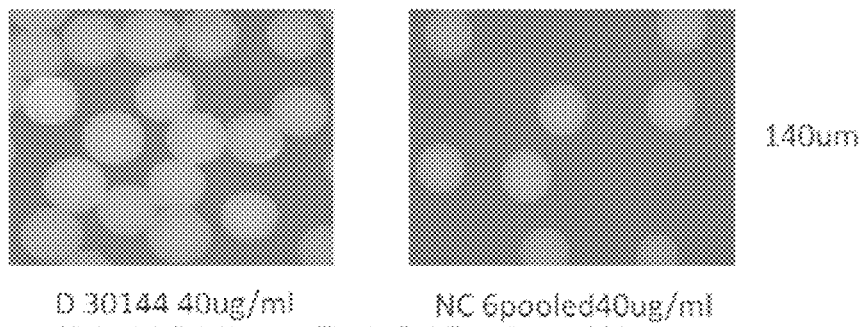
FIG. 21 shows a validation of P1aag5 (putative hit 5 or JC3B-R8) on TentaGel beads in a comparison of diseased AD serum versus healthy control (pooled) at 40 ug/mL.

FIG. 21 shows validation of use of a peptoid (JC3B-R8) in a tentagel based screen for Alzheimer's. 140 micron (um) beads were used and the serum concentration was 40 ug/mL. There was a clear distinction between diseased beads and non-diseased (normal control) beads.

Figure 50:
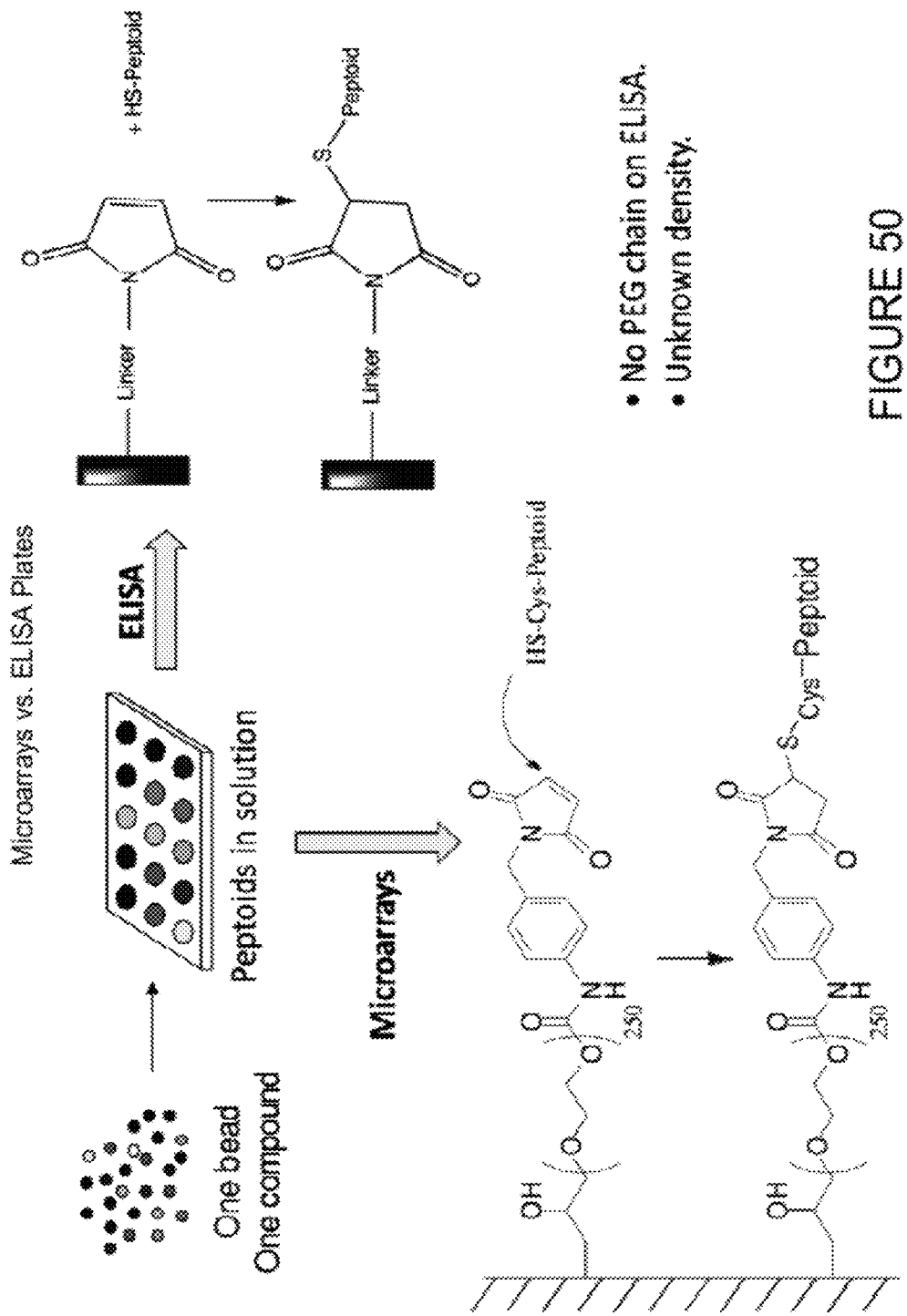
FIG. 50 shows a simple schematic of the preparation of and distinction between peptoids that are used in microarrays versus those peptoids that are placed on ELISA plates. Schematic for how peptoid microarrays are made: individual beads are segregated into the wells of microtiter plates and the peptoids are cleaved from the beads to make a concentrated stock solution. Note that each well will now contain a single kind of peptoid. Several thousand peptoids are then spotted onto chemically-modified glass microscope slides in such a way that they bind covalently to the surface. Several thousand slides can be produced highly reproducibly from a single synthetic library. The ELISA production is similar except that there is no PEG chain on the surface but the density of peptoids on the ELISA plate may be different than it is on the microarrays.

FIG. 50 shows a simple schematic of the preparation of and distinction between peptoids that are used in microarrays versus those peptoids that are placed on ELISA plates. Schematic for how peptoid microarrays are made: individual beads are segregated into the wells of microtiter plates and the peptoids are cleaved from the beads to make a concentrated stock solution. Note that each well will now contain a single kind of peptoid. Several thousand peptoids are then spotted onto chemically-modified glass microscope slides in such a way that they bind covalently to the surface. Several thousand slides can be produced highly reproducibly from a single synthetic library. The ELISA production is similar except that there is no PEG chain on the surface but the density of peptoids on the ELISA plate may be different than it is on the microarrays.

FIG. 51 shows ELISA experiments with a clear distinction between normal control and diseased serum at a serum dilution of 1:800 using horseradish peroxidase linked to a secondary antibody that detects the disease associated antibody-peptoid complex. The colorless substrate is added and changes color (blue) upon reaction with the bound HRP enzyme.

Figure 52A:
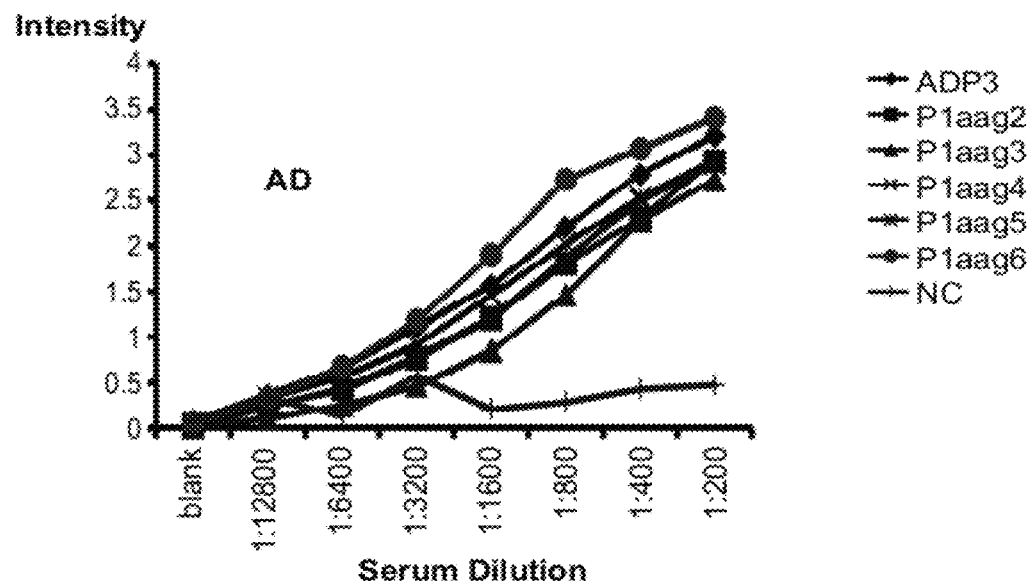
FIG. 52 shows titration data that compares various AD peptoids in an ELISA test at various serum dilutions of diseased serum (A) versus normal serum (B). There is no intensity of the signals in the normal serum but clear distinction and intensity of all of the AD peptoids as the concentration increases from 1:12,800 to 1:200.
Figure 52B:
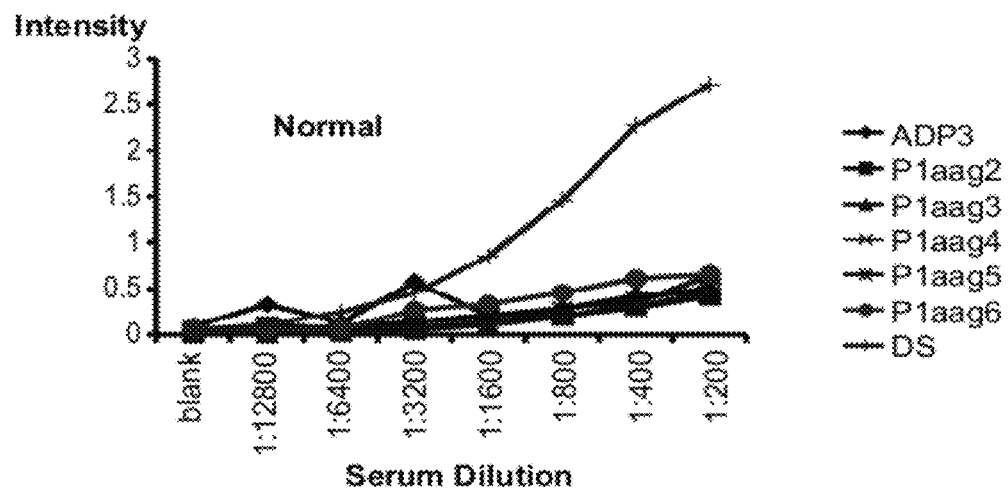

FIG. 52 shows titration data that compares various AD peptoids in an ELISA test at various serum dilutions of diseased serum (A) versus normal serum (B). There is no intensity of the signals in the normal serum but clear distinction and intensity of all of the AD peptoids as the concentration increases from 1:12,800 to 1:200.

Figure 53:
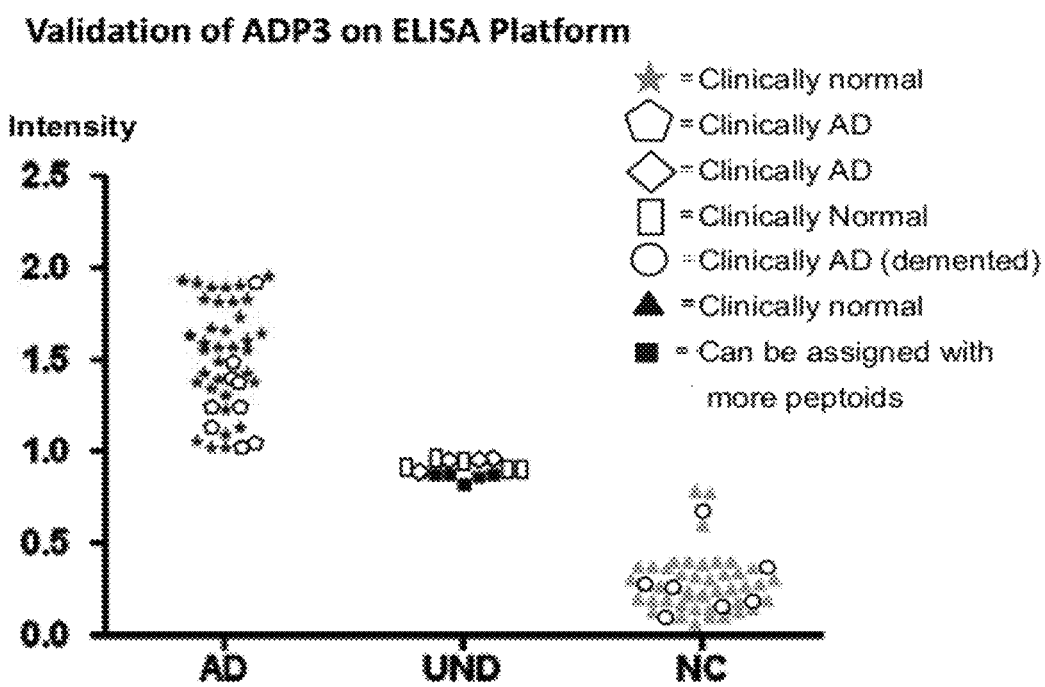
FIG. 53 provides a diagram that validates the correlation between the clinical diagnosis of the unblinded sample set of AD patients at various stages of Alzheimer's disease (or not) versus the data obtained from the same patient serum samples (blinded) and which were screened against ADP3 peptoid to detect disease associated antibodies. The results shown are from a blinded study of plasma samples from Mayo Clinic Jacksonville. UND=Undecided. The plot was derived from taking a single serum concentration (1:800) dilution. A reading of >1 was considered positive, a reading between 1 and 0.7 was considered undecided and a reading below 0.7 was considered negative.

FIG. 53 provides a diagram that validates the correlation between the clinical diagnosis of the unblinded sample set of AD patients at various stages of Alzheimer's disease (or not) versus the data obtained from the same patient serum samples (blinded) and which were screened against ADP3 peptoid to detect disease associated antibodies. The results shown are from a blinded study of plasma samples from Mayo Clinic Jacksonville. UND=Undecided. The plot was derived from taking a single serum concentration (1:800) dilution. A reading of >1 was considered positive, a reading between 1 and 0.7 was considered undecided and a reading below 0.7 was considered negative.

Figure 54:
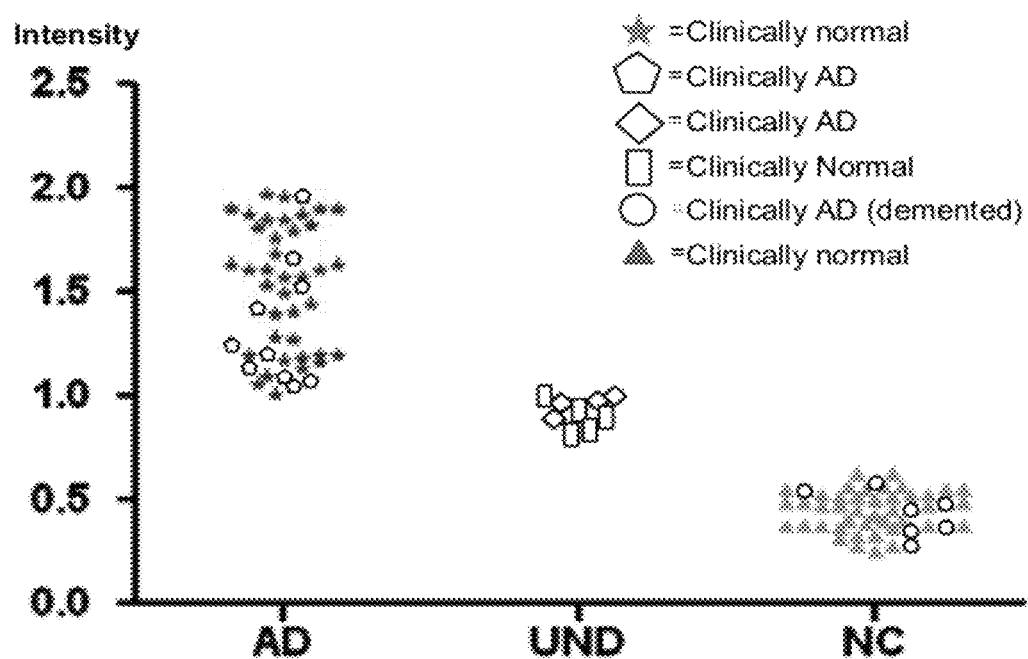
FIG. 54 provides a diagram that validates the correlation between the clinical diagnosis of the unblinded sample set of AD patients at various stages of Alzheimer's disease (or not) versus the data obtained from the same patient serum samples (blinded) and which were screened against the various AD peptoids (plot is average value of results of 9 peptoids) of the invention to detect disease associated antibodies. The results shown are from a blinded study of plasma samples from Mayo Clinic Jacksonville. UND=Undecided. The plot was derived from taking a single serum concentration (1:800) dilution. A reading of >1 was considered positive, a reading between 1 and 0.7 was considered undecided and a reading below 0.7 was considered negative.

FIG. 54 provides a diagram that validates the correlation between the clinical diagnosis of the unblinded sample set of AD patients at various stages of Alzheimer's disease (or not) versus the data obtained from the same patient serum samples (blinded) and which were screened against the various AD peptoids (plot is average value of results of 9 peptoids) of the invention to detect disease associated antibodies. The results shown are from a blinded study of plasma samples from Mayo Clinic Jacksonville. UND=Undecided. The plot was derived from taking a single serum concentration (1:800) dilution. A reading of >1 was considered positive, a reading between 1 and 0.7 was considered undecided and a reading below 0.7 was considered negative.

Figure 55:
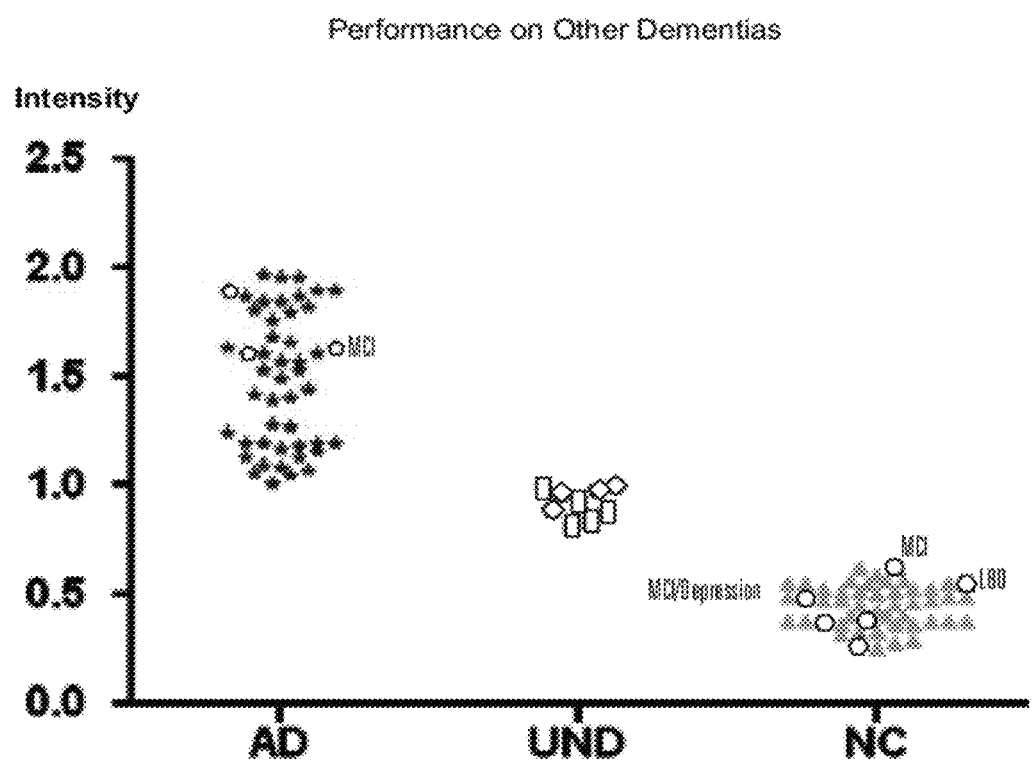
FIG. 55 provides a diagram that validates the correlation between the clinical diagnosis of the unblinded sample set of AD patients at various stages of Alzheimer's disease (or not) versus the data obtained from the same patient serum samples (blinded) and which were screened against the various AD peptoids of the invention to detect disease associated antibodies. The results shown are from a blinded study of plasma samples from Mayo Clinic Jacksonville. UND=Undecided. The plot was derived from taking a single serum concentration (1:800) dilution. A reading of >1 was considered positive, a reading between 1 and 0.7 was considered undecided and a reading below 0.7 was considered negative. The data also shows performance on other dementias where MCI/depression samples are labeled and Lewis Body Dementia samples are marked as well. The data shows that at least three MCI patients have serum samples with detectable amounts above 1 of the antibodies captured by the AD selective peptoids of the invention.

FIG. 55 provides a diagram that validates the correlation between the clinical diagnosis of the unblinded sample set of AD patients at various stages of Alzheimer's disease (or not) versus the data obtained from the same patient serum samples (blinded) and which were screened against the various AD peptoids of the invention to detect disease associated antibodies. The results shown are from a blinded study of plasma samples from Mayo Clinic Jacksonville. UND=Undecided. The plot was derived from taking a single serum concentration (1:800) dilution. A reading of >1 was considered positive, a reading between 1 and 0.7 was considered undecided and a reading below 0.7 was considered negative. The data also shows performance on other dementias where MCI/depression samples are labeled and Lewis Body Dementia samples are marked as well. The data shows that at least three MCI patients have serum samples with detectable amounts above 1 of the antibodies captured by the AD selective peptoids of the invention.

Figure 56A:
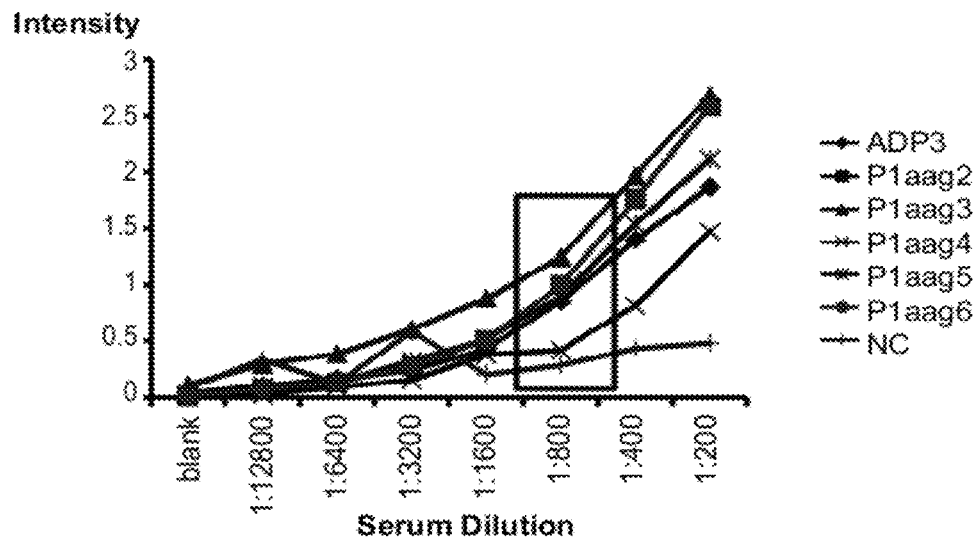
FIGS. 56A-D provide data on that subset of samples from patients that have disagreements between the Opko Health peptoid diagnostic assay using multiple AD peptoids versus the clinical diagnosis after this information was provided when unblinded.
Figure 56B:
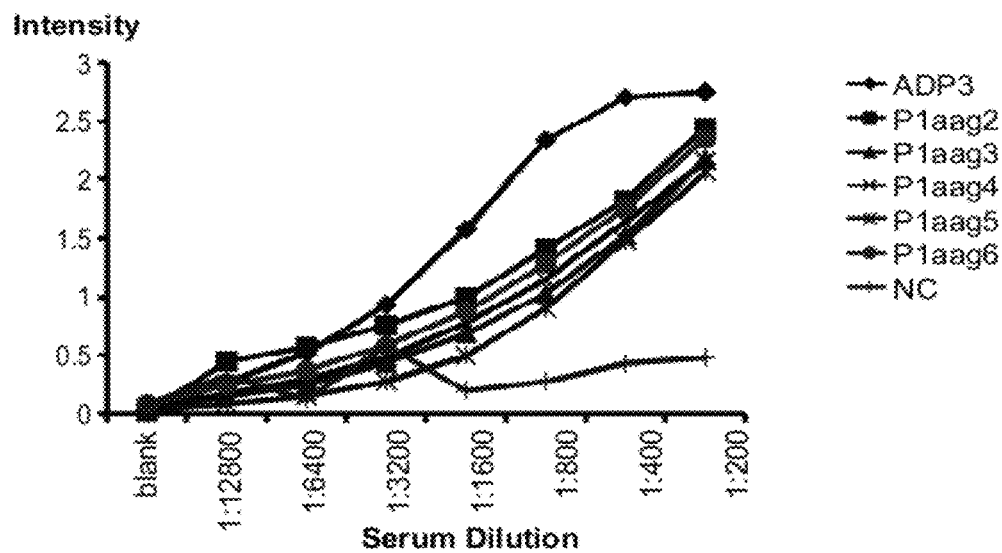
Figure 56C:
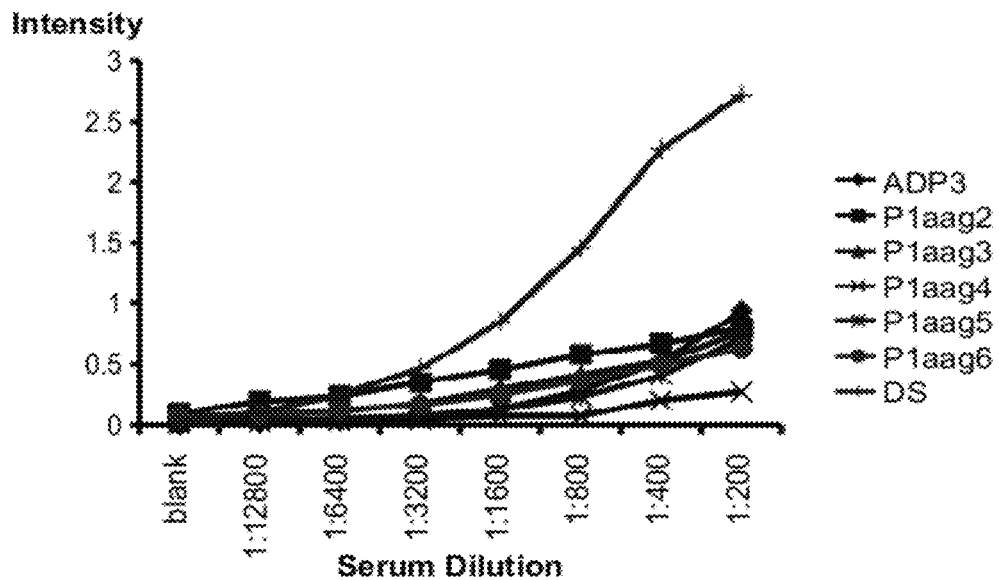
Figure 56D:
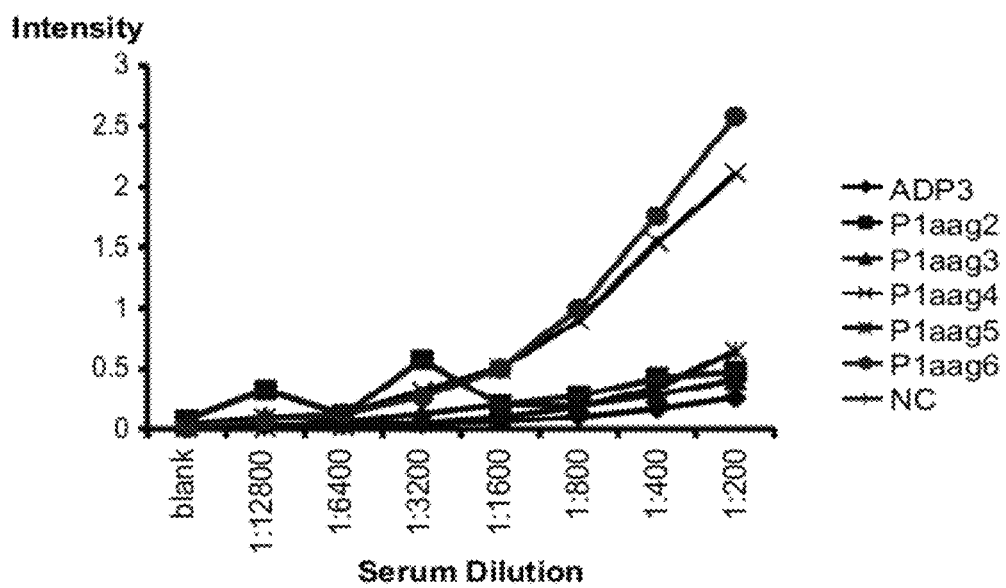

FIGS. 56A-D provide data on that subset of samples from patients that have disagreements between the Opko Health peptoid diagnostic assay using multiple AD peptoids versus the clinical diagnosis after this information was provided when unblinded. FIG. 56A shows the data for peptoids ADP3 and others as shown for a patient that was diseased clinically but for which the Opko peptoid P1aag4 was below 1.0 (UND at a single point; Titration AD positive). All other Opko peptoids were positive for AD (i.e., above 1.0). FIG. 56B shows that all Opko peptoids were positive for disease associated antibodies in a patient that was currently diagnosed as normal (non-demented) suggesting pre-AD. FIG. 56C shows that none of the Opko AD peptoids showed an intensity above 1 at any dilution point in a patient that was clinically diagnosed with AD suggesting that this patient had some other form of dementia. FIG. 56D shows that in a clinically positive AD patient, multiple Opko AD peptoids were not positive for disease associated antibodies but two peptoids (P1aag6 and P1aag4) were positive, thus UND at a single point and UND even after titration.

Figures 57, 58:
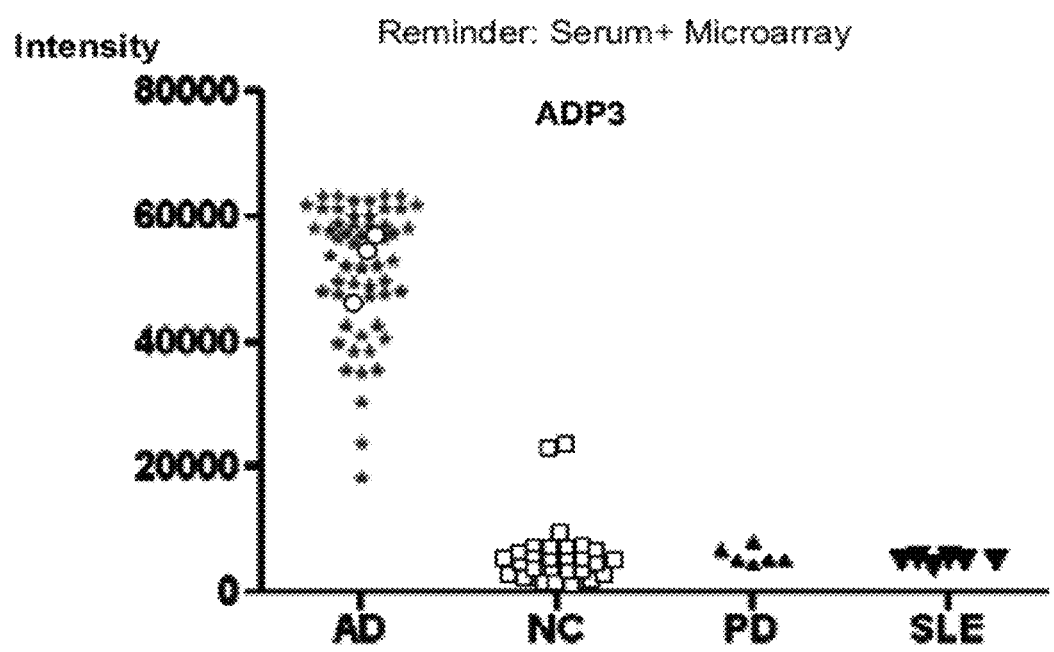
FIG. 57 shows the cluster diagram generated from previous AD samples using a microarray spotted with ADP3. There is a clear correlation between diseased versus control in the microarray data and data generated using the ELISA platform.
FIG. 58 provides a summary of ELISA analysis using a total of 106 serum samples tested.

FIG. 57 shows the cluster diagram generated from previous AD samples using a microarray spotted with ADP3. There is a clear correlation between diseased versus control in the microarray data and data generated using the ELISA platform. FIG. 57 also shows that the ADP3 peptoid is selected for disease associated antibodies associated with Alzheimer's disease and not Parkinsons or Lupus (SLE).

FIG. 58 provides a summary of ELISA analysis using a total of 106 serum samples tested. With this data, 9 samples could not be called (clinically 4 AD, 5 normal) from the single point data. Examination of titration curves assigned 3 of the 9 to be in agreement with the clinical data. 6 remain unclear (disagreement amongst different peptoids).

Figure 59A:
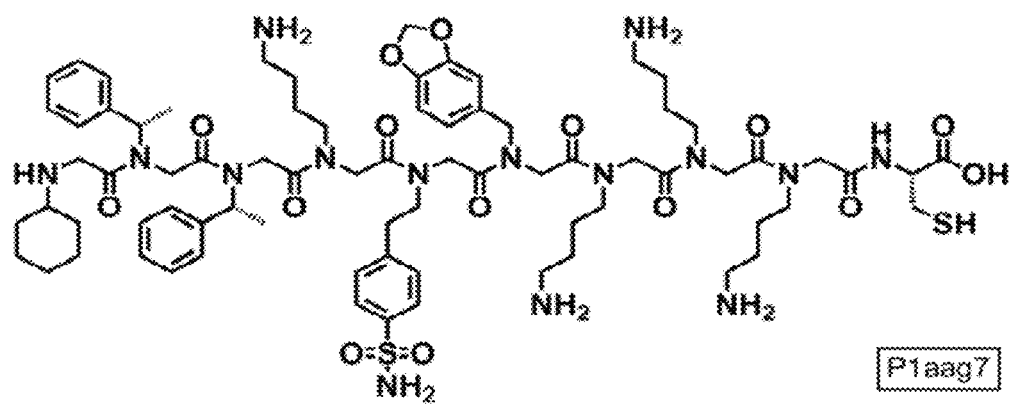
FIG. 59 provides the chemical structures of P1aag7-9.
Figure 59B:
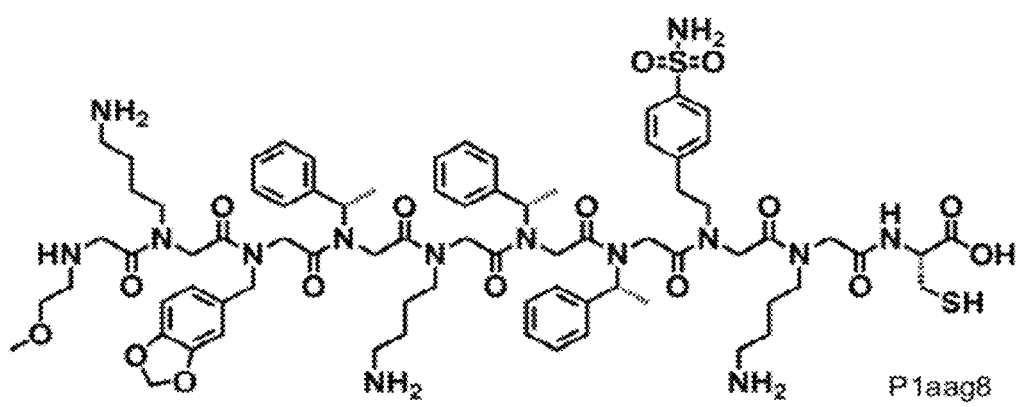
Figure 59C:
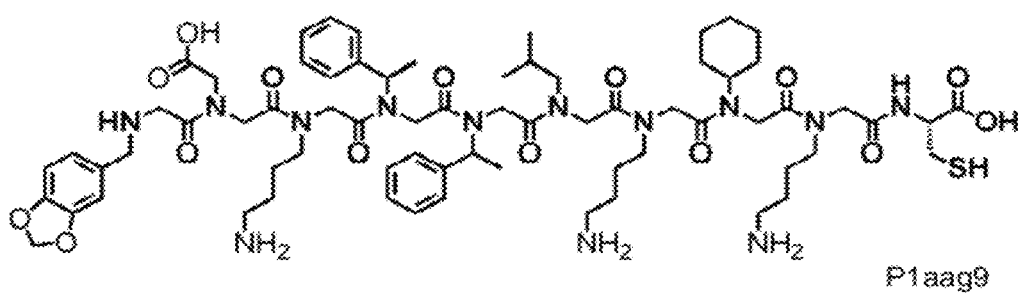

FIG. 59 provides the chemical structures of P1aag7-9.

The data presented in the above Figures with respect to an Opko diagnostic method to detect disease associated antibodies associated with Alzheimer's disease confirm that the methods disclosed and recited herein are powerful tools to confirm and/or predict the onset of Alzheimer's and/or confirm that the neurological disease or disorder is some other neurological disorder like mild cognitive impairment. The data clearly support earlier filed patent applications that claim and disclose certain peptoids and methods to detect disease associated antibodies. Herein, completely novel peptoids discovered through an entirely new and novel and more rapid screening process were validated in multiple platforms including microarrays and in ELISA against clinical data in patients having various stages of Alzheimer's disease symptoms and correlated significantly with the actual clinical data after unblinding.

Example 4 Pancreatic Cancer Screening

Peptoid libraries were generated to perform screens of serum from pancreatic cancer patients. Two libraries (JC3B and JC5B) were synthesized. 26 total hits were obtained in the screens against pancreatic cancer biomarkers. The JC3B library comprised amines selected from diaminobutane; R-methylbenzylamine; isobutylamine; cyclohexylamine; piperonylamine; 4-(aminoethyl)benzenesulfonamide; furfurylamine and 2-methoxyethylamine. The JC5B library was built from amines selected from isobutylamine; 2-methoxyethylamine; diaminobutane; furfurylamine; cyclohexylamine; R-methylbenzylamine; piperonylamine and 4-(aminoethyl)benzenesulfonamide. Pooled 6 samples of each pancreatic disease serum and control serum were used for screening. JC3B conditions: used 5 ul of each diseased serum sample in 4 ml PBS blocking buffer and used 5 ul each normal serum sample in 4 ml 1×TBST. JC5B conditions: Used 10 ug/ml diseased serum in 4 ml PBS blocking buffer and used 150 ug/ml control serum in 4 ml 1×TBST. Dnay bead screen: added 50 ul goat anti-human IgG DYNA beads to 1 ml 1×TBST. A DYNA bead screen was performed to remove non-specific hits. Quantum dot screen: Added 10 ul/1 ml goat anti-human IgG Quantum Dot 655 to 1×TBST; screened using the UV microscope to remove hits. Hit Validation: JC3B: added 2 ul of each control PC sample into 1 ml 1×TBST to screen hits; remove red (non-specific) beads; added 2 ul of each disease PC sample into 1 ml blocking buffer to screen hits; remove read beads (real hits) and cleave for sequencing. This was performed on both DYNA bead hits and Q dot hits. 12 hits were re-confirmed. JC5B: Added 50 ug/ml of pooled disease samples into 1 ml blocking buffer to hits; added 15 ug/ml pooled control samples into 1×TBST to hits; remove red beads (real hits) and cleave for sequencing; performed this on both DYNA bead hits and Q dot hits. 14 hits reconfirmed.

Figure 22:
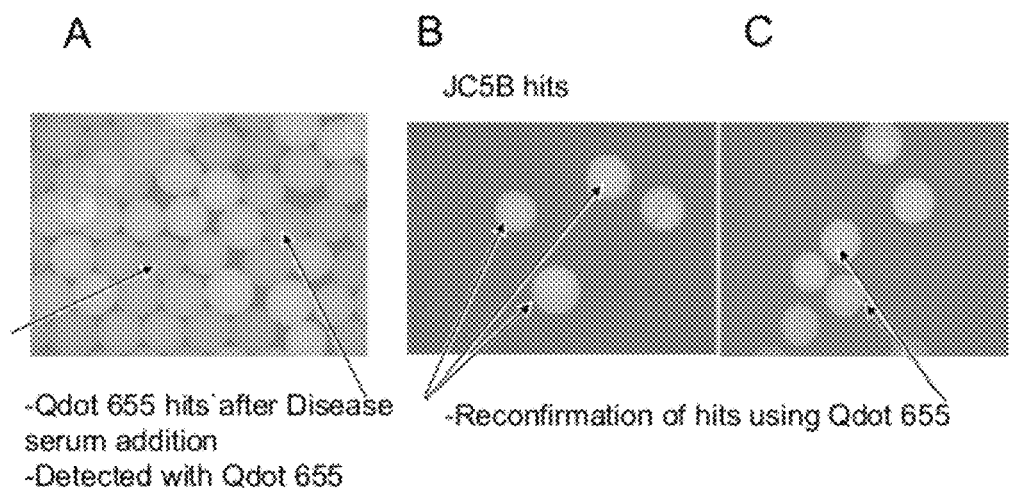
FIG. 22A shows the peptoid hits in the pancreatic cancer screen using QDot 655 and using the JC5B library.
FIGS. 22B and C show reconfirmation of hits using QDot 655 (arrows point to hits).

FIG. 22 (left picture) The peptoid library was incubated with serum from Pancreatic Cancer patients. Afterwards, the library was incubated with a secondary detection antibody (goat anti-human IgG tagged with Quantum dot 655 (Invitrogen). Hit beads were detected under a UV microscope containing a DAPI filter, and beads that were red in color were picked as hits to be sequenced for further testing.

(right picture): After Pancreatic Cancer Disease hits were isolated from the peptoid library, a 1% SDS wash was performed to strip the hits from any residual antibody. Beads were then incubated with individual serum samples from pancreatic cancer patients, and then with goat anti-human human IgG Quantum Got 655. Beads were then visualized under a UV microscope to determine if hits would re-confirm with individual samples. The consistently reconfirmed hits were chosen to sequence.

Figure 23:
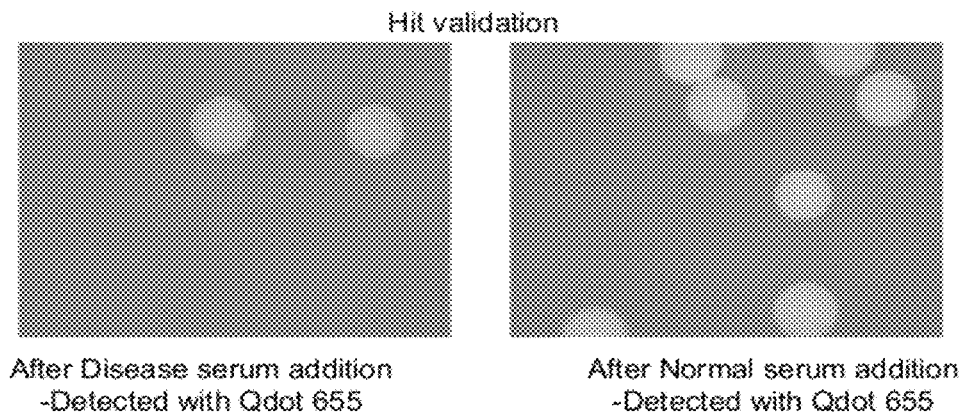
FIG. 23 shows pancreatic peptoid hit validation and compares disease serum addition and detection with QDot 655 versus normal serum addition.

FIG. 23: (left) Hit validation pictures demonstrate the efficacy of the Tentagel screen. After Pancreatic Cancer Disease hits were isolated from the peptoid library, a 1% SDS wash was performed to strip the hits from any residual antibody. Beads were then incubated with individual serum samples from pancreatic cancer patients, and then with goat anti-human IgG Quantum Got 655. Beads were then visualized under a UV microscope to determine if hits would re-confirm with individual samples. The consistently reconfirmed hits were chosen to sequence.

(right) Another SDS wash was performed on the hit beads, and the beads were then incubated with control serum, then with goat anti-human IgG Quantum Got 655. Beads were then visualized under a UV microscope to determine if hits would re-confirm with individual samples. The consistently reconfirmed hits were chosen to sequence.

Figure 24:
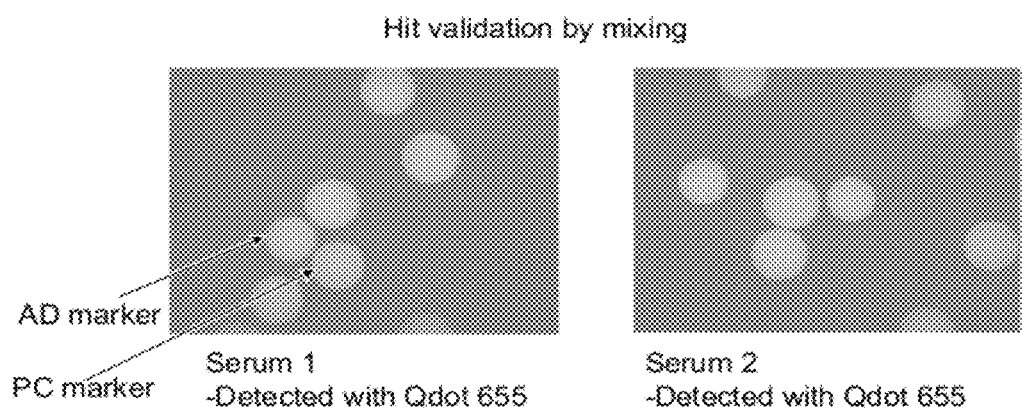
FIG. 24 shows hit validation by mixing AD markers and PC markers. The data shows that the PC marker was detected while there was no detectable antibody on the AD peptoid bead in the pancreatic cancer serum (Serum 1).

FIG. 24 shows hit validation in the pancreatic cancer screen by mixing. The data shows that the markers are specific for the particular disease (PC versus AD).

Figure 25:
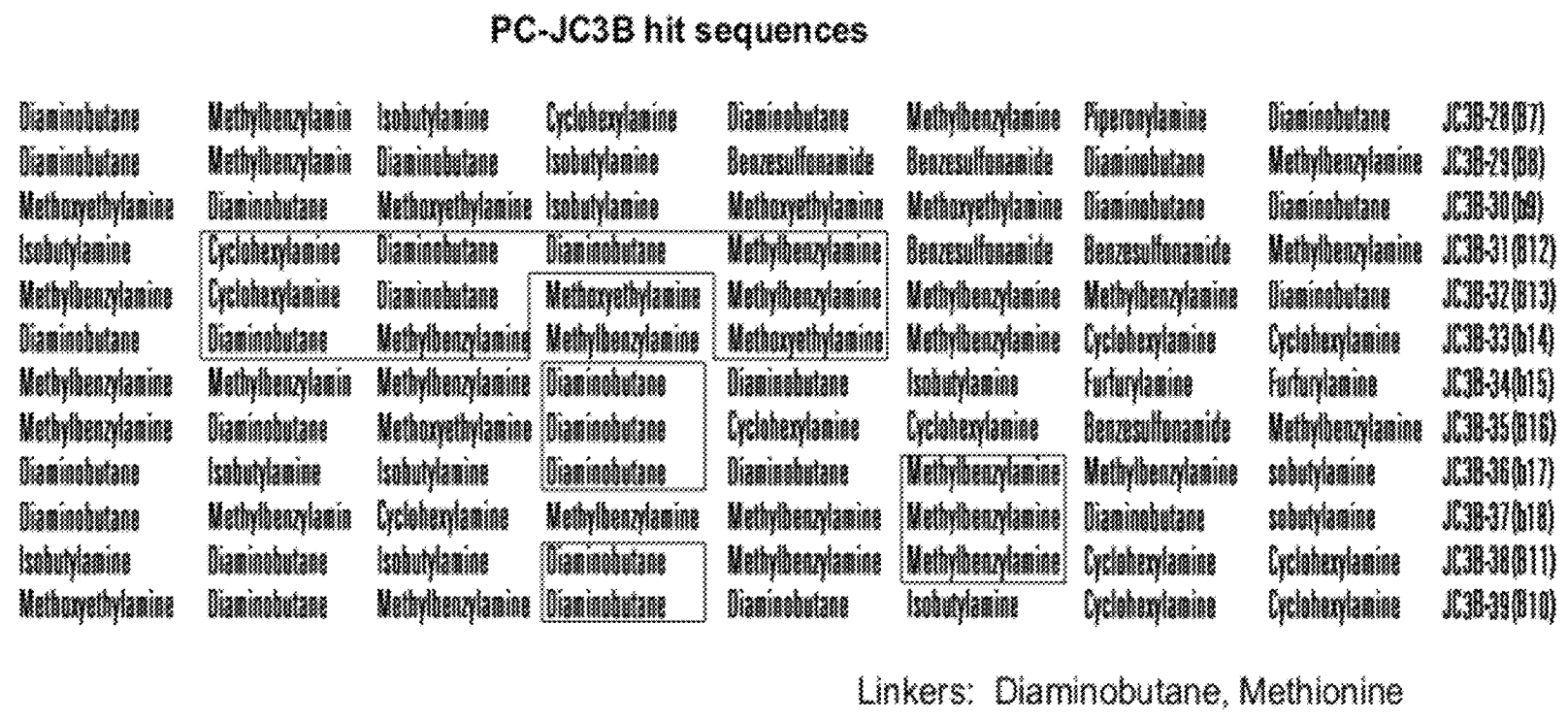

FIG. 25 shows the pancreatic cancer ligands (putative hits) from the JC3B library.

Figure 26:
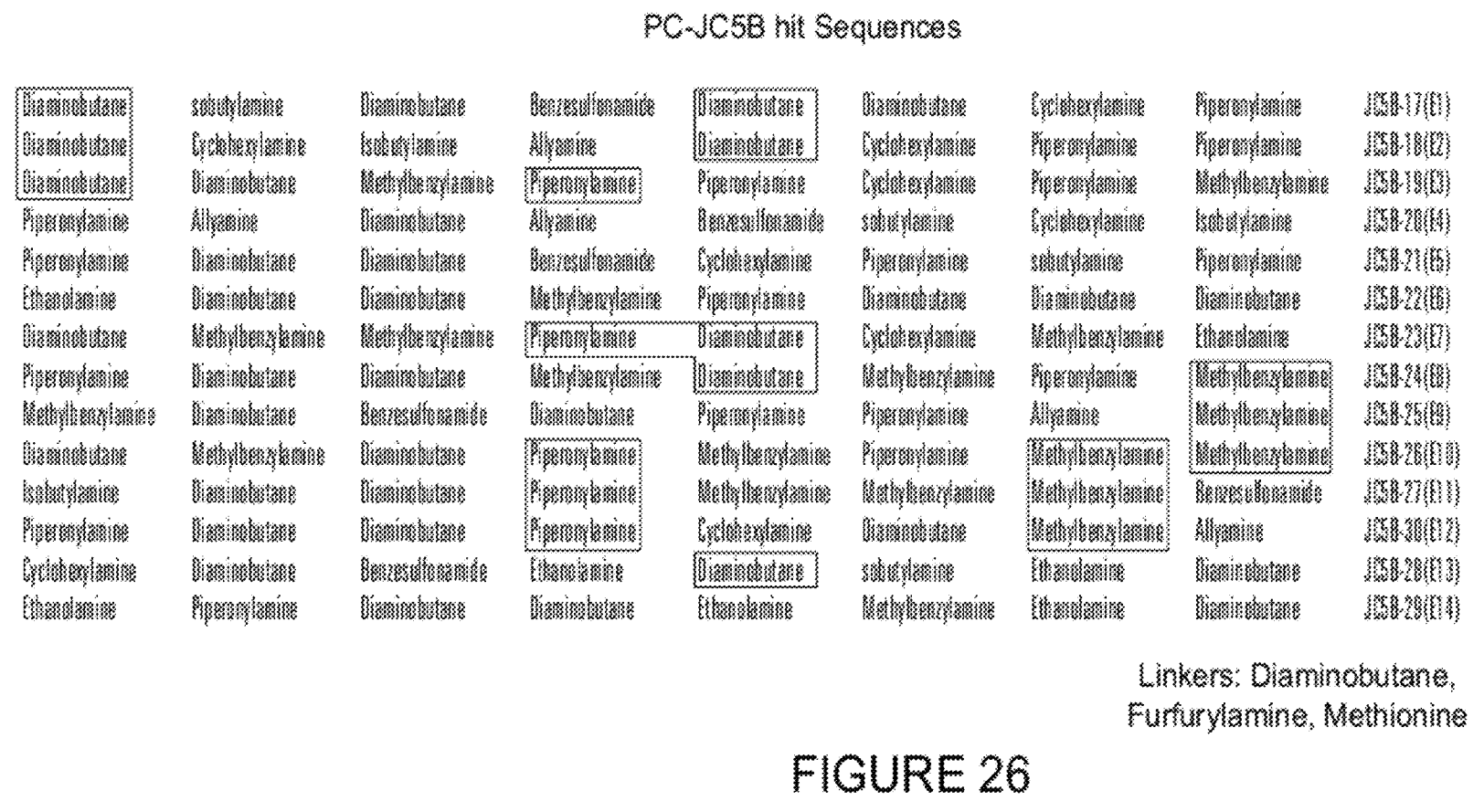

FIG. 26 shows the pancreatic cancer ligands (putative hits) from the JC5B library.

Example 5 Lupus Screening

Figure 27:
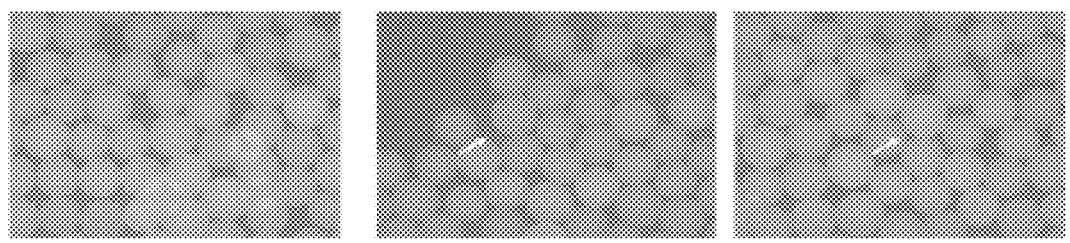
FIGS. 27A, B and C show the results of an SLE (Lupus) screen. A is normal control and B and C are SLE serum from two different groups 1 and 2. The arrows point to the hits.

FIG. 27 shows the SLE hits in an SLE library screen versus a normal control. The KN1B library was used and discovered as useful in this particular screen. The exact same protocol was used in the Lupus screening as delineated above for the Pancreatic cancer screen and for the AD screen except for the library and the serum samples.

FIG. 28 shows the putative SLE hits.

Figure 29:
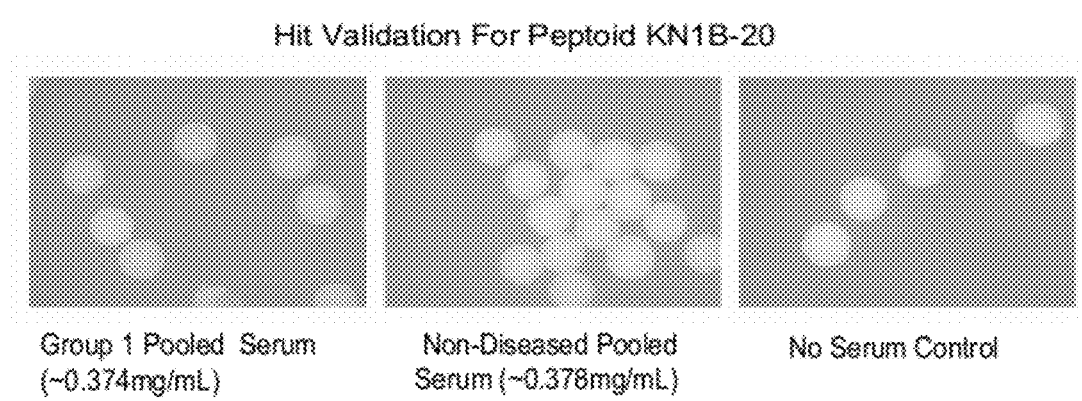
FIG. 29 shows a hit validation for peptoid KN1B-20. Group 1 is pooled diseased serum at a concentration of about 0.374 mg/mL (left picture)(the hits are shown with a red tinge on the bead). Non-diseased pooled serum (center picture) is provided at a concentration of about 0.378 mg/mL and the far right picture shows a no serum control.

FIG. 29 shows a hit validation study.

Diagnostic Kits and Methods

FIG. 30 shows the binding of one of the SLE (lupus) peptoids to ELISA plates using two different binding methods. In the first case, biotin is used as the "moiety" which "binds to" the ELISA plate through a Streptavidin treated plate (this is a non-covalent bond). The peptoid has a fluroescein tag. In the second case, the cysteine on the peptoid covalently attaches to a maleimide treated ELISA plate. In both cases, the data shows that at mM concentrations of greater than about 3 mM a significant fluorescence signal is seen.

Figure 31:
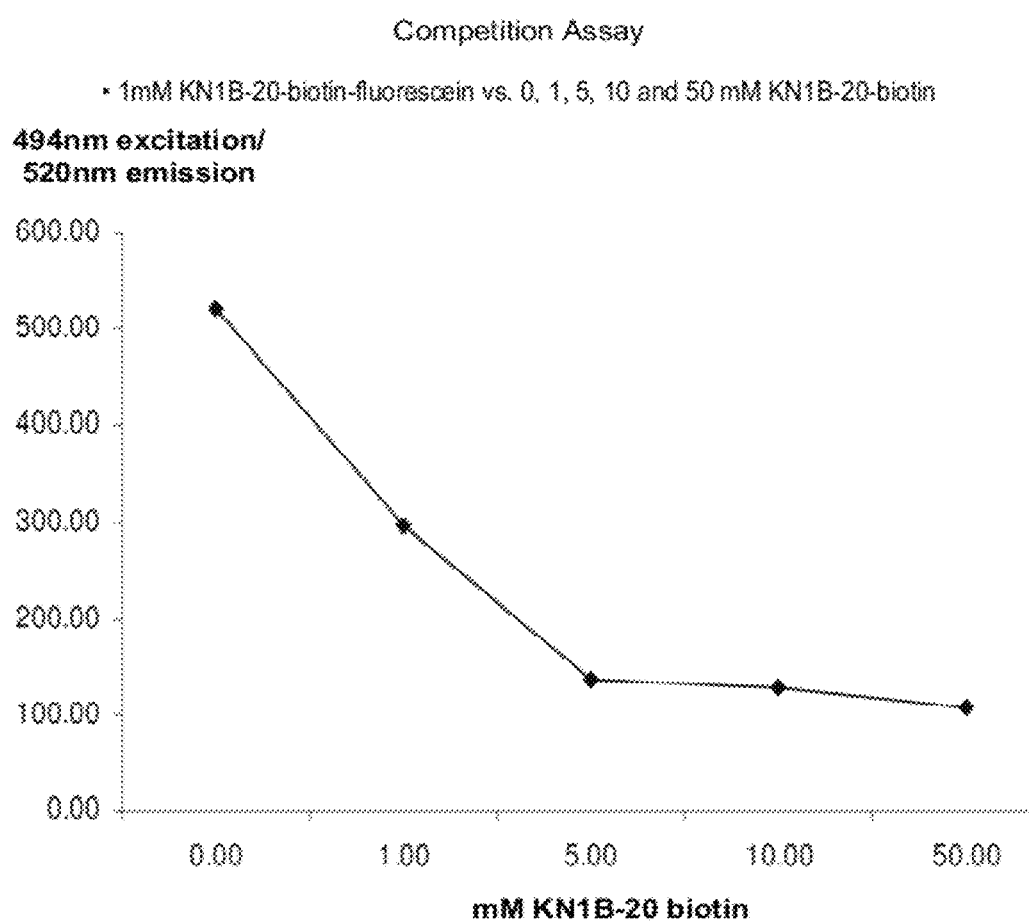
FIG. 31 shows a competition assay between plate bound KN1B-20-biotin-fluorescein versus free KN1B-20-biotin in solution at various concentrations. Signal dampening occurs as the concentration of free KN1B-20-biotin increases from equimolar concentrations of bound versus free.

FIG. 31 shows a competition assay between plate bound KN1B-20-biotin-fluorescein versus free KN1B-20-biotin in solution at various concentrations. Signal dampening occurs as the concentration of free KN1B-20-biotin increases from equimolar concentrations of bound versus free.

Figure 32:
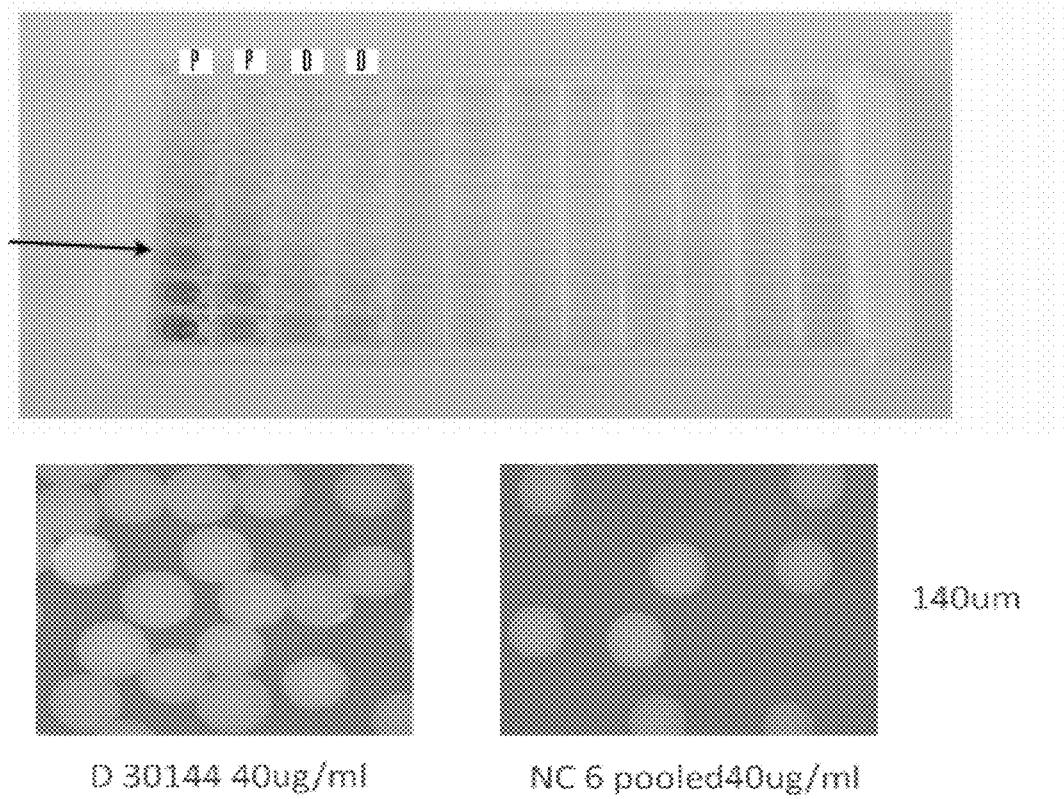
FIG. 32 shows an ELISA plate having peptoid at various concentrations and clearly shows a difference between diseased serum (AD)(P column 1) and normal control serum (column 3) [1:200 doubling each well to 1:400, 1:800, 1:1,600, 1:3,200, 1:6,400, 1:12,800]. The arrow points to the 1:800 dilution in 1×TBST buffer. The peptoid concentration in the wells is 10 mM.

FIG. 32 shows an ELISA plate having peptoid at 10 mM and clearly shows a difference between diseased serum (column1) (AD) and normal control serum (column 3) at various sera dilutions [1:200 doubling to 1:400, 1:800, 1:1,600, 1:3,200, 1:6,400, 1:12,800]. The peptoid wells having AD peptoid ADP3 have peptoid concentrations of 10 mM. Similarly, FIG. 32 shows the clear distinction between diseased samples and normal control samples for a tentagel platform at 40 ug/ml concentration of diluted serum on 140 micron beads.

Figure 33:
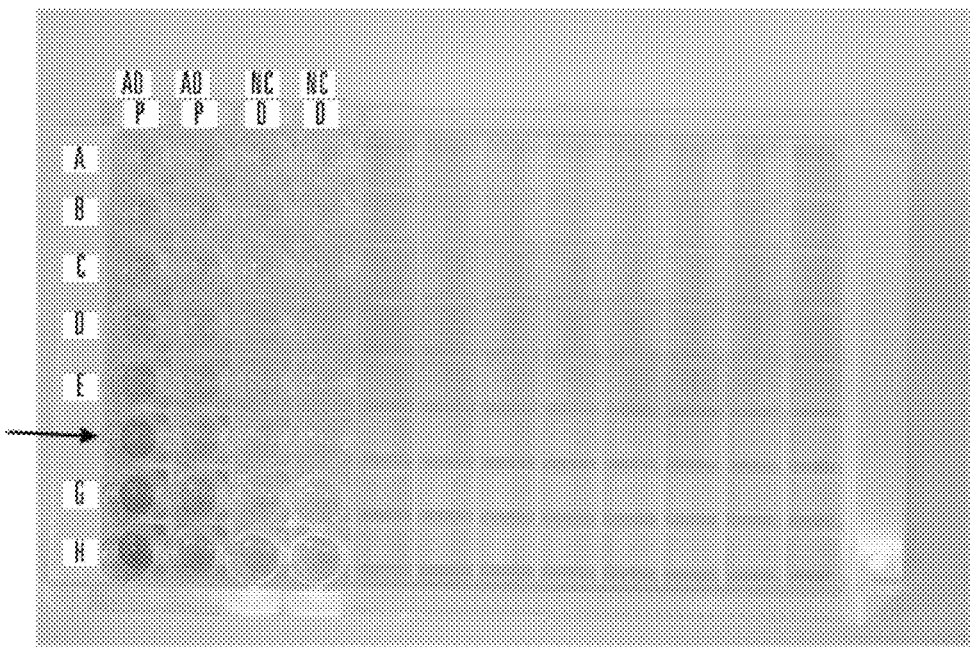
FIG. 33 shows an ELISA plate with 10 mM ADP3 and at various dilutions of AD sera versus control sera. The arrow points to the 1:800 dilution.

FIG. 33 shows an ELISA plate having peptoid at various concentrations and clearly shows a difference between diseased serum (AD) and normal control serum at various dilutions [1:200 to 1:12,800]. The arrow shows the data for 10 mM ADP3 at 1:800 sera dilution.

Figure 34:
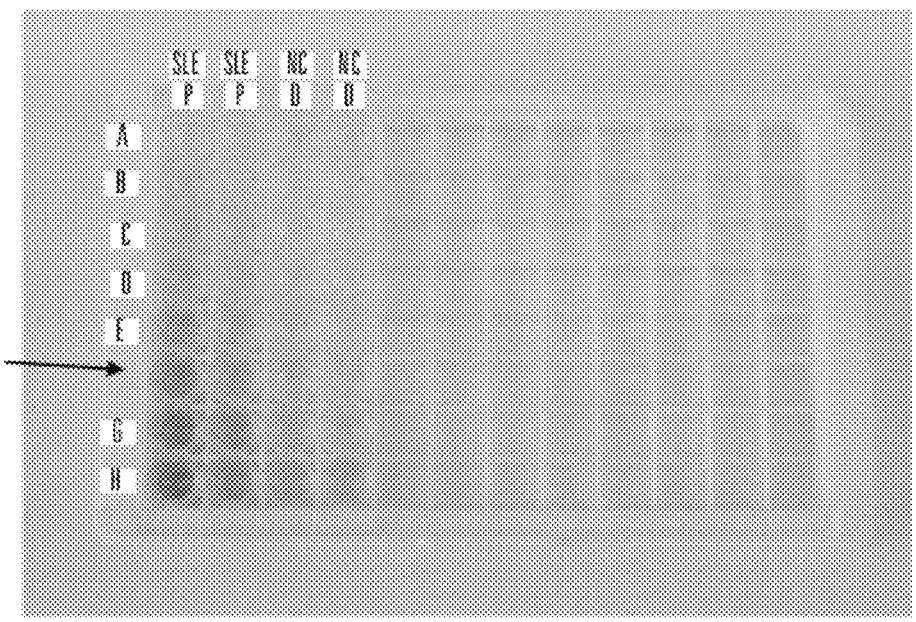
FIG. 34 shows an ELISA plate with 10 mM SLE-KN1B-20 and at various dilutions of AD sera versus control sera. The arrow points to the 1:800 dilution.

FIG. 34 shows an ELISA plate having peptoid at 10 mM and clearly shows a difference between diseased serum (SLE) and normal control serum at various sera dilutions [1:200-1:12,800]. The data shows a clear distinction using SLE-KN1B-20 (10 mM) between diseased serum and control. Plasma may also be utilized in all screening methods provided total protein is accounted for.

Figure 35:
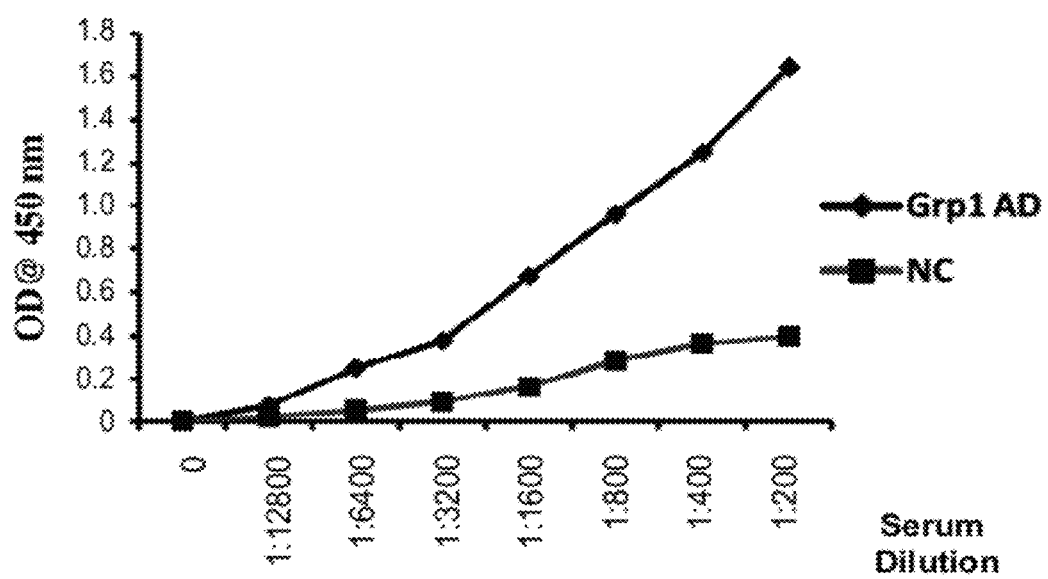
FIG. 35 shows an AD serum ELISA graph using 10 mM ADP3 prepared in binding buffer at various serum dilutions. Separation between normal and diseased serum occurred over the dilution range of 1:200 through approximately 1:10,000. The starting dilutions were 1:200 (Group 1AD serum 0.394 mg/mL and non-diseased serum at 0.386 mg/mL).

FIG. 35 shows an AD serum ELISA graph using 10 mM ADP3 prepared in binding buffer at various serum dilutions. Separation between normal and diseased serum occurred over the dilution range of 1:200 through approximately 1:10,000. The starting dilutions were 1:200 (Group 1AD serum 0.394 mg/mL and non-diseased serum at 0.386 mg/mL).

Figure 36:
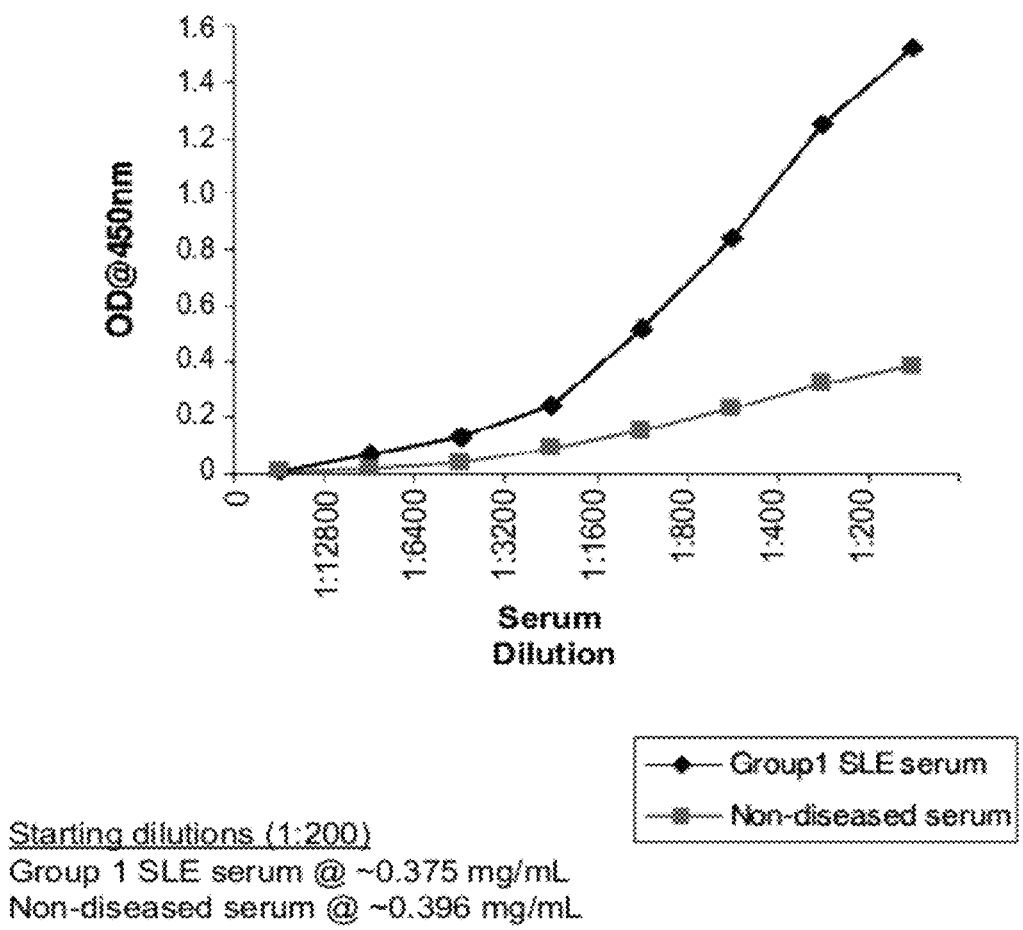
FIG. 36 shows an SLE serum ELISA graph using 10 mM KN1B-20 prepared in binding buffer at various serum dilutions. Separation between normal and diseased serum occurred over the dilution range of 1:200 through approximately 1:10,000. The starting dilutions were 1:200 (Group 1 SLE serum 0.375 mg/mL and non-diseased serum at 0.396 mg/mL).

FIG. 36 shows an SLE serum ELISA graph using 10 mM KN1B-20 prepared in binding buffer at various serum dilutions. Separation between normal and diseased serum occurred over the dilution range of 1:200 through approximately 1:10,000. The starting dilutions were 1:200 (Group 1 SLE serum 0.375 mg/mL and non-diseased serum at 0.396 mg/mL).

Figure 37:
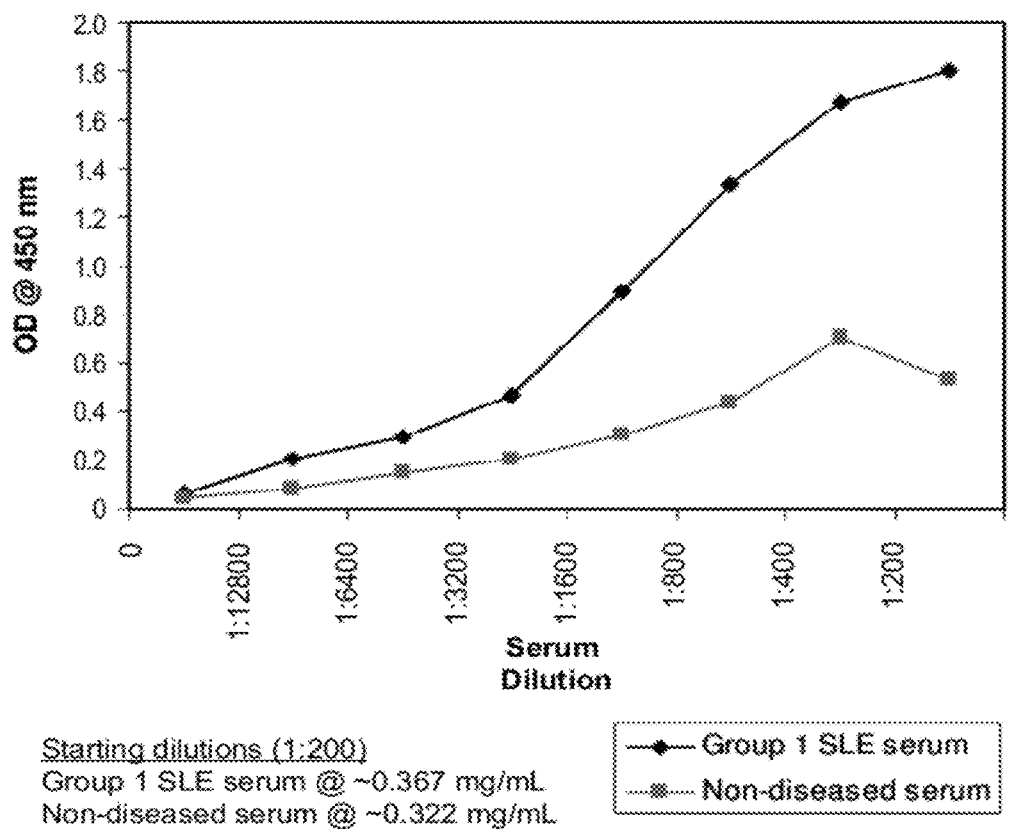
FIG. 37 shows

FIG. 37 shows an SLE serum ELISA graph using 10 mM KN1B-20 prepared in DMSO at various serum dilutions. Separation between normal and diseased serum occurred over the dilution range of 1:200 through approximately 1:10,000. The starting dilutions were 1:200 (Group 1 SLE serum 0.367 mg/mL and non-diseased serum at 0.322 mg/mL).

Figure 38:
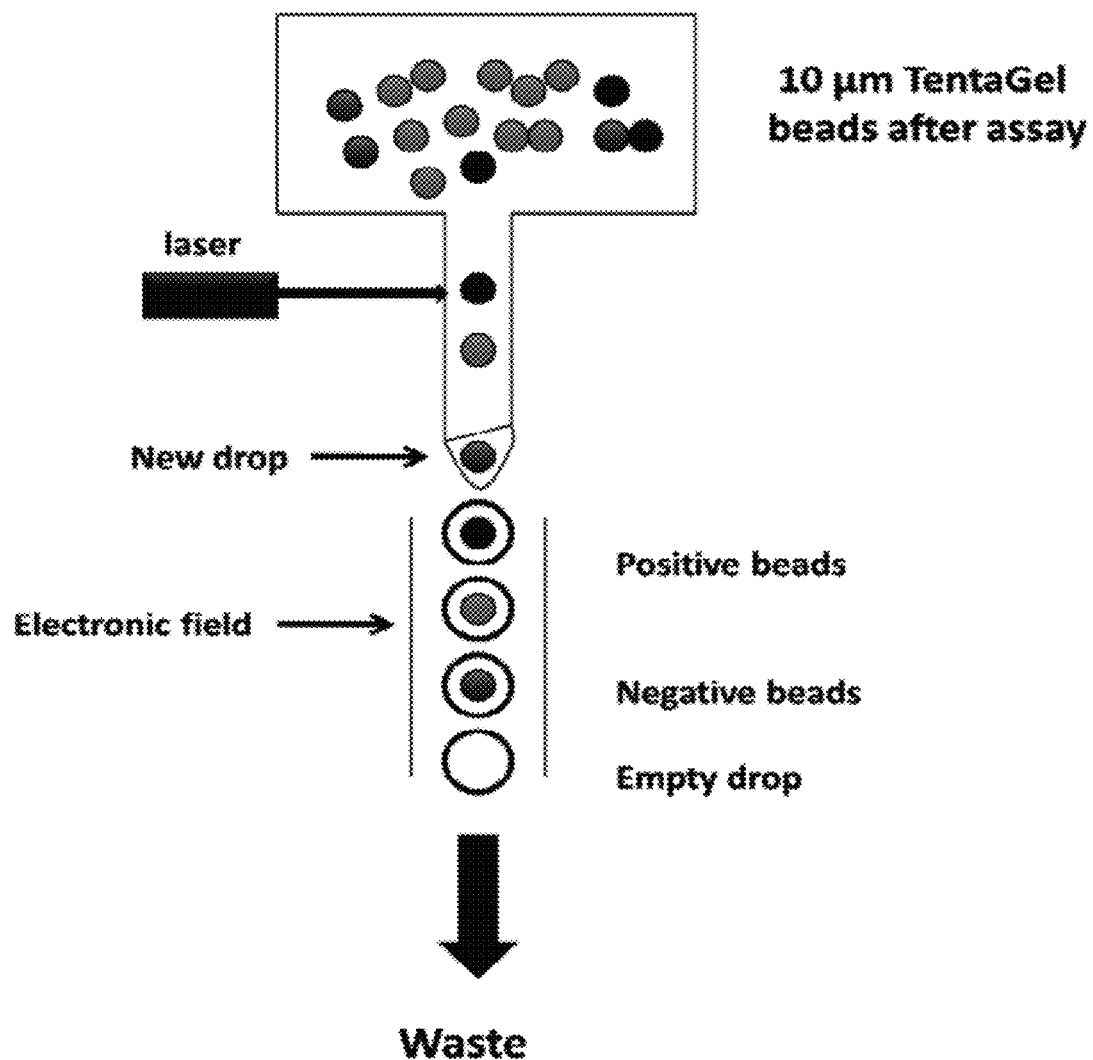
FIG. 38 shows a FACS platform for Tentagel beads hits validation.

FIG. 38 shows a FACS platform for Tentagel beads hits validation.

FIG. 39 shows the degree of separation between beads having an acetyl group and beads having a 2,5-dintrophenyl group (DNP) at various concentrations of sera (100 ug/mL to 1,000 ug/mL) and in response to treatment with an anti-DNP labeled secondary antibody. The Mean fluorescence intensity (MFI) separation was greatest at the higher dilution of 1,000 ug/mL sera.

Figure 40:
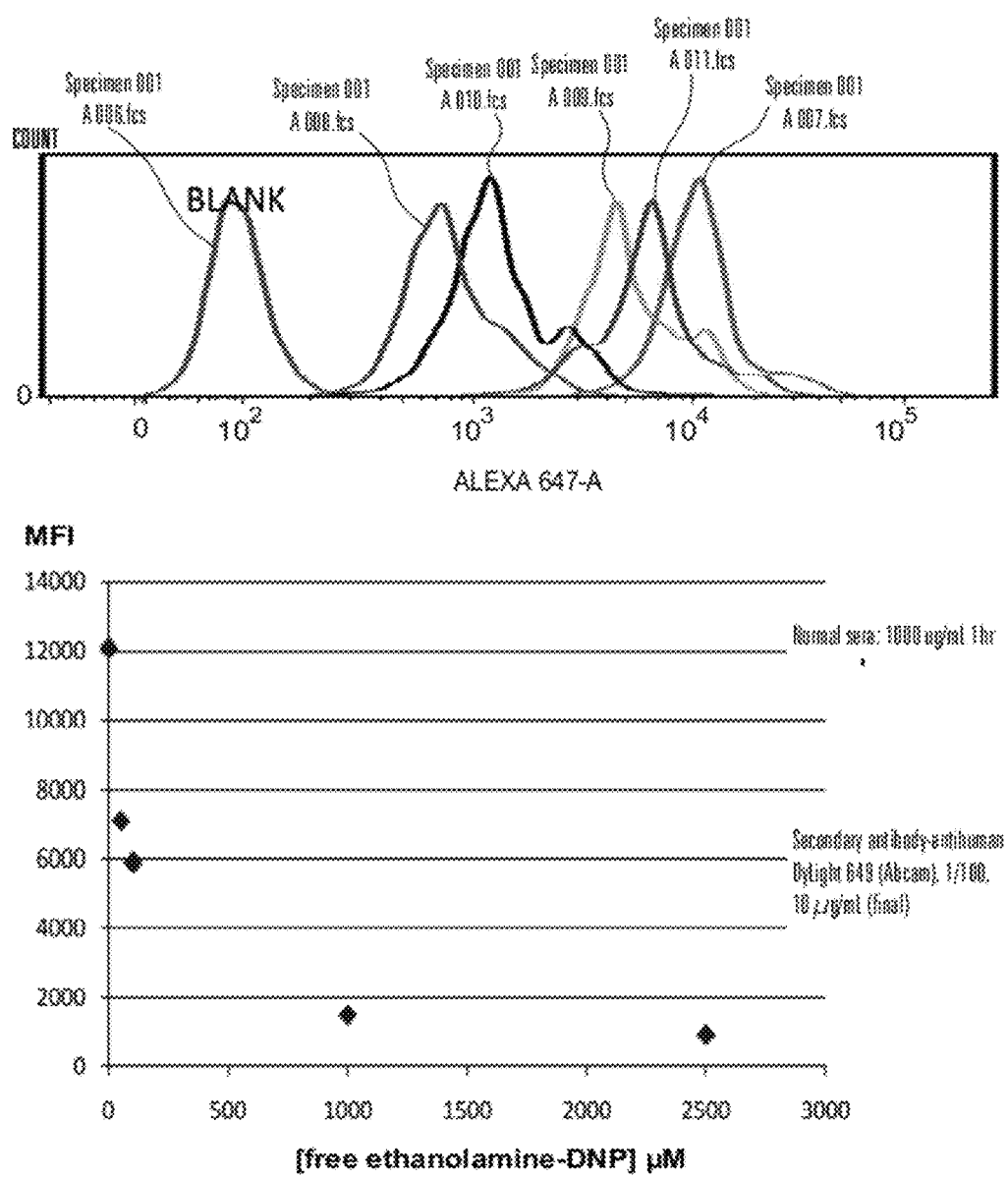
FIG. 40 shows that there is a direct competition between free ethanolamine-DNP and the binding of DNP (on a plate) to anti-DNP antibody at 1,000 ug/mL sera concentration.

FIG. 40 shows that there is a direct competition between free ethanolamine-DNP and the binding of DNP (on a plate) to anti-DNP antibody at 1,000 ug/mL sera concentration.

Figure 41A:
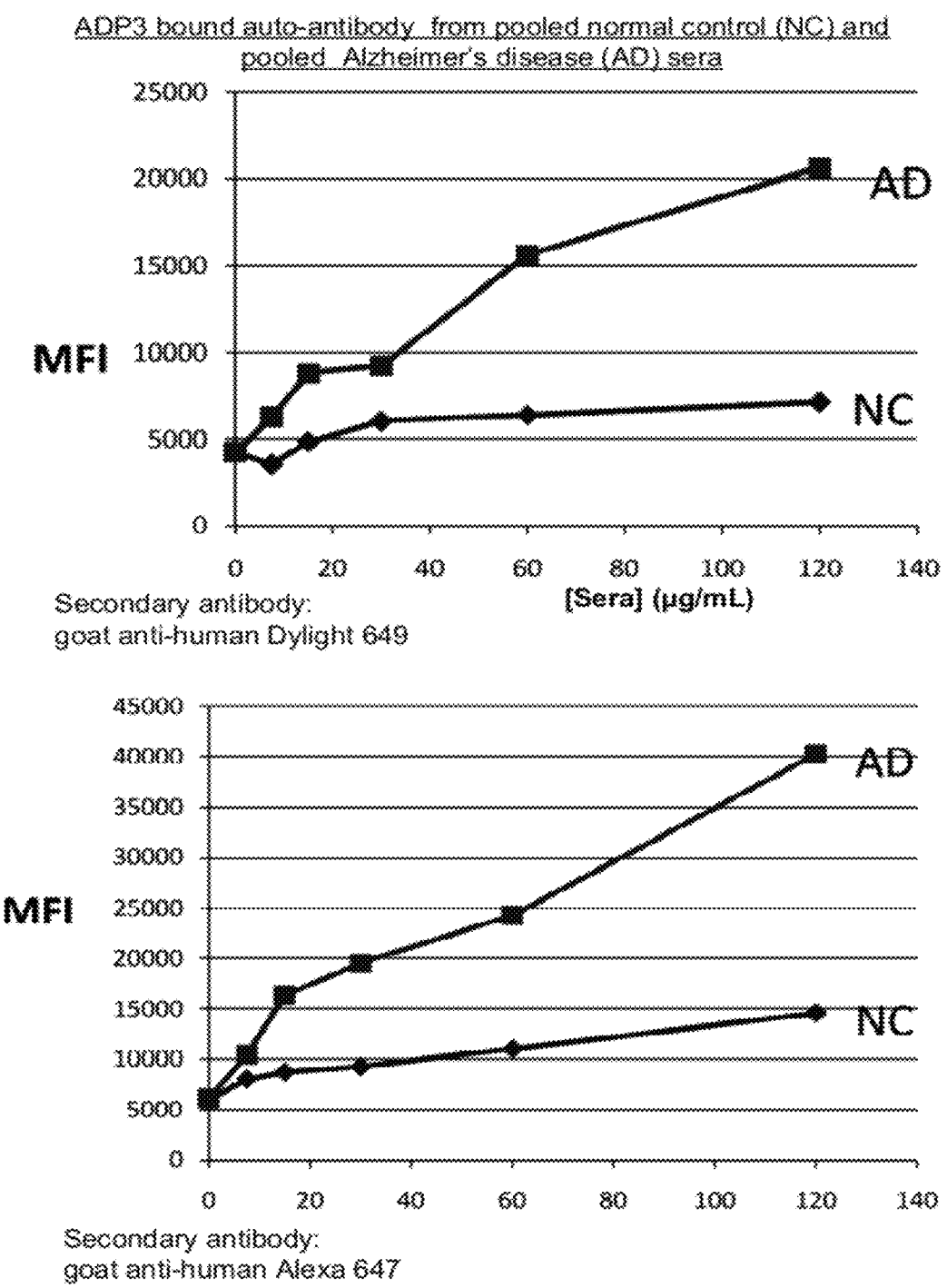
FIG. 41 shows ADP3 bound anti-antibody from pooled normal control sera and pooled AD sera. The data shows good separation at sera concentration ranges of 20 and 140 ug/mL using two different secondary antibodies (goat anti-human Dylight 649 and goat anti-human Alexa 647).
Figure 41B:
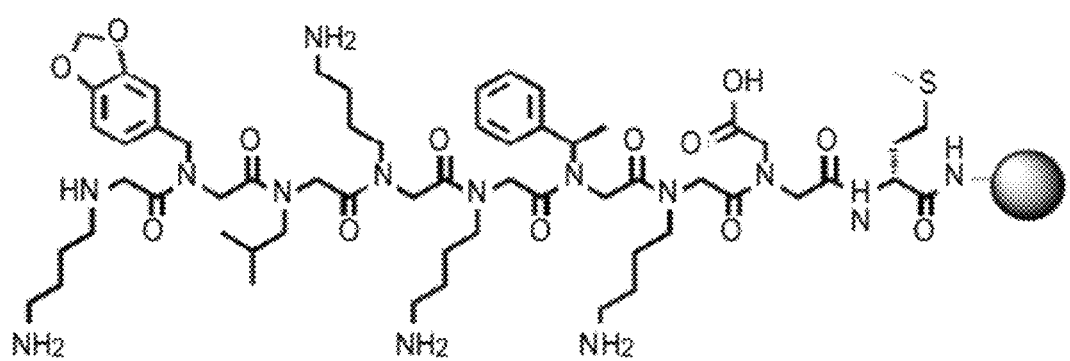

FIG. 41 shows ADP3 bound anti-antibody from pooled normal control sera and pooled AD sera. The data shows good separation at sera concentration ranges of 20 and 140 ug/mL using two different secondary antibodies (goat anti-human Dylight 649 and goat anti-human Alexa 647).

Figure 42:
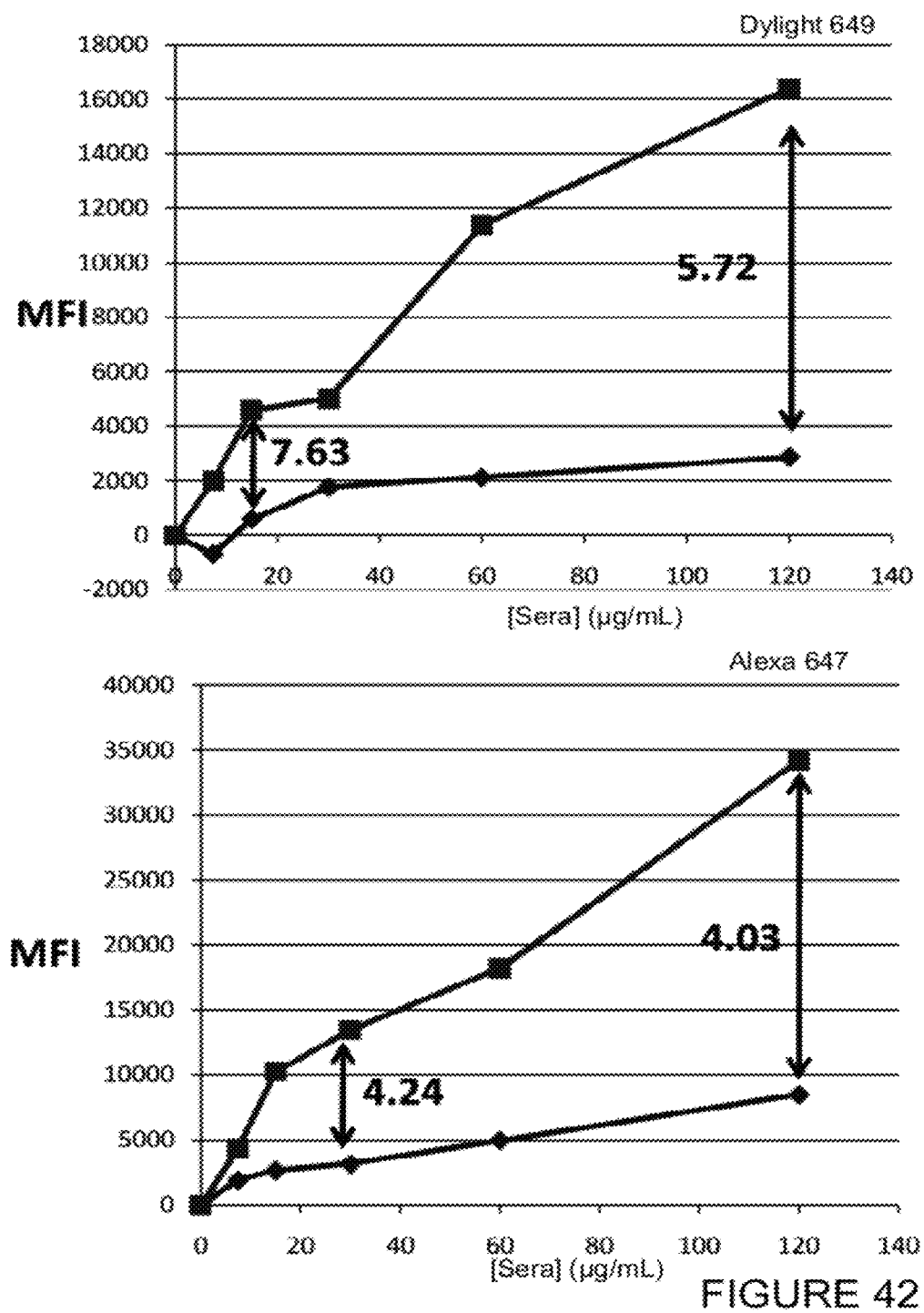
FIG. 42 shows ADP3 bound auto-antibody from normal control and AD sera after background subtraction at various sera concentration ranges. There is a significant degree of separation at most sera concentration ranges from less than 20 ug/mL to 120 ug/mL or greater.

FIG. 42 shows ADP3 bound auto-antibody from normal control and AD sera after background subtraction at various sera concentration ranges. There is a significant degree of separation at most sera concentration ranges from less than 20 ug/mL to 120 ug/mL or greater.

Figure 43B:
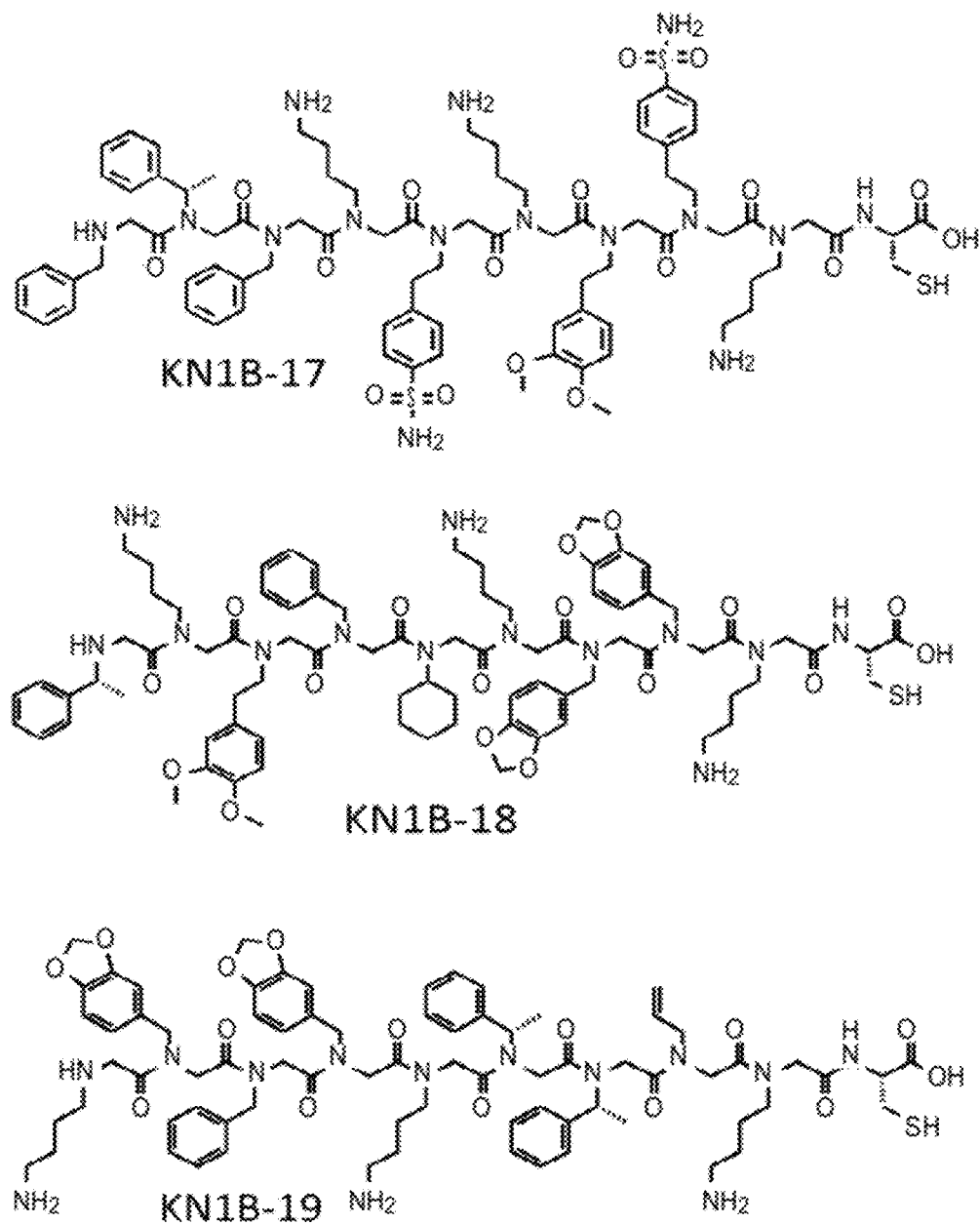

FIGS. 43 and 44 show the structures of the SLE (lupus) resynthesized peptoid ligand hits.

Figure 45:
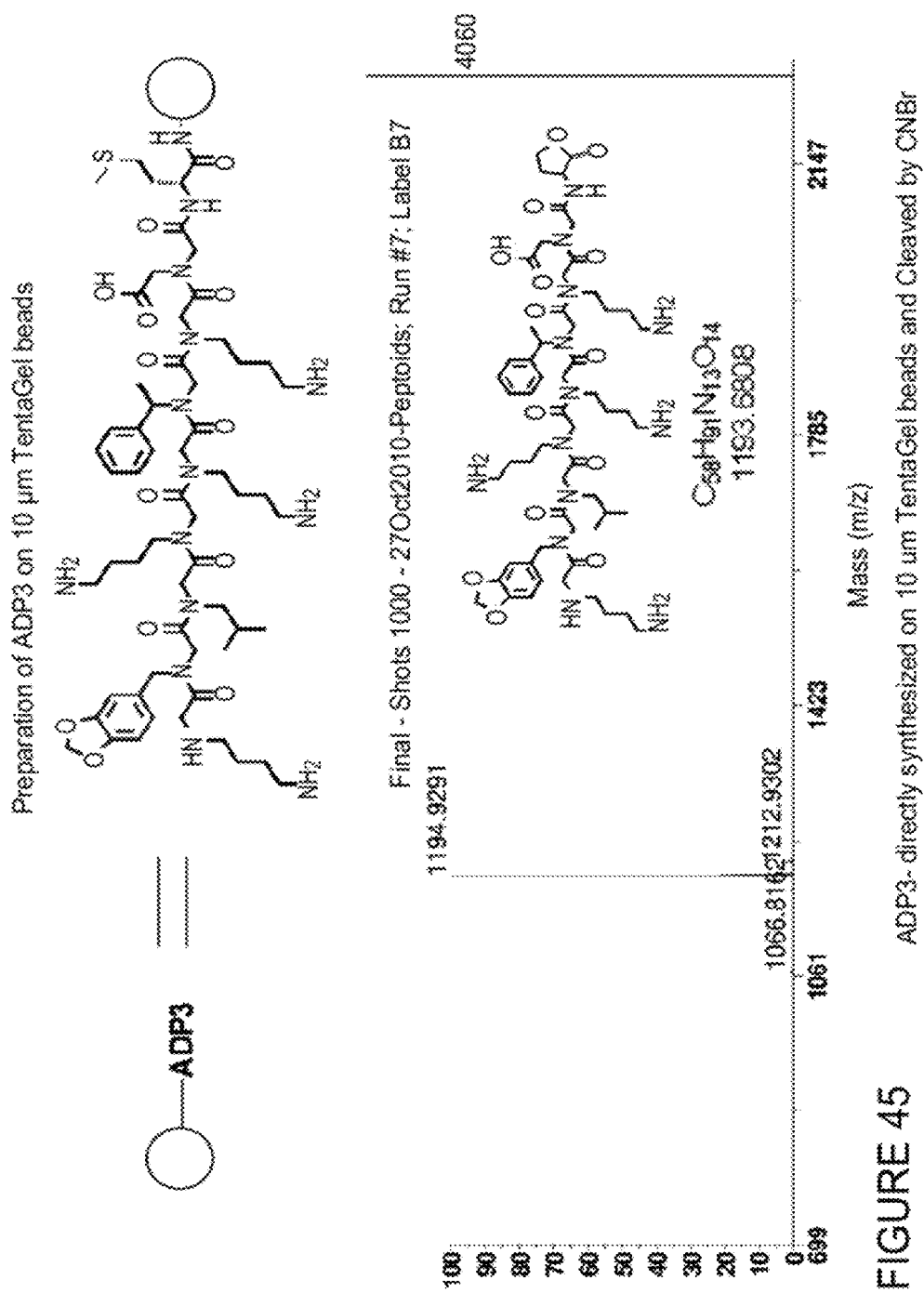
FIG. 45 shows the preparation of ADP3 on 10 um Tentagel beads and the subsequent cleavage using CNBr along with a mass spectrometry reading of the lactone shown.

FIG. 45 shows the preparation of ADP3 on 10 um Tentagel beads and the subsequent cleavage using CNBr along with a mass spectrometry reading of the lactone shown.

Figure 46:
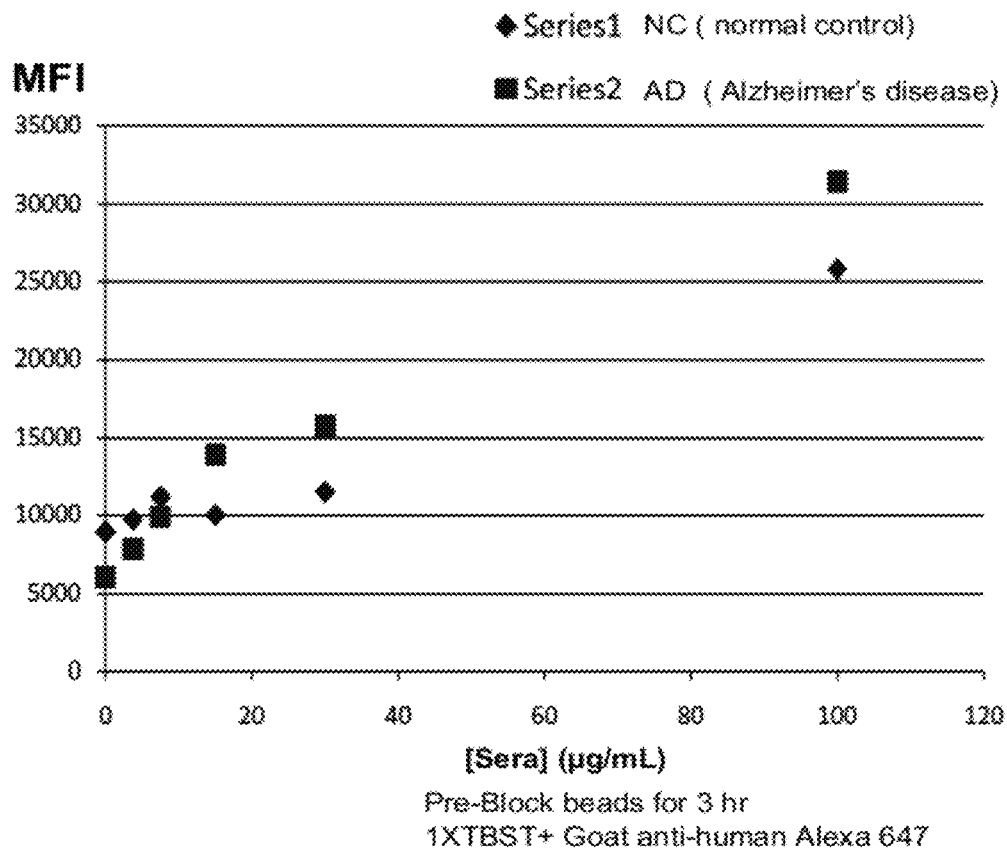
FIG. 46 shows ADP3 bound autoantibody from normal control and Alzheimer's disease sera at different concentrations. The beads were preblocked for 3 hours with 1×TBST and then detected using Goat anti-human Alexa 647 secondary antibody.

FIG. 46 shows ADP3 bound autoantibody from normal control and Alzheimer's disease sera at different concentrations. The beads were preblocked for 3 hours with 1×TBST and then detected using Goat anti-human Alexa 647 secondary antibody.

Figure 47:
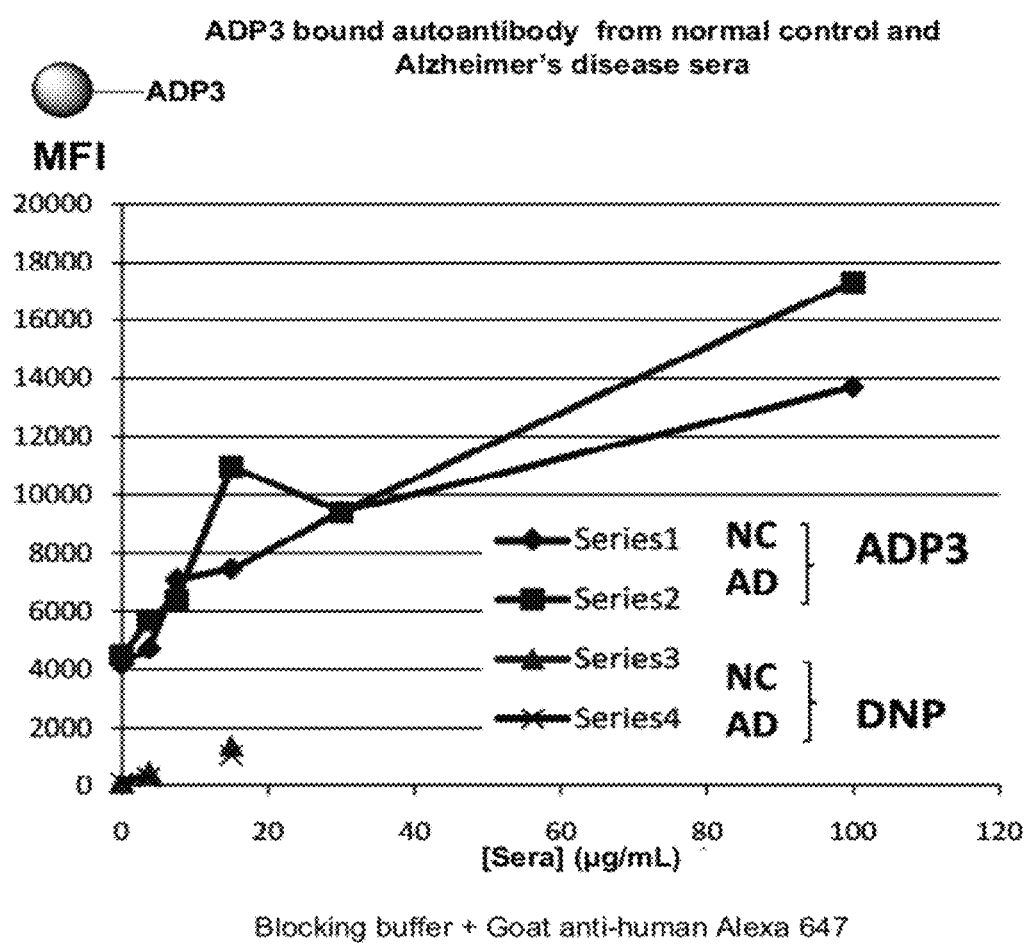
FIG. 47 shows the ADP3 bound autoantibody from normal control and Alzheimer's disease sera at different sera concentrations and also shows DNP values.

FIG. 47 shows the ADP3 bound autoantibody from normal control and Alzheimer's disease sera at different sera concentrations and also shows DNP values.

Figure 48:
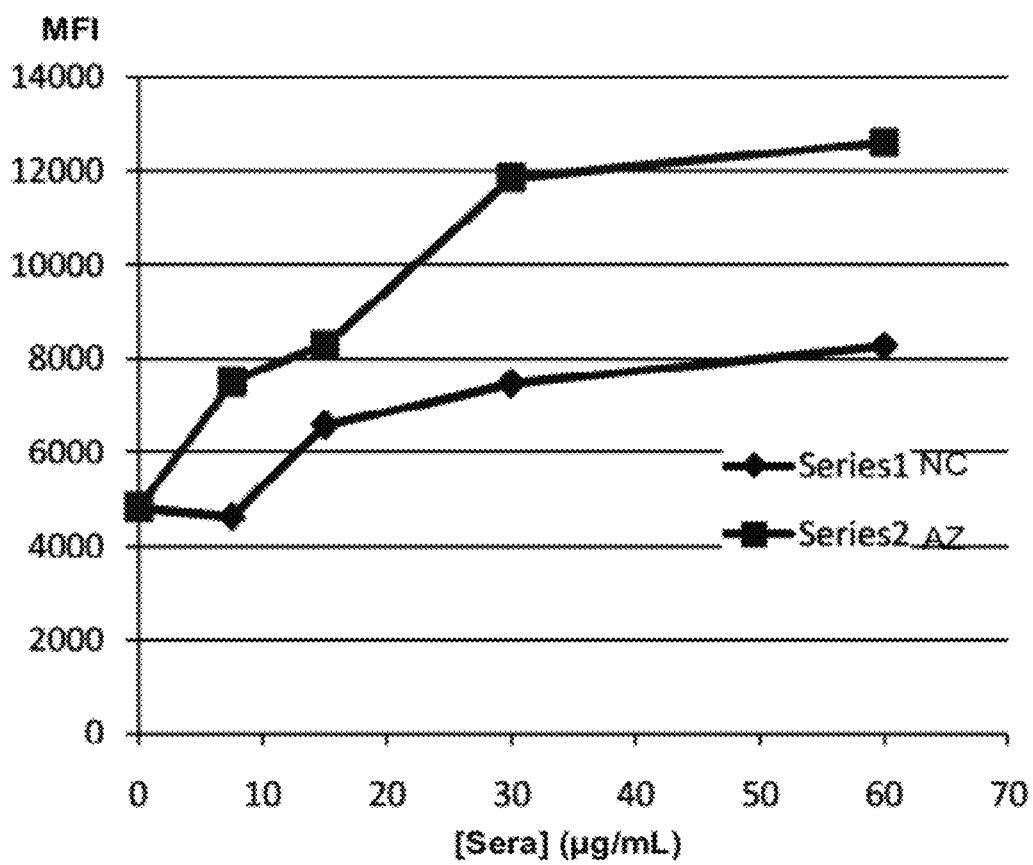
FIGS. 48 and 49 show ADP3 bound autoantibody from normal controls versus Alzheimer's disease sera using pre-blocking conditions such as E. coli lysate and lysine.
Figure 49:
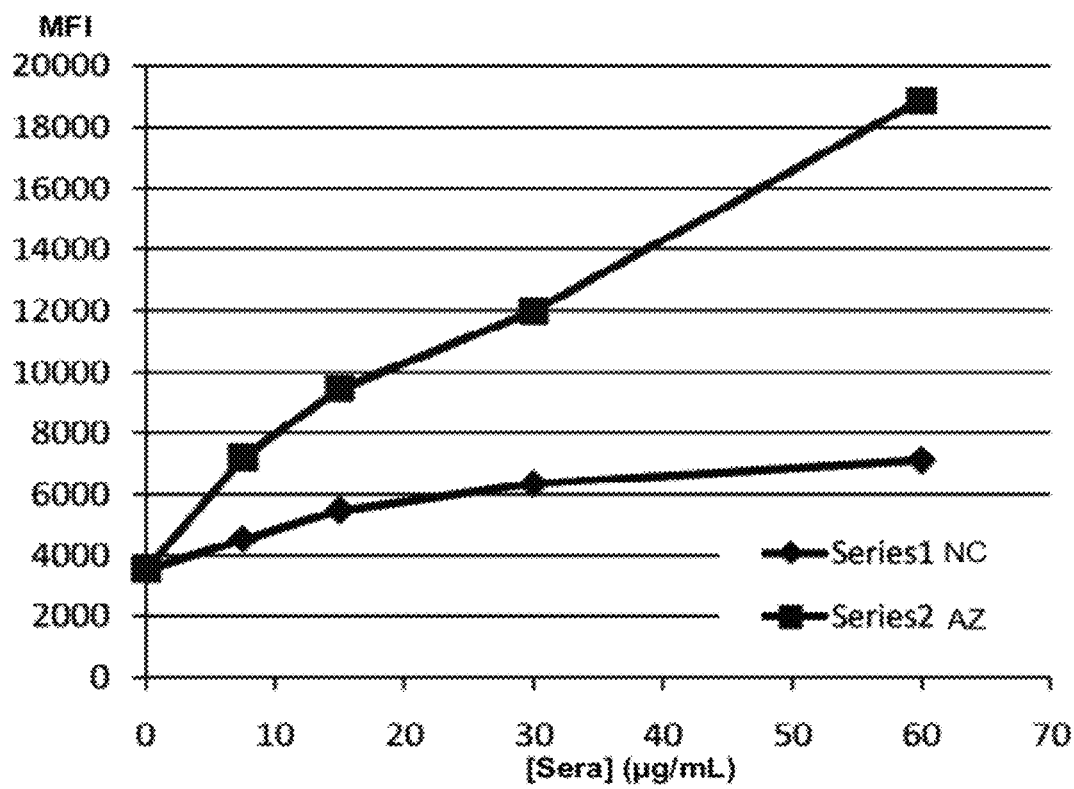

FIGS. 48 and 49 show ADP3 bound autoantibody from normal controls versus Alzheimer's disease sera using preblocking conditions such as E. coli lysate and lysine.

ELISA Protocol 96 well Maleimide-activated plates were obtained from Thermo Scientific, and washed three times with 400 ul/well wash buffer (0.1M sodium phosphate, 0.15M sodium chloride, 0.05% Tween 20, pH 7.2), using a plate washer from Beckman Coulter. The peptoid of interest was diluted to 10 mM in PBS binding buffer (0.1M sodium phosphate, 0.15M sodium chloride, 10 mM EDTA, pH 7.2), and 200 ul of the peptoid solution was added to the appropriate wells. The plate was then allowed to incubate in the dark for two hours at room temperature with shaking at 500 rpm. The peptoid solution was then aspirated from the wells using the plate washer, and again washed three times with 400 ul/well of wash buffer. L-Cysteine HCL: H20 (Thermo Scientific) was diluted to 10 ug/mL in binding buffer, and 200 ul per well was added. The plate was then incubated for one hour in the dark at room temperature with shaking at 500 rpm, and washed three times. 200 ul StartingBlock™ (PBS) Blocking Buffer (Thermo Scientific) was added to the wells and the plate was incubated for one hour at 4° Celsius in the dark with shaking at 500 rpm. The plate was washed three times with the plate washer, and serum samples were prepared by serially diluting in binding buffer from 1:200 downward. Concentrations of the 1:200 sample stocks were taken using a nano-drop (Thermo Scientific), to make sure that they were similar. Each diluted sample was vortexed before preparing the next dilution. 200 ul of the appropriate dilution for serum (both disease and normal) was added to the plate, as well as binding buffer without serum as a control. The serum was allowed to incubate for two hours at room temperature in the dark with 500 rpm shaking. The plate was again washed, and 200 ul of a 1:30,000 dilution of goat anti-human IgG HRP (Millipore) in binding buffer was added to the appropriate wells and incubated at room temperature for 30 minutes with 500 rpm shaking in the dark. The plate was washed three times, and 100 ul of TMB (3,3',5,5'-tetramethylbenzidine) solution was added to each well, and color was allowed to develop for 30 minutes on the bench in the dark. 100 ul of 2M Sulfuric acid stop solution was added to stop the reaction, and the wells were read at an absorbance of 450 using a plate reader.

Thus, in each case and with respect to each disease or any disease, the process of the invention may be utilized to rapidly discover disease associated biomarkers and ligands which bind to such markers. These ligands—this larger pool of ligands-can then be used for multiple diagnostic and/or therapeutic purposes. The diagnostic platforms include microarrays, bead based methods and ELISA systems. The conditions utilized above comprise an important aspect of the invention. These conditions include dilution ranges for sera as well as the concentration of a particular peptoid on a bead or in a well and detection methods. The number of beads having a peptoid on a bead may vary depending upon the particular test kit or screening kit. These numbers may also vary depending upon whether beads/ligands are used in the initial screening protocol and method recited herein and/or are used in a test kit based upon the discovery of a high affinity ligand.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A random ligand library for screening a complex biological fluid comprising a compound of formula I on a support,

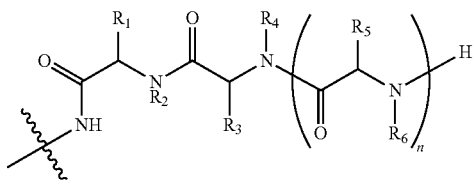

I wherein $R_1$ is —$(C_1$-$C_6)SCH_3$;

$R_2$ is selected from H;

and $R_3$-$R_6$ are independently selected from the groups consisting of —$C_1$-$C_6$alkyl, —$C_1$-$C_6$alkyl$SCH_3$, —$C_0$-$C_6$alkyl$C_2$-$C_6$alkenyl, —$C_0$-$C_6$alkyl $C_2$-$C_6$alkynyl, —$C_1$-$C_6$ COOH, —$C_1$-$C_6$alkylOH, —$C_1$-$C_6$alkyl$NH_2$, —$C_3$-$C_8$cyclo alkyl, —$C_1$-$C_6$alkylaryl, —$C_1$-$C_6$alkylheteroaryl, —$C_1$-$C_6$alkylNC(O)$C_1$-$C_6$alkyl, and —$C_1$-$C_6$alkylcycloamide, wherein any of the aryl or heteroaryl groups may be independently substituted with OH, Cl, F, Br, —$OCH_3$, —$SO_2NH_2$ or —O—$CH_2$—O—, wherein n is 3-11, and wherein said library comprises 200,000 to 150 million distinct ligands.

2. The random ligand library for screening a complex biological fluid according to claim 1 comprising a compound of formula I on a support,

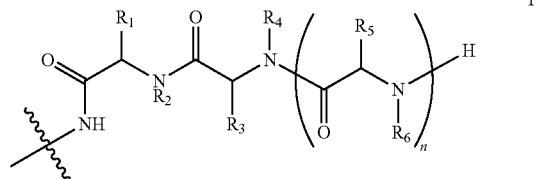

I wherein the compound is produced by a process which comprises use of a reactant selected from the group consisting of
(A) furfurylamine; benzylamine; N-(2-aminoethyl)acetamide; N-(3-aminopropyl)-2-pyrrolidinone; ethanolamine; glycine; diaminobutane; allylamine; piperonylamine; methylbenzylamine; isobutylamine; 4-(2-aminoethyl)benzenesulfonamide; and cyclohexylamine; or
(B) methoxyethylamine; piperonylamine; cyclohexylamine; diaminobutane; methylbenzylamine; furfurylamine; and 4-(2-aminoethyl)benzenesulfonamide; or
(C) furfurylamine, ethanolamine; glycine; diaminobutane; allylamine; piperonylamine; methylbenzylamine; isobutylamine; and 4-(2-aminoethyl)benzenesulfonamide; or
(D) furfurylamine, N-(2-aminoethyl)acetamide; N-(3-aminopropyl)-2-pyrrolidinone; ethanolamine; glycine; diaminobutane; allylamine; piperonylamine; methylbenzylamine; isobutylamine; and 4-(2-aminoethyl)benzenesulfonamide; or
(E) cysteine, glycine, allylamine, ethanolamine, isobutylamine, methylbenzylamine, piperonylamine, methionine, cyclohexylamine, 3,4-dimethoxyphenethylamine, benzylamine, N-(2-aminoethyl)acetamide, N-(3-aminopropyl)-2-pyrrolidone, 4-(2-aminoethyl)benzenesulfonamide and furfurylamine; and wherein, $R_1$ is selected from the group consisting —$(C_1$-$C_6)SCH_3$;

$R_2$ is selected from H;

$R_3$ and $R_5$ are independently selected from the groups consisting of —$C_1$-$C_6$alkyl, —$C_1$-$C_6$alkyl$SCH_3$, —$C_0$-$C_6$alkyl$C_2$-$C_6$alkenyl, —$C_0$-$C_6$alkyl $C_2$-$C_6$alkynyl, —$C_1$-$C_6$ COOH, —$C_1$-$C_6$alkylOH, —$C_1$-$C_6$alkyl$NH_2$, —$C_3$-$C_8$cyclo alkyl, —$C_1$-$C_6$alkylaryl, —$C_1$-$C_6$alkylheteroaryl, —$C_1$-$C_6$alkylNC(O)$C_1$-$C_6$alkyl, and —$C_1$-$C_6$alkylcycloamide, wherein any of the aryl or heteroaryl groups may be independently substituted with OH, Cl, F, Br, —$OCH_3$, —$SO_2NH_2$ or —O—$CH_2$—O—;

$R_4$ is selected from the group consisting of furfuryl and —$(C_1$-$C_6$alkyl)$NH_2$, $R_6$ is selected from the group consisting of consisting of 1-yl-allyl, 1-yl-2-hydroxyethyl, isobutyl, 1-yl-n-butylamine, methylbenzyl, piperonyl, cyclohexyl, 1-yl-2-(3,4-dimethoxyphenyl)ethyl, benzyl, 1-yl-2-(acetamide)ethyl, 1-yl-3N-(2-pyrrolidinone)propyl, 1-yl-2-(4-benzenesulfonamide)ethyl, and furfuryl; and n is 3-11.

3. The ligand library according to claim 2 wherein the support is selected from a bead or resin.

4. The ligand library according to claim 3 wherein the bead or resin comprises a PEG linker of less than 10 monomeric units.

* * * * *